US009458128B2

(12) United States Patent
Ahlmark et al.

(10) Patent No.: US 9,458,128 B2
(45) Date of Patent: Oct. 4, 2016

(54) CATECHOL O-METHYLTRANSFERASE ACTIVITY INHIBITING COMPOUNDS

(71) Applicant: Orion Corporation, Espoo (FI)

(72) Inventors: Marko Ahlmark, Espoo (FI); David Din Belle, Espoo (FI); Mika Kauppala, Helsinki (FI); Anne Luiro, Helsinki (FI); Taina Pajunen, Espoo (FI); Jarmo Pystynen, Espoo (FI); Eija Tiainen, Espoo (FI); Matti Vaismaa, Espoo (FI); Josef Messinger, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 14/403,023

(22) PCT Filed: May 23, 2013

(86) PCT No.: PCT/FI2013/000026
§ 371 (c)(1),
(2) Date: Nov. 21, 2014

(87) PCT Pub. No.: WO2013/175053
PCT Pub. Date: Nov. 28, 2013

(65) Prior Publication Data
US 2015/0218124 A1    Aug. 6, 2015

Related U.S. Application Data

(60) Provisional application No. 61/651,217, filed on May 24, 2012, provisional application No. 61/777,162, filed on Mar. 12, 2013.

(51) Int. Cl.
| *C07C 205/56* | (2006.01) |
| *C07C 255/57* | (2006.01) |
| *C07C 255/53* | (2006.01) |
| *C07C 255/51* | (2006.01) |
| *C07C 229/42* | (2006.01) |
| *C07D 333/60* | (2006.01) |
| *C07C 255/54* | (2006.01) |
| *C07D 333/24* | (2006.01) |
| *C07C 311/29* | (2006.01) |
| *C07D 207/337* | (2006.01) |
| *C07D 277/30* | (2006.01) |
| *C07D 295/192* | (2006.01) |
| *C07D 213/57* | (2006.01) |
| *C07D 307/54* | (2006.01) |
| *C07D 307/80* | (2006.01) |
| *C07D 309/06* | (2006.01) |
| *C07D 309/12* | (2006.01) |
| *C07D 231/12* | (2006.01) |
| *C07D 231/14* | (2006.01) |
| *C07D 333/28* | (2006.01) |

(Continued)

(52) U.S. Cl.
CPC .......... *C07D 333/60* (2013.01); *A61K 31/198* (2013.01); *A61K 31/277* (2013.01); *A61K 31/341* (2013.01); *A61K 31/343* (2013.01); *A61K 31/381* (2013.01); *A61K 31/382* (2013.01); *A61K 31/40* (2013.01); *A61K 31/5377* (2013.01); *C07C 255/53* (2013.01); *C07C 255/54* (2013.01); *C07C 255/57* (2013.01); *C07C 255/59* (2013.01); *C07C 309/66* (2013.01); *C07C 311/29* (2013.01); *C07C 317/46* (2013.01); *C07C 323/29* (2013.01); *C07C 323/62* (2013.01); *C07D 207/337* (2013.01); *C07D 211/14* (2013.01); *C07D 213/57* (2013.01); *C07D 213/62* (2013.01); *C07D 231/12* (2013.01); *C07D 231/14* (2013.01); *C07D 277/30* (2013.01); *C07D 277/34* (2013.01); *C07D 277/74* (2013.01); *C07D 295/155* (2013.01); *C07D 295/192* (2013.01); *C07D 307/54* (2013.01); *C07D 307/80* (2013.01); *C07D 307/81* (2013.01); *C07D 309/06* (2013.01); *C07D 309/12* (2013.01); *C07D 309/22* (2013.01); *C07D 333/24* (2013.01); *C07D 333/28* (2013.01); *C07D 333/70* (2013.01)

(58) Field of Classification Search
CPC . C07C 205/56; C07C 255/57; C07C 255/53; C07C 255/51; C07C 207/37; C07C 333/24; C07C 333/60; C07C 307/52; C07C 307/82
See application file for complete search history.

(56) References Cited

U.S. PATENT DOCUMENTS 3,974,184 A    8/1976   Umezawa et al.
5,236,952 A *  8/1993   Bernauer .............. C07C 45/298
                                                        514/520

(Continued)

FOREIGN PATENT DOCUMENTS

CN    101643465 A    2/2010
CN    102755312 A    10/2012

(Continued)

OTHER PUBLICATIONS

Zhu et al. JOC (2010) 75, 7240-7257.*

(Continued)

*Primary Examiner* — Nyeemah A Grazier
(74) *Attorney, Agent, or Firm* — Finnegan, Henderson, Farabow, Garrett & Dunner, LLP

(57) ABSTRACT

Compounds of formula (I), wherein $R_1$ is as defined in the claims, exhibit COMT enzyme inhibiting activity and are thus useful as COMT inhibitors. Methods of treatment and pharmaceutical dosage forms are also disclosed.

52 Claims, No Drawings

(51) Int. Cl.

| | | |
|---|---|---|
| C07D 333/70 | (2006.01) | |
| C07D 277/34 | (2006.01) | |
| C07D 277/74 | (2006.01) | |
| C07D 211/14 | (2006.01) | |
| C07D 295/155 | (2006.01) | |
| C07D 213/62 | (2006.01) | |
| C07C 255/59 | (2006.01) | |
| C07C 309/66 | (2006.01) | |
| C07C 317/46 | (2006.01) | |
| C07C 323/62 | (2006.01) | |
| A61K 31/198 | (2006.01) | |
| A61K 31/277 | (2006.01) | |
| A61K 31/341 | (2006.01) | |
| A61K 31/343 | (2006.01) | |
| A61K 31/381 | (2006.01) | |
| A61K 31/382 | (2006.01) | |
| A61K 31/40 | (2006.01) | |
| A61K 31/5377 | (2006.01) | |
| C07C 323/29 | (2006.01) | |
| C07D 307/81 | (2006.01) | |
| C07D 309/22 | (2006.01) | |

(56) References Cited

U.S. PATENT DOCUMENTS

| | | | |
|---|---|---|---|
| 5,446,194 A | 8/1995 | Backstrom et al. | |
| 5,489,731 A | 2/1996 | Ditrich | |
| 5,698,755 A | 12/1997 | Beller et al. | |
| 6,150,412 A * | 11/2000 | Pystynen | C07C 59/74 514/381 |
| 6,194,627 B1 | 2/2001 | Geissler et al. | |
| 6,215,035 B1 | 4/2001 | Choudhary et al. | |
| 6,291,383 B1 | 9/2001 | Zapf et al. | |
| 2003/0018219 A1 | 1/2003 | Choudhary et al. | |

FOREIGN PATENT DOCUMENTS

| | | |
|---|---|---|
| EP | 2 246 338 A1 | 11/2010 |
| EP | 2 305 633 A1 | 4/2011 |
| JP | 2008/308493 A | 12/2006 |
| JP | 2008/308494 A | 12/2008 |
| JP | 2008/308495 A | 12/2008 |
| JP | 2011/021010 A | 2/2011 |
| JP | 2012/051884 A | 3/2012 |
| JP | 2012/051885 A | 3/2012 |
| WO | WO 96/37456 | 11/1996 |
| WO | WO 98/27973 | 7/1998 |
| WO | WO 00/37423 | 6/2000 |
| WO | WO 01/68083 A1 | 9/2001 |
| WO | WO 01/98250 A1 | 12/2001 |
| WO | WO 01/98251 A1 | 12/2001 |
| WO | WO 02/02548 A1 | 1/2002 |
| WO | WO 02/22551 A1 | 3/2002 |
| WO | WO 03/059346 A1 | 7/2003 |
| WO | WO 2004/112729 A2 | 12/2004 |
| WO | WO 2005/058228 A2 | 6/2005 |
| WO | WO 2006/051154 A1 | 5/2006 |
| WO | WO 2007/010085 A2 | 1/2007 |
| WO | WO 2007/013830 A1 | 2/2007 |
| WO | WO 2007/056143 A2 | 5/2007 |
| WO | WO 2007/063789 A1 | 6/2007 |
| WO | WO 2007/076875 A2 | 7/2007 |
| WO | WO 2007/117165 A1 | 10/2007 |
| WO | WO 2008/024963 A1 | 2/2008 |
| WO | WO 2008/058402 A1 | 5/2008 |
| WO | WO 2009/081892 A1 | 7/2009 |
| WO | WO 2010/011318 A2 | 1/2010 |
| WO | WO 2010/111504 A2 | 9/2010 |
| WO | WO 2011/109254 A1 | 9/2011 |
| WO | WO 2011/109261 A1 | 9/2011 |
| WO | WO 2011/109267 A1 | 9/2011 |
| WO | WO 2012/088438 A1 | 6/2012 |
| WO | WO 2012/146936 A1 | 11/2012 |

OTHER PUBLICATIONS

Borgulya, et al.; "Catechol-$O$-Methyltransferase-Inhibiting Pyrocatechol Derivatives: Synthesis and Structure-Activity Studies"; Helv. Chim. Acta; vol. 72, p. 952 (1989).

Copeland; "Evaluation of Enzyme Inhibitors in Drug Discovery: A Guide for Medicinal Chemists and Pharmacologists"; John Wiley & Sons, Inc., Hoboken, NJ; pp. 185-187 (2005).

Kim, et al.; "Pharmacokinetic Evaluation and Modeling of Formulated Levodopa Intranasal Delivery Systems"; Eur. J. Pharm. Sci.; vol. 38, p. 525 (2009).

Kurkela, et al.; "Microplate Screening Assay to Identify Inhibitors of Human Catechol-$O$-Methyltransferase"; Anal. Biochem.; vol. 331, p. 198 (2004).

Lotta, et al.; "PLS Modelling of Structure-Activity Relationships of Catechol $O$-Methyltransferase Inhibitors"; J. Comput.-Aided Mol. Des.; vol. 6, p. 253 (1992).

Männistö, et al.; "Properties of Novel Effective and Highly Selective Inhibitors of Catechol-O-Methyltransferase"; Life Sci.; vol. 43, pp. 1465-1471 (1988).

Palma, et al.; "Computation of the Binding Affinities of Catechol-$O$-Methyltransferase Inhibitors: Multisubstate Relative Free Energy Calculations"; J. Comput. Chem.; vol. 33, p. 970 (2012).

Shinagawa; "Molecular Orbital Studies on the Structure-Activity Relationships of Catechol O-Methyltransferase Inhibitors"; Japan, J. Pharmacol.; vol. 58, p. 95 (1992).

Taskinen, et al.; "QSAR and Binding Model for Inhibition of Rat Liver Catechol-O-Methyl-Transferase by 1,5-Substituted-3,4-Dihydroxybenzenes"; Quant. Struct.-Act. Relat.; vol. 8, p. 210 (1989).

Tervo, et al.; "A Structure-Activity Relationship Study of Catechol-$O$-Methyltransferase Inhibitors Combining Molecular Docking and 3D QSAR Methods"; J. Comput.-Aided Mol. Des.; vol. 17, p. 797 (2003).

English abstract of CN 101643465 A.
English abstract of CN 102755312 A.
English abstract of JP 2008/308493 A.
English abstract of JP 2008/308494 A.
English abstract of JP 2008/308495 A.
English abstract of JP 2011/021010 A.
English abstract of JP 2012/051884 A.
English abstract of JP 2012/051885 A.
English abstract of WO 2007/063789 A1.
English abstract of WO 2009/081892 A1.
International Search Report for PCT/FI2013/000026 dated Sep. 13, 2013.

* cited by examiner

CATECHOL O-METHYLTRANSFERASE ACTIVITY INHIBITING COMPOUNDS

This is a national stage application under §371 of International Patent Application No. PCT/FI2013/000026, filed May 23, 2013, which claims the benefit of priority of U.S. Provisional Application No. 61/651,217, filed May 24, 2012, and U.S. Provisional Application No. 61/777,162, filed Mar. 12, 2013, and, all of which are incorporated herein by reference.

FIELD OF THE INVENTION

The present invention relates to pharmacologically active 2-substituted 4,5-dihydroxyisophthalonitriles, or pharmaceutically acceptable salts and esters thereof, as well as to pharmaceutical compositions containing them and to their use as inhibitors of the catechol O-methyltransferase (COMT) enzyme.

BACKGROUND OF THE INVENTION

Dopamine is deficient in the brain of patients suffering from Parkinson's disease. Levodopa is used orally in the treatment of Parkinson's disease. Levodopa is a dopamine precursor, which is converted to dopamine in the brain. However, only a small portion of orally administered levodopa reaches the brain, because levodopa is metabolized in the peripheral system by COMT as well as by dopa decarboxylase (DDC). COMT metabolizes levodopa by converting it to 3-O-methyldopa, which is therapeutically ineffective and detrimental when competing with levodopa. COMT inhibitors have been shown to be effective in clinical use for the treatment of Parkinson's disease as an adjunct to levodopa therapy.

It is generally thought that the levodopa concentration in plasma reflects the levodopa levels in the brain. It is thus desirable to achieve a high levodopa concentration in plasma. However, optimal levodopa concentration in plasma is not achieved, for example, with the currently used COMT inhibitor entacapone.

COMT inhibitors have also been indicated to be useful in the treatment of, for example, hypertension, heart failure and depression (U.S. Pat. No. 5,446,194) as well as inhibitors for the prevention of diabetic vascular dysfunctions (WO 98/27973). COMT inhibitors have also been disclosed as being useful for treating or controlling pain (WO 01/68083) as well as for treating restless legs syndrome (RLS), which is also known as Ekbom's syndrome (WO 2006/051154). RLS is characterized by an irresistible urge to move the legs accompanied by other unpleasant sensations deep within the legs.

Some compounds with COMT inhibiting activity are known in the art. Isoflavone derivatives as COMT inhibitors have been disclosed in U.S. Pat. No. 3,974,184 and CN 101643465 A. Catechol derivatives as COMT inhibitors have been disclosed in U.S. Pat. No. 5,236,952, U.S. Pat. No. 5,446,194, WO 96/37456, WO 00/37423, WO 01/98250, WO 01/98251, WO 02/02548, WO 02/22551, WO 2004/112729, WO 2005/058228, WO 2007/010085, WO 2007/013830, WO 2007/063789, WO 2007/117165, JP 2008308493, JP 2008308494, JP 2008308495, EP 2246338 A1, WO 2009/081892, EP 2305633 A1, JP 2011021010, JP 2012051884, and JP 2012051885. 3-Hydroxypyridin-4(1H)-one derivatives, 3-hydroxypyridin-2(1H)-one derivatives, and 5-hydroxypyrimidin-4(3H)-one derivatives as COMT inhibitors have been disclosed in WO 2011/109254, WO 2011/109261, and WO 2011/109267, respectively. Flavone derivatives as COMT inhibitors have been disclosed in CN 102755312 A.

SUMMARY OF THE INVENTION

An object of the present invention is to provide further inhibitors of the catechol O-methyltransferase enzyme that can be used for the treatment of diseases or conditions wherein inhibition of COMT is indicated to be useful. Accordingly, an object of the present invention is to provide further compounds to be used as COMT inhibiting agents in the treatment of mammals, including humans and animals. Furthermore, pharmaceutical compositions containing the present compounds are provided.

The COMT inhibitors of the invention provide in levodopa therapy an improved levodopa concentration in plasma.

DETAILED DESCRIPTION OF THE INVENTION

The present invention relates to compounds having the general formula I,

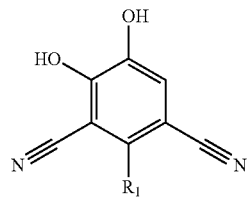

wherein
$R_1$ is $(C_1\text{-}C_6)$alkyl, $(C_2\text{-}C_6)$alkenyl, $(C_2\text{-}C_6)$alkynyl, $(C_3\text{-}C_7)$cycloalkyl, $(C_4\text{-}C_{10})$cycloalkenyl, aryl, $(R_2)_2C\!=\!C\!-\!$, halogen, hydroxy, $(C_1\text{-}C_6)$alkoxy, $(C_1\text{-}C_6)$alkyl-S—, $(C_4\text{-}C_{10})$cycloalkenyloxy, $(C_4\text{-}C_{10})$cycloalkenyl-S—, aryloxy, aryl-S—, heteroaryloxy, heteroaryl-S—, $(R_3)_2N\!-\!$, $(R_4)_2C\!=\!N\!-\!$, heterocyclyl, heteroaryl, aryl$(C_1\text{-}C_6)$alkyl, (1-amino-1-carboxymethyl)-$(C_1\text{-}C_6)$alkyl, halo$(C_1\text{-}C_6)$alkyl, hydroxy$(C_1\text{-}C_6)$alkyl, $(C_1\text{-}C_6)$alkoxy$(C_1\text{-}C_6)$alkyl, $(C_1\text{-}C_6)$alkyl-S—$(C_1\text{-}C_6)$alkyl, $(R_3)_2N\!-\!(C_1\text{-}C_6)$alkyl, heterocyclyl$(C_1\text{-}C_6)$alkyl, carboxy$(C_2\text{-}C_6)$alkenyl, $(C_3\text{-}C_7)$cycloalkyl$(C_2\text{-}C_6)$alkenyl, aryl$(C_2\text{-}C_6)$alkenyl, $(C_1\text{-}C_6)$alkoxy$(C_2\text{-}C_6)$alkenyl, heterocyclyl$(C_2\text{-}C_6)$alkenyl, heteroaryl$(C_2\text{-}C_6)$alkenyl, carboxy$(C_2\text{-}C_6)$alkynyl, $(C_3\text{-}C_7)$cycloalkyl$(C_2\text{-}C_6)$alkynyl, aryl$(C_2\text{-}C_6)$alkynyl, $(C_1\text{-}C_6)$alkoxy$(C_2\text{-}C_6)$alkynyl, heterocyclyl$(C_2\text{-}C_6)$alkynyl, heteroaryl$(C_2\text{-}C_6)$alkynyl, halo$(C_1\text{-}C_6)$alkoxy, hydroxy$(C_1\text{-}C_6)$alkoxy, $(C_1\text{-}C_6)$alkoxy$(C_1\text{-}C_6)$alkoxy, $(C_1\text{-}C_6)$alkyl-$(C\!=\!O)\!-\!O\!-\!$, $R_5\!-\!(S\!=\!O)\!-\!$, $R_5\!-\!(O\!=\!S\!=\!O)\!-\!$, hydroxy$(C_1\text{-}C_6)$alkoxy$(C_1\text{-}C_6)$alkyl, $(C_1\text{-}C_6)$alkoxy-$(C\!=\!O)\!=\!(C_2\text{-}C_6)$alkenyl or $(C_1\text{-}C_6)$alkyl-$(C\!=\!O)\!-\!O\!-\!(C_1\text{-}C_6)$alkyl, wherein said $(C_4\text{-}C_{10})$cycloalkenyl, aryl, heterocyclyl, heteroaryl or $(C_3\text{-}C_7)$cycloalkyl as such or as part of another group is unsubstituted or substituted with 1, 2 or 3 substituent(s) $R_6$;
$R_2$ is, independently at each occurrence, carboxy or aryl, wherein said aryl is, independently at each occurrence, unsubstituted or substituted with 1, 2 or 3 substituent(s) $R_6$;
$R_3$ is, independently at each occurrence, H, $(C_1\text{-}C_6)$alkyl, $(C_3\text{-}C_7)$cycloalkyl, aryl, $(C_3\text{-}C_7)$cycloalkyl$(C_1\text{-}C_6)$alkyl hydroxy$(C_1\text{-}C_6)$alkyl or $(C_1\text{-}C_6)$alkoxy$(C_1\text{-}C_6)$alkyl, wherein said $(C_3\text{-}C_7)$cycloalkyl or aryl as such or as part of another group is, independently at each occurrence, unsubstituted or substituted with 1 substituent being $(C_1-C_6)$alkyl, halogen, hydroxy, $(C_1-C_6)$alkoxy or hydroxy$(C_1-C_6)$alkyl;

$R_4$ is, independently at each occurrence, H or aryl, wherein said aryl is, independently at each occurrence, unsubstituted or substituted with 1 substituent being $(C_1-C_6)$alkyl, halogen or $(C_1-C_6)$alkoxy;

$R_5$ is $(C_1-C_6)$alkyl, aryl, hydroxy or $(C_1-C_6)$alkoxy, wherein said aryl is unsubstituted or substituted with 1, 2 or 3 substituent(s) $R_6$;

$R_6$ is, independently at each occurrence, $(C_1-C_6)$alkyl, $(C_2-C_6)$alkenyl, carboxy, cyano, aryl, halogen, hydroxy, $(C_1-C_6)$alkoxy, $(C_1-C_6)$alkyl-S—, $(C_4-C_{10})$cycloalkenyloxy, $(C_4-C_{10})$cycloalkenyl-S—, aryloxy, aryl-S—, heteroaryloxy, heteroaryl-S—, $(R_7)_2N$—, heteroaryl, carboxy$(C_1-C_6)$alkyl, aryl$(C_1-C_6)$alkyl, halo$(C_1-C_6)$alkyl, hydroxy$(C_1-C_6)$alkyl, $(C_1-C_6)$alkoxy$(C_1-C_6)$alkyl, heterocyclyl$(C_1-C_6)$alkyl, $(C_1-C_6)$alkyl-(C=O)—, $(C_1-C_6)$alkoxy-(C=O)—, heterocyclyl-(C=O)—, $(R_7)_2N$—(C=O)—, halo$(C_1-C_6)$alkoxy, $R_8$—(S=O)—, $R_8$—(O=S=O)—, $(C_1-C_6)$alkoxy-(C=O)—$(C_1-C_6)$alkyl, $(R_7)_2N$—(C=O)—$(C_1-C_6)$alkyl or $(C_1-C_6)$alkoxy$(C_1-C_6)$alkoxy-(C=O)—, wherein said aryl, heteroaryl or heterocyclyl as such or as part of another group is, independently at each occurrence, unsubstituted or substituted with 1 substituent being $(C_1-C_6)$alkyl;

or $R_6$ and $R_6$ both attached to the same carbon ring atom form, together with the carbon ring atom to which they are attached, a —(C=O)— group;

$R_7$ is, independently at each occurrence, H, $(C_1-C_6)$alkyl, $(C_3-C_7)$cycloalkyl or carboxy$(C_1-C_6)$alkyl, wherein said $(C_3-C_7)$cycloalkyl is, independently at each occurrence, unsubstituted or substituted with 1 substituent being $(C_1-C_6)$alkyl;

$R_8$ is, independently at each occurrence, $(C_1-C_6)$alkyl, hydroxy, $(C_1-C_6)$alkoxy or $(R_9)_2N$—;

$R_9$ is, independently at each occurrence, $(C_1-C_6)$alkyl;

or a pharmaceutically acceptable salt or ester thereof.

In one embodiment of the invention, the invention relates to compounds of formula I, wherein $R^1$ is $(C_1-C_6)$alkyl, $(C_2-C_6)$alkenyl, $(C_2-C_6)$alkynyl, $(C_4-C_{10})$cycloalkenyl, aryl, halogen, hydroxy, $(C_4-C_{10})$cycloalkenyloxy, aryloxy, aryl-S—, heteroaryl-S—, $(R_3)_2N$—, $(R_4)_2C=N$—, heterocyclyl, heteroaryl, aryl$(C_1-C_6)$alkyl, hydroxy$(C_1-C_6)$alkyl, $(R_3)_2N$—$(C_1-C_6)$alkyl, heterocyclyl$(C_1-C_6)$alkyl, carboxy$(C_2-C_6)$alkenyl, $(C_3-C_7)$cycloalkyl$(C_2-C_6)$alkenyl, aryl$(C_2-C_6)$alkenyl, $(C_1-C_6)$alkoxy$(C_2-C_6)$alkenyl, heteroaryl$(C_2-C_6)$alkenyl, aryl$(C_2-C_6)$alkynyl, $(C_1-C_6)$alkoxy$(C_2-C_6)$alkynyl, $R_5$—(S=O)—, $R_5$—(O=S=O)— or $(C_1-C_6)$alkoxy-(C=O)—$(C_2-C_6)$alkenyl, wherein said $(C_4-C_{10})$cycloalkenyl, aryl, heterocyclyl, heteroaryl or $(C_3-C_7)$cycloalkyl as such or as part of another group is unsubstituted or substituted with 1, 2 or 3 substituent(s) $R_6$;

$R_3$ is, independently at each occurrence, H, $(C_1-C_6)$alkyl, $(C_3-C_7)$cycloalkyl, aryl, $(C_3-C_7)$cycloalkyl$(C_1-C_6)$alkyl, hydroxy$(C_1-C_6)$alkyl or $(C_1-C_6)$alkoxy$(C_1-C_6)$alkyl, wherein said $(C_3-C_7)$cycloalkyl or aryl as such or as part of another group is unsubstituted or substituted with 1 substituent being $(C_1-C_6)$alkyl;

$R_4$ is, independently at each occurrence, H or aryl, wherein said aryl is, independently at each occurrence, substituted with 1 substituent being $(C_1-C_6)$alkyl, halogen or $(C_1-C_6)$alkoxy;

$R_5$ is aryl, wherein said aryl is substituted with 1 substituent $R_6$;

$R_6$ is, independently at each occurrence, $(C_1-C_6)$alkyl, $(C_2-C_6)$alkenyl, carboxy, cyano, aryl, halogen, hydroxy, $(C_1-C_6)$alkoxy, $(C_1-C_6)$alkyl-S—, aryloxy, heteroaryl, carboxy$(C_1-C_6)$alkyl, aryl$(C_1-C_6)$alkyl, halo$(C_1-C_6)$alkyl, hydroxy$(C_1-C_6)$alkyl; $(C_1-C_6)$alkoxy$(C_1-C_6)$alkyl, heterocycyl$(C_1-C_6)$alkyl, $(C_1-C_6)$alkyl-(C=O)—, $(C_1-C_6)$alkoxy-(C=O)—, heterocyclyl-(C=O)—, $(R_7)_2N$—(C=O)—, halo$(C_1-C_6)$alkoxy, $R_8$—(O=S=O)—, $(C_1-C_6)$alkoxy-(C=O)—$(C_1-C_6)$alkyl, $(R_7)_2N$—(C=O)—$(C_1-C_6)$alkyl or $(C_1-C_6)$alkoxy$(C_1-C_6)$alkoxy-(C=O)—, wherein said aryl, heteroaryl or heterocyclyl as such or as part of another group is, independently at each occurrence, unsubstituted or substituted with 1 substituent being $(C_1-C_6)$alkyl;

or $R_6$ and $R_6$ both attached to the same carbon ring atom form, together with the carbon ring atom to which they are attached, a —(C=O)— group;

$R_7$ is, independently at each occurrence, H, $(C_1-C_6)$alkyl, $(C_3-C_7)$cycloalkyl or carboxy$(C_1-C_6)$alkyl, wherein said $(C_3-C_7)$cycloalkyl is unsubstituted;

$R_8$ is, independently at each occurrence, $(C_1-C_6)$alkyl or $(R_9)_2N$—;

$R_9$ is, independently at each occurrence, $(C_1-C_6)$alkyl.

In one embodiment of the invention, the invention relates to compounds of formula I, wherein $R_1$ is $(C_1-C_6)$alkyl, $(C_2-C_6)$alkenyl, $(C_2-C_6)$alkynyl, $(C_4-C_{10})$cycloalkenyl, aryl, halogen, $(C_4-C_{10})$cycloalkenyloxy, aryloxy, aryl-S—, heteroaryl-S—, $(R_3)_2N$—, $(R_4)_2C=N$—, heterocyclyl, heteroaryl, aryl$(C_1-C_6)$alkyl, $(R_3)_2N$—$(C_1-C_6)$alkyl, carboxy$(C_2-C_6)$alkenyl, $(C_3-C_7)$cycloalkyl$(C_2-C_6)$alkenyl or aryl$(C_2-C_6)$alkenyl, wherein said $(C_4-C_{10})$cycloalkenyl, aryl, heterocyclyl, heteroaryl or $(C_3-C_7)$cycloalkyl as such or as part of another group is unsubstituted or substituted with 1, 2 or 3 substituent(s) $R_6$;

$R_3$ is, independently at each occurrence, H, $(C_1-C_6)$alkyl or $(C_1-C_6)$alkoxy$(C_1-C_6)$alkyl;

$R_4$ is, independently at each occurrence, H or aryl, wherein said aryl is, independently at each occurrence, substituted with 1 substituent being $(C_1-C_6)$alkyl;

$R_5$ is $(C_1-C_6)$alkyl, aryl, hydroxy or $(C_1-C_6)$alkoxy, wherein said aryl is unsubstituted or substituted with 1, 2 or 3 substituent(s) $R_6$;

$R_6$ is, independently at each occurrence, $(C_1-C_6)$alkyl, cyano, aryl, halogen, hydroxy, $(C_1-C_6)$alkoxy, $(C_1-C_6)$alkyl- $R_4$ is, independently at each occurrence, H or aryl, wherein said aryl is, independently at each occurrence, substituted with 1 substituent being $(C_1-C_6)$alkyl, halogen or $(C_1-C_6)$alkoxy;

$R_6$ is, independently at each occurrence, $(C_1-C_6)$alkyl, cyano, aryl, halogen, hydroxy, $(C_1-C_6)$alkoxy, $(C_1-C_6)$alkyl- S—, carboxy($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, heterocyclyl-(C=O)—, $(R_7)_2$N—(C=O)— or $R_8$—(O=S=O)—, wherein said aryl or heterocyclyl as such or as part of another group is unsubstituted;

$R_7$ is, independently at each occurrence, H or ($C_1$-$C_6$)alkyl;
$R_8$ is, independently at each occurrence, ($C_1$-$C_6$)alkyl.

In one embodiment of the invention, the invention relates to compounds of formula I, wherein
$R_1$ is ($C_1$-$C_6$)alkyl, ($C_2$-$C_6$)alkenyl, aryl, halogen, aryloxy, aryl-S—, $(R_3)_2$N—, heterocyclyl, heteroaryl, aryl($C_1$-$C_6$)alkyl or aryl($C_2$-$C_6$)alkenyl, wherein said aryl, heterocyclyl or heteroaryl as such or as part of another group is unsubstituted or substituted with 1, 2 or 3 substituent(s) $R_6$;
$R_3$ is, independently at each occurrence, H or ($C_1$-$C_6$)alkyl;
$R_6$ is, independently at each occurrence, ($C_1$-$C_6$)alkyl, halogen, hydroxy, ($C_1$-$C_6$)alkoxy, carboxy($C_1$-$C_6$)alkyl, halo($C_1$-$C_6$)alkyl or $(R_7)_2$N—(C=O)—;
$R_7$ is, independently at each occurrence, H or ($C_1$-$C_6$)alkyl.

In one embodiment of the invention, the invention relates to compounds of formula I, wherein
$R_1$ is ($C_2$-$C_6$)alkenyl, aryl, halogen, aryloxy, aryl-S—, $(R_3)_2$N—, heteroaryl, aryl($C_1$-$C_6$)alkyl or aryl($C_2$-$C_6$)alkenyl, wherein said aryl or heteroaryl as such or as part of another group is unsubstituted or substituted with 1 or 2 substituent(s) $R_6$;
$R_3$ is, independently at each occurrence, H or ($C_1$-$C_6$)alkyl;
$R_6$ is, independently at each occurrence, ($C_1$-$C_6$)alkyl, halogen, ($C_1$-$C_6$)alkoxy, carboxy($C_1$-$C_6$)alkyl or halo($C_1$-$C_6$)alkyl.

In one embodiment of the invention, the invention relates to compounds of formula I, wherein
$R_1$ is ($C_2$-$C_6$)alkenyl, aryl, halogen, aryl-S—, heteroaryl or aryl($C_1$-$C_6$)alkyl, wherein said aryl
or heteroaryl as such or as part of another group is unsubstituted or substituted with 1 or 2 substituent(s) $R_6$;
$R_6$ is, independently at each occurrence, ($C_1$-$C_6$)alkyl, halogen or ($C_1$-$C_6$)alkoxy.

In one embodiment of the invention, the invention relates to compounds of formula I, wherein
$R_1$ is ($C_2$-$C_6$)alkenyl, halogen, aryl-S— or aryl($C_1$-$C_6$)alkyl, wherein said aryl as part of another group is unsubstituted or substituted with 1 or 2 substituent(s) $R_6$;
$R_6$ is, independently at each occurrence, ($C_1$-$C_6$)alkyl, halogen or ($C_1$-$C_6$)alkoxy.

In one embodiment of the invention, the invention relates to compounds of formula I, wherein
$R_1$ is ($C_2$-$C_6$)alkenyl, aryl, aryl-S—, heteroaryl or aryl($C_1$-$C_6$)alkyl, wherein said aryl or heteroaryl as such or as part of another group is substituted with 1 or 2 substituent(s) $R_6$;
$R_6$ is, independently at each occurrence, ($C_1$-$C_6$)alkyl or ($C_1$-$C_6$)alkoxy.

In one embodiment of the invention, the invention relates to compounds of formula I, wherein
$R_1$ is ($C_2$-$C_6$)alkenyl, aryl-S or aryl($C_1$-$C_6$)alkyl, wherein said aryl as part of another group is substituted with 1 or 2 substituent(s) $R_6$;
$R_6$ is, independently at each occurrence, ($C_1$-$C_6$)alkyl or ($C_1$-$C_6$)alkoxy.

In one embodiment of the invention, the invention relates to compounds of formula I, wherein $R_1$ is ($C_2$-$C_6$)alkenyl.

In one embodiment of the invention, the invention relates to compounds of formula I, wherein
$R_1$ is aryl, wherein said aryl is unsubstituted or substituted with 1 or 2 substituent(s) $R_6$;
$R_6$ is, independently at each occurrence, ($C_1$-$C_6$)alkyl, halogen or ($C_1$-$C_6$)alkoxy.

In one embodiment of the invention, the invention relates to compounds of formula I, wherein
$R_1$ is aryl-S—, wherein said aryl is unsubstituted or substituted with 1 or 2 substituent(s) $R_6$;
$R_6$ is, independently at each occurrence, ($C_1$-$C_6$)alkyl, halogen or ($C_1$-$C_6$)alkoxy.

In one embodiment of the invention, the invention relates to compounds of formula I, wherein
$R_1$ is heteroaryl, wherein said heteroaryl is unsubstituted or substituted with 1 or 2 substituent(s) $R_6$;
$R_6$ is, independently at each occurrence, ($C_1$-$C_6$)alkyl, halogen or ($C_1$-$C_6$)alkoxy.

In one embodiment of the invention, the invention relates to compounds of formula I, wherein
$R_1$ is aryl($C_1$-$C_6$)alkyl, wherein said aryl is substituted with 1 or 2 substituent(s) $R_6$;
$R_6$ is, independently at each occurrence, ($C_1$-$C_6$)alkyl or ($C_1$-$C_6$)alkoxy.

In one embodiment of the invention, the invention relates to compounds of formula I, wherein the compound is 2-bromo-4,5-dihydroxyisophthalonitrile, 4,5-dihydroxy-2-(phenylethynyl)isophthalonitrile, 4,5-dihydroxy-2-(prop-1-ynyl)isophthalonitrile, 4,5-dihydroxy-2-(1-methyl-1H-pyrrol-2-yl)isophthalonitrile, 4,5-dihydroxy-2-(thiophen-2-yl)isophthalonitrile, 2-(furan-2-yl)-4,5-dihydroxyisophthalonitrile, 3',4',5'-trifluoro-3,4-dihydroxybiphenyi-2,6-dicarbonitrile, 4,5-dihydroxy-2-(naphthalen-1-yl)isophthalonitrile, 4'-tert-butyl-3,4-dihydroxybiphenyl-2,6-dicarbonitrile, 3,4-dihydroxy-4'-(hydroxymethyl)biphenyl-2,6-dicarbonitrile, 4,5-dihydroxy-2-(naphthalen-2-yl)isophthalonitrile, 3,4-dihydroxy-4'-(isopropylthio)biphenyl-2,6-dicarbonitrile, 3,4-dihydroxy-4'-(methylthio)biphenyl-2,6-dicarbonitrile, 3,4-dihydroxy-4'-isopropoxybiphenyl-2,6-dicarbonitrile, 4'-(ethylthio)-3,4-dihydroxybiphenyl-2,6-dicarbonitrile, 3,4-dihydroxy-4'-isopropoxy-3',5'-dimethylbiphenyl-2,6-dicarbonitrile, 4'-butyl-3,4-dihydroxybiphenyl-2,6-dicarbonitrile, 3,4-dihydroxy-2',4',5'-trimethylbiphenyl-2,6-dicarbonitrile, 3,4-dihydroxy 2',5'-dimethylbiphenyl-2,6-dicarbonitrile, 2-cyclohexenyl-4,5-dihydroxyisophthalonitrile, 3'-ethyl-3,4-dihydroxybiphenyl-2,6-dicarbonitrile, 3,4-dihydroxybiphenyl-2,4',6-tricarbonitrile, 3,4-dihydroxy-4'-(isopropylsulfonyl)biphenyl-2,6-dicarbonitrile, 2',6'-dicyano-3',4'-dihydroxy-N,N-dimethylbiphenyl-4-sulfonamide, (E)-4,5-dihydroxy-2-(pent-1-enyl)isophthalonitrile, 2',6'-dicyano-3',4'-dihydroxybiphenyl-3-carboxylic acid, 3,4-dihydroxy-4'-(1-methoxyethyl)biphenyl-2,6-dicarbonitrile, (E)-2-(3,3-dimethylbut-1-enyl)-4,5-dihydroxyisophthalonitrile, 3,4-dihydroxy-2'-methylbiphenyl-2,6-dicarbonitrile, (E)-2-(2-cyclohexylvinyl)-4,5-dihydroxyisophthalonitrile, (Z)-4,5-dihydroxy-2-(prop-1-enyl)isophthalonitrile, 3-(2',6'-dicyano-3',4'-dihydroxybiphenyl-4-yl)propanoic acid, 3,4-dihydroxy-3'-(hydroxymethyl)biphenyl-2,6-dicarbonitrile, 3,4-dihydroxy-3'-(methoxymethyl)biphenyl-2,6-dicarbonitrile, 2',6'-dicyano-3',4'-dihydroxy-N,N-dipropylbiphenyl-4-carboxamide, (E)-4,5-dihydroxy-2-(prop-1-enyl)isophthalonitrile, 3,4-dihydroxybiphenyl-2,6-dicarbonitrile, 3',4'-dichloro-3,4-dihydroxybiphenyl-2,6-dicarbonitrile, 3,4-dihydroxy-3'-(trifluoromethyl)biphenyl-2,6-dicarbonitrile, 2-(furan-3-yl)-4,5-dihydroxyisophthalonitrile, 3,4-dihydroxy-4'-(trifluoromethyl)biphenyl-2,6-dicarbonitrile, 4,5-dihydroxy-2-(thiophen-3-yl)isophthalonitrile, 4,5-dihydroxy-2-(5-methylfuran-2-yl)isophthalonitrile, 4,5-dihydroxy-2-(5-methylthiophen-2-yl)isophthalonitrile, 2-benzyl-4,5-dihydroxyisophthalonitrile, 2-(benzofuran-2-yl)-4,5-dihydroxyisophthalonitrile, 2-(5-chlorothiophen-2-yl)-4,5-dihydroxyisophthalonitrile, 2-(benzo[b]thiophen-2- yl)-4,5-dihydroxyisophthalonitrile, (E)-4,5-dihydroxy-2-styrylisophthalonitrile, 4'-ethyl-3,4-dihydroxybiphenyl-2,6-dicarbonitrile, 3,4-dihydroxy-3',5'-dimethylbiphenyl-2,6-dicarbonitrile, 4,5-dihydroxy-2-(phenylthio)isophthalonitrile, 4,5-dihydroxy-2-(p-tolylthio)isophthalonitrile, 4,5-dihydroxy-2-(4-methylbenzyl)isophthalonitrile, 2-(4-fluorobenzyl)-4,5-dihydroxyisophthalonitrile, 4,5-dihydroxy-2-(4-hydroxybenzyl)isophthalonitrile, 4,5-dihydroxy-2-(2-methoxybenzyl)isophthalonitrile, 4,5-dihydroxy-2-(4-(trifluoromethoxy)benzyl)isophthalonitrile, 2-(3-fluoro-4-methoxybenzyl)-4,5-dihydroxyisophthalonitrile, 2-(2-fluorobenzyl)-4,5-dihydroxyisophthalonitrile, 4,5-dihydroxy-2-(2-methylbenzyl)isophthalonitrile, 2-(2,5-dimethylbenzyl)-4,5-dihydroxyisophthalonitrile, 2-(3-fluoro-5-methylbenzyl)-4,5-dihydroxyisophthalonitrile, 3-(2,6-dicyano-3,4-dihydroxybenzyl)benzoic acid, 2-(4-fluoro-3-methylbenzyl)-4,5-dihydroxyisophthalonitrile, 4,5-dihydroxy-2-(3-methylbenzyl)isophthalonitrile, 2-(5-fluoro-2-methoxybenzyl)-4,5-dihydroxyisophthalonitrile, 2-(3,5-dimethylbenzyl)-4,5-dihydroxyisophthalonitrile, 4,5-dihydroxy-2-(4-isopropylbenzyl)isophthalonitrile, 2-(4-ethylbenzyl)-4,5-dihydroxyisophthalonitrile, 4,5-dihydroxy-2-(naphthalen-1-ylmethyl)isophthalonitrile, 5-(2,6-dicyano-3,4-dihydroxybenzyl)-2-hydroxybenzoic acid, 2-(2,4-dimethylbenzyl)-4,5-dihydroxyisophthalonitrile, 2-(3,6-dihydro-2H-pyran-4-yl)-4,5-dihydroxyisophthalonitrile, 2-cyclopentenyl-4,5-dihydroxyisophthalonitrile, (E)-3-(2,6-dicyano-3,4-dihydroxyphenyl)acrylic acid, (E)-4,5-dihydroxy-2-(3-methoxyprop-1-enyl)isophthalonitrile, 4,5-dihydroxy-2-(5-(morpholinomethyl)thiophen-2-yl)isophthalonitrile, 3,4-dihydroxy-4'-(morpholine-4-carbonyl)biphenyl-2,6-dicarbonitrile, 2-(5'-hexyl-2,2'-bithiophen-5-yl)-4,5-dihydroxyisophthalonitrile, 2-(1-benzyl-1H-pyrazol-4-yl)-4,5-dihydroxyisophthalonitrile, 2-(5-hexylthiophen-2-yl)-4,5-dihydroxyisophthalonitrile, (Z)-2-(but-2-enyl)-4,5-dihydroxyisophthalonitrile, 4,5-dihydroxy-2-(3-methylbut-2-enyl)isophthalonitrile, (E)-2-(but-2-enyl)-4,5-dihydroxyisophthalonitrile, 4,5-dihydroxy-2-methylisophthalonitrile, 4,5-dihydroxy-2-(2-methylprop-1-enyl)isophthalonitrile, 3,4-dihydroxy-3'-methylbiphenyl-2,6-dicarbonitrile, 4,5-dihydroxy-2-vinylisophthalonitrile, 4,5-dihydroxy-2-(prop-1-en-2-yl)isophthalonitrile, 2-(2-ethoxythiazol-5-yl)-4,5-dihydroxyisophthalonitrile, 2-allyl-4,5-dihydroxyisophithalonitrile, 3'-(tert-butoxymethyl)-3,4-dihydroxybiphenyl-2,6-dicarbonitrile, tert-butyl 2',6'-dicyano-3',4'-dihydroxybiphenyl-3-carboxylate, 3,4-dihydroxybiphenyl-2,3',6-tricarbonitrile, 2',6'-dicyano-3',4'-dihydroxy-N,N-dipropylbiphenyl-3-carboxamide, 2',6'-dicyano-N-cyclohexyl-3',4'-dihydroxybiphenyl-4-carboxamide, 2',6'-dicyano-N-cyclohexyl-3',4'-dihydroxybiphenyl-3-carboxamide, 2',6'-dicyano-N,N-diethyl-3',4'-dihydroxybiphenyl-4-carboxamide, 2',6'-dicyano-N,N-diethyl-3',4'-dihydroxybiphenyl-3-carboxamide, 2',6'-dicyano-N-ethyl-3',4'-dihydroxybiphenyl-3-carboxamide, 2',6'-dicyano-3',4'-dihydroxy-N,N-dimethylbiphenyl-3-carboxamide, 4'-fluoro-3,4-dihydroxybiphenyl-2,6-dicarbonitrile, 3',4'-difluoro-3,4-dihydroxybiphenyl-2,6-dicarbonitrile, 4'-fluoro-3,3',4'-trihydroxybiphenyl-2,6-dicarbonitrile, (E)-4,5-dihydroxy-2-(3-phenylprop-1-enyl)isophthalonitrile, 4'-fluoro-3,4-dihydroxy-3'-methoxybiphenyl-2,6-dicarbonitrile, 5-(2,6-dicyano-3,4-dihydroxyphenyl)thiophene-2-carboxylic acid, 3,4-dihydroxy-4'-(methylsulfonyl)biphenyl-2,6-dicarbonitrile, 3,4-dihydroxy-4'-propoxybiphenyl-2,6-dicarbonitrile, 2',6'-dicyano-3',4'-dihydroxybiphenyl-4-carboxylic acid, 4'-chloro-3,4-dihydroxy-3'-methylbiphenyl-2,6-dicarbonitrile, 4,5-dihydroxy-2-(5-phenylthiophen-2-yl)isophthalonitrile, 3,4-dihydroxy-4'-isopropylbiphenyl-2,6-dicarbonitrile, 3,4-dihydroxy-4'-propylbiphenyl-2,6-dicarbonitrile, 4,5-dihydroxy-2-(1-phenylvinyl)isophthalonitrile, 2',6'-dicyano-3',4'-dihydroxybiphenyl-2-carboxylic acid, 4-(2,6-dicyano-3,4-dihydroxybenzyl)benzoic acid, (E)-4,5-dihydroxy-2-(4-methoxystyryl)isophthalonitrile, 3,4-dihydroxy-3',4'-dimethylbiphenyl-2,6-dicarbonitrile, (E)-4,5-dihydroxy-2-(4-methylstyryl)isophthalonitrile, 4,5-dihydroxy-2-(6-hydroxynaphthalen-2-yl)isophthalonitrile, 4'-fluoro-3,4-dihydroxy-3'-methylbiphenyl-2,6-dicarbonitrile, 4,5-dihydroxy-2-(3-methylbut-2-en-2-yl)isophthalonitrile, 2-(2,5-dimethylthiophen-3-yl)-4,5-dihydroxyisophthalonitrile, 2-(2,3-difluoro-4-methylbenzyl)-4,5-dihydroxyisophthalonitrile, 2-(4=(2,6-dicyano-3,4-dihydroxybenzyl)phenyl)propanoic acid, (E)-2-(3-cyclopentylprop-1-enyl)-4,5-dihydroxyisophthalonitrile, 4,5-dihydroxy-2-(1-isobutyl-1H-pyrazol-4-yl)isophthalonitrile, 2-(4-(2,6-dicyano-3,4-dihydroxyphenyl)-1H-pyrazol-1-yl) acetic acid, 4,5-dihydroxy-2-(1-methyl-1H-pyrazol-4-yl)isophthalonitrile, 4,5-dihydroxy-2-(3-methoxyprop-1-ynyl)isophthalonitrile, (E)-4,5-dihydroxy-2-(2-(thiophen-3-yl)vinyl)isophthalonitrile, (E)-2-(2-cyclopropylvinyl)-4,5-dihydroxyisophthalonitrile, 2',6'-dicyano-3',4'-dihydroxybiphenyl-4-carboxamide, 3,4-dihydroxy-3',4'-dimethoxybiphenyl-2,6-dicarbonitrile, 3,4-dihydroxy-3'-isopropylbiphenyl-2,6-dicarbonitrile, 2-(2,3-dihydrobenzofuran-5-yl)-4,5-dihydroxyisophthalonitrile, 4,5-dihydroxy-2-(6-methoxynaphthalen-2-yl)isophthalonitrile, 4,5-dihydroxy-2-(4-(hydroxymethyl)benzyl)isophthalonitrile, 2-(2,6-difluoro-3-methylbenzyl)-4,5-dihydroxyisophthalonitrile, 4,5-dihydroxy-2-(4-(trifluoromethyl)phenylthio)isophthalonitrile, 2-(2,4-dimethylphenylthio)-4,5-dihydroxyisophthalonitrile, methyl 3-(4-(2,6-dicyano-3,4-dihydroxyphenylthio)phenyl)propanoate, 4,5-dihydroxy-2-(p-tolyloxy)isophthalonitrile, (E)-2-(2,4-difluorostyryl)-4,5-dihydroxyisophthalonitrile, (E)-4,5-dihydroxy-2-(3-(trifluoromethyl)styryl)isophthalonitrile, (E)-4,5-dihydroxy-2-(4-methylpent-1-enyl)isophthalonitrile, (E)-2-(3,5-difluorostyryl)-4,5-dihydroxyisophthalonitrile, 2-(4-(2,6-dicyano-3,4-dihydroxybenzyl)phenyl)acetic acid, 2-(4-chlorobenzyl)-4,5-dihydroxyisophthalonitrile, 3,4-dihydroxy-4'-methylbiphenyl-2,6-dicarbonitrile, 3-(4-(2,6-dicyano-3,4-dihydroxybenzyl)phenyl)propanoic acid, 4,5-dihydroxy-2-(4-(trifluoromethyl)benzyl)isophthalonitrile, (E)-4,5-dihydroxy-2-(4-(trifluoromethyl)styryl)isophthalonitrile, 4,5-dihydroxy-2-(p-tolylsulfinyl)isophthalonitrile, 4-(2,6-dicyano-3,4-dihydroxyphenylthio)benzoic acid, 2-(4-ethylphenylthio)-4,5-dihydroxyisophthalonitrile, 2-(4-chlorophenylthio)-4,5-dihydroxyisophthalonitrile, 4,5-dihydroxy-2-(o-tolylthio)isophthalonitrile, methyl 4-(2,6-dicyano-3,4-dihydroxyphenylthio)benzoate, 2-(2-chlorophenylthio)-4,5-dihydroxyisophthalonitrile, methyl 2-(2,6-dicyano-3,4-dihydroxyphenylthio)benzoate, 2-(4-(2,6-dicyano-3,4-dihydroxyphenylthio)phenyl)acetic acid, 2-(2,6-dicyano-3,4-dihydroxyphenylthio)benzoic acid, 3-(4-(2,6-dicyano-3,4-dihydroxyphenylthio)phenyl)propanoic acid, 4,5-dihydroxy-2-(4-methoxyphenylthio)isophthalonitrile, methyl 2-(4-(2,6-dicyano-3,4-dihydroxybenzyl)phenyl)acetate, 4,5-dihydroxy-2-(3-methoxyphenylthio)isophthalonitrile, methyl 4-(2,6-dicyano-3,4-dihydroxyphenoxy)benzoate, 4,5-dihydroxy-2-(pyridin-4-ylthio)isophthalonitrile, 3-(2,6-dicyano-3,4-dihydroxyphenylthio)benzoic acid, 2-(4-cyanophenylthio)-4,5-dihydroxyisophthalonitrile, 4,5-dihydroxy-2-(naphthalen-2-ylthio)isophthalonitrile, 2-(4-(2,6-dicyano-3,4-dihydroxybenzyl)phenyl)-N,N-diethylacetamide, 2-(4- ethylphenoxy)-4,5-dihydroxyisophthalonitrile, 2-(4-acetylphenoxy)-4,5-dihydroxyisophthalonitrile, 4,5-dihydroxy-2-(1-oxo-2,3-dihydro-1H-inden-5-yloxy)isophthalonitrile, 2-(2',6'-dicyano-3',4'-dihydroxybiphenyl-4-yl)acetic acid, 2-(2,4-dimethylphenoxy)-4,5-dihydroxyisophthalonitrile, 2-(4-chlorophenoxy)-4,5-dihydroxyisophthalonitrile, 4,5-dihydroxy-2-(4-(trifluoromethyl)phenoxy)isophthalonitrile, 4,5-dihydroxy-2-(1H-inden-3-yl)isophthalonitrile, 4,5-dihydroxy-2-(morpholinomethyl)isophthalonitrile, 2-((diethylamino)methyl)-4,5-dihydroxyisophthalonitrile hydrochloride, 4,5-dihydroxy-2-(((2-hydroxyethyl)amino)methyl)isophthalonitrile hydrochloride (1:1), 4,5-dihydroxy-2-(3-hydroxypropyl)isophthalonitrile, 2-amino-4,5-dihydroxyisophthalonitrile, 4,5-dihydroxy-2-(pyrrolidin-1-yl)isophthalonitrile, 2-(2,6-dimethylmorpholino)-4,5-dihydroxyisophthalonitrile, 4,5-dihydroxy-2-morpholinoisophthalonitrile, 4,5-dihydroxy-2-(isopropylamino)isophthalonitrile, 4,5-dihydroxy-2-(3-methoxypropylamino)isophthalonitrile, 2,4,5-trihydroxyisophthalonitrile, 2-ethyl-4,5-dihydroxyisophthalonitrile, 3,4-dihydroxy-4'-methoxybiphenyl-2,6-dicarbonitrile, 3,4-dihydroxy-3'-(morpholine-4-carbonyl)biphenyl-2,6-dicarbonitrile, N-butyl-2',6'-dicyano-3',4'-dihydroxybiphenyl-4-carboxamide, 2-(3,3-dimethylbutyl)-4,5-dihydroxyisophthalonitrile, 4,5-dihydroxy-2-(piperidin-1-yl)isophthalonitrile, 2-(hexylamino)-4,5-dihydroxyisophthalonitrile, 2-(cyclohexylamino)-4,5-dihydroxyisophthalonitrile, 4,5-dihydroxy-2-(2-methoxyethylamino)isophthalonitrile, 2-(4-benzylpiperidin-1-yl)-4,5-dihydroxyisophthalonitrile, 4,5-dihydroxy-2-(pentan-3-ylamino)isophthalonitrile, (E)-2-(4-ethylbenzylideneamino)-4,5-dihydroxyisophthalonitrile, (E)-4,5-dihydroxy-2-(4-methoxybenzylideneamino)isophthalonitrile, (E)-2-(4-fluorobenzylideneamino)-4,5-dihydroxyisophthalonitrile, 4,5-dihydroxy-2-tosylisophthalonitrile, 4-(2,6-dicyano-3,4-dihydroxyphenoxy)benzoic acid, 2-(benzo[d]thiazol-2-ylthio)-4,5-dihydroxyisophthalonitrile, 2-(4-fluorophenylthio)-4,5-dihydroxyisophthalonitrile, 2-(biphenyl-4-ylmethyl)-4,5-dihydroxyisophthalonitrile, 2-(4-chloro-2-methylbenzyl)-4,5-dihydroxyisophthalonitrile, 2-(2-ethylbenzyl)-4,5-dihydroxyisophthalonitrile, 2-(2,3-dihydro-1H-inden-5-yloxy)-4,5-dihydroxyisophthalonitrile, enantiomer A of 4,5-dihydroxy-2-(p-tolylsulfinyl)isophthalonitrile, enantiomer B of 4,5-dihydroxy-2-(p-tolylsulfinyl)isophthalonitrile, 2-((cyclohexylmethyl)amino)-4,5-dihydroxyisophthalonitrile, 4,5-dihydroxy-2-(4-phenoxyphenylthio)isophthalonitrile, 4,5-dihydroxy-2-(pyridin-3-yl)isophthalonitrile, 4,5-dihydroxy-2-(4-(2,2,2-trifluoroethyl)benzyl)isophthalonitrile, 4,5-dihydroxy-2-(4-methyl-2-(trifluoromethyl)benzyl)isophthalonitrile, 4,5-dihydroxy-2-((4-(morpholine-4-carbonyl)phenyl)thio)isophthalonitrile, 4,5-dihydroxy-2-(methyl(p-tolyl)amino)isophthalonitrile or 4,5-dihydroxy-2-((6-methoxynaphthalen-2-yl)methyl)isophthalonitrile.

The terms employed herein have the meanings indicated below. The term "at least one" employed in the meanings below refers to one or several, such as one. For example, the term "at least one hydroxy($C_1$-$C_6$)alkoxy group" refers to one or several hydroxy($C_1$-$C_6$)alkoxy groups, such as one hydroxy($C_1$-$C_6$)alkoxy group.

The term "($C_1$-$C_6$)alkyl", as employed herein as such or as part of another group, refers to a straight or branched chain saturated hydrocarbon group having 1, 2, 3, 4, 5 or 6 carbon atom(s). Representative examples of ($C_1$-$C_6$)alkyl include, but are not limited to, methyl, ethyl, propyl, isopropyl, butyl, isobutyl, tert-butyl, pent-3-yl, hexyl, and 3,3-dimethylbutyl.

The term "($C_2$-$C_6$)alkenyl", as employed herein as such or as part of another group, refers to a straight or branched chain hydrocarbon group having 2, 3, 4, 5 or 6 carbon atoms and at least one carbon-carbon double bond. Representative examples of ($C_2$-$C_6$)alkenyl include, but are not limited to, vinyl, prop-1-en-1-yl, prop-1-en-2-yl, allyl, but-2-en-1-yl, 2-methylprop-1-en-1-yl, pent-1-en-1-yl, 3-methylbut-2-en-1-yl, 3-methylbut-2-en-2-yl, 4-methylpent-1-en-1-yl, and 3,3-dimethylbut-1-en-1-yl.

The term "($C_2$-$C_6$)alkynyl", as employed herein as such or as part of another group, refers to a straight or branched chain hydrocarbon group having 2, 3, 4, 5 or 6 carbon atoms and at least one carbon-carbon triple bond. Representative examples of ($C_2$-$C_6$)alkynyl include, but are not limited to, ethynyl, prop-1-yn-1-yl, and 3,3-dimethylbut-1-yn-1-yl.

The term "($C_3$-$C_7$)cycloalkyl", as employed herein as such or as part of another group, refers to a saturated cyclic hydrocarbon group having 3, 4, 5, 6 or 7 carbon atoms. Representative examples of ($C_3$-$C_7$)cycloalkyl include, but are not limited to, cyclopropyl, cyclopentyl, and cyclohexyl.

The term "($C_4$-$C_{10}$)cycloalkenyl", as employed herein as such or as part of another group, refers to a monocyclic hydrocarbon group having 3, 4, 5, 6 or 7 carbon atoms and at least one carbon-carbon double bond or to an 8, 9 or 10 membered partially unsaturated bicyclic hydrocarbon group. When the ($C_4$-$C_{10}$)cycloalkenyl group is an 8, 9 or 10 membered partially unsaturated bicyclic hydrocarbon group, one of the rings is optionally aromatic. Representative examples of ($C_4$-$C_{10}$)cycloalkenyl include, but are not limited to, cyclopent-1-en-1-yl, cyclohex-1-en-1-yl, and 2,3-dihydro-1H-inden-5-yl.

The term "aryl", as employed herein as such or as part of another group, refers to an aromatic monocyclic hydrocarbon group having 6 carbon atoms or to an aromatic bicyclic hydrocarbon group having 10 carbon atoms. Representative examples of aryl include, but are not limited to, phenyl and naphthalen-2-yl.

The term "halo" or "halogen", as employed herein as such or as part of another group, refers to fluorine, chlorine, bromine or iodine.

The term "hydroxy", as employed herein as such or as part of another group, refers to a —OH group.

The term "($C_1$-$C_6$)alkoxy", as employed herein as such or as part of another group, refers to an ($C_1$-$C_6$)alkyl group, as defined herein, appended to the parent molecular moiety through an oxygen atom. Representative examples of ($C_1$-$C_6$)alkoxy include, but are not limited to, methoxy, ethoxy, propoxy, isopropoxy, tert-butoxy, and neopentyloxy.

The term "($C_4$-$C_{10}$)cycloalkenyloxy", as employed herein, refers to a ($C_4$-$C_{10}$)cycloalkenyl group, as defined herein, appended to the parent molecular moiety through an oxygen atom. Representative examples of ($C_4$-$C_{10}$)cycloalkenyloxy include, but are not limited to, cyclopent-1-en-1-yloxy and 2,3-dihydro 1H-inden-5-yloxy.

The term "aryloxy", as employed herein, refers to an aryl group, as defined herein, appended to the parent molecular moiety through an oxygen atom. Representative examples of aryloxy include, but are not limited to, phenoxy and naphthalen-1-yloxy.

The term "heteroaryl", as employed herein as such or as part of another group, refers to a 5, 6 or 7 membered aromatic monocyclic group containing 1, 2, 3 or 4 ring heteroatom(s) each independently selected from N, O, and S or to an 8, 9 or 10 membered aromatic bicyclic group containing 1, 2, 3 or 4 ring heteroatom(s) each independently selected from N, O, and S. Representative examples of heteroaryl include, but are not limited to, 1H pyrrol-2-yl, furan-2-yl, thiophen-2-yl, thiophen-3-yl, 1H-pyrazol-4-yl, thiazol-5-yl, benzofuran-2-yl, benzo[b]thiophen-2-yl, and benzo[d][1,3]dioxol-5-yl.

The term "heteroaryloxy", as employed herein, refers to a heteroaryl group, as defined herein, appended to the parent molecular moiety through an oxygen atom. Representative examples of heteroaryloxy include, but are not limited to, pyridin-4-yloxy and benzo[d][1,3]dioxol-5-yloxy.

The term "heterocyclyl", as employed herein as such or as part of another group, refers to a 5, 6 or 7 membered saturated or partially unsaturated monocyclic group containing 1 or 2 ring heteroatom(s) each independently selected from N, O, and S or to an 8, 9 or 10 membered saturated or partially unsaturated bicyclic group containing 1 or 2 ring heteroatom(s) each independently selected from N, O, and S. When the heterocyclyl group is an 8, 9 or 10 membered partially unsaturated bicyclic group, one of the rings is optionally aromatic. Representative examples of heterocyclyl include, but are not limited to, pyrrolidin-1-yl, piperidin-1-yl, 3,6-dihydro-2H-pyran-4-yl, morpholino, and 2,3-dihydrobenzofuran-5-yl.

The term "aryl($C_1$-$C_6$)alkyl", as employed herein, refers to an aryl group, as defined herein, appended to the parent molecular moiety through an ($C_1$-$C_6$)alkyl group, as defined herein. Representative examples of aryl($C_1$-$C_6$)alkyl include, but are not limited to, benzyl, 2-phenethyl, and 3-phenylpropyl.

The term "halo($C_1$-$C_6$)alkyl", as employed herein, refers to at least one halogen, as defined herein, appended to the parent molecular moiety through an ($C_1$-$C_6$)alkyl group, as defined herein. When there are several halogens, the halogens can be attached to the same or different carbon atom and the halogens can be identical or different. Representative examples of halo($C_1$-$C_6$)alkyl include, but are not limited to, trifluoromethyl and 3-bromopropyl.

The term "hydroxy($C_1$-$C_6$)alkyl", as employed herein, refers to at least one hydroxy group, as defined herein, appended to the parent molecular moiety through an ($C_1$-$C_6$)alkyl group, as defined herein. When there are several hydroxy groups, the hydroxy groups can be attached to the same or different carbon atom. Representative examples of hydroxy($C_1$-$C_6$)alkyl include, but are not limited to, hydroxymethyl, 2-hydroxyethyl, and 3-hydroxypropyl.

The term "($C_1$-$C_6$)alkoxy($C_1$-$C_6$)alkyl", as employed herein as such or as part of another group, refers to at least one ($C_1$-$C_6$)alkoxy group, as defined herein, appended to the parent molecular moiety through an ($C_1$-$C_6$)alkyl group, as defined herein. When there are several ($C_1$-$C_6$)alkoxy groups, the ($C_1$-$C_6$)alkoxy groups can be attached to the same or different carbon atom and the ($C_1$-$C_6$)alkoxy groups can be identical or different. Representative examples of ($C_1$-$C_6$)alkoxy($C_1$-$C_6$)alkyl include, but are not limited to, methoxymethyl, 1-methoxyethyl, 2-methoxyethyl, 3-methoxypropyl, and tert-butoxymethyl.

The term "heterocyclyl($C_1$-$C_6$)alkyl" as employed herein, refers to a heterocyclyl group, as defined herein, appended to the parent molecular moiety through an ($C_1$-$C_6$)alkyl group, as defined herein. Representative examples of heterocyclyl($C_1$-$C_6$)alkyl include, but are not limited to, morpholinomethyl and 3-(pyrrolidin-1-yl)propyl.

The term "carboxy", as employed herein as such or as part of another group, refers to a —COOH group.

The term "carboxy($C_2$-$C_6$)alkenyl", as employed herein, refers to a carboxygroup, as defined herein, appended to the parent molecular moiety through an ($C_2$-$C_6$)alkenyl group, as defined herein. Representative examples of carboxy($C_2$-$C_6$)alkenyl include, but are not limited to, 2-carboxyvinyl and 2-carboxyallyl.

The term "($C_3$-$C_7$)cycloalkyl($C_2$-$C_6$)alkenyl", as employed herein, refers to a ($C_3$-$C_7$)cycloalkyl group, as defined herein, appended to the parent molecular moiety through an ($C_2$-$C_6$)alkenyl group, as defined herein. Representative examples of ($C_3$-$C_7$)cycloalkyl($C_2$-$C_6$)alkenyl include, but are not limited to, 2-cyclopropylvinyl, 2-cyclohexylvinyl, and 3-cyclopentylprop-1-en-1-yl.

The term "aryl($C_2$-$C_6$)alkenyl", as employed herein, refers to an aryl group, as defined herein, appended to the parent molecular moiety through an ($C_2$-$C_6$)alkenyl group, as defined herein. Representative examples of aryl($C_2$-$C_6$)alkenyl include, but are not limited to, styryl, 1-phenylvinyl, and 3-phenylprop-1-en-1-yl.

The term "($C_1$-$C_6$)alkoxy($C_2$-$C_6$)alkenyl", as employed herein, refers to at least one ($C_1$-$C_6$)alkoxy group, as defined herein, appended to the parent molecular moiety through an ($C_2$-$C_6$)alkenyl group, as defined herein. When there are several ($C_1$-$C_6$)alkoxy groups, the ($C_1$-$C_6$)alkoxy groups can be attached to the same or different carbon atom and the ($C_1$-$C_6$)alkoxy groups can be identical or different. Representative examples of ($C_1$-$C_6$)alkoxy($C_2$-$C_6$)alkenyl include, but are not limited to, 3-methoxyprop-1-en-1-yl and 3-ethoxyprop-1-en-2-yl.

The term "heterocyclyl($C_2$-$C_6$)alkenyl", as employed herein, refers to a heterocyclyl group, as defined herein, appended to the parent molecular moiety through an ($C_2$-$C_6$)alkenyl group, as defined herein. Representative examples of heterocyclyl($C_2$-$C_6$)alkenyl include, but are not limited to, 4-(pyrrolidin-1-yl)but-2-en-1-yl and 3-methyl-4-morpholinobut-2-en-2-yl.

The term "heteroaryl($C_2$-$C_6$)alkenyl", as employed herein, refers to a heteroaryl group, as defined herein, appended to the parent molecular moiety through an ($C_2$-$C_6$)alkenyl group, as defined herein. Representative examples of heteroaryl($C_2$-$C_6$)alkenyl include, but are not limited to, 2-(thiophen-3-yl)vinyl and 3-methyl-4-(1H-pyrazol-4-yl)but-2-en-2-yl.

The term "carboxy($C_2$-$C_6$)alkynyl", as employed herein, refers to a carboxy group, as defined herein, appended to the parent molecular moiety through an ($C_2$-$C_6$)alkynyl group, as defined herein. Representative examples of carboxy($C_2$-$C_6$)alkynyl include, but are not limited to, carboxyethynyl and 3-carboxyprop-1-yn-1-yl.

The term "($C_3$-$C_7$)cycloalkyl($C_2$-$C_6$)alkynyl", as employed herein, refers to a ($C_3$-$C_7$)cycloalkyl group, as defined herein, appended to the parent molecular moiety through an ($C_2$-$C_6$)alkynyl group, as defined herein. Representative examples of ($C_3$-$C_7$)cycloalkyl($C_2$-$C_6$)alkynyl include, but are not limited to, cyclopropylethynyl and 3-cyclopentylprop-1-yn-1-yl.

The term "aryl($C_2$-$C_6$)alkynyl", as employed herein, refers to an aryl group, as defined herein, appended to the parent molecular moiety through an ($C_2$-$C_6$)alkynyl group, as defined herein. Representative examples of aryl($C_2$-$C_6$)alkynyl include, but are not limited to, phenylethynyl and 3-(naphthalen-1-yl)prop-1-yn-1-yl.

The term "($C_1$-$C_6$)alkoxy($C_2$-$C_6$)alkynyl", as employed herein, refers to at least one ($C_1$-$C_6$)alkoxy group, as defined herein, appended to the parent molecular moiety through an ($C_2$-$C_6$)alkynyl group, as defined herein. When there are several ($C_1$-$C_6$)alkoxy groups, the ($C_1$-$C_6$)alkoxy groups can be attached to the same or different carbon atom and the ($C_1$-$C_6$)alkoxy groups can be identical or different. Representative examples of $(C_1-C_6)$alkoxy$(C_2-C_6)$alkynyl include, but are not limited to, tert-butoxyethynyl and 3-methoxyprop-1-yn-1-yl.

The term "heterocyclyl$(C_2-C_6)$alkynyl", as employed herein, refers to a heterocyclyl group, as defined herein, appended to the parent molecular moiety through an $(C_2-C_6)$alkynyl group, as defined herein. Representative examples of heterocyclyl$(C_2-C_6)$alkynyl include, but are not limited to, morpholinoethynyl and 3-(piperidin-1-yl)prop-1-yn-1-yl.

The term "heteroaryl$(C_2-C_6)$alkynyl", as employed herein, refers to a heteroaryl group, as defined herein, appended to the parent molecular moiety through an $(C_2-C_6)$alkynyl group, as defined herein. Representative examples of heteroaryl$(C_2-C_6)$alkynyl include, but are not limited to, thiophen-3-ylethynyl and 3-(1H-pyrazol-4-yl)prop-1-yn-1-yl.

The term "halo$(C_1-C_6)$alkoxy", as employed herein, refers to at least one halogen, as defined herein, appended to the parent molecular moiety through an $(C_1-C_6)$alkoxy group, as defined herein. When there are several halogens, the halogens can be attached to the same or different carbon atom and the halogens can be identical or different. Representative examples of halo$(C_1-C_6)$alkoxy include, but are not limited to, trifluoromethoxy and 1,1,2,2-tetrafluoroethoxy.

The term "hydroxy$(C_1-C_6)$alkoxy", as employed herein as such or as part of another group, refers to at least one hydroxy group, as defined herein, appended to the parent molecular moiety through an $(C_1-C_6)$alkoxy group, as defined herein. When there are several hydroxy groups, the hydroxy groups can be attached to the same or different carbon atom. Representative examples of hydroxy$(C_1-C_6)$alkoxy include, but are not limited to, hydroxymethoxy and 3-hydroxy-2,2-dimethylpropoxy.

The term "$(C_1-C_6)$alkoxy$(C_1-C_6)$alkoxy", as employed herein as such or as part of another group, refers to at least one $(C_1-C_6)$alkoxy group, as defined herein, appended to the parent molecular moiety through an $(C_1-C_6)$alkoxy group, as defined herein. The $(C_1-C_6)$alkoxy groups can be identical or different. When there are several $(C_1-C_6)$alkoxy groups appended to the parent molecular moiety through an $(C_1-C_6)$alkoxy group, the $(C_1-C_6)$alkoxy groups can be attached to the same or different carbon atom. Representative examples of $(C_1-C_6)$alkoxy$(C_1-C_6)$alkoxy include, but are not limited to, 2-methoxyethoxy and 3-methoxy-2,2-dimethylpropoxy.

The term "hydroxy$(C_1-C_6)$alkoxy$(C_1-C_6)$alkyl", as employed herein, refers to at least one hydroxy$(C_1-C_6)$alkoxy group, as defined herein, appended to the parent molecular moiety through an $(C_1-C_6)$alkyl group, as defined herein. When there are several hydroxy$(C_1-C_6)$alkoxy groups, the hydroxy$(C_1-C_6)$alkoxy groups can be attached to the same or different carbon atom and the hydroxy$(C_1-C_6)$alkoxy groups can be identical or different. Representative examples of hydroxy$(C_1-C_6)$alkoxy$(C_1-C_6)$alkyl include, but are not limited to, (3-hydroxy-2,2-dimethylpropoxy)methyl and 2-(hydroxymethoxy)prop-2-yl.

The term "$(C_3-C_7)$cycloalkyl$(C_1-C_6)$alkyl", as employed herein, refers to a $(C_3-C_7)$cycloalkyl group, as defined herein, appended to the parent molecular moiety through an $(C_1-C_6)$alkyl group, as defined herein. Representative examples of $(C_3-C_7)$cycloalkyl$(C_1-C_6)$alkyl include, but are not limited to, cyclohexylmethyl and 2-cyclopentylethyl.

The term "cyano", as employed herein, refers to —CN group.

The term "carboxy$(C_1-C_6)$alkyl", as employed herein, refers to a carboxy group, as defined herein, appended to the parent molecular moiety through an $(C_1-C_6)$alkyl group, as defined herein. Representative examples of carboxy$(C_1-C_6)$alkyl include, but are not limited to, carboxymethyl, 1-carboxyethyl, and 2-carboxyethyl.

The term "$(C_1-C_5)$alkyl", as employed herein, refers to a straight or branched chain saturated hydrocarbon group having 1, 2, 3, 4 or 5 carbon atom(s). Representative examples of $(C_1-C_5)$alkyl include, but are not limited to, methyl, ethyl, propyl, isopropyl, pentyl, and neopentyl.

Pharmaceutically acceptable salts, e.g. metal salts and acid addition salts, with both organic and inorganic acids, are well known in the field of pharmaceuticals. Representative examples of pharmaceutically acceptable metal salts include, but are not limited to, lithium, sodium, potassium, calcium, magnesium, aluminum and zinc salts. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, and ascorbates.

Pharmaceutically acceptable esters of hydroxy groups may be prepared by known methods using pharmaceutically acceptable carboxylic acids that are conventional in the field of pharmaceuticals. Representative examples of pharmaceutically acceptable esters of hydroxy groups include, but are not limited to, esters formed with butyric acid and pentanoic acid.

Pharmaceutically acceptable esters of carboxy groups may be prepared by known methods using pharmaceutically acceptable alcohols that are conventional in the field of pharmaceuticals. Representative examples of pharmaceutically acceptable esters of carboxy groups include, but are not limited to, esters formed with propan-1-ol, butan-1-ol, and 2-methylpropan-1-ol.

The invention includes within its scope all the possible geometric isomers, e.g. Z and E isomers (cis and trans isomers), of the compounds as well as all the possible optical isomers, e.g. diastereomers and enantiomers, of the compounds. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof conventional resolution methods, e.g. fractional crystallization, may be used.

The invention includes within its scope all the possible tautomers, or equilibrium mixtures thereof, of the compounds. In tautomers a hydrogen migrates from one atom of the compound to another atom of the compound. Representative examples of tautomers include, but are not limited to, keto/enol and nitroso/oxime.

The compounds of formula I can be prepared by a variety of synthetic routes analogously to or according to methods known in the literature using suitable starting materials.

While many general methods are available for the generation of a cyano group, most of them are not directly usable in the field of catechol chemistry. For instance, the Sandmeyer reaction provides an extremely reactive catecholic amine as an intermediate which creates serious preparative challenges.

Some methods useful for the preparation of the compounds of formula I are described below. The dicyano grouping can be constructed efficiently using simple starting materials essentially via two ways, either synthesizing two formyl groups simultaneously or building the second formyl group on a benzaldehyde derivative. In both cases the formyl groups are subsequently transformed into cyano groups in good yield. Further transformations provide a useful intermediate from which numerous final products can be formed.

Scheme 1. Starting from 2-methoxy-5-methylphenol

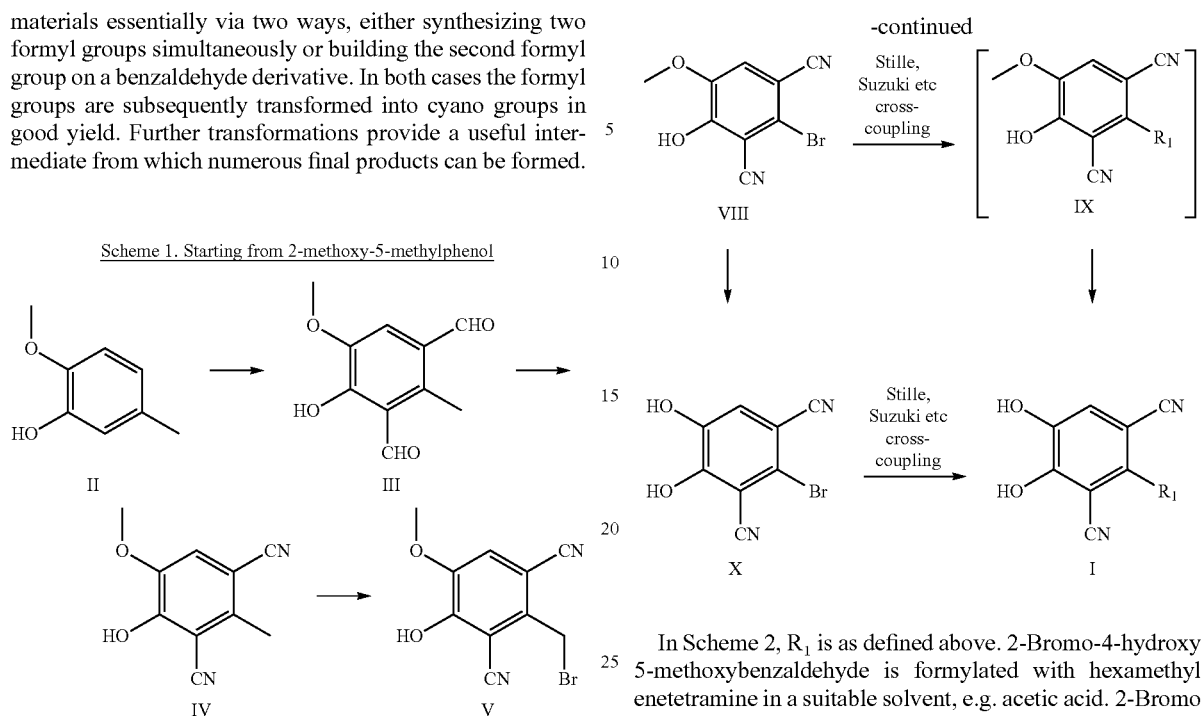

In Scheme 1, 2-methoxy-5-methylphenol is formylated with hexamethylenetetramine in a suitable solvent, e.g. acetic acid. 4-Hydroxy-5-methoxy-2-methylisophthalaldehyde is converted to 4-hydroxy-5-methoxy-2-methylisophthalonitrile with hydroxylamine hydrochloride in a suitable solvent, e.g. formic acid. 4-Hydroxy-5-methoxy-2-methylisophthalonitrile is brominated with N-bromosuccinimide in a suitable solvent, e.g. dichloromethane, to yield 2-(bromomethyl)-4-hydroxy-5-methoxyisophthalonitrile. The bromine atom is then converted to the desired functional group and the desired product is obtained by carrying out a demethylation with a Lewis acid in a suitable solvent, e.g. with aluminum chloride in acetonitrile or with boron tribromide in dichloromethane.

In Scheme 2, $R_1$ is as defined above. 2-Bromo-4-hydroxy-5-methoxybenzaldehyde is formylated with hexamethylenetetramine in a suitable solvent, e.g. acetic acid. 2-Bromo-4-hydroxy-5-methoxyisophthalaldehyde is converted to 2-bromo-4-hydroxy-5-methoxyisophthalonitrile with hydroxylamine hydrochloride in a suitable solvent, e.g. formic acid. The bromine atom is replaced with substituent $R_1$, for instance, by a Suzuki cross-coupling reaction. 2-Bromo-4-hydroxy-5-methoxyisophthalonitrile is reacted with a suitable boronic acid derivative in a suitable solvent, e.g. 1,4-dioxane/water. Intermediate IX obtained is then demethylated. Alternatively, the demethylation is carried out before replacing the bromine atom with substituent $R_1$. The demethylation is carried out with a Lewis acid in a suitable solvent, e.g. with aluminum chloride in acetonitrile or with boron tribromide in dichloromethane. Intermediate IX is not necessarily isolated from the reaction mixture. Another route for the conversion of 2-bromo-4-hydroxy-5-methoxyisophthalaldehyde to product I is depicted in Scheme 5.

Scheme 2. Starting from 2-bromo-4-hydroxy-5-methoxybenzaldehyde

Scheme 3. Starting from a 5-substituted 2-methoxyphenol

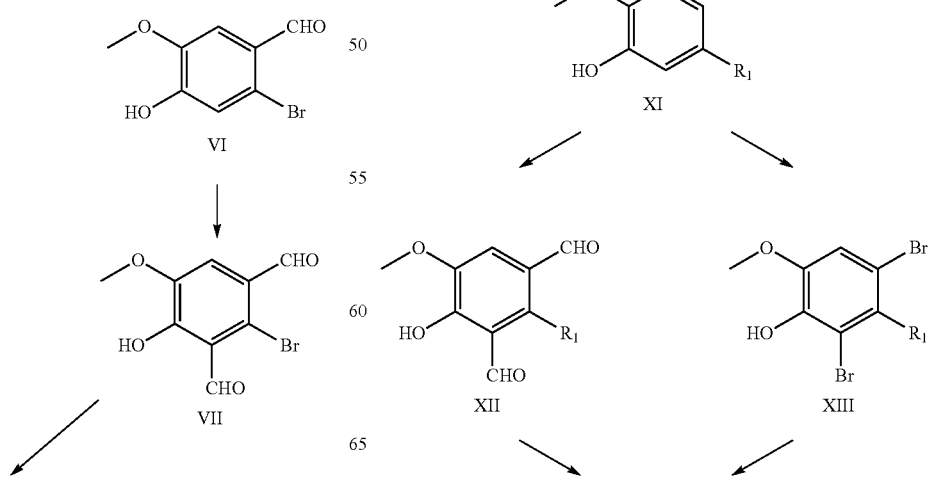

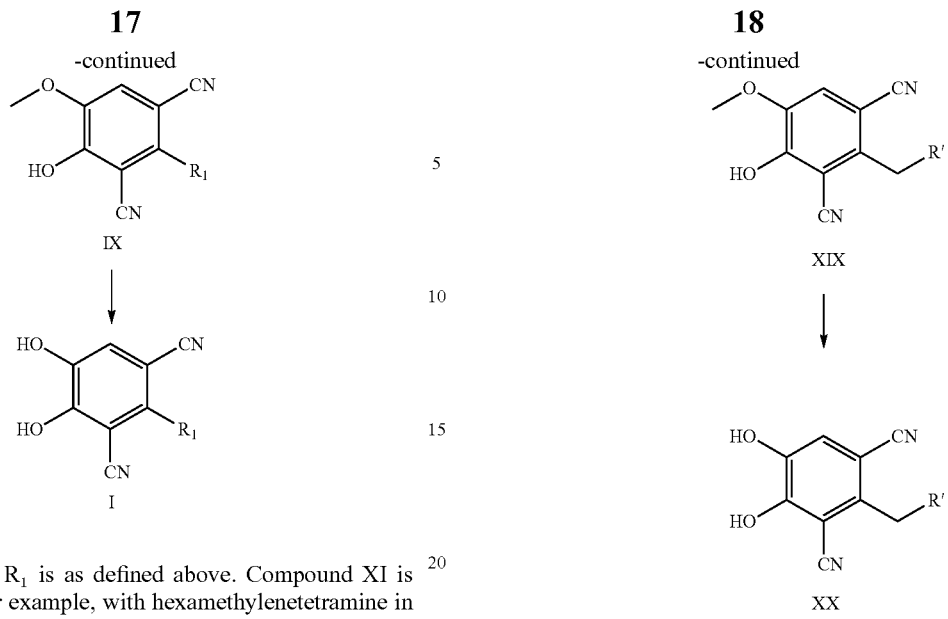

In Scheme 3, $R_1$ is as defined above. Compound XI is diformylated, for example, with hexamethylenetetramine in a suitable solvent such as acetic acid or trifluoroacetic acid, or dibrominated, for example, with bromine in a suitable solvent such as a mixture of dichloromethane and acetic acid. Dicyano derivative IX is obtained by reacting diformyl derivative XII with hydroxylamine hydrochloride in a suitable solvent such as formic acid or by reacting dibromo derivative XIII with copper(I) cyanide in a suitable solvent such as N,N-dimethylformamide. Dicyano derivative IX is demethylated with a Lewis acid in a suitable solvent, e.g. with aluminum chloride in acetonitrile or with boron tribromide in dichloromethane.

In Scheme 4, Bn is benzyl, R' is, for example, $(C_1-C_5)$alkyl or aryl, R'' is, for example, $(C_1-C_5)$alkyl, R''' is, for example, aryl, and X is halogen. 3-Benzyloxy-4-methoxybenzaldehyde is converted to alcohol XV using a suitable Grignard reagent. Compound XVI is obtained by hydrogenating alcohol XV. When R' is, for example, $(C_1-C_5)$alkyl, compound XVI can be diformylated, for example, with hexamethylenetetramine in a suitable solvent such as acetic acid or trifluoroacetic acid. When R' is, for example, aryl, compound XVI can be dibrominated, for example, with bromine in a suitable solvent such as a mixture of dichloromethane and acetic acid. Dicyano derivative XIX is obtained by reacting diformyl derivative XVII with hydroxylamine hydrochloride in a suitable solvent such as formic acid or by reacting dibromo derivative XVIII with copper(I) cyanide in a suitable solvent such as N,N-dimethylformamide. Dicyano derivative XIX is demethylated with a Lewis acid in a suitable solvent, e.g. with aluminum chloride in acetonitrile or with boron tribromide in dichloromethane.

Scheme 4. Starting from 3-benzyloxy-4-methoxybenzaldehyde

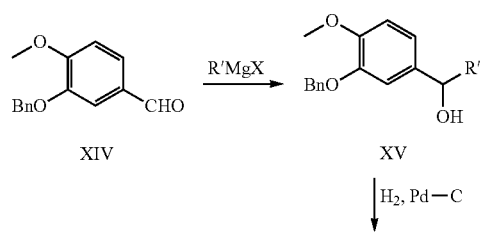

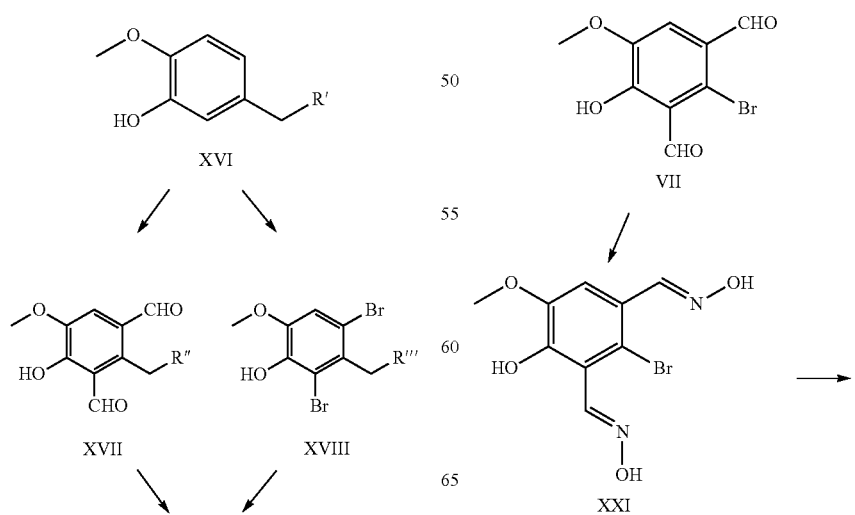

Scheme 5. Conversion of 2-bromo-4-hydroxy-5-methoxyisophthalaldehyde

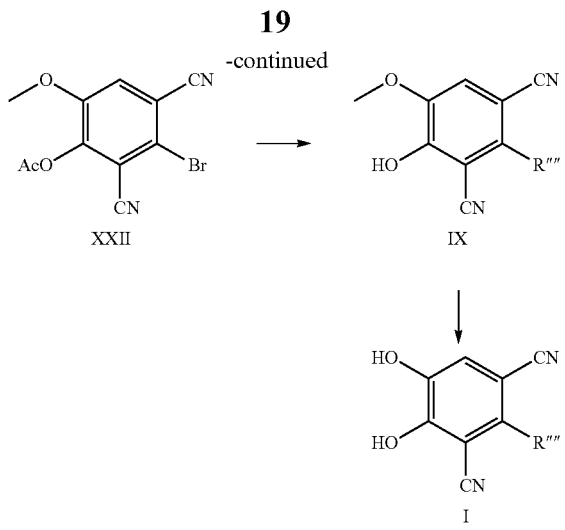

In Scheme 5, Ac is acetyl and R"" is, for example, aryl-S— or heteroaryl-S—. 2-Bromo-4-hydroxy-5-methoxyisophthalaldehyde, which can be prepared as depicted in Scheme 2, is converted to (1E,1'E)-2-bromo-6-hydroxy-3-((E)-(hydroxyimino)methyl)-5-methoxybenzaldehyde oxime with hydroxylamine hydrochloride in a suitable solvent, e.g. tetrahydrofuran. Treating (1E,1'E)-2-bromo-6-hydroxy-3-((E)-(hydroxyimino)methyl)-5-methoxybenzaldehyde oxime with acetic anhydride yields 3-bromo-2,4-dicyano-6-methoxyphenyl acetate. Dicyano derivative IX is obtained by reacting 3-bromo-2,4-dicyano-6-methoxyphenyl acetate with a suitable thiol in a suitable solvent, e.g. N,N-dimethylformamide. Dicyano derivative IX is demethylated with a Lewis acid in a suitable solvent, e.g. with aluminum chloride in acetonitrile or with boron tribromide in dichloromethane.

It is obvious for a person skilled in the art that any starting material or intermediate in the reactions described above can be protected, if necessary, in a manner well known in the chemical field. For instance, ethyl vanillin can be used instead of vanillin. Any protected functionality can subsequently be deprotected in a manner known in the art.

Stepwise routes can be used. For instance, the dicyano target can be prepared from a suitable starting compound in the following order: 1) monobromination, 2) monoformylation, 3) conversion of CHO to CN, and 4) conversion of Br to CN. The order of all of these separate steps of bromination, formylation, conversion of CHO to CN and conversion of Br to CN can be optionally changed. For instance, one can start with a formylation. Likewise, if desired, conversion of Br to CN can be carried out prior to conversion of CHO to CN.

The synthetic routes described above are meant to illustrate the preparation of the compounds of formula I and the preparation is by no means limited thereto, i.e., there are also other possible synthetic methods which are within the general knowledge of a person skilled in the art. For instance, formylation can be accomplished also via lithiation of an aromatic methoxy halogenide, e.g. an aromatic methoxy bromide, or an aromatic methoxy dihalogenide, e.g. an aromatic methoxy dibromide, oxidation of a methyl group or reduction of a carboxy group. An aromatic formyl group can be converted into a hydroxy group via a Dakin reaction.

The compounds of formula I may be converted, if desired, into their pharmaceutically acceptable salt or ester form using methods well known in the art.

The present invention will be explained in more detail by the following examples. The examples are meant for illustrating purposes only and do not limit the scope of the invention defined in the claims.

Unless otherwise noted, all the starting materials were obtained from commercial suppliers and used without further purification. The abbreviations have the meanings indicated below.

AcOH acetic acid
AIBN 2,2'-azobisisobutyronitrile
DBU 1,8-diazabicyclo[5,4,0]undec-7-ene
DCM dichloromethane
DIPEA N,N-diisopropylethylamine
DMAP 4-dimethylaminopyridine
DMF N,N-dimethylformamide
DMSO dimethylsulfoxide
DPEPhos (oxybis(2,1-phenylene))bis(diphenylphosphine)
EtOAc ethyl acetate
mCPBA m-chloroperoxybenzoic acid
NBS N-bromosuccinimide
Pd(dppf)Cl$_2$ (1,1'-bis(diphenylphosphino)ferrocene)palladium dichloride
Pd$_2$(dba)$_3$ Tris(dibenzylideneacetone)dipalladium(0)
TFA trifluoroacetic acid
THF tetrahydrofuran

PREPARATION OF INTERMEDIATES

Intermediate A1

4-Hydroxy-5-methoxy-2-methylisophthalonitrile

4-Hydroxy-5-methoxy-2-methylisophthalaldehyde

2-Methoxy-5-methylphenol (11.0 g) and hexamethylenetetramine (23.8 g) in AcOH (280 ml) were refluxed for 15 h. Concentrated HCl (20 ml) was added and the mixture was refluxed for 3 h. The solvent volume was reduced to 40-50 ml. The mixture was cooled for 1 h in an ice bath. The precipitate was filtered off and washed with ethanol. Water was added to the filtrate and the mixture was extracted thrice with DCM. The combined organic phases were dried (Na$_2$SO$_4$) and evaporated to dryness. The residue was triturated with ethanol and cooled in an ice bath. The solid was filtered off and washed with ethanol. Concentrated HCl (45 ml) was added to the solid and refluxed for 1 h. The reaction mixture was cooled in an ice bath, filtered and washed with ethanol (5 ml). Yield 2.9 g $^1$H NMR (400 MHz, DMSO-d$_6$) ppm 12.02 (s, 1H) 10.48 (s, 1H) 10.28 (s, 1H) 7.56 (s, 1H) 2.79 (s, 3H)

4-Hydroxy-5-methoxy-2-methylisophthalonitrile

4-Hydroxy-5-methoxy-2-methylisophthalaldehyde (5.2 g), hydroxylamine hydrochloride (5.58 g) and anhydrous sodium acetate (8.79 g) in formic acid (30 ml) were refluxed for 5 h. The reaction mixture was cooled in an ice bath and the precipitate was filtered off and washed with water. Yield 4.6 g $^1$H NMR (400 MHz, DMSO-d$_6$) ppm 11.47 (br s, 1H) 7.55 (s, 1H) 3.88 (s, 3H)

Intermediate A2

2-Bromo-4-hydroxy-5-methoxyisophthalonitrile

2-Bromo-4-hydroxy-5-methoxyisophthalaldehyde

2-Bromo-4-hydroxy-5-methoxybenzaldehyde (0.75 g) and hexamethylenetetramine (0.91 g) in AcOH (30 ml) was heated under reflux for 4 h. AcOH was evaporated and 4 M HCl (30 ml) was added. The mixture was first refluxed for 2 h and stirred overnight at room temperature. The solid product was filtered, washed with water and dried. Yield 0.38 g $^1$H NMR (400 MHz, DMSO-$d_6$) ppm 10.37 (s, 1H) 10.24 (s, 1H) 7.50 (s, 1H) 3.90 (s, 3H)

2-Bromo-4-hydroxy-5-methoxyisophthalonitrile

2-Bromo-4-hydroxy-5-methoxyisophthalaldehyde (11.6 g) and hydroxylamine hydrochloride (9.3 g) were dissolved in hot formic acid (155 ml). The solution was heated to boiling point followed by addition of anhydrous sodium acetate (22.0 g). The mixture was refluxed for 2 h. Acetic anhydride (18.2 g) was added dropwise to the hot reaction mixture and refluxed for 4 h. The mixture was allowed to cool to room temperature overnight, and then stirred in an ice bath. The solid was filtered, washed with ice cold water (20 ml) and dried. Yield 10.6 g $^1$H NMR (400 MHz, DMSO-$d_6$) ppm 12.10 (br s, 1H) 7.75 (s, 1H) 3.91 (s, 3H)

Intermediate A3

2-Bromo-4,5-dihydroxyisophthalonitrile

The preparation of 2-bromo-4-hydroxy-5-methoxyisophthalonitrile is described above. Sieve dry acetonitrile (75 ml) was cooled in an ice bath. Aluminum chloride (3.16 g) was added slowly to the solvent so that temperature was kept below 30° C. The mixture was stirred at room temperature for 10 min. Sodium iodine (2.4 g) was added and the solution was stirred for 15 min. 2-Bromo-4-hydroxy-5-methoxyisophthalonitrile (2.0 g) was added and the reaction mixture was heated at 70° C. for 5 h after which it was stirred at room temperature overnight. 4 M HCl (20 ml) and a solution of sodium sulfate (1.3 g) in water (40 ml) were successively added to the cool reaction mixture. The mixture was extracted thrice with EtOAc (50 ml) and the combined organic phases were washed with 2 M HCl (50 ml), water (50 ml) and brine (50 ml). The washed organic phase was dried ($Na_2SO_4$), filtered and evaporated to dryness. Yield 1.89 g $^1$H NMR (400 MHz, DMSO-$d_6$) ppm 11.15 (br s, 2H) 7.32 (s, 2H)

Intermediate A4

4-Bromo-3,5-dicyano-1,2-phenylene diacetate

The preparation of 2-bromo-4,5-dihydroxyisophthalonitrile is described above. 2-Bromo-4,5-dihydroxyisophthalonitrile (1.80 g), acetic anhydride (10 ml) and sulfuric acid (20 μl) was stirred at room temperature overnight. The reaction mixture was poured slowly to ice water (50 ml) stirring simultaneously the water mixture. The product was filtered, washed with water and dried in vacuum (30° C.). Yield 2.19 g $^1$H NMR (400 MHz, chloroform-d) ppm 7.79 (s, 1H) 2.43 (s, 3H) 2.34 (s, 3H)

Intermediate A5

2-Bromo-4,5-diisopropoxyisophthalonitrile

The preparation of 2-bromo-4,5-dihydroxyisophthalonitrile is described above. To a warm mixture of 2-bromo-4,5-dihydroxyisophthalonitrile (10.0 g) and potassium carbonate (23.1 g) in DMF (160 ml) was added 2-iodopropane (16.7 ml) dropwise over 1 h. The reaction mixture was heated at 85° C. for 6 h after which it was poured into cold water and pH was adjusted to 12. The precipitate was filtered, washed with water and dried in vacuum. Yield 9.3 g $^1$H NMR (400 MHz, DMSO-$d_6$) ppm 8.00 (s, 1H) 4.85 (m, 1H) 4.82 (m, 1H) 1.32 (s, 6H) 1.30 (s, 6H)

Intermediate A6

3-Bromo-2,4-dicyano-6-methoxyphenyl acetate (1E,1'E)-2-Bromo-6-hydroxy-3-((E)-(hydroxyimino) methyl)-5-methoxybenzaldehyde oxime The preparation of 2-bromo-4-hydroxy-5-methoxyisophthalaldehyde is described above. 2-Bromo-4-hydroxy-5-methoxyisophthalaldehyde (15.9 g) and hydroxylamine hydrochloride (17.0 g) were dissolved in THF (500 ml). Pyridine (19.9 ml) was added. The solution was heated at 90° C. for 3 h. After concentration to half of the original volume, ice and 4 M HCl solution (40 ml) was added. The mixture was stirred for 30 min. The solid was filtered, washed with 1 M HCl and ice cold water and dried. Yield 17.4 g $^1$H NMR (400 MHz, DMSO-$d_6$) ppm 12.10 (br s, 1H) 7.75 (s, 1H) 3.91 (s, 3H)

3-Bromo-2,4-dicyano-6-methoxyphenyl acetate (1E,1'E)-2-Bromo-6-hydroxy-3-((E)-(hydroxyimino) methyl)-5-methoxybenzaldehyde oxime (15.0 g) was dissolved in acetic anhydride (96 ml). The mixture was refluxed for 2 h. The mixture was allowed to cool to room temperature overnight. Toluene and water were added and solvents were evaporated. After 30 min stirring with ice cold water, the solid was filtered, washed with ice cold water and dried. Yield 11.0 g $^1$H NMR (400 MHz, DMSO-$d_6$) ppm 8.19 (s, 1H) 3.92 (s, 3H) 2.44 (s, 3H)

Intermediate A7

3-Bromo-2,4-dicyano-6-methoxyphenyl tert-butyl carbonate

The preparation of 2-bromo-4-hydroxy-5-methoxyisophthalonitrile is described above. To a stirred solution of 2-bromo-4-hydroxy-5-methoxyisophthalonitrile (5.57 g) in acetonitrile (200 ml) was added in one portion DMAP (1.3 g) and di-tert-butyl dicarbonate (33.6 g). After refluxing for 4 h the mixture was cooled in an ice bath, filtered and evaporated to dryness. EtOAc was added and the mixture was filtered through silica gel. The filtrate was evaporated to dryness. Yield 4.79 g $^1$H NMR (400 MHz, DMSO-$d_6$) ppm 7.98 (s, 1H) 3.88 (s, 3H) 1.42 (s, 9H)

Intermediate A8

5-(Benzyloxy)-2-bromo-4-hydroxyisophthalonitrile

The preparation of 2-bromo-4,5-dihydroxyisophthalonitrile is described above. 2-Bromo-4,5-dihydroxyisophthalonitrile (450 mg) was dissolved in DMF (7 ml). Cesium carbonate (1.84 g) and benzyl chloride (0.46 ml) were added and stirred at 70° C. for 1.5 h. The reaction was quenched with ice water and the mixture was stirred for 10 min. The precipitated solid was filtered, washed with water and dried under vacuum. Yield 520 mg $^1$H NMR (400 MHz, DMSO-$d_6$) ppm 7.31-7.40 (m, 5H) 6.78 (s, 1H) 4.94 (s, 2H)

PREPARATION OF COMPOUNDS OF THE INVENTION

Example 1

2-Bromo-4,5-dihydroxyisophthalonitrile

The preparation of the title compound is described above.
$^1$H NMR (400 MHz, DMSO-$d_6$) ppm 11.15 (br s, 2H) 7.32 (s, 2H)

Example 2

4,5-Dihydroxy-2-(phenylethynyl)isophthalonitrile 2,6-Di-tert-butyl-4-methylphenol (13.6 mg) and tetrakis(triphenylphosphine)palladium (28.6 mg) was added to a solution of 4-bromo-3,5-dicyano-1,2-phenylene diacetate (200 mg) in dry toluene (18 ml). A solution of phenylethynyltri-n-butyltin (315 mg) in dry toluene (2 ml) was added to the reaction mixture under nitrogen atmosphere. The reaction mixture was heated under reflux for 6 h. The mixture was filtered through celite. The filtrate was evaporated to dryness. THF (30 ml) and 1 M NaOH (40 ml) was added to the resultant product and solution was stirred for 1 h. The solution was washed thrice with toluene (10 ml). The water phase was made acidic with 4 M HCl under cooling. The product was filtered, washed with water and dried at 40° C. in vacuum. Yield 45 mg $^1$H NMR (400 MHz, DMSO-$d_6$) ppm 7.54-7.60 (m, 2H) 7.47-7.53 (m, 3H) 7.35 (s, 1H)

Example 3

4,5-Dihydroxy-2-(prop-1-ynyl)isophthalonitrile

The title compound was prepared from 4-bromo-3,5-dicyano-1,2-phenylene diacetate (200 mg) by the method of Example 2 using tributylpropynylstannane (254 mg) instead of phenylethynyltri-n-butyltin. Yield 78 mg $^1$H NMR (400 MHz, DMSO-$d_6$) ppm 11.40 (br s, 2H) 7.25 (s, 1H) 2.18 (s, 3H)

Example 4

4,5-Dihydroxy-2-(1-methyl-1H-pyrrol-2-yl)isophthalonitrile

The title compound was prepared from 4-bromo-3,5-dicyano-1,2-phenylene diacetate (500 mg) by the method of Example 2 using 1-methyl-2-(tributylstannyl)-1H-pyrrole (716 mg) instead of phenylethynyltri-n-butyltin. Yield 280 mg $^1$H NMR (400 MHz, DMSO-$d_6$) ppm 11.39 (br s, 2H) 7.33 (s, 1H) 6.94-6.97 (m, 1H) 6.20 (m, J=3.50, 1.80 Hz, 1H) 6.12 (m, J=3.50, 2.80 Hz, 1H) 3.47 (s, 3H)

Example 5

4,5-Dihydroxy-2-(thiophen-2-yl)isophthalonitrile

The title compound was prepared from 4-bromo-3,5-dicyano-1,2-phenylene diacetate (200 mg) by the method of Example 2 using 2-(tributylstannyl)thiophene (462 mg) instead of phenylethynyltri-n-butyltin. Yield 60 mg $^1$H NMR (400 MHz, DMSO-$d_6$) ppm 11.41 (br s, 2H) 7.80 (dd, J=5.0, 1.3 Hz, 1H) 7.31-7.36 (m, 2H) 7.22 (dd, J=3.8 Hz, 1H)

Example 6

2-(Furan-2-yl)-4,5-dihydroxyisophthalonitrile

The title compound was prepared from 4-bromo-3,5-dicyano-1,2-phenylene diacetate (200 mg) by the method of Example 2 using 2-(tributylstannyl)furan (442 mg) instead of phenylethynyltri-n-butyltin. Yield 100 mg $^1$H NMR (400 MHz, DMSO-$d_6$) ppm 11.43 (br s, 2H) 7.94 (br s, 1H) 7.34 (s, 1H) 6.88-7.08 (m, 1H) 6.72 (br s, 1H)

Example 7

3',4',5'-Trifluoro-3,4-dihydroxybiphenyl-2,6-dicarbonitrile

To a solution of 4-bromo-3,5-dicyano-1,2-phenylene diacetate (500 mg) in acetonitrile (3 ml), water (4 ml) and ethanol (3 ml) in a vial, was added 3,4,5-trifluorophenylboronic acid (354 mg), bis(triphetylphosphine)palladium(II) chloride (61 mg) and sodium carbonate (492 mg). The reaction mixture was microwave-irradiated for 60 min at 130° C. The mixture was filtered through pall filter, basified with 2 M NaOH (50 ml), washed with toluene (50 ml). The aqueous phase was then acidified with 4 M HCl under cooling. The product was filtered, washed with water and recrystallized with water/ethanol 10/2 mixture. Yield 140 mg $^1$H NMR (400 MHz, DMSO-$d_6$) ppm 11.38 (br s, 2H) 7.58-7.69 (m, 2H) 7.36 (s, 1H)

Example 8

4,5-Dihydroxy-2-(naphthalen-1-yl)isophthalonitrile

The title compound was prepared from 4-bromo-3,5-dicyano-1,2-phenylene diacetate (200 mg) and naphthalene-1-boronic acid (149 mg) instead of 3,4,5-trifluorophenylboronic acid as described in Example 7. Yield 126 mg $^1$H NMR (400 MHz, DMSO-$d_6$) ppm 11.47 (br s, 2H) 8.08 (dd, J=1.00 Hz, 2H) 7.56-7.67 (m, 2H) 7.49-7.56 (m, 2H) 7.43 (s, 1H) 7.37 (d, J=1.00 Hz, 1H)

Example 9

4'-tert-Butyl-3,4-dihydroxybiphenyl-2,6-dicarbonitrile

The title compound was prepared from 4-bromo-3,5-dicyano-1,2-phenylene diacetate (300 mg) and 4-tert-butylphenylboronic acid (248 mg) instead of 3,4,5-trifluorophenylboronic acid as described in Example 7. Reaction conditions: 20 min at 150° C. Yield 115 mg $^1$H NMR (400 MHz, DMSO-d$_6$) ppm 11.67 (br s, 1H) 11.06 (br s, 1H) 7.52-7.59 (m, 2H) 7.39-7.43 (m, 2H) 7.34 (s, 1H) 1.34 (s, 9H)

Example 10

3,4-Dihydroxy-4'-(hydroxymethyl)biphenyl-2,6-dicarbonitrile

The title compound was prepared from 4-bromo-3,5-dicyano-1,2-phenylene diacetate (1 g) and 4-(hydroxymethyl)benzeneboronic acid (564 mg) instead of 3,4,5-trifluorophenylboronic acid as described in Example 7. Reaction conditions: 30 min at 130° C. Yield 639 mg $^1$H NMR (400 MHz, DMSO-d$_6$) ppm 11.34 (br s, 1H) 7.44 (m, J=8.10, 8.10, 8.10 Hz, 4H) 7.34 (s, 1H) 5.33 (br s, 1H) 4.59 (s, 2H)

Example 11

4,5-Dihydroxy-2-(naphthalen-2-yl)isophthalonitrile

The title compound was prepared from 4-bromo-3,5-dicyano-1,2-phenylene diacetate (200 mg) and naphthalene-2-boronic acid (138 mg) instead of 3,4,5-trifluorophenylboronic acid as described in Example 7. Yield 160 mg $^1$H NMR (400 MHz, DMSO-d$_6$) ppm 11.77 (br s, 1H) 11.06 (br s, 1H) 7.98-8.11 (m, 4H) 7.56-7.67 (m, 3H) 7.40 (s, 1H)

Example 12

3,4-Dihydroxy-4'-(isopropylthio)biphenyl-2,6-dicarbonitrile

The title compound was prepared from 4-bromo-3,5-dicyano-1,2-phenylene diacetate (200 mg and 4-isopropylthiophenylboronic acid (158 mg) instead of 3,4,5-trifluorophenylboronic acid as described in Example 7. Reaction conditions: 45 min at 150° C. Yield 135 mg $^1$H NMR (400 MHz, DMSO-d$_6$) ppm 11.72 (br s, 1H) 11.08 (br s, 1H) 7.45-7.49 (m, 2H) 7.40-7.44 (m, 2H) 7.35 (s, 1H) 3.64 (m, J=13.30, 6.70, 6.70 Hz, 1H) 1.30 (d, J=6.78 Hz, 6H)

Example 13

3,4-Dihydroxy-4'-(methylthio)biphenyl-2,6-dicarbonitrile

The title compound was prepared from 4-bromo-3,5-dicyano-1,2-phenylene diacetate (200 mg) and 4-(methylthio)phenylboronic acid (135 mg) instead of 3,4,5-trifluorophenylboronic acid as described in Example 7. Yield 151 mg $^1$H NMR (400 MHz, DMSO-d$_6$) ppm 11.32-12.19 (m, 1H) 10.74-11.28 (m, 1H) 7.36-7.44 (m, 4H) 7.34 (s, 1H) 2.54 (s, 3H)

Example 14

3,4-Dihydroxy-4'-isopropoxybiphenyl-2,6-dicarbonitrile

The title compound was prepared from 4-bromo-3,5-dicyano-1,2-phenylene diacetate (600 mg) and 4-isopropoxyphenylboronic acid (334 mg) instead of 3,4,5-trifluorophenylboronic acid as described in Example 7. Reaction conditions: 15 min at 150° C. Yield 365 mg $^1$H NMR (400 MHz, DMSO-d$_6$) ppm 11.25 (br s, 1H) 7.25-7.44 (m, 3H) 7.03 (d, J=8.03 Hz, 2H) 4.65-4.76 (m, 1H) 1.31 (d, J=5.77 Hz, 6H)

Example 15

4'-(Ethylthio)-3,4-dihydroxybiphenyl-2,6-dicarbonitrile

The title compound was prepared from 4-bromo-3,5-dicyano-1,2-phenylene diacetate (200 mg) and 4-(ethylthio)benzeneboronic acid (146 mg) instead of 3,4,5-trifluorophenylboronic acid as described in Example 7. Yield 143 mg $^1$H NMR (400 MHz, DMSO-d$_6$) ppm 11.76 (br s, 1H) 11.05 (br s, 1H) 7.41 (s, 4H) 7.34 (s, 1H) 3.07 (m, J=7.30, 7.30, 7.30 Hz, 2H) 1.29 (t, J=7.28 Hz, 3H)

Example 16

3,4-Dihydroxy-4'-isopropoxy-3',5'-dimethylbiphenyl-2,6-dicarbonitrile

The title compound was prepared from 4-bromo-3,5-dicyano-1,2-phenylene diacetate (200 mg) and 3,5-dimethyl-4-isopropoxyphenylboronic acid (167 mg) instead of 3,4,5-trifluorophenylboronic acid as described in Example 7. Yield 109 mg $^1$H NMR (400'MHz, DMSO-d$_6$) ppm 11.63 (br s, 1H) 10.98 (br s, 1H) 7.31 (s, 1H) 7.11 (s, 2H) 4.22-4.30 (m, 1H) 2.26 (s, 6H) 1.26 (d, J=6.27 Hz, 6H)

Example 17

4'-Butyl-3,4-dihydroxybiphenyl-2,6-dicarbonitrile

The title compound was prepared from 4-bromo-3,5-dicyano-1,2-phenylene diacetate (200 mg) and 4-n-butylbenzeneboronic acid (143 mg) instead of 3,4,5-trifluorophenylboronic acid as described in Example 7. Reaction conditions: 15 min at 150° C. Yield 88 mg $^1$H NMR (400 MHz, DMSO-d$_6$) ppm 11.28 (br s, 2H) 7.29-7.41 (m, 5H) 2.66 (t, J=7.65 Hz, 2H) 1.61 (m, J=7.70, 7.70 Hz, 2H) 1.29-1.40 (m, 2H) 0.92 (t, J=7.40 Hz, 3H)

Example 18

3,4-Dihydroxy-2',4',5'-trimethylbiphenyl-2,6-dicarbonitrile

The title compound was prepared from 4-bromo-3,5-dicyano-1,2-phenylene diacetate (200 mg) and 2,4,5-trimethylphenylboronic acid (132 mg) instead of 3,4,5-trifluorophenylboronic acid as described in Example 7. Reaction conditions: 15 min at 150° C. Yield 122 mg $^1$H NMR (400 MHz, DMSO-d$_6$) ppm 11.37 (br s, 2H) 7.33 (s, 1H) 7.13 (s, 1H) 6.96 (s, 1H) 2.25 (s, 3H) 2.21 (s, 3H) 2.00 (s, 3H)

Example 19

3,4-Dihydroxy-2',5'-dimethylbiphenyl-2,6-dicarbonitrile

The title compound was prepared from 4-bromo-3,5-dicyano-1,2-phenylene diacetate (200 mg) and 2,5-dimethylbenzeneboronic acid (121 mg) instead of 3,4,5-trifluorophenylboronic acid as described in Example 7. Reaction conditions: 15 min at 150° C. Yield 102 mg $^1$H NMR (400 MHz, DMSO-$d_6$) ppm 10.37-12.37 (m, 2H) 7.35 (s, 1H) 7.23-7.27 (m, 1H) 7.18-7.23 (m, 1H) 7.00-7.04 (m, 1H) 2.31 (s, 3H) 2.03 (s, 3H)

Example 20

2-Cyclohexenyl-4,5-dihydroxyisophthalonitrile

The title compound was prepared from 4-bromo-3,5-dicyano-1,2-phenylene diacetate (200 mg) and cyclohexen-1-ylboronic acid (94 mg) instead of 3,4,5-trifluorophenylboronic acid as described in Example 7. Reaction conditions: 15 min at 150° C. Yield 112 mg $^1$H NMR (400 MHz, DMSO-$d_6$) ppm 10.57-11.63 (m, 2H) 7.21 (s, 1H) 5.78 (br s, 1H) 2.22 (br s, 2H) 2.15 (br s, 2H) 1.72 (i, J=4.30 Hz, 2H) 1.63 (m, J=4.50 Hz, 2H)

Example 21

3'-Ethyl-3,4-dihydroxybiphenyl-2,6-dicarbonitrile

The title compound was prepared from 4-bromo-3,5-dicyano-1,2-phenylene diacetate (250 mg) and 3-ethylphenylboronic acid (116 mg) instead of 3,4,5-trifluorophenylboronic acid as described in Example 7. Reaction conditions: 15 min at 150° C. Yield 204 mg $^1$H NMR (400 MHz, DMSO-$d_6$) ppm 10.86-11.94 (m, 2H) 7.42 (s, 1H) 7.29-7.37 (m, 3H) 7.28 (s, 1H) 2.68 (d, J=7.53 Hz, 2H) 1.22 (t, J=7.65 Hz, 3H)

Example 22

3,4-Dihydroxybiphenyl-2,4',6-tricarbonitrile

The title compound was prepared from 4-bromo-3,5-dicyano-1,2-phenylene diacetate (200 mg) and 4-cyanophenylboronic acid (109 mg) instead of 3,4,5-trifluorophenylboronic acid as described in Example 7. Reaction conditions: 45 min at 150° C. Yield 127 mg $^1$H NMR (400 MHz, DMSO-$d_6$) ppm 11.49 (br s, 2H) 8.00-8.04 (m, 2H) 7.69-7.74 (m, 2H) 7.39 (s, 1H)

Example 23

3,4-Dihydroxy-4'-(isopropylsulfonyl)biphenyl-2,6-dicarbonitrile

The title compound was prepared from 4-bromo-3,5-dicyano-1,2-phenylene diacetate (200 mg) and 4-(isopropylsulfonylphenyl)boronic acid (169 mg) instead of 3,4,5-trifluorophenylboronic acid as described in Example 7. Reaction conditions: 45 min at 150° C. Yield 148 mg $^1$H NMR (400 MHz, DMSO-$d_6$) ppm 10.83-12.08 (m, 2H) 7.95-8.07 (m, 2H) 7.75-7.83 (m, 2H) 7.39 (s, 1H) 3.48-3.60 (m, 1H) 1.19 (d, J=6.78 Hz, 6H)

Example 24

2',6'-Dicyano-3',4'-dihydroxy-N,N-dimethylbiphenyl-4-sulfonamide

The title compound was prepared from 4-bromo-3,5-dicyano-1,2-phenylene diacetate (200 mg) and N,N-dimethyl-4-boronobenzenesulfonamide (170 mg) instead of 3,4,5-trifluorophenylboronic acid as described in Example 7. Reaction conditions: 15 min at 150° C. Yield 159 mg $^1$H NMR (400 MHz, DMSO-$d_6$) ppm 11.51 (br s, 2H) 7.88-7.93 (m, 2H) 7.75-7.80 (m, 2H) 7.40 (s, 1H) 2.67 (s, 6H)

Example 25

(E)-4,5-Dihydroxy-2-(pent-1-enyl)isophthalonitrile

The title compound was prepared from 4-bromo-3,5-dicyano-1,2-phenylene diacetate (200 mg) and 1-pentenylboronic acid (85 mg) instead of 3,4,5-trifluorophenylboronic acid as described in Example 7. Reaction conditions: 15 min at 150° C. Yield 100 mg $^1$H NMR (400 MHz, DMSO-$d_6$) ppm 11.18 (br s, 2H) 7.25 (s, 1H) 6.44-6.50 (m, 2H) 2.21-2.28 (m, 2H) 1.49 (m, 2H) 0.95 (t, J=7.40 Hz, 3H)

Example 26

2',6'-Dicyano-3',4'-dihydroxybiphenyl-3-carboxylic acid

The title compound was prepared from 4-bromo-3,5-dicyano-1,2-phenylene diacetate (200 mg) and 3-carboxyphenylboronic acid (308 mg) instead of 3,4,5-trifluorophenylboronic acid as described in Example 7. Reaction conditions: 30 min at 130° C. Yield 388 mg $^1$H NMR (400 MHz, DMSO-$d_6$) ppm 13.20 (br s, 1H) 11.47 (br s, 2H) 8.08 (d, J=7.78 Hz, 1H) 8.01 (s, 1H) 7.75 (d, J=7.80 Hz, 1H) 7.67 (t, J=7.65 Hz, 1H) 7.37 (s, 1H)

Example 27

3,4-Dihydroxy-4'-(1-methoxyethyl)biphenyl-2,6-dicarbonitrile

The title compound was prepared from 4-bromo-3,5-dicyano-1,2-phenylene diacetate (250 mg) and (4-(1-methoxyethyl)phenyl)boronic acid (139 mg) instead of 3,4,5-trifluorophenylboronic acid as described in Example 7. Reaction conditions: 15 min at 130° C. Yield 63 mg $^1$H NMR (400 MHz, DMSO-$d_6$) ppm 11.21 (br s, 2H) 7.45 (s, 4H) 7.34 (s, 1H) 3.18 (s, 3H) 1.39 (d, J=6.27 Hz, 3H)

Example 28

(E)-2-(3,3-Dimethylbut-1-enyl)-4,5-dihydroxyisophthalonitrile

The title compound was prepared from 4-bromo-3,5-dicyano-1,2-phenylene diacetate (500 mg) and 3,3-dimethyl-1-butenylboronic acid (297 mg) instead of 3,4,5-trifluorophenylboronic acid as described in Example 7. Reaction conditions: 20 min at 150° C. Yield 280 mg $^1$H NMR (400 MHz, DMSO-$d_6$) ppm 11.13 (br s, 2H) 7.23 (s, 1H) 6.47 (d, J=16.31 Hz, 1H) 6.36 (d, J=16.31 Hz, 1H) 1.11 (s, 9H)

Example 29

3,4-Dihydroxy-2'-methylbiphenyl-2,6-dicarbonitrile

The title compound was prepared from 4-bromo-3,5-dicyano-1,2-phenylene diacetate (250 mg) and o-tolylboronic acid (105 mg) instead of 3,4,5-trifluorophenylboronic acid as described in Example 7. Reaction conditions: 20 min at 150° C. Yield 17 mg $^1$H NMR (400 MHz, DMSO-d$_6$) ppm 7.00-7.87 (m, 4H) 7.27 (s, 1H) 2.51 (s, 3H)

Example 30

(E)-2-(2-Cyclohexylvinyl)-4,5-dihydroxyisophthalonitrile

The title compound was prepared from 4-bromo-3,5-dicyano-1,2-phenylene diacetate (200 mg) and 2-cyclohexylethenylboronic acid (95 mg) instead of 3,4,5-trifluorophenylboronic acid as described in Example 7. Reaction conditions: 15 min at 130° C. Yield 92 mg $^1$H NMR (400 MHz, DMSO-d$_6$) ppm 11.62 (br s, 1H) 10.92 (br s, 2H) 7.24 (s, 1H) 6.43 (d, J=2.26 Hz, 2H) 2.17-2.27 (m, 1H) 1.68-1.81 (m, 4H) 1.63 (d, J=11.54 Hz, 1H) 1.13-1.37 (m, 5H)

Example 31

(Z)-4,5-Dihydroxy-2-(prop-1-enyl)isophthalonitrile

The title compound was prepared from 4-bromo-3,5-dicyano-1,2-phenylene diacetate (2 g) and (Z)-prop-1-enylboronic acid (744 mg) instead of 3,4,5-trifluorophenylboronic acid as described in Example 7. Reaction conditions: 20 min at 120° C. Yield 990 mg $^1$H NMR (400 MHz, DMSO-d$_6$) ppm 11.21 (br s, 2H) 11.19 (br s, 1H) 7.28 (s, 1H) 6.40-6.53 (m, 1H) 6.05-6.17 (m, 1H) 1.63 (d, J=7.03 Hz, 3H)

Example 32

3-(2',6'-Dicyano-3',4'-dihydroxybiphenyl-4-yl)propanoic acid

The title compound was prepared from 4-bromo-3,5-dicyano-1,2-phenylene diacetate (200 mg) and 4-(2-carboxyethyl)benzeneboronic acid (144 mg) instead of 3,4,5-trifluorophenylboronic acid as described in Example 7. Reaction conditions: 30 min at 130° C. Yield 33 mg $^1$H NMR (400 MHz, DMSO-d$_6$) ppm 11.89-12.43 (m, 1H) 10.78-11.86 (m, 2H) 7.38 (s, 4H) 7.33 (s, 1H) 2.91 (t, J=7.65 Hz, 2H) 2.61 (t, J=7.65 Hz, 2H)

Example 33

3,4-Dihydroxy-3'-(hydroxymethyl)biphenyl-2,6-dicarbonitrile

The title compound was prepared from 4-bromo-3,5-dicyano-1,2-phenylene diacetate (500 mg) and 3-(hydroxymethyl)benzeneboronic acid (282 mg) instead of 3,4,5-trifluorophenylboronic acid as described in Example 7. Reaction conditions: 30 min at 130° C. Yield 256 mg $^1$H NMR (400 MHz, DMSO-d$_6$) ppm 11.36 (br s, 2H) 7.42-7.52 (m, 2H) 7.38 (s, 1H) 7.29-7.36 (m, 2H) 5.30 (br s, 1H) 4.58 (s, 2H)

Example 34

3,4-Dihydroxy-3'-(methoxymethyl)biphenyl-2,6-dicarbonitrile

The title compound was prepared from 4-bromo-3,5-dicyano-1,2-phenylene diacetate (500 mg and 3-methoxyethylphenylboronic acid (308 mg) instead of 3,4,5-trifluorophenylboronic acid as described in Example 7. Reaction conditions: 30 min at 150° C. Yield 370 mg $^1$H NMR (400 MHz, DMSO-d$_6$) ppm 11.35 (br s, 2H) 7.48-7.54 (m, 1H) 7.42-7.48 (m, 1H) 7.35-7.42 (m, 3H) 4.49 (s, 2H) 3.31 (s, 3H)

Example 35

2',6'-Dicyano-3',4'-dihydroxy-N,N-dipropylbiphenyl-4-carboxamide

The title compound was prepared from 4-bromo-3,5-dicyano-1,2-phenylene diacetate (300 mg) and 4-(dipropylcarbamoyl)phenylboronic acid (301 mg) instead of 3,4,5-trifluorophenylboronic acid as described in Example 7. Reaction conditions: 10 min at 150° C. Yield 150 mg $^1$H NMR (400 MHz, DMSO-d$_6$) ppm 11.38 (br s, 2H) 7.50-7.56 (m, 2H) 7.43-7.50 (m, 2H) 7.36 (s, 1H) 3.39 (br s, 2H) 3.11 (br s, 2H) 1.62 (br s, 2H) 1.49 (br s, 2H) 0.92 (br s, 3H) 0.65 (br s, 3H)

Example 36

(E)-4,5-Dihydroxy-2-(prop-1-enyl)isophthalonitrile

The title compound was prepared from 4-bromo-3,5-dicyano-1,2-phenylene diacetate (1 g) and trans-propenylboronic acid (372 mg) instead of 3,4,5-trifluorophenylboronic acid as described in Example 7. Reaction conditions: 20 min at 150° C. The product was recrystallized from ethanol-water solution. Yield 564 mg $^1$H NMR (400 MHz, DMSO-d$_6$) ppm 7.24 (s, 1H) 6.38-6.61 (m, 2H) 1.93 (d, J=4.02 Hz, 3H)

Example 37

3,4-Dihydroxybiphenyl-2,6-dicarbonitrile

3-Hydroxy-4-methoxybiphenyl-2,6-dicarbonitrile

To a mixture of 2-bromo-4-hydroxy-5-methoxyisophthalonitrile (0.25 g) and phenylboronic acid (0.15 g) in ethanol (1 ml) and water (5 ml) was added tetrakis(triphenylphosphine)palladium (0.04 mg) and 2 M sodium carbonate (1.63 ml). The stirred reaction was refluxed for 3 h. The hot reaction mixture was filtered over pall filter. After cooling, the obtained precipitate was acidified with 2 M HCl (5 ml), filtered, washed with water and dried to give 3-hydroxy-4-methoxybiphenyl-2,6-dicarbonitrile. Yield 0.14 g $^1$H NMR (400 MHz, DMSO-d$_6$) ppm 7.49 (s, 1H) 6.96-7.24 (m, 4H) 3.94 (s, 3H)

3,4-Dihydroxybiphenyl-2,6-dicarbonitrile

To a dry mixture of 3-hydroxy-4-methoxybiphenyl-2,6-dicarbonitrile (141 mg) in DCM (5 ml) under nitrogen atmosphere was added 1 M boron tribromide solution in DCM (2.82 ml) at 0° C. The reaction mixture was warmed slowly to room temperature with stirring for 3½ h. The reaction mixture was poured into methanol (5 ml)/ice mixture. After evaporation of the solvent, water (10 ml) was added and the mixture was stirred for 1 h, followed by filtration, washing with water and drying in vacuum to give the title compound. Yield 115 mg ¹H NMR (400 MHz, DMSO-d₆) ppm 11.35 (br s, 2H) 7.50-7.55 (m, 3H) 7.44-7.49 (m, 2H) 7.35 (s, 1H)

Example 38

3',4'-Dichloro-3,4-dihydroxybiphenyl-2,6-dicarbonitrile

Using the procedure described in Example 37, 3',4'-dichloro-3-hydroxy-4-methoxybiphenyl-2,6-dicarbonitrile (107 mg), prepared from 3,4-dichlorophenylboronic acid and 2-bromo-4-hydroxy-5-methoxyisophthalonitrile, was demethylated to give the title compound. Yield 96 mg ¹H NMR (400 MHz, DMSO-d₆) ppm 11.38 (br s, 2H) 7.84 (d, J=2.01 Hz, 1H) 7.82 (d, J=8.28 Hz, 1H) 7.51 (dd, J=8.28, 2.26 Hz, 1H) 7.35 (s, 1H)

Example 39

3,4-Dihydroxy-3'-(trifluoromethyl)biphenyl-2,6-dicarbonitrile

Using the procedure described in Example 37, 3-hydroxy-4-methoxy-3'-(trifluoromethyl) biphenyl-2,6-dicarbonitrile (320 mg), prepared from 3-(trifluoromethyl)phenylboronic acid and 2-bromo-4-hydroxy-5-methoxyisophthalonitrile, was demethylated to give the title compound. Yield 239 mg ¹H NMR (400 MHz, DMSO-d₆) ppm 11.19 (br s, 2H) 7.87-7.92 (m, 2H) 7.75-7.85 (m, 2H) 7.36 (s, 1H)

Example 40

2-(Furan-3-yl)-4,5-dihydroxyisophthalonitrile

Using the procedure described in Example 37, 2-(furan-3-yl)-4-hydroxy-5-methoxyisophthalonitrile (60 mg), prepared from furan-3-boronic acid and 2-bromo-4-hydroxy-5-methoxyisophthalonitrile, was demethylated to give the title compound. Yield 56 mg ¹H NMR (400 MHz, DMSO-d₆) ppm 11.68 (br s, 1H) 11.15 (br s, 1H) 8.00-8.12 (m, 1H) 7.82-7.91 (m, 1H) 7.33 (s, 1H) 6.75-6.84 (m, 1H)

Example 41

3,4-Dihydroxy-4'-(trifluoromethyl)biphenyl-2,6-dicarbonitrile

Using the procedure described in Example 37, 3-hydroxy-4-methoxy-4'-(trifluoromethyl) biphenyl-2,6-dicarbonitrile (145 mg), prepared from 4-tri(fluoromethyl)phenylboronic acid and 2-bromo-4-hydroxy-5-methoxyisophthalonitrile, was demethylated to give the title compound. Yield 139 mg ¹H NMR (400 MHz, DMSO-d₆) ppm 11.41 (br s, 2H) 7.92 (d, J=8.03 Hz, 2H) 7.74 (d, J=8.03 Hz, 2H) 7.38 (s, 1H)

Example 42

4,5-Dihydroxy-2-(thiophen-3-yl)isophthalonitrile

Using the procedure described in Example 37, 4-hydroxy-5-methoxy-2-(thiophen-3-yl) isophthalonitrile (210 mg), prepared from thiophene-3-boronic acid and 2-bromo-4-hydroxy-5-methoxyisophthalonitrile, was demethylated to give the title compound. Yield 110 mg ¹H NMR (400 MHz, DMSO-d₆) ppm 11.56 (br s, 1H) 11.12 (br s, 1H) 7.83 (dd, J=3.0, 1.2 Hz, 1H) 7.72 (dd, J=5.0 Hz, 1H) 7.33 (s, 1H) 7.30 (dd, 1H)

Example 43

4,5-Dihydroxy-2-(5-methylfuran-2-yl)isophthalonitrile

Using the procedure described in Example 37, 4-hydroxy-5-methoxy-2-(5-methylfuran-2-yl)isophthalonitrile (150 mg), prepared from 5-methylfuran-2-boronic acid and 2-bromo-4-hydroxy-5-methoxyisophthialonitrile, was demethylated to give the title compound. Yield 90 mg ¹H NMR (400 MHz, DMSO-d₆) ppm 11.39 (br s, 2H) 7.31 (s, 1H) 6.88 (d, J=3.3 Hz, 1H) 6.21-6.48 (m, 1H) 2.35 (s, 3H)

Example 44

4,5-Dihydroxy-2-(5-methylthiophen-2-yl)isophthalonitrile

Using the procedure described in Example 37, 4-hydroxy-5-methoxy-2-(5-methylthiophen-2-yl)isophthalonitrile (250 mg), prepared from 5-methylthiophene-2-boronic acid and 2-bromo-4-hydroxy-5-methoxyisophthalonitrile, was demethylated to give the title compound. Yield 130 mg ¹H NMR (400 MHz, DMSO-d₆) ppm 11.41 (br s, 2H) 7.31 (s, 1H) 7.13 (d, J=3.5 Hz, 1H) 6.88-6.95 (m, 1H) 2.52 (br s, 3H)

Example 45

2-Benzyl-4,5-dihydroxyisophthalonitrile

2-Benzyl-4-hydroxy-5-methoxyisophthalonitrile

To a mixture of 2-bromo-4-hydroxy-5-methoxyisophthalonitrile (1.0 g) and benzylboronic acid pinacol ester (0.53 ml) in 1,4-dioxane (5 ml) and water (5 ml) was added Pd(dppf)Cl₂ complex with CH₂Cl₂ (1:1) (0.260 g) and cesium carbonate (3.8 g). The stirred reaction was microwave-irradiated at 120° C. for 30 min. The hot reaction mixture was filtered over pall filter. After cooling, the obtained precipitate was acidified with 2 M HCl (5 ml), filtered, washed with water and dried to give 2-benzyl-4-hydroxy-5-methoxyisophthalonitrile. Yield 0.77 g ¹H NMR (400 MHz, DMSO-d₆) ppm 7.49 (s, 1H) 6.96-7.24 (m, 4H) 3.94 (s, 3H)

2-Benzyl-4,5-dihydroxyisophthalonitrile

2-Benzyl-4-hydroxy-5-methoxyisophthalonitrile (1.5 g) was demethylated using boron tribromide as described in Example 37 to give the title compound. Yield 0.77 g ¹H NMR (DMSO-d₆) ppm 10.8-11.6 (br, 2H) 7.29 (s, 1H) 7.15-7.35 (m, 5H) 4.16 (s, 2H)

Example 46

2-(Benzofuran-2-yl)-4,5-dihydroxyisophthalonitrile

Using the procedure described in Example 37, 2-(benzofuran-2-yl)-4-hydroxy-5-methoxyisophthalonitrile (320 mg), prepared from 2-benzofuranboronic acid and 2-bromo- 4-hydroxy-5-methoxyisophthalonitrile, was demethylated to give the title compound. Yield 200 ng $^1$H NMR (400 MHz, DMSO-d$_6$) ppm 11.60 (br s, 2H) 7.80 (d, J=7.8 Hz, 1H) 7.68 (d, J=8.3 Hz, 1H) 7.40-7.48 (m, 3H) 7.32-7.39 (m, 1H)

Example 47

2-(5-Chlorothiophen-2-yl)-4,5-dihydroxyisophthalonitrile

Using the procedure described in Example 37, 2-(5-chlorothiophen-2-yl)-4-hydroxy-5-methoxyisophthalonitrile (27 mg), prepared from 5-chlorothiophene-2-boronic acid and 2-bromo-4-hydroxy-5-methoxyisophthalonitrile, was demethylated to give the title compound. Yield 20 mg $^1$H NMR (400 MHz, DMSO-d$_6$) ppm 11.35 (br s, 2H) 7.34 (s, 1H) 7.27 (d, J=3.9 Hz, 1H) 7.24 (d, 1H)

Example 48

2-(Benzo[b]thiophen-2-yl)-4,5-dihydroxyisophthalonitrile

Using the procedure described in Example 37, 2-(benzo[b]thiophen-2-yl)-4-hydroxy-5-methoxyisophthalonitrile (70 mg), prepared from 2-bromo-4-hydroxy-5-methoxyisophthalonitrile and thianaphthene-2-boronic acid, was demethylated to give the title compound. Yield 50 mg $^1$H NMR (400 MHz, DMSO-d$_6$) ppm 10.43-12.58 (m, 2H) 8.04-8.11 (m, 1H) 7.94-8.01 (m, 1H) 7.67 (s, 1H) 7.44-7.51 (m, 2H) 7.39 (s, 1H)

Example 49

(E)-4,5-Dihydroxy-2-styrylisophthalonitrile

Using the procedure described in Example 37, (E)-4-hydroxy-5-methoxy-2-styrylisophthalonitrile (100 mg), prepared from 2-bromo-4-hydroxy-5-methoxyisophthalonitrile and trans-2-phenylvinylboronic acid, was demethylated to give the title compound. Yield 79 mg $^1$H NMR (400 MHz, DMSO-d$_6$) ppm 7.61 (d, J=7.28 Hz, 2H) 7.41-7.48 (m, 2H) 7.21-7.41 (m, 4H)

Example 50

4'-Ethyl-3,4-dihydroxybiphenyl-2,6-dicarbonitrile

Using the procedure described in Example 37, 4'-ethyl-3-hydroxy-4-methoxybiphenyl-2,6-dicarbonitrile (150 mg), prepared from 2-bromo-4-hydroxy-5-methoxyisophthalonitrile and 4-ethylbenzeneboronic acid, was demethylated to give the title compound. Yield 100 mg $^1$H NMR (400 MHz, DMSO-d$_6$) ppm 7.33-7.41 (m, 5H) 2.70 (m, J=7.50, 7.50, 7.50 Hz, 2H) 1.25 (t, J=7.53 Hz, 3H)

Example 51

3,4-Dihydroxy-3',5'-dimethylbiphenyl-2,6-dicarbonitrile

Using the procedure described in Example 37, 3-hydroxy-4-methoxy-3',5'-dimethylbiphenyl-2,6-dicarbonitrile (115 mg), prepared from 2-bromo-4-hydroxy-5-methoxyisophthalonitrile and 3,5-dimethylbenzeneboronic acid, was demethylated to give the title compound. Yield 70 mg $^1$H NMR (400 MHz, DMSO-d$_6$) ppm 7.32 (s, 1H) 7.14 (s, 1H) 7.04 (s, 2H) 2.33 (s, 6H)

Example 52

4,5-Dihydroxy-2-(phenylthio)isophthalonitrile

4-Hydroxy-5-methoxy-2-(phenylthio)isophthalonitrile

To a mixture of 2-bromo-4-hydroxy-5-methoxyisophthalonitrile (0.5 g) in THF (8 ml) was added phenyl disulfide (0.26 g) and Pd(dppf)Cl$_2$ complex with CH$_2$Cl$_2$ (1:1) (0.13 g). The stirred reaction was refluxed for 24 h. The hot reaction mixture was filtered over pall filter.

After cooling, the obtained precipitate was acidified with 2 M HCl (5 ml), filtered, washed with water and dried to give 4-hydroxy-5-methoxy-2-(phenylthio)isophthalonitrile. Yield 0.45 g $^1$H NMR (400 MHz, DMSO-d$_6$) ppm 7.29 (s, 1H) 7.01-7.18 (m, 4H) 3.68 (s, 2H)

4,5-Dihydroxy-2-(phenylthio)isophthalonitrile

4-Hydroxy-5-methoxy-2-(phenylthio)isophthalonitrile (400 mg) was demethylated using boron tribromide as described in Example 37 to give the title compound. Yield 164 mg $^1$H NMR (400 MHz, DMSO-d$_6$) ppm 7.25-7.40 (m, 6H)

Example 53

4,5-Dihydroxy-2-(p-tolylthio)isophthalonitrile

4-Hydroxy-5-methoxy-2-(p-tolylthio)isophthalonitrile (400 mg), which was prepared as described in Example 52, except that p-tolyl disulfide was used instead of phenyl disulfide, was demethylated using boron tribromide as described in Example 37 to give the title compound. Yield 65 mg $^1$H NMR (400 MHz, DMSO-d$_6$) ppm 11.45 (br s, 2H) 7.36 (s, 1H) 7.17 (d, J=8.28 Hz, 2H) 7.12 (d, J=8.28 Hz, 2H) 2.27 (s, 3H)

Example 54

4,5-Dihydroxy-2-(4-methylbenzyl)isophthalonitrile

4-Hydroxy-5-methoxy-2-(4-methylbenzyl)isophthalonitrile

To a mixture of 2-bromo-4-hydroxy-5-methoxyisophthalonitrile (1.00 g) and 4,4,5,5-tetramethyl-2-(4-methylbenzyl)-1,3,2-dioxaborolane (1.38 g) in ethanol (2.5 ml) and water (22 ml) was added Pd(dppf)Cl$_2$ complex with CH$_2$Cl$_2$ (1:1) (0.26 g) and sodium hydrogen carbonate (1.32 g). The stirred reaction was refluxed for 3 h. The hot reaction mixture was filtered over pall filter. After cooling, the obtained precipitate was acidified with 2 M HCl (10 ml), filtered, washed with water and dried to give 4-hydroxy-5-methoxy-2-(4-methylbenzyl)isophthalonitrile. Yield 0.53 g $^1$H NMR (400 MHz, DMSO-d$_6$) ppm 7.66 (s, 1H) 6.96-7.24 (m, 4H) 4.13 (s, 2H) 3.90 (s, 3H) 2.26 (s, 3H)

4,5-Dihydroxy-2-(4-methylbenzyl)isophthalonitrile

4-Hydroxy-5-methoxy-2-(4-methylbenzyl)isophthalonitrile (1.00 g) in acetonitrile (15 ml) was slowly added to a solution of aluminum chloride (0.95 g) and sodium iodide (1.07 g) in acetonitrile (15 ml) 0° C. The reaction mixture was heated at 50° C. for 3 h. Methanol (50 ml) was added and the solution was evaporated to dryness. 2 M NaOH (10 ml) and toluene (20 ml) was added and the mixture was stirred for 1 h. The aqueous phase was washed twice with toluene (10 ml) and made acidic by concentrated HCl at 0° C. The product was filtered, washed with water and dried to give the title compound. Yield 0.90 g $^1$H NMR (400 MHz, DMSO-$d_6$) ppm 7.29 (s, 1H) 6.92-7.21 (m, 4H) 4.10 (s, 2H) 2.25 (s, 3H)

Example 55

2-(4-Fluorobenzyl)-4,5-dihydroxyisophthalonitrile 2-(4-Fluorobenzyl)-4-hydroxy-5-methoxyisophthalonitrile 2-(4-Fluorobenzyl)-4-hydroxy-5-methoxyisophthalonitrile was prepared from 2-bromo-4-hydroxy-5-methoxyisophthalonitrile (1.00 g) and 2-(4-fluorobenzyl)-4,4,5,5-tetramethyl-1,3,2-dioxaborolane (1.30 g) instead of 4,4,5,5-tetramethyl-2-(4-methylbenzyl)-1,3,2-dioxaborolane using the procedure analogous to Example 54. Yield 0.53 g $^1$H NMR (400 MHz, DMSO-$d_6$) ppm 7.68 (s, 1H) 7.04-7.29 (m, 4H) 4.18 (s, 2H) 3.90 (s, 3H)

2-(4-Fluorobenzyl)-4,5-dihydroxyisophthalonitrile 2-(4-Fluorobenzyl)-4-hydroxy-5-methoxyisophthalonitrile (200 mg) was converted to the title compound using the procedure analogous to Example 54. Yield 96 mg $^1$H NMR (400 MHz, DMSO-$d_6$) ppm 7.29 (s, 1H) 7.12-7.23 (m, 4H) 4.14 (s, 2H)

Example 56

4,5-Dihydroxy-2-(4-hydroxybenzyl)isophthalonitrile

Using the procedure analogous to Example 54, 4-hydroxy-5-methoxy-2-(4-methoxybenzyl)isophthalonitrile (250 mg), prepared from 4-methoxybenzylboronic acid pinacol ester and 2-bromo-4-hydroxy-5-methoxyisophthalonitrile (1.00 g), was demethylated to give the title compound. Yield 96 mg $^1$H NMR (400 MHz, DMSO-$d_6$) ppm 7.37 (s, 1H) 6.96 (d, J=1.00 Hz, 2H) 6.69 (d, J=1.00 Hz, 2H) 4.01 (s, 2H)

Example 57

4,5-Dihydroxy-2-(2-methoxybenzyl)isophthalonitrile

Using the procedure analogous to Example 54, 4-hydroxy-5-methoxy-2-(2-methoxybenzyl)isophthalonitrile (116 mg), prepared from 2-bromo-4-hydroxy-5-methoxyisophthalonitrile and 2-(2-methoxybenzyl)-4,4,5,5-tetramethyl-1,3,2-dioxaborolane, was demethylated to give the title compound. Yield 17.6 mg $^1$H NMR (400 MHz, DMSO-$d_6$) ppm 7.28 (s, 1H) 7.23 (t, J=7.28 Hz, 1H) 6.99 (d, J=8.28 Hz, 1H) 6.84 (t, J=7.40 Hz, 1H) 6.70 (d, J=7.28 Hz, 1H) 4.07 (s, 2H) 3.81 (s, 3H)

Example 58

4,5-Dihydroxy-2-(4-(trifluoromethoxy)benzyl)isophthalonitrile

Using the procedure analogous to Example 54, 4-hydroxy-5-methoxy-2-(4-(trifluoromethoxy)benzyl)isophthalonitrile (260 mg), prepared from 2-bromo-4-hydroxy-5-methoxyisophthalonitrile and 4-(trifluoromethoxy)benzylboronic acid pinacol ester, was demethylated to give the title compound. Yield 130 mg $^1$H NMR (400 MHz, DMSO-$d_6$) ppm 7.25-7.36 (m, 5H) 4.18 (s, 2H)

Example 59

2-(3-Fluoro-4-methoxybenzyl)-4,5-dihydroxy-isophthalonitrile

Using the procedure analogous to Example 54, 2-(3-fluoro-4-methoxybenzyl)-4,5-dihydroxyisophthalonitrile (600 mg), prepared from 2-bromo-4-hydroxy-5-methoxyisophthalonitrile and 2-(3-fluoro-4-methoxybenzyl)-4,4,5,5-tetramethyl-1,3,2-dioxaborolane, was demethylated to give the title compound. Yield 175 mg $^1$H NMR (400 MHz, DMSO-$d_6$) ppm 7.36 (s, 1H) 7.11 (t, J=8.78 Hz, 1H) 7.01 (dd, J=1.00 Hz, 1H) 6.91 (br d, J=1.00 Hz, 1H) 4.09 (s, 2H) 3.80 (s, 3H)

Example 60

2-(2-Fluorobenzyl)-4,5-dihydroxyisophthalonitrile

Using the procedure analogous to Example 54, 2-(2-fluorobenzyl)-4-hydroxy-5-methoxyisophthalonitrile (200 mg), prepared from 2-bromo-4-hydroxy-5-methoxyisophthalonitrile and 2-(2-fluorobenzyl)-4,4,5,5-tetramethyl-1,3,2-dioxaborolane, was demethylated to give the title compound. Yield 86 mg $^1$H NMR (400 MHz, DMSO-$d_6$) ppm 7.27-7.34 (m, 2H) 7.16-7.24 (m, 1H) 7.13 (t, J=7.53 Hz, 1H) 6.95 (t, J=7.53 Hz, 1H) 4.17 (s, 2H)

Example 61

4,5-Dihydroxy-2-(2-methylbenzyl)isophthalonitrile

Using the procedure analogous to Example 54, 4-hydroxy-5-methoxy-2-(2-methylbenzyl)isophthalonitrile (550 mg), prepared from 2-bromo-4-hydroxy-5-methoxyisophthalonitrile and 4,4,5,5-tetramethyl-2-(2-methylbenzyl)-1,3,2-dioxaborolane, was demethylated to give the title compound. Yield 152 mg $^1$H NMR (400 MHz, DMSO-$d_6$) ppm 7.33 (s, 1H) 7.22 (d, J=7.07 Hz, 1H) 7.12 (d, J=7.07 Hz, 1H) 7.07 (d, J=7.58 Hz, 1H) 6.47 (d, J=7.58 Hz, 1H) 4.10 (s, 2H) 2.38 (s, 3H)

Example 62

2-(2,5-Dimethylbenzyl)-4,5-dihydroxyisophthalonitrile

Using the procedure analogous to Example 54, (2,5-dimethylbenzyl)-4-hydroxy-5-methoxyisophthalonitrile (578 mg), prepared from 2-bromo-4-hydroxy-5-methoxyisophthalonitrile and 2-(2,5-dimethylbenzyl)-4,4,5,5-tetramethyl-1,3,2-dioxaborolane, was demethylated to give the title compound. Yield 39 mg ¹H NMR (400 MHz, DMSO-d$_6$) ppm 7.33 (s, 1H) 7.10 (d, J=7.28 Hz, 1H) 6.93 (d, J=7.03 Hz, 1H) 6.28 (br s, 1H) 4.06 (brs, 2H) 2.32 (s, 3H) 2.13 (s, 3H)

Example 63

2-(3-Fluoro-5-methylbenzyl)-4,5-dihydroxy-isophthalonitrile

Using the procedure analogous to Example 54, 2-(3-fluoro-5-methylbenzyl)-4-hydroxy-5-methoxyisophthalonitrile (600 mg), prepared from 2-bromo-4-hydroxy-5-methoxyisophthalonitrile and 2-(3-fluoro-5-methylbenzyl)-4,4,5,5-tetramethyl-1,3,2-dioxaborolane, was demethylated to give the title compound. Yield 91 mg ¹H NMR (400 MHz, DMSO-d$_6$) ppm 7.30 (s, 1H) 6.91 (d, J=9.79 Hz, 1H) 6.80 (s, 1H) 6.75 (d, J=9.79 Hz, 1H) 4.13 (s, 2H) 2.27 (s, 3H)

Example 64

3-(2,6-Dicyano-3,4-dihydroxybenzyl)benzoic acid

Using the procedure analogous to Example 54, 3-(2,6-dicyano-3-hydroxy-4-methoxybenzyl)benzoic acid (300 mg), prepared from 2-bromo-4-hydroxy-5-methoxyisophthalonitrile and methyl 3-((4,4,5,5-tetramethyl-1,3,2-dioxaborolan-2-yl)methyl)benzoate, was demethylated to give the title compound. Yield 43 mg ¹H NMR (400 MHz, DMSO-d$_6$) ppm 7.75 (s, 1H) 7.26-7.56 (m, 4H) 4.22 (s, 2H)

Example 65

2-(4-Fluoro-3-methylbenzyl)-4,5-dihydroxy-isophthalonitrile

Using the procedure analogous to Example 54, 2-(4-fluoro-3-methylbenzyl)-4-hydroxy-5-methoxyisophthalonitrile (600 mg), prepared from 2-bromo-4-hydroxy-5-methoxyisophthalonitrile and 2-(4-fluoro-3-methylbenzyl)-4,4,5,5-tetramethyl-1,3,2-dioxaborolane, was demethylated to give the title compound. Yield 24 mg ¹H NMR (400 MHz, DMSO-d$_6$) ppm 7.29 (s, 1H) 7.03-7.12 (m, 2H) 6.99 (br s, 1H) 4.10 (br s, 2H) 2.19 (br s, 3H)

Example 66

4,5-Dihydroxy-2-(3-methylbenzyl)isophthalonitrile

Using the procedure analogous to Example 54, 4-hydroxy-5-methoxy-2-(3-methylbenzyl)isophthalonitrile (600 mg), prepared from 2-bromo-4-hydroxy-5-methoxyisophthalonitrile and 4,4,5,5-tetramethyl-2-(3-methylbenzyl)-1,3,2-dioxaborolane, was demethylated to give the title compound. Yield 43 mg ¹H NMR (400 MHz, DMSO-d$_6$) ppm 11.57 (br s, 1H) 10.93 (br, 1H) 7.29 (br s, 1H) 7.19 (br s, 1H) 6.79-7.09 (m, 3H) 4.11 (s, 2H) 2.26 (s, 3H)

Example 67

2-(5-Fluoro-2-methoxybenzyl)-4,5-dihydroxy-isophthalonitrile

Using the procedure analogous to Example 54, 2-(5-fluoro-2-methoxybenzyl)-4-hydroxy-5-methoxyisophthalonitrile (400 mg), prepared from 2-bromo-4-hydroxy-5-methoxyisophthalonitrile and 2-(5-fluoro-2-methoxybenzyl)-4,4,5,5-tetramethyl-1,3,2-dioxaborolane, was demethylated to give the title compound. Yield 7 mg ¹H NMR (400 MHz, DMSO-d$_6$) ppm 11.09 (br s, 1H) 10.95 (br s, 1H) 7.29 (s, 1H) 6.92-7.11 (m, 2H) 6.55 (d, J=9.03 Hz, 1H) 4.06 (s, 2H) 3.79 (s, 3H)

Example 68

2-(3,5-Dimethylbenzyl)-4,5-dihydroxyisophthalonitrile

Using the procedure analogous to Example 54, 2-(3,5-dimethylbenzyl)-4-hydroxy-5-methoxyisophthalonitrile (578 mg), prepared from 2-bromo-4-hydroxy-5-methoxyisophthalonitrile and 2-(3,5-dimethylbenzyl)-4,4,5,5-tetramethyl-1,3,2-dioxaborolane, was demethylated to give the title compound. Yield 120 mg ¹H NMR (400 MHz, DMSO-d$_6$) ppm 7.30 (s, 1H) 6.86 (s, 1H) 6.76 (s, 2H) 4.07 (s, 2H) 2.21 (s, 6H)

Example 69

4,5-Dihydroxy-2-(4-isopropylbenzyl)isophthalonitrile

Using the procedure analogous to Example 54, 4-hydroxy-2-(4-isopropylbenzyl)-5-methoxyisophthalonitrile (600 mg), prepared from 2-bromo-4-hydroxy-5-methoxyisophthalonitrile and 2-(4-isopropylbenzyl)-4,4,5,5-tetramethyl-1,3,2-dioxaborolane, was demethylated to give the title compound. Yield 21 mg ¹H NMR (400 MHz, DMSO-d$_6$) ppm 7.28 (s, 1H) 7.18 (d, J=1.00 Hz, 2H) 7.10 (d, J=1.00 Hz, 2H) 4.10 (s, 2H) 2.79-2.88 (m, 1H) 1.17 (d, J=6.78 Hz, 6H)

Example 70

2-(4-Ethylbenzyl)-4,5-dihydroxyisophthalonitrile 2-(4-Ethylbenzyl)-4-hydroxy-5-methoxyisophthalonitrile To a mixture of 2-bromo-4-hydroxy-5-methoxyisophthalonitrile (2.57 g) and 2-(4-ethylbenzyl)-4,4,5,5-tetramethyl-1,3,2-dioxaborolane (3.75 g) in ethanol (5 ml) and water (40 ml) was added Pd(dppf)Cl$_2$ complex with CH$_2$Cl$_2$ (1:1) (0.67 g) and sodium hydrogen carbonate (3.40 g). The stirred reaction was refluxed for 3 h. The hot reaction mixture was filtered over pall filter. After cooling, the obtained precipitate was acidified with 2 M HCl (20 ml), filtered, washed with water and dried to give 2-(4-ethylbenzyl)-4-hydroxy-5-methoxyisophthalonitrile. Yield 2.31 g ¹H NMR (400 MHz, DMSO-d$_6$) ppm 7.41 (s, 1H) 7.08-7.17 (m, 4H) 4.08 (s, 2H) 3.82 (s, 3H) 2.55 (q, J=7.61 Hz, 2H) 1.14 (t, J=7.53 Hz, 3H)

2-(4-Ethylbenzyl)-4,5-dihydroxyisophthalonitrile

Using the procedure described in Example 54, 2-(4-ethylbenzyl)-4-hydroxy-5-methoxyisophthalonitrile (2.31 g) was converted to the title compound. Yield 2.15 g ¹H NMR (400 MHz, DMSO-d$_6$) ppm 7.28 (s, 1H) 7.12-7.17 (m, 2H) 7.07-7.12 (m, 2H) 4.11 (s, 2H) 2.53-2.59 (m, 2H) 1.14 (t, J=7.65 Hz, 3H)

Example 71

4,5-Dihydroxy-2-(naphthalen-1-ylmethyl)isophthalonitrile

Using the procedure analogous to Example 54, 4-hydroxy-5-methoxy-2-(naphtalen-1-ylmethyl)isophthalonitrile (100 mg), prepared from 2-bromo-4-hydroxy-5-methoxyisophthalonitrile and 4,4,5,5-tetramethyl-2-(naphthalen-1-ylmethyl)-1,3,2-dioxaborolane, was demethylated to give the title compound. Yield 40 mg $^1$H NMR (400 MHz, DMSO-$d_6$) ppm 8.50-6.50 (m, 8H) 4.72 (m, 2H)

Example 72

5-(2,6-Dicyano-3,4-dihydroxybenzyl)-2-hydroxybenzoic acid

Using the procedure analogous to Example 54, 5-(2,6-dicyano-3-hydroxy-4-methoxybenzyl)-2-hydroxybenzoic acid (300 mg), prepared from 2-bromo-4-hydroxy-5-methoxyisophthalonitrile and 2-hydroxy-5-((4,4,5,5-tetramethyl-1,3,2-dioxaborolan-2-yl)methyl)benzoic acid, was demethylated to give the title compound. Yield 38 mg $^1$H NMR (400 MHz, DMSO-$d_6$) ppm 11.29-11.80 (m, 1H) 10.95 (br s, 1H) 7.33 (s, 1H) 7.10 (d, J=7.78 Hz, 1H) 6.93 (d, J=7.78 Hz, 1H) 6.27 (s, 1H) 4.06 (s, 2H)

Example 73

2-(2,4-Dimethylbenzyl)-4,5-dihydroxyisophthalonitrile

2-(2,4-Dimethylbenzyl)-4-hydroxy-5-methoxyisophthalonitrile

To a mixture of 2-bromo-4-hydroxy-5-methoxyisophthalonitrile (0.86 g) and 2-(2,4-dimethylbenzyl)-4,4,5,5-tetramethyl-1,3,2-dioxaborolane (1.13 g) in ethanol (2.5 ml) and water (22 ml) was added Pd(dppf)Cl$_2$ complex with CH$_2$Cl$_2$ (1:1) (0.21 g) and sodium hydrogen carbonate (1.10 g). The stirred reaction was refluxed for 3 h. The hot reaction mixture was filtered over pall filter. After cooling, the obtained precipitate was acidified with 2 M HCl (10 ml), filtered, washed with water and dried to give 2-(2,4-dimethylbenzyl)-4-hydroxy-5-methoxyisophthalonitrile. Yield 0.43 g $^1$H NMR (400 MHz, DMSO-$d_6$) ppm 7.70 (s, 1H) 7.04 (s, 1H) 6.87 (d, J=7.78 Hz, 1H) 6.34 (d, J=7.78 Hz, 1H) 4.08 (s, 2H) 3.93 (s, 3H) 2.34 (s, 3H) 2.22 (s, 3H)

2-(2,4-Dimethylbenzyl)-4,5-dihydroxyisophthalonitrile

Using the procedure described in Example 54, 2-(2,4-dimethylbenzyl)-4-hydroxy-5-methoxyisophthalonitrile (0.43 g) was converted to the title compound. Yield 0.40 g $^1$H NMR (400 MHz, DMSO-$d_6$) ppm 7.31 (s, 1H) 7.02 (s, 1H) 6.86 (d, J=8.03 Hz, 1H) 6.34 (d, J=7.78 Hz, 1H) 4.04 (s, 2H) 2.33 (s, 3H) 2.21 (s, 3H)

Example 74

2-(3,6-Dihydro-2H-pyran-4-yl)-4,5-dihydroxyisophthalonitrile 3,6-Dihydro-2H-pyran-4-boronic acid pinacol ester (156 mg), bis(triphenylphosphine)palladium(II) chloride (24 mg) and sodium carbonate (197 mg) in water solution (2 ml) was added to a solution of 4-bromo-3,5-dicyano-1,2-phenylene diacetate (200 mg), ethanol (2 ml) and acetonitrile (2 ml). The reaction mixture was microwave-irradiated for 15 min at 130° C. The reaction mixture was poured in ice water and 2 M NaOH (15 ml) and toluene (20 ml) was added. The mixture was stirred for half an hour. The water phase was washed with toluene (20 ml) and then made acidic by addition of 4 M HCl (10 ml) under cooling. The product was filtered, washed with water and dried to give the title compound. Yield 133 mg:

$^1$H NMR (400 MHz, DMSO-$d_6$) ppm 7.26 (s, 1H) 5.95 (br s, 1H) 4.21 (d, J=2.51 Hz, 2H) 3.81 (t, J=5.14 Hz, 2H) 2.30-2.37 (m, 2H)

Example 75

2-Cyclopentenyl-4,5-dihydroxyisophthalonitrile

The title compound was prepared from 4-bromo-3,5-dicyano-1,2-phenylene diacetate (200 mg) by the procedure analogous to Example 74 using as reactant 1-cyclopentenylboronic acid pinacol ester (144 mg) instead of 3,6-dihydro-2H-pyran-4-boronic acid pinacol ester. Reaction conditions: 0.4 h at 130° C. Yield 114 mg $^1$H NMR (400 MHz, DMSO-$d_6$) ppm 7.25 (s, 1H) 6.02 (br s, 1H) 2.60-2.76 (m, 2H) 2.10-2.30 (m, 2H) 1.92-2.08 (m, 2H)

Example 76

(E)-3-(2,6-Dicyano-3,4-dihydroxyphenyl)acrylic acid

The title compound was prepared from 4-bromo-3,5-dicyano-1,2-phenylene diacetate (500 mg) by the procedure analogous to Example 74 using as reactant 2-(ethoxycarbonyl)vinylboronic acid pinacol ester (420 mg) instead of 3,6-dihydro-2H-pyran-4-boronic acid pinacol ester. Reaction conditions: 0.4 h at 150° C. Yield 260 mg $^1$H NMR (400 MHz, DMSO-$d_6$) ppm 7.65 (d, J=16.31 Hz, 1H) 7.32 (s, 1H) 6.74 (d, J=16.06 Hz, 1H)

Example 77

(E)-4,5-Dihydroxy-2-(3-methoxyprop-1-enyl)isophthalonitrile

The title compound was prepared from 4-bromo-3,5-dicyano-1,2-phenylene diacetate (200 mg) by the procedure analogous to Example 74 using as reactant trans-3-methoxy-1-propenylboronic acid pinacol ester (147 mg) instead of 3,6-dihydro-2H-pyran-4-boronic acid pinacol ester. Reaction conditions: 30 min at 130° C. Yield 70 mg $^1$H NMR (400 MHz, DMSO-$d_6$) ppm 7.26 (s, 1H) 6.40-6.77 (m, 2H) 4.02-4.20 (m, 2H) 3.33 (s, 3H)

Example 78

4,5-Dihydroxy-2-(5-(morpholinomethyl)thiophen-2-yl)isophthalonitrile

The title compound was prepared from 4-bromo-3,5-dicyano-1,2-phenylene diacetate (200 mg) by the procedure analogous to Example 74 using as reactant 5-(morpholinomethyl)-2-thiopheneboronic acid pinacol ester (249 mg)

instead of 3,6-dihydro-2H-pyran-4-boronic acid pinacol ester. Reaction conditions: 10 min at 150° C. Yield 80 mg $^1$H NMR (400 MHz, DMSO-$d_6$) ppm 7.48 (d, J=3.51 Hz, 1H) 7.45 (s, 1H) 7.36 (d, J=3.76 Hz, 1H) 4.64 (s, 2H) 3.87 (br s, 4H) 3.18 (br s, 4H)

Example 79

3,4-Dihydroxy-4'-(morpholine-4-carbonyl)biphenyl-2,6-dicarbonitrile

The title compound was prepared from 4-bromo-3,5-dicyano-1,2-phenylene diacetate (300 mg) by the procedure analogous to Example 74 using as reactant (4-(morpholine-4-carbonyl)phenyl)boronic acid pinacol ester (383 mg) instead of 3,6-dihydro-2H-pyran-4-boronic acid pinacol ester. Reaction conditions: 10 min at 140° C. Yield 120 mg $^1$H NMR (400 MHz, DMSO-$d_6$) ppm 7.99-8.12 (m, 2H) 7.58-7.68 (m, 2H) 7.37 (s, 1H) 3.16-3.74 (m, 4H)

Example 80

2-(5'-Hexyl-2,2'-bithiophen-5-yl)-4,5-dihydroxy-isophthalonitrile

The title compound was prepared from 4-bromo-3,5-dicyano-1,2-phenylene diacetate (200 mg) by the procedure analogous to Example 74 using as reactant 5'-hexyl-2,2'-bithiophene-5-boronic acid pinacol ester (303 mg) instead of 3,6-dihydro-2H-pyran-4-boronic acid pinacol ester. Reaction conditions: 10 min at 140° C. Yield 22 mg $^1$H NMR (400 MHz, DMSO-$d_6$) ppm 7.33 (s, 1H) 7.30 (d, J=3.76 Hz, 1H) 7.27 (d, J=1.00 Hz, 1H) 7.20 (d, J=3.51 Hz, 1H) 6.84 (d, J=3.26 Hz, 1H) 2.80 (t, J=7.28 Hz, 2H) 1.58-1.68 (m, 2H) 1.23-1.39 (m, 6H) 0.81-0.91 (m, 3H)

Example 81

2-(1-Benzyl-1H-pyrazol-4-yl)-4,5-dihydroxy-isophthalonitrile

The title compound was prepared from 4-bromo-3,5-dicyano-1,2-phenylene diacetate (300 mg) by the procedure analogous to Example 74 using as reactant 1-benzyl-4-(4,4,5,5-tetramethyl-1,3,2-dioxaborolan-2-yl)-1H-pyrazole (317 mg) instead of 3,6-dihydro-2H-pyran-4-boronic acid pinacol ester. Reaction conditions: 10 min at 140° C. Yield 82 mg $^1$H NMR (400 MHz, DMSO-$d_6$) ppm 8.37 (s, 1H) 7.88 (s, 1H) 7.33-7.50 (m, 6H) 5.54 (s, 2H)

Example 82

2-(5-Hexylthiophen-2-yl)-4,5-dihydroxyisophthalonitrile

The title compound was prepared from 4-bromo-3,5-dicyano-1,2-phenylene diacetate (300 mg) by the procedure analogous to Example 74 using as reactant 5-hexyl-2-thiopheneboronic acid pinacol ester (355 mg) instead of 3,6-dihydro-2H-pyran-4-boronic acid pinacol ester. Reaction conditions: 10 min at 140° C. Yield 40 mg $^1$H NMR (400 MHz, DMSO-$d_6$) ppm 7.31 (s, 1H) 7.14 (d, J=1.00 Hz, 1H) 6.93 (br s, 1H) 2.84 (t, J=7.15 Hz, 2H) 1.61-1.70 (m, 2H) 1.23-1.36 (m, 6H) 0.86 (br s, 3H)

Example 83

(Z)-2-(But-2-enyl)-4,5-dihydroxyisophthalonitrile cis-Crotylboronic acid pinacol ester (99 mg), bis(triphenylphosphine)palladium(II) chloride (29 mg) and sodium carbonate (133 mg) was added 2-bromo-4,5-dihydroxyisophthalonitrile (100 mg) solution containing ethanol (1 ml), acetonitrile (1 ml) and water (1 ml) as a solvent. The reaction mixture was stirred and microwave-irradiated for 45 min at 120° C. The reaction mixture was filtered through celite and poured in ice water. 2 M NaOH (15 ml) and toluene (20 ml) was added. The mixture was stirred for half an hour. The water phase was washed twice with toluene (20 ml) and made acidic by adding 4 M HCl keeping the temperature at 0-5° C. The solid product was filtered, washed with water and toluene and dried. Yield 36.6 mg $^1$H NMR (400 MHz, DMSO-$d_6$) ppm 7.5 (s, 1H) 5.92 (dd, J=10.29, 5.77 Hz, 1H) 5.54 (dd, J=10.42, 5.65 Hz, 1H) 3.73-3.74 (d, J=5.00 Hz, 2H) 1.68 (d, J=5.02 Hz, 3H)

Example 84

4,5-Dihydroxy-2-(3-methylbut-2-enyl)isophthalonitrile

3-Methyl-2-butenylboronic acid pinacol ester (392 mg), bis(triphenylphosphine)palladium(II) chloride (47 mg) and sodium carbonate (426 mg) was added in 2-bromo-4,5-dihydroxyisophthalonitrile (320 mg) solution containing ethanol (5 ml), acetonitrile (5 ml) and water (5 ml) as a solvent. The reaction mixture was stirred and microwave-irradiated for 60 min at 120° C. The reaction mixture was filtered through celite and organic solvents were evaporated. 0.1 M NaOH was added and the mixture was washed with toluene and EtOAc. The water phase was made acidic by adding HCl. The solid product was filtered, washed with water and toluene and dried. Yield 306 mg $^1$H NMR (400 MHz, DMSO-$d_6$) δ ppm 7.23 (s, 1H) 5.09 (t, J=7.03 Hz, 1H) 3.49 (d, J=7.03 Hz, 2H) 1.75 (s, 3H) 1.68 (s, 3H)

Example 85

(E)-2-(But-2-enyl)-4,5-dihydroxyisophthalonitrile

The title compound was prepared from 2-bromo-4,5-dihydroxyisophthalonitrile (100 mg) as described in Example 83 using trans-crotylboronic acid pinacol ester (99 mg) instead of cis-crotylboronic acid pinacol ester. Reaction conditions: 60 min at 120° C. Yield 30 mg $^1$H NMR (400 MHz, DMSO-$d_6$) ppm 7.5 (s, 1H) 5.92 (dd, J=10.29, 5.77 Hz, 1H) 5.56 (dd, J=10.42, 5.65 Hz, 1H) 3.73-3.75 (d, J=5.00 Hz, 2H) 1.72 (d, J=5.02 Hz, 3H)

Example 86

4,5-Dihydroxy-2-methylisophthalonitrile

To a mixture of 4-hydroxy-5-methoxy-2-methylisophthalonitrile (565 mg), DCM (30 ml) and acetonitrile (30 ml) under nitrogen atmosphere was added 1 M boron tribromide solution in DCM (6.0 ml) at −20° C. The reaction mixture was allowed to warm overnight to room temperature. Water (0.3 ml) was added to the reaction mixture followed by addition of methanol until clear reaction mixture was achieved. The mixture was evaporated to dryness and the remainder was chromatographed over silica gel with EtOAc/AcOH solvent mixture. Yield 0.27 g $^1$H NMR (400 MHz, DMSO-d$_6$) ppm 10.97 (br s, 2H) 7.17 (s, 1H) 2.44 (s, 3H)

Example 87

4,5-Dihydroxy-2-(2-methylprop-1-enyl)isophthalonitrile

The title compound was prepared from 4-bromo-3,5-dicyano-1,2-phenylene diacetate (395 mg) by the method of Example 2 using 2-methylpropene-1-tributylstannane (528 mg) instead of phenylethynyltri-n-butyltin. Yield 198 mg $^1$H NMR (400 MHz, DMSO-d$_6$) ppm 11.20 (br s, 2H) 7.27 (s, 1H) 6.20-6.26 (m, 1H) 1.92 (d, J=1.25 Hz, 3H) 1.62 (d, J=1.00 Hz, 3H)

Example 88

3,4-Dihydroxy-3'-methylbiphenyl-2,6-dicarbonitrile

The title compound was prepared from 4-bromo-3,5-dicyano-1,2-phenylene diacetate (352 mg) by the method of Example 2 using tributyl(m-tolyl)stannane (235 mg) instead of phenylethynyltri-n-butyltin. Yield 273 mg $^1$H NMR (400 MHz, DMSO-d$_6$) ppm 11.31 (br s, 2H) 7.37-7.44 (m, 1H) 7.29-7.36 (m, 2H) 7.21-7.29 (m, 2H) 2.38 (s, 3H)

Example 89

4,5-Dihydroxy-2-vinylisophthalonitrile

The title compound was prepared from 4-bromo-3,5-dicyano-1,2-phenylene diacetate (200 mg) by the method of Example 2 using tributyl(vinyl)stannane (255 mg) instead of phenylethynyltri-n-butyltin. Yield 50 mg $^1$H NMR (400 MHz, DMSO-d$_6$) ppm 11.30 (br s, 2H) 7.28 (s, 1H) 6.83 (dd, J=17.57, 11.54 Hz, 1H) 6.03 (d, J=17.57 Hz, 1H) 5.78 (d, J=11.54 Hz, 1H)

Example 90

4,5-Dihydroxy-2-(prop-1-en-2-yl)isophthalonitrile

The title compound was prepared from 4-bromo-3,5-dicyano-1,2-phenylene diacetate (500 mg) by the method of Example 2 using 2-(tributylstannyl)propene (641 mg) instead of phenylethynyltri-n-butyltin. Yield 210 mg $^1$H NMR (400 MHz, DMSO-d$_6$) ppm 11.35 (br s, 1H) 7.26 (s, 1H) 5.49 (s, 1H) 5.09 (s, 1H) 2.07 (s, 3H)

Example 91

2-(2-Ethoxythiazol-5-yl)-4,5-dihydroxyisophthalonitrile

The title compound was prepared from 4-bromo-3,5-dicyano-1,2-phenylene diacetate (200 mg) by the method of Example 2 using 2-ethoxy-5-(tributylstannyl)thiazole (311 mg) instead of phenylethynyltri-n-butyltin. Yield 60 mg $^1$H NMR (400 MHz, DMSO-d$_6$) ppm 11.36 (br s, 1H) 7.40 (s, 1H) 7.34 (s, 1H) 4.50 (m, J=7.00, 7.00, 7.00 Hz, 2H) 1.40 (t, J=6.90 Hz, 3H)

Example 92

2-Allyl-4,5-dihydroxyisophthalonitrile

The title compound was prepared from 4-bromo-3,5-dicyano-1,2-phenylene diacetate (250 mg) by the method of Example 2 using allyltri-n-butyltin (512 mg) instead of phenylethynyltri-n-butyltin. Yield 28 mg $^1$H NMR (400 MHz, DMSO-d$_6$) ppm 10.7-11.8 (br, s, 2H) 7.25 (s, 1H) 5.90 (m, 1H) 5.11 (m, 1H) 4.95 (m, 1H) 3.52 (m, 2H)

Example 93

3'-(tert-Butoxymethyl)-3,4-dihydroxybiphenyl-2,6-dicarbonitrile

The title compound was prepared from 4-bromo-3,5-dicyano-1,2-phenylene diacetate (500 mg) and (3-(tert-butoxymethyl)phenyl)boronic acid (322 mg) instead of 3,4,5-trifluorophenylboronic acid as described in Example 7. Reaction conditions: 30 min at 150° C. Yield 250 mg $^1$H NMR (400 MHz, DMSO-d$_6$) ppm 11.27 (br s, 2H) 7.41-7.53 (m, 2H) 7.29-7.41 (m, 3H) 4.49 (s, 2H) 1.24 (s, 9H)

Example 94 tert-Butyl 2',6'-dicyano-3',4'-dihydroxybiphenyl-3-carboxylate

The title compound was prepared from 4-bromo-3,5-dicyano-1,2-phenylene diacetate (500 mg) and 3-tert-butoxycarbonylphenylboronic acid (344 mg) instead of 3,4,5-trifluorophenylboronic acid as described in Example 7. Reaction conditions: 30 min at 150° C. Yield 67 mg $^1$H NMR (400 MHz, DMSO-d$_6$) ppm 11.43 (br s, 2H) 8.03 (d, J=8.03 Hz, 1H) 7.96 (s, 1H) 7.74 (d, J=7.28 Hz, 1H) 7.67 (t, J=7.53 Hz, 1H) 7.36 (s, 1H) 1.56 (s, 9H)

Example 95

3,4-Dihydroxybiphenyl-2,3',6-tricarbonitrile

The title compound was prepared from 4-bromo-3,5-dicyano-1,2-phenylene diacetate (500 mg) and 3-cyanophenylboronic acid (227 mg) instead of 3,4,5-trifluorophenylboronic acid as described in Example 7. Reaction conditions: 30 min at 150° C. Yield 141 mg $^1$H NMR (400 MHz, DMSO-d$_6$) ppm 11.39 (br s, 1H) 8.06 (s, 1H) 8.01 (d, J=7.78 Hz, 1H) 7.86 (d, J=8.03 Hz, 1'H) 7.76 (t, J=7.91 Hz, 1H) 7.39 (s, 1H)

Example 96

2',6'-Dicyano-3',4'-dihydroxy-N,N-dipropylbiphenyl-3-carboxamide

The title compound was prepared from 4-bromo-3,5-dicyano-1,2-phenylene diacetate (300 mg) and 3-(dipropylcarbamoyl)phenylboronic acid (231 mg) instead of 3,4,5-trifluorophenylboronic acid as described in Example 7. Reaction conditions: 10 min at 150° C. Yield 40 mg $^1$H NMR (400 MHz, DMSO-d$_6$) ppm 11.36 (br s, 2H) 7.59 (t, J=7.65 Hz, 1H) 7.51 (d, J=7.78 Hz, 1H) 7.46 (d, J=7.53 Hz, 1H) 7.34-7.40 (m, 2H) 3.27-3.35 (m, 2H) 3.19 (br s, 2H) 1.60 (br s, 2H) 1.45 (br s, 2H) 0.91 (br s, 3H) 0.65 (br s, 3H)

Example 97

2',6'-Dicyano-N-cyclohexyl-3',4'-dihydroxybiphenyl-4-carboxamide

The title compound was prepared from 4-bromo-3,5-dicyano-1,2-phenylene diacetate (300 mg) and 4-(cyclohexylaminocarbonyl)phenylboronic acid (275 mg) instead of 3,4,5-trifluorophenylboronic acid as described in Example 7. Reaction conditions: 5 min at 150° C. Yield 190 mg
$^1$H NMR (400 MHz, DMSO-$d_6$) ppm 11.38 (br s, 2H) 8.36 (d, J=7.78 Hz, 1H) 7.95 (d, J=1.00 Hz, 2H) 7.56 (d, J=1.00 Hz, 2H) 7.37 (s, 1H) 3.79 (br s, 1H) 1.84 (br s, 2H) 1.76 (br s, 2H) 1.62 (d, J=12.05 Hz, 1H) 1.30-1.40 (m, 4H) 1.14 (m, J=8.50 Hz, 1H)

Example 98

2',6'-Dicyano-N-cyclohexyl-3',4'-dihydroxybiphenyl-3-carboxamide

The title compound was prepared from 4-bromo-3,5-dicyano-1,2-phenylene diacetate (300 mg) and 3-(cyclohexylaminocarbonyl)phenylboronic acid (275 mg) instead of 3,4,5-trifluorophenylboronic acid as described in Example 7. Reaction conditions: 5 min at 150° C. Yield 120 mg
$^1$H NMR (400 MHz, DMSO-$d_6$) ppm 11.35 (br s, 2H) 8.29 (d, J=7.78 Hz, 1H) 7.99 (br s, 1H) 7.94 (s, 1H) 7.61 (d, J=4.52 Hz, 2H) 7.37 (s, 1H) 3.78 (br s, 1H) 1.83 (br s, 2H) 1.74 (br s, 2H) 1.61 (d, J=12.05 Hz, 1H) 1.31 (m, J=9.50, 9.50 Hz, 4H) 1.14 (br s, 1H)

Example 99

2',6'-Dicyano-N,N-diethyl-3',4'-dihydroxybiphenyl-4-carboxamide

The title compound was prepared from 4-bromo-3,5-dicyano-1,2-phenylene diacetate (300 mg) and 4-(N,N-diethylaminocarbonyl)phenylboronic acid (246 mg) instead of 3,4,5-trifluorophenylboronic acid as described in Example 7. Reaction conditions: 10 min at 140° C. Yield 100 mg
$^1$H NMR (400 MHz, DMSO-$d_6$) ppm 7.42-7.62 (m, 4H) 7.36 (s, 1H) 3.44 (t, J=1.00 Hz, 4H) 1.15 (br q, J=1.00, 1.00, 1.00 Hz, 6H)

Example 100

2',6'-Dicyano-N,N-diethyl-3',4'-dihydroxybiphenyl-3-carboxamide

The title compound was prepared from 4-bromo-3,5-dicyano-1,2-phenylene diacetate (300 mg) and 3-(N,N-diethylaminocarbonyl)phenylboronic acid (246 mg) instead of 3,4,5-trifluorophenylboronic acid as described in Example 7. Reaction conditions: 10 min at 140° C. Yield 100 mg
$^1$H NMR (400 MHz, DMSO-$d_6$) ppm 11.34 (br s, 2H) 7.56-7.63 (m, 1H) 7.48 (d, J=7.28 Hz, 1H) 7.52 (d, J=7.78 Hz, 1H) 7.40 (s, 1H) 7.34 (s, 1H) 3.44 (br s, 4H) 1.14 (br s, 3H) 1.05 (br s, 3H)

Example 101

2',6'-Dicyano-N-ethyl-3',4'-dihydroxybiphenyl-3-carboxamide

The title compound was prepared from 4-bromo-3,5-dicyano-1,2-phenylene diacetate (300 ing) and 3-(N-ethylaminocarbonyl)phenylboronic acid (215 mg) instead of 3,4,5-trifluorophenylboronic acid as described in Example 7. Reaction conditions: 10 min at 140° C. Yield 100 mg
$^1$H NMR (400 MHz, DMSO-$d_6$) ppm 11.40 (br s, 2H) 8.56 (m, J=5.00, 5.00 Hz, 1H) 7.96-8.02 (m, 1H) 7.94 (s, 1H) 7.62 (d, J=4.77 Hz, 2H) 7.38 (s, 1H) 3.25-3.35 (m, 2H) 1.14 (t, J=7.15 Hz, 3H)

Example 102

2',6'-Dicyano-3',4'-dihydroxy-N,N-dimethylbiphenyl-3-carboxamide

The title compound was prepared from 4-bromo-3,5-dicyano-1,2-phenylene diacetate (300 mg) and N,N-dimethylbenzamide-3-boronic acid (215 mg) instead of 3,4,5-trifluorophenylboronic acid as described in Example 7. Reaction conditions: 10 min at 140° C. Yield 60 mg
$^1$H NMR (400 MHz, DMSO-$d_6$) ppm 7.57-7.63 (m, 1H) 7.51-7.57 (m, 2H) 7.48 (s, 1H) 7.36 (s, 1H) 3.00 (br s, 3H) 2.95 (br s, 3H)

Example 103

4'-Fluoro-3,4-dihydroxybiphenyl-2,6-dicarbonitrile

The title compound was prepared from 4-bromo-3,5-dicyano-1,2-phenylene diacetate (100 mg) and 4-fluorobenzeneboronic acid (43 mg) instead of 3,4,5-trifluorophenylboronic acid as described in Example 7. Reaction conditions: 20 min at 130° C. Yield 50 mg
$^1$H NMR (400 MHz, DMSO-$d_6$) ppm 7.50-7.57 (m, 2H) 7.37 (t, J=8.78 Hz, 2H) 7.32 (s, 1H)

Example 104

3',4'-Difluoro-3,4-dihydroxybiphenyl-2,6-dicarbonitrile

The title compound was prepared from 4-bromo-3,5-dicyano-1,2-phenylene diacetate (100 mg) and 3,4-difluorophenylboronic acid (49 mg) instead of 3,4,5-trifluorophenylboronic acid as described in Example 7. Reaction conditions: 20 min at 130° C. Yield 34 mg
$^1$H NMR (400 MHz, DMSO-$d_6$) ppm 7.66-7.73 (m, 1H) 7.57-7.66 (m, 1H) 7.37 (br s, 1H) 7.33 (s, 1H)

Example 105

4'-Fluoro-3,3',4-trihydroxybiphenyl-2,6-dicarbonitrile

The title compound was prepared from 4-bromo-3,5-dicyano-1,2-phenylene diacetate (100 mg) and 4-fluoro-3-hydroxyphenylboronic acid (48 mg) instead of 3,4,5-trifluorophenylboronic acid as described in Example 7. Reaction conditions: 20 min at 130° C. Yield 32 mg
$^1$H NMR (400 MHz, DMSO-$d_6$) ppm 7.23-7.31 (m, 3H) 7.00 (d, J=8.28 Hz, 1H) 6.86 (br s, 1H)

Example 106

(E)-4,5-Dihydroxy-2-(3-phenylprop-1-enyl)isophthalonitrile

The title compound was prepared from 4-bromo-3,5-dicyano-1,2-phenylene diacetate (100 mg) and (E)-3-phenylpropen-1-yl-boronic acid (65 mg) instead of 3,4,5-trifluorophenylboronic acid as described in Example 7. Reaction conditions: 20 min at 150° C. Yield 57 mg $^1$H NMR (400 MHz, DMSO-d$_6$) ppm 7.26-7.35 (m, 4H) 7.20-7.26 (m, 2H) 6.54-6.69 (m, 2H) 3.63 (d, J=6.27 Hz, 2H)

Example 107

4'-Fluoro-3,4-dihydroxy-3'-methoxybiphenyl-2,6-dicarbonitrile

The title compound was prepared from 4-bromo-3,5-dicyano-1,2-phenylene diacetate (106 mg) and 3-fluoro-4-methoxyphenylboronic acid (72 mg) instead of 3,4,5-trifluorophenylboronic acid as described in Example 7. Reaction conditions: 45 min at 150° C. Yield 63.5 mg $^1$H NMR (400 MHz, DMSO-d$_6$) ppm 7.41 (d, J=10.79 Hz, 1H) 7.24-7.35 (m, 3H) 3.92 (s, 3H)

Example 108

5-(2,6-Dicyano-3,4-dihydroxyphenyl)thiophene-2-carboxylic acid

The title compound was prepared from 4-bromo-3,5-dicyano-1,2-phenylene diacetate (300 mg) and 5-boronothiophene-2-carboxylic acid (208 mg) instead of 3,4,5-trifluorophenylboronic acid as described in Example 7. Reaction conditions: 45 min at 150° C. Yield 127 mg $^1$H NMR (400 MHz, DMSO-d$_6$) ppm 7.79 (d, J=3.76 Hz, 1H) 7.39 (d, J=4.02 Hz, 1H) 7.35 (s, 1H)

Example 109

3,4-Dihydroxy-4'-(methylsulfonyl)biphenyl-2,6-dicarbonitrile

The title compound was prepared from 4-bromo-3,5-dicyano-1,2-phenylene diacetate (108 mg) and 4-(methanesulfonyl)phenylboronic acid (87 mg) instead of 3,4,5-trifluorophenylboronic acid as described in Example 7. Reaction conditions: 45 min at 150° C. Yield 60 mg $^1$H NMR (400 MHz, DMSO-d$_6$) ppm 10.72-12.36 (m, 2H) 8.08 (br d, J=8.30 Hz, 2H) 7.78 (br d, J=8.50 Hz, 2H) 7.38 (s, 1H) 3.33 (s, 3H)

Example 110

3,4-Dihydroxy-4'-propoxybiphenyl-2,6-dicarbonitrile

The title compound was prepared from 4-bromo-3,5-dicyano-1,2-phenylene diacetate (200 mg) and 3-propoxyphenylboronic acid (167 mg) instead of 3,4,5-trifluorophenylboronic acid as described in Example 7. Reaction conditions: 20 min at 150° C. Yield 30 mg $^1$H NMR (400 MHz, DMSO-d$_6$) ppm 7.38 (d, J=1.00 Hz, 2H) 7.34 (s, 1H) 7.06 (d, J=1.00 Hz, 2H) 4.00 (t, J=6.53 Hz, 2H) 1.71-1.81 (m, 2H) 1.01 (t, J=7.40 Hz, 3H)

Example 111

2',6'-Dicyano-3',4'-dihydroxybiphenyl-4-carboxylic acid

The title compound was prepared from 4-bromo-3,5-dicyano-1,2-phenylene diacetate (400 mg) and 4-carboxyphenylboronic acid (247 mg) instead of 3,4,5-trifluorophenylboronic acid as described in Example 7. Reaction conditions: 30 min at 140° C. Yield 270 mg $^1$H NMR (400 MHz, DMSO-d$_6$) ppm 8.07 (d, J=1.00 Hz, 2H) 7.61 (d, J=1.00 Hz, 2H) 7.38 (s, 1H)

Example 112

4'-Chloro-3,4-dihydroxy-3'-methylbiphenyl-2,6-dicarbonitrile

The title compound was prepared from 4-bromo-3,5-dicyano-1,2-phenylene diacetate (200 mg) and (4-chloro-3-methylphenyl)boronic acid (127 mg) instead of 3,4,5-trifluorophenylboronic acid as described in Example 7. Reaction conditions: 45 min at 150° C. Yield 54 mg $^1$H NMR (400 MHz, DMSO-d$_6$) ppm 7.57 (d, J=8.28 Hz, 1H) 7.47 (d, J=1.76 Hz, 1H) 7.34 (s, 1H) 7.33 (d, J=2.26 Hz, 1H) 2.39 (s, 3H)

Example 113

4,5-Dihydroxy-2-(5-phenylthiophen-2-yl)isophthalonitrile

The title compound was prepared from 4-bromo-3,5-dicyano-1,2-phenylene diacetate (200 mg) and 5-phenyl-2-thienylboronic acid (164 mg) instead of 3,4,5-trifluorophenylboronic acid as described in Example 7. Reaction conditions: 45 min at 150° C. Yield 71 mg $^1$H NMR (400 MHz, DMSO-d$_6$) ppm 7.72 (d, J=7.28 Hz, 2H) 7.63 (d, J=3.51 Hz, 1H) 7.44-7.50 (m, 2H) 7.34-7.40 (m, 3H)

Example 114

3,4-Dihydroxy-4'-isopropylbiphenyl-2,6-dicarbonitrile

The title compound was prepared from 4-bromo-3,5-dicyano-1,2-phenylene diacetate (200 mg) and 4-isopropylphenylboronic acid (152 mg) instead of 3,4,5-trifluorophenylboronic acid as described in Example 7. Reaction conditions: 20 min at 150° C. Yield 66 mg $^1$H NMR (400 MHz, DMSO-d$_6$) ppm 7.39 (s, 4H) 7.34 (s, 1H) 2.92-3.03 (m, 1H) 1.26 (d, J=7.03 Hz, 6H)

Example 115

3,4-Dihydroxy-4'-propylbiphenyl-2,6-dicarbonitrile

The title compound was prepared from 4-bromo-3,5-dicyano-1,2-phenylene diacetate (200 mg) and 4-propylphenylboronic acid (152 mg) instead of 3,4,5-trifluorophenylboronic acid as described in Example 7. Reaction conditions: 20 min at 150° C. Yield 80 mg $^1$H NMR (400 MHz, DMSO-d$_6$) ppm 7.31-7.40 (m, 5H) 2.64 (t, J=7.65 Hz, 2H) 1.60-1.71 (m, 2H) 0.93 (t, J=7.40 Hz, 3H)

Example 116

4,5-Dihydroxy-2-(1-phenylvinyl)isophthalonitrile

The title compound was prepared from 4-bromo-3,5-dicyano-1,2-phenylene diacetate (500 mg) and 1-phenylvinylboronic acid (321 mg) instead of 3,4,5-trifluorophenylboronic acid as described in Example 7. Reaction conditions: 45 min at 130° C. Yield 370 mg $^1$H NMR (400 MHz, DMSO-$d_6$) ppm 7.32-7.40 (m, 4H) 7.24-7.28 (m, 2H) 6.17 (s, 1H) 5.44 (s, 1H)

Example 117

2',6'-Dicyano-3',4'-dihydroxybiphenyl-2-carboxylic acid

The title compound was prepared from 4-bromo-3,5-dicyano-1,2-phenylene diacetate (200 mg) and 2-carboxyphenylboronic acid (134 mg) instead of 3,4,5-trifluorophenylboronic acid as described in Example 7. Reaction conditions: 45 min at 130° C. Yield 106 mg $^1$H NMR (400 MHz, DMSO-$d_6$) ppm 8.08 (d, J=7.78 Hz, 1H) 8.01 (s, 1H) 7.75 (d, J=7.78 Hz, 1H) 7.67 (m, J=7.70, 7.70 Hz, 1H) 7.38 (s, 1H)

Example 118

4-(2,6-Dicyano-3,4-dihydroxybenzyl)benzoic acid

2-((4-(Chloromethyl)benzyl)oxy)tetrahydro-2H-pyran

A mixture of (4-(chloromethyl)phenyl)methanol (25.3 g), DCM (280 ml), 3,4-dihydro-2H-pyran (39.6 ml) and pyridin-1-ium 4-methylbenzenesulfonate (4.1 g) was stirred at room temperature for 3 h. Saturated aqueous solution of sodium hydrogen carbonate (250 ml) and DCM (550 ml) were added to the mixture and the layers were separated. The organic phase was extracted with saturated aqueous solution of sodium hydrogen carbonate (250 ml) and brine (250 ml), dried (Na$_2$SO$_4$), filtered and concentrated. Toluene (350 ml) was added to the residue and the solution was concentrated to give the title compound. Yield 43.0 g $^1$H NMR (200 MHz, DMSO-$d_6$) ppm 7.32-7.44 (m, 4H) 4.75 (s, 2H) 4.67-4.73 (m, 1H) 4.56 (dd, 2H) 3.73-3.84 (m, 1H) 3.42-3.52 (m, 1H) 1.47-1.79 (m, 6H)

4,4,5,5-Tetramethyl-2-(4-(((tetrahydro-2H-pyran-2-yl)oxy)methyl)benzyl)-1,3,2-dioxaborolane Bis(triphenylphosphine)palladium(II) chloride (1.75 g), N-ethyl-N-isopropylpropan-2-amine (30.95 g) and 4,4,5,5-tetramethyl-1,3,2-dioxaborolane (17.5 ml) were added to a solution of 2-((4-(chloromethyl)benzyl)oxy)tetrahydro-2H-pyran (21.2 g) in 1,2-dichloroethane (320 ml) under nitrogen atmosphere. The mixture was heated under reflux for 10 h. Toluene (1000 ml) was added at room temperature. The reaction mixture was washed with brine (1150 ml), dried (Na$_2$SO$_4$), filtered and concentrated. The crude product was dissolved in n-heptane (800 ml). The precipitate formed was filtered off and washed with n-heptane. The combined n-heptane filtrates were concentrated and the residue was purified by silica column chromatography (n-heptane/EtOAc 9:1+0.5% triethylamine). Yield 13.72

$^1$H NMR (200 MHz, DMSO-$d_6$) ppm 7.06-7.21 (m, 4H) 4.64-4.68 (m, 1H) 4.48 (dd, 2H) 3.74-3.85 (m, 1H) 3.41-3.52 (m, 1H) 2.19 (s, 2H) 1.41-1.80 (m, 6H) 1.17 (s, 12H)

4-Hydroxy-5-methoxy-2-(4-(((tetrahydro-2H-pyran-2-yl)oxy)methyl)benzyl)isophthalonitrile A mixture of 4,4,5,5-tetramethyl-2-(4-(((tetrahydro-2H-pyran-2-yl)oxy)methyl)benzyl)-1,3,2-dioxaborolane (5.03 g), 2-bromo-4-hydroxy-5-methoxyisophthalonitrile (3.06 g), Pd(dppf)Cl$_2$ complex with CH$_2$Cl$_2$ (1:1) (1.11 g), sodium hydrogen carbonate (5.09 g), water (84 ml) and ethanol (1.5 ml) was bubbled with nitrogen gas at room temperature. The mixture was heated under reflux under nitrogen atmosphere for 1.5 h. DCM (130 ml) was added to the mixture at room temperature and the mixture was filtered through celite. Celite was washed with water (100 ml) and DCM (100 ml) and pH of the combined filtrates was adjusted to 7 with 0.5 M HCl solution. The layers were separated and separation was eased with addition of water (200 ml). The aqueous phase was extracted with DCM (2×100 ml, 2×50 ml) and the combined organic phases were dried (Na$_2$SO$_4$), filtered and concentrated.

The crude product was purified by silica column chromatography (DCM/methanol 100:0→90:10+0.5% triethylamine). Yield 3.68 g $^1$H NMR (200 MHz, DMSO-$d_6$) ppm 7.17-7.28 (m, 4H) 6.82 (s, 1H) 4.61-4.68 (m, 1H) 4.49 (dd, 2H) 3.96 (s, 2H) 3.73-3.84 (m, 1H) 3.65 (s, 3H) 3.61 (s, 1H) 3.39-3.50 (m, 1H) 1.45-1.77 (m, 6H)

4-(2,6-Dicyano-3-hydroxy-4-methoxybenzyl)benzoic acid

A mixture of 4-hydroxy-5-methoxy-2-(4-(((tetrahydro-2H-pyran-2-yl)oxy)methyl)benzyl)isophthalonitrile (4.70 g) in acetone (96 ml) was cooled in ice bath and Jones reagent (24.0 ml) was added in small portions. The mixture was stirred at room temperature for 2 h. Isopropanol (5 ml) was added to the mixture and the solution was filtered to remove chromium salts. The chromium salts were washed with acetone (150 ml) and acetone was combined with the filtrate. Water (200 ml) was added to the solution and the solution was concentrated until the product started to precipitate. The concentrate was filtered and the precipitate was washed with water (100 ml). The precipitate was dissolved in EtOAc (50 ml) and washed with 0.5 M HCl solution (2×40 ml) and brine (20 ml). Water (50 ml) was added to the organic phase and pH of the solution was adjusted to >10 with 15% NaOH solution. The phases were separated and the organic phase was washed with water (30 ml). The pH of the combined aqueous solutions was adjusted to 1-2 with 4 M HCl solution. The precipitate was filtered, washed with water (30 ml) and DCM (20 ml) and dried in vacuum at 50° C. Yield 1.47 g $^1$H NMR (200 MHz, DMSO-$d_6$) ppm 12.89 (br s, 1H) 12.02 (br s, 1H) 7.89 (d, 2H) 7.71 (s, 1H) 7.27 (d, 2H) 4.27 (s, 2H) 3.91 (s, 3H)

4-(2,6-Dicyano-3,4-dihydroxybenzyl)benzoic acid

1 M boron tribromide solution (5.6 ml) was added slowly to 4-(2,6-dicyano-3-hydroxy-4-methoxybenzyl)benzoic acid (1.45 g) in DCM (36 ml) under nitrogen atmosphere at 0° C. Stirring was continued at room temperature and more 1 M boron tribromide solution was added six times [after 1.5 h (5.6 ml), after 2.5 h (5.6 ml), after 4 h (5.6 ml), after 5.5 h (5.3 ml), after 22 h (5.3 ml) and after 25.5 h (5.3 ml)]. After total of 47 h stirring, the reaction mixture was poured into ice water (140 ml) and stirred for 1.5 h. The mixture was filtered and the precipitate was washed with water (100 ml)

and n-heptane (20 ml). The precipitate was dissolved in 1 M NaOH solution (60 ml) and the solution was extracted thrice with EtOAc (35 ml). The pH of the aqueous solution was adjusted to 1-2 with 4 M HCl solution and the solution was extracted twice with EtOAc (30 ml). The combined organic phases were washed with water (30 ml) and brine (30 ml), dried ($Na_2SO_4$), filtered and concentrated to give the title compound. Yield 1.55 g $^1$H NMR (200 MHz, DMSO-$d_6$) ppm 12.9 (br s, 1H) 11.4 (br s, 1H) 7.2-8.0 (m, 5H) 4.25 (s, 2H)

Example 119

(E)-4,5-Dihydroxy-2-(4-methoxystyryl)isophthalonitrile

Using the procedure described in Example 37, (E)-4-hydroxy-5-methoxy-2-(4-methoxystyryl)isophthalonitrile (117 mg), prepared from 2-bromo-4-hydroxy-5-methoxy-isophthalonitrile and trans-2-(4-methoxyphenyl)vinylboronic acid, was demethylated to give the title compound. Yield 56 mg $^1$H NMR (400 MHz, DMSO-$d_6$) ppm 11.29 (br s, 2H) 6.78-7.60 (m, 7H) 3.80 (s, 3H)

Example 120

3,4-Dihydroxy-3',4'-dimethylbiphenyl-2,6-dicarbonitrile

Using the procedure described in Example 37, 3-hydroxy-4-methoxy-3',4'-dimethylbiphenyl-2,6-dicarbonitrile (50 mg), prepared from 2-bromo-4-hydroxy-5-methoxy-isophthalonitrile and 3,4-dimethylbenzeneboronic acid, was demethylated to give the title compound. Yield 36 mg $^1$H NMR (400 MHz, DMSO-$d_6$) ppm 7.33 (s, 1H) 7.28 (d, J=7.53 Hz, 1H) 7.22 (s, 1H) 7.14-7.19 (m, 1H) 2.29 (d, J=5.27 Hz, 6H)

Example 121

(E)-4,5-Dihydroxy-2-(4-methylstyryl)isophthalonitrile

Using the procedure described in Example 37, (E)-4-hydroxy-5-methoxy-2-(4-methylstyryl)isophthalonitrile (95 mg), prepared from 2-bromo-4-hydroxy-5-methoxy-isophthalonitrile and trans-2-(4-methylphenyl)vinylboronic acid, was demethylated to give the title compound. Yield 71 mg $^1$H NMR (400 MHz, DMSO-$d_6$) ppm 7.50 (d, J=1.00 Hz, 2H) 7.32 (d, J=1.00 Hz, 2H) 7.25 (d, J=1.00 Hz, 2H) 7.18 (d, J=1.00 Hz, 1H) 2.34 (s, 3H)

Example 122

4,5-Dihydroxy-2-(6-hydroxynaphthalen-2-yl)isophthalonitrile

Using the procedure described in Example 37, 4-hydroxy-5-methoxy-2-(6-methoxynaphthalen-2-yl)isophthalonitrile (105 mg), prepared from 2-bromo-4-hydroxy-5-methoxy-isophthalonitrile and 6-methoxy-2-naphthaleneboronic acid, was demethylated to give the title compound. Yield 45 mg $^1$H NMR (400 MHz, DMSO-$d_6$) ppm 7.88 (s, 1H) 7.86 (d, J=8.78 Hz, 1H) 7.81 (d, J=8.53 Hz, 1H) 7.44 (m, J=8.50, 1.80 Hz, 1H) 7.36 (s, 1H) 7.19-7.22 (m, 1H) 7.17 (m, J=8.80, 2.30 Hz, 1H)

Example 123

4'-Fluoro-3,4-dihydroxy-3'-methylbiphenyl-2,6-dicarbonitrile

Using the procedure described in Example 37, 4'-fluoro-3-hydroxy-4-methoxy-3'-methylbiphenyl-2,6-dicarbonitrile (215 mg), prepared from 2-bromo-4-hydroxy-5-methoxy-isophthalonitrile and 4-fluoro-3-methylphenylboronic acid, was demethylated to give the title compound. Yield 140 mg $^1$H NMR (400 MHz, DMSO-$d_6$) ppm 7.40 (d, J=7.28 Hz, 1H) 7.25-7.36 (m, 3H) 2.28-2.31 (m, 3H)

Example 124

4,5-Dihydroxy-2-(3-methylbut-2-en-2-yl)isophthalonitrile

To a dry mixture of aluminum chloride (66 mg), sodium iodide (74 mg) and acetonitrile (1 ml) under nitrogen atmosphere was added 4-hydroxy-5-methoxy-2-(3-methylbut-2-en-2-yl)isophthalonitrile (12 mg), which was prepared as described in Example 54, except that 3-methylbut-2-en-2-ylboronic acid was used instead of 4,4,5,5-tetramethyl-2-(4-methylbenzyl)-1,3,2-dioxaborolane. The mixture was heated for 3 h at 60° C. and stirred overnight at room temperature. 2 M HCl (0.3 ml) and sodium sulfite (31 mg) was added to the mixture and the solution was heated for 30 min at 50° C. The product was extracted with EtOAc, the solvent was evaporated and the residue was dried. The product was recrystallized from toluene-isopropanol solution. Yield 6 mg $^1$H NMR (400 MHz, methanol-$d_4$) ppm 7.15 (s, 1H) 1.95 (s, 3H) 1.88 (s, 3H) 1.48-1.55 (m, 3H)

Example 125

2-(2,5-Dimethylthiophen-3-yl)-4,5-dihydroxy-isophthalonitrile 2-(2,5-Dimethylthiophen-2-yl)-4-hydroxy-5-methoxy-isophthalonitrile (65 mg), which was prepared as described in Example 54, except that potassium 2,5-dimethylthiophene-3-trifluoroborate was used instead of 4,4,5,5-tetramethyl-2-(4-methylbenzyl)-1,3,2-dioxaborolane, was converted to the title compound using the procedure analogous to Example 54. Yield 36 mg $^1$H NMR (400 MHz, methanol-$d_4$) ppm 7.26 (s, 1H) 6.62 (d, J=1.14 Hz, 1H) 2.44 (s, 3H) 2.28 (s, 3H)

Example 126

2-(2,3-Difluoro-4-methylbenzyl)-4,5-dihydroxy-isophthalonitrile

Using the procedure analogous to Example 54, 2-(2,3-difluoro-4-methylbenzyl)-4-hydroxy-5-methoxyisophthalonitrile (200 mg), prepared from 2-bromo-4-hydroxy-5-methoxyisophthalonitrile and 2-(2,3-difluoro-4-methylbenzyl)-4,4,5,5-tetramethyl-1,3,2-dioxaborolane, was demethylated to give the title compound. Yield 30 mg ¹H NMR (400 MHz, DMSO-d₆) ppm 7.29 (s, 1H) 7.02 (t, J=7.40 Hz, 1H) 6.65 (t, J=7.28 Hz, 1H) 4.16 (s, 2H) 2.24 (s, 3H)

Example 127

2-(4-(2,6-Dicyano-3,4-dihydroxybenzyl)phenyl) propanoic acid

Using the procedure analogous to Example 54, 2-(4-(2,6-dicyano-3-hydroxy-4-methoxybenzyl)phenyl) propanoic acid (600 mg), prepared from 2-bromo-4-hydroxy-5-methoxyisophthalonitrile and 2-(4-((4,4,5,5-tetramethyl-1,3,2-dioxaborolan-2-yl)methyl)phenyl)propanoic acid, was demethylated to give the title compound. Yield 27.5 mg ¹H NMR (400 MHz, DMSO-d₆) ppm 7.26-7.31 (m, 1H) 7.09-7.26 (m, 4H) 4.12 (s, 2H) 3.62 (quin, J=7.15 Hz, 1H) 1.34 (d, J=1.00 Hz, 3H)

Example 128

(E)-2-(3-Cyclopentylprop-1-enyl)-4,5-dihydroxy-isophthalonitrile

The title compound was prepared from 4-bromo-3,5-dicyano-1,2-phenylene diacetate (300 mg) by the procedure analogous to Example 74 using as reactant trans-3-cyclopentylpropen-1-ylboronic acid pinacol ester (285 mg) instead of 3,6-dihydro-2H-pyran-4-boronic acid pinacol ester. Reaction conditions: 10 min at 140° C. Yield 25 mg ¹H NMR (400 MHz, DMSO-d₆) ppm 7.24 (s, 1H) 6.47 (s, 2H) 2.21-2.32 (m, 2H) 1.95 (m, J=14.70, 7.30, 7.30 Hz, 1H) 1.70-1.86 (m, 2H) 1.56-1.66 (m, 2H) 1.42-1.54 (m, 2H) 1.13-1.27 (m, 2H)

Example 129

4,5-Dihydroxy-2-(1-isobutyl-1H-pyrazol-4-yl) isophthalonitrile

The title compound was prepared from 4-bromo-3,5-dicyano-1,2-phenylene diacetate (300 mg) by the procedure analogous to Example 74 using as reactant 1-isobutyl-4-(4,4,5,5-tetramethyl-1,3,2-dioxaborolan-2-yl)-1H-pyrazole (279 mg) instead of 3,6-dihydro-2H-pyran-4-boronic acid pinacol ester. Reaction conditions: 10 min at 140° C. Yield 70 mg ¹H NMR (400 MHz, DMSO-d₆) ppm 8.08 (s, 1H) 7.72 (s, 1H) 7.30 (s, 1H) 4.00 (d, J=7.28 Hz, 2H) 2.13 (m, J=13.60, 6.90, 6.90 Hz, 1H) 0.86 (d, J=6.53 Hz, 6H)

Example 130

2-(4-(2,6-Dicyano-3,4-dihydroxyphenyl)-1H-pyrazol-1-yl) acetic acid

The title compound was prepared from 4-bromo-3,5-dicyano-1,2-phenylene diacetate (310 mg) by the procedure analogous to Example 74 using as reactant (4-(4,4,5,5-tatramethyl-[1,3,2]dioxaborolan-2-yl)-pyrazol-1-yl)-acetic acid ethyl ester (121 mg) instead of 3,6-dihydro-2H-pyran-4-boronic acid pinacol ester. Reaction conditions: 20 min at 150° C. The reaction mixture was filtered through celite and poured into ice water and 2 M NaOH and toluene was added to the mixture. The water phase was washed with toluene and was made acidic with concentrated HCl. The product was filtered, washed with water and toluene and dried. Yield 57 mg ¹H NMR (400 MHz, DMSO-d₆) ppm 8.14 (s, 1H) 7.78 (s, 1H) 7.31 (s, 1H) 5.06 (s, 2H)

Example 131

4,5-Dihydroxy-2-(1-methyl-1H-pyrazol-4-yl) isophthalonitrile

The title compound was prepared from 4-bromo-3,5-dicyano-1,2-phenylene diacetate (100 mg) by the procedure analogous to Example 74 using as reactant 1-methyl-4-(4,4,5,5-tetramethyl-1,3,2-dioxaborolan-2-yl)-1H-pyrazole (90 mg) instead of 3,6-dihydro-2H-pyran-4-boronic acid pinacol ester. Reaction conditions: 20 min at 150° C. Yield 51 mg ¹H NMR (400 MHz, DMSO-d₆) ppm 8.08 (s, 1H) 7.71 (s, 1H) 7.30 (s, 1H) 3.92 (s, 3H)

Example 132

4,5-Dihydroxy-2-(3-methoxyprop-1-ynyl)isophthalonitrile

The title compound was prepared from 4-bromo-3,5-dicyano-1,2-phenylene diacetate (100 ing) by the procedure analogous to Example 74 using as reactant 3-methoxy-1-propyn-1-ylboronic acid pinacol ester (80 mg) instead of 3,6-dihydro-2H-pyran-4-boronic acid pinacol ester. Reaction conditions: 20 min at 150° C. Yield 36 mg ¹H NMR (400 MHz, DMSO-d₆) ppm 7.28 (s, 1H) 4.44 (s, 2H) 3.33 (br s, 3H)

Example 133

(E)-4,5-Dihydroxy-2-(2-(thiophen-3-yl)vinyl) isophthalonitrile

The title compound was prepared from 4-bromo-3,5-dicyano-1,2-phenylene diacetate (100 mg) by the procedure analogous to Example 74 using as reactant trans-2-(thiophen-3-yl)vinylboronic acid pinacol ester (95 mg) instead of 3,6-dihydro-2H-pyran-4-boronic acid pinacol ester. Reaction conditions: 20 min at 150° C. Yield 59 mg ¹H NMR (400 MHz, DMSO-d₆) ppm 7.74 (d, J=2.26 Hz, 1H) 7.62 (m, J=4.90, 2.90 Hz, 1H) 7.49 (d, J=5.02 Hz, 1H) 7.26-7.37 (m, 2H) 7.08 (d, J=16.56 Hz, 1H)

Example 134

(E)-2-(2-Cyclopropylvinyl)-4,5-dihydroxyisophthalonitrile

The title compound was prepared from 4-bromo-3,5-dicyano-1,2-phenylene diacetate (100 mg) by the procedure analogous to Example 74 using as reactant (E)-2-cyclopropylvinylboronic acid pinacol ester (72 mg) instead of 3,6-dihydro-2H-pyran-4-boronic acid pinacol ester. Reaction conditions: 20 min at 150° C. Yield 52 mg ¹H NMR (400 MHz, DMSO-d₆) ppm 7.21 (s, 1H) 6.57 (dd, J=15.81, 9.54 Hz, 1H) 5.97 (dd, J=15.81, 9.54 Hz, 1H) 1.58-1.79 (m, 1H) 0.77-0.96 (m, 2H) 0.47-0.68 (m, 2H)

Example 135

2',6'-Dicyano-3',4'-dihydroxybiphenyl-4-carboxamide

4-Aminocarbonylphenyl boronic acid (173 mg), bis(triphenylphosphine)palladium(II) chloride (73 mg) and sodium carbonate (333 mg) were added to 2-bromo-4,5-dihydroxyisophthalonitrile (250 mg) dissolved in acetonitrile (2 ml), ethanol (2 ml) and water (1 ml). The reaction mixture was stirred and microwave-irradiated for 60 min at 130° C. 2 N NaOH was added and the reaction mixture was washed with toluene. The aqueous phase was made acidic by adding HCl. The solid product was filtered, washed with water and dried. Yield 166 mg $^1$H NMR (DMSO-d$_6$) ppm 11.0-11.8 (br s, 2H) 8.13 (br s, 1H) 7.98 (d, J=8.28 Hz, 1H) 7.56 (d, J=8.36 Hz, 1H) 7.52 (br s, 1H) 7.36 (s, 1H)

Example 136

3,4-Dihydroxy-3',4'-dimethoxybiphenyl-2,6-dicarbonitrile 3,4-Diethoxyphenylboronic acid (152 mg), palladium(II) acetate (7.5 mg) and DBU (166 mg) were added to 2-bromo-4,5-dihydroxyisophthalonitrile (200 mg) dissolved in ethanol (1 ml) and water (1 ml). The reaction mixture was stirred and microwave-irradiated for 10 min at 150° C. The reaction mixture was filtered through celite and the organic solvent was evaporated. 0.1 M NaOH was added and the mixture was washed with toluene and EtOAc. The aqueous phase was made acidic by adding HCl. The solid product was filtered, washed with water and dried. Yield 100 mg $^1$H NMR (DMSO-d$_6$) ppm 10.8-11.7 (br s, 2H) 7.33 (s, 1H) 7.09 (d, J=8.36 Hz, 1H) 7.09 (d, J=2.04 Hz, 1H) 7.01 (dd, J=8.28, 2.04 Hz, 1H) 3.93 (s, 3H) 3.79 (s, 3H)

Example 137

3,4-Dihydroxy-3'-isopropylbiphenyl-2,6-dicarbonitrile

The title compound was prepared from 4-bromo-3,5-dicyano-1,2-phenylene diacetate (200 mg) and 3-isopropylphenylboronic acid (122 mg) instead of 3,4,5-trifluorophenylbororiic acid as described in Example 7. Reaction conditions: 20 min at 150° C. Yield 86 mg $^1$H NMR (400 MHz, DMSO-d$_6$) ppm 11.00-11.63 (m, 2H) 7.10-7.51 (m, 5H) 2.97 (dt, J=13.80, 6.90 Hz, 1H) 1.24 (d, J=7.03 Hz, 6H)

Example 138

2-(2,3-Dihydrobenzofuran-5-yl)-4,5-dihydroxyisophthalonitrile

The title compound was prepared from 4-bromo-3,5-dicyano-1,2-phenylene diacetate (200 mg) and 2,3-dihydrobenzofuran-5-boronic acid (132 mg) instead of 3,4,5-trifluorophenylboronic acid as described in Example 7. Reaction conditions: 45 min at 150° C. Yield 127 mg $^1$H NMR (400 MHz, DMSO-d$_6$) ppm 7.35 (s, 1H) 7.32 (s, 1H) 7.17 (dd, J=8.16, 1.63 Hz, 1H) 6.88 (d, J=8.28 Hz, 1H) 4.61-4.67 (m, 2H) 3.21-3.27 (m, 2H)

Example 139

4,5-Dihydroxy-2-(6-methoxynaphthalen-2-yl)isophthalonitrile

The title compound was prepared from 4-bromo-3,5-dicyano-1,2-phenylene diacetate (200 mg) and 6-methoxy-2-naphthaleneboronic acid (150 mg) instead of 3,4,5-trifluorophenylboronic acid as described in Example 7. Reaction conditions: 45 min at 150° C. Yield 64 mg:

$^1$H NMR (400 MHz, DMSO-d$_6$) ppm 1.99 (s, 3H) 6.96-8.22 (m, 7H)

Example 140

4,5-Dihydroxy-2-(4-(hydroxymethyl)benzyl)isophthalonitrile

4-Bromo-3,5-dicyano-1,2-phenylene dimethanesulfonate

Triethylamine (17.0 ml) was added to 2-bromo-4,5-dihydroxyisophthalonitrile (10.1 g) in 1:1 mixture of DCM and THF (100 ml) at 0° C. under nitrogen atmosphere. Methanesulfonyl chloride (12.92 g) was added slowly to the mixture followed by addition of DMAP (0.52 g). Stirring was continued at room temperature for 21 h and the mixture was concentrated. EtOAc was added (300 ml) and the insoluble material was filtered off and washed with EtOAc (50 ml). The combined organic phases were washed with 1 M HCl solution (2×150 ml), water (150 ml) and brine (150 ml), dried (Na$_2$SO$_4$), filtered and concentrated. Yield 15.2 g. The crude product was purified by flash chromatography (EtOAc/n-heptane). The combined fractions were concentrated to smaller volume and the precipitate was filtered. The precipitate was recrystallized from EtOAc and n-heptane (added to hot solution) and dried in vacuum at 50° C.

$^1$H NMR (200 MHz, DMSO-d$_6$) ppm 7.88 (s, 1H) 3.46 (s, 3H) 2.38 (s, 3H)

3,5-Dicyano-4-(4-(((tetrahydro-2H-pyran-2-yl)oxy)methyl)benzyl)-1,2-phenylene dimethanesulfonate The preparation of 4,4,5,5-tetramethyl-2-(4-(((tetrahydro-2H-pyran-2-yl)oxy)methyl)benzyl)-1,3,2-dioxaborolane is described in Example 118. A mixture of 4,4,5,5-tetramethyl-2-(4-(((tetrahydro-2H-pyran-2-yl)oxy)methyl)benzyl)-1,3,2-dioxaborolane (8.00 g), 4-bromo-3,5-dicyano-1,2-phenylene dimethanesulfonate (7.61 g), Pd(dppf)Cl$_2$ complex with CH$_2$Cl$_2$ (1:1) (1.77 g), sodium hydrogen carbonate (8.09 g), water (128 ml) and ethanol (16 ml) was bubbled with nitrogen gas at room temperature. The mixture was heated under reflux under nitrogen atmosphere for 2 h. DCM (240 ml) was added to the mixture at room temperature and the mixture was filtered through celite. Celite was washed with water (120 ml) and DCM (120 ml) and the layers of the combined filtrates were separated. The organic phase was washed with water (150 ml) and EtOAc (150 inl) was added to the aqueous phase before adjusting pH to 7 with 15% HCl solution. The layers were separated and the aqueous phase was extracted thrice with EtOAc (150 ml). The combined organic phases were dried (Na$_2$SO$_4$), filtered and concentrated. The crude product was recrystallized from ethanol (75 ml, all did not dissolve). The precipitate was dried in vacuum at 25° C. overnight. Yield 2.74 g ¹H NMR (200 MHz, DMSO-d₆) ppm 7.10-7.40 (m, 5H) 4.50-4.70 (m, 2H) 4.30-4.45 (d, 1H) 3.98 (s, 2H) 3.70-3.85 (m, 1H) 3.20-3.55 (m, 5H) 1.30-1.85 (m, 6H)

4,5-Dihydroxy-2-(4-(hydroxymethyl)benzyl) isophthalonitrile

The pH of a solution of 3,5-dicyano-4-(4-(((tetrahydro-2H-pyran-2-yl)oxy)methyl)benzyl)-1,2-phenylene dimethanesulfonate (4.60 g) in methanol (100 ml) was adjusted to about 2 by addition of 25% HCl solution in isopropanol (2.25 ml). More methanol (50 ml) was added, but 3,5-dicyano-4-(4-(((tetrahydro-2H-pyran-2-yl)oxy)methyl)benzyl)-1,2-phenylene dimethanesulfonate was not completely dissolved. The mixture was stirred at room temperature for 5 h. The pH was adjusted to about 12 by addition of 5 M aqueous solution of NaOH. The mixture was heated under reflux for 35 min and then pH was adjusted back to acidic (about pH 1) by addition of HCl (55 ml). The mixture was stirred in ice bath and then the precipitate was filtered and washed twice with water (10 ml). The precipitate was dried in vacuum at 25° C. overnight and at 40° C. over another night. Yield 2.19 g ¹H NMR (200 MHz, DMSO-d₆) ppm 11.2 (br s, 1H) 6.9-7.3 (m, 5H) 4.4 (s, 2H) 4.1 (s, 2H)

Example 141

2-(2,6-Difluoro-3-methylbenzyl)-4,5-dihydroxy-isophthalonitrile

Using the procedure analogous to Example 54, 2-(2,6-difluoro-3-methylbenzyl)-4-hydroxy-5-methoxyisophthalonitrile (600 mg), prepared from 2-bromo-4-hydroxy-5-methoxyisophthalonitrile and 2-(2,6-difluoro-3-methylbenzyl)-4,4,5,5-tetramethyl-1,3,2-dioxaborolane, was demethylated to give the title compound. Yield 20 mg ¹H NMR (400 MHz, DMSO-d₆) ppm 7.41 (s, 1H) 7.12-6.85 (m, 2H) 4.32 (s, 2H) 2.17 (s, 3H)

Example 142

4,5-Dihydroxy-2-(4-(trifluoromethyl)phenylthio) isophthalonitrile 4,5-Diisopropoxy-2-(4-(trifluoromethyl)phenylthio) isophthalonitrile 4-(Trifluoromethyl)thiophenol (0.28 g) was added to a mixture of 2-bromo-4,5-diisopropoxyisophthalonitrile (0.51 g) and cesium carbonate (2 equiv.) in DMF followed by stirring at room temperature overnight. The reaction mixture was poured into cold water and pH was adjusted to 12. The precipitate was filtered, washed with water and dried in vacuum. Yield 0.67 g ¹H NMR (400 MHz, DMSO-d₆) ppm 8.09 (s, 1H) 7.70 (d, 2H) 7.35 (d, 2H) 4.86-4.95 (m, 1H) 4.77-4.89 (m, 1H) 1.36 (d, 6H) 1.31 (d, 6H)

4,5-Dihydroxy-2-(4-(trifluoromethyl)phenylthio) isophthalonitrile

To a mixture of 4,5-diisopropoxy-2-(4-(trifluoromethyl) phenylthio)isophthalonitrile (0.3 g) in DCM under nitrogen atmosphere was added 1 M boron tribromide solution in DCM (2-5 equiv.) at 0° C. The reaction mixture was left to warm slowly to room temperature with stirring for 2 h. The reaction mixture was poured into methanol. After evaporation of the solvent, 2 M NaOH solution was added and the mixture was stirred for 30 min, washed with EtOAc, cooled and acidified with HCl to give solid product which was filtered, washed with water and dried in vacuum. Yield 0.16 g ¹H NMR (400 MHz, DMSO-d₆) ppm 7.68 (d, 2H) 7.42 (s, 1H) 7.30 (d, 2H)

Example 143

2-(2,4-Dimethylphenylthio)-4,5-dihydroxyisophthalonitrile 2-(2,4-Dimethylphenylthio)-4,5-diisopropoxy-isophthalonitrile 2-(2,4-Dimethylphenylthio)-4,5-diisopropoxyisophthalonitrile was prepared from 2-bromo-4,5-diisopropoxy-isophthalonitrile (0.25 g) and 2,4-dimethylthiophenol (0.12 ml) instead of 4-(trifluoromethyl)thiophenol as described in Example 142. Yield 0.28 g ¹H NMR (400 MHz, DMSO-d₆) ppm 7.33 (d, 1H) 6.92-7.13 (m, 2H) 6.76 (d, 1H) 4.83-4.91 (m, 1H) 4.76-4.86 (m, 1H) 2.35 (s, 3H) 2.24 (s, 3H) 1.36 (d, 6H) 1.30 (d, 6H)

2-(2,4-Dimethylphenylthio)-4,5-dihydroxyisophthalonitrile

The title compound was prepared from 2-(2,4-dimethylphenylthio)-4,5-diisopropoxyisophthalonitrile instead of 4,5-diisopropoxy-2-(4-(trifluoromethyl)phenylthio) isophthalonitrile as described in Example 142. 2-(2,4-Dimethylphenylthio)-4,5-dihydroxyisophthalonitrile was purified by chromatography. Yield 80 mg ¹H NMR (400 MHz, DMSO-d₆) ppm 7.34 (s, 1H) 7.09 (s, 1H) 6.94 (dd, 1H) 6.70 (d, 1H) 2.34 (s, 3H) 2.23 (s, 3H)

Example 144

Methyl 3-(4-(2,6-dicyano-3,4-dihydroxyphenylthio) phenyl)propanoate 3-(4-(2,6-Dicyano-3,4-diisopropoxyphenylthio)phenyl)propanoic acid 3-(4-(2,6-Dicyano-3,4-diisopropoxyphenylthio)phenyl) propanoic acid was prepared from 2-bromo-4,5-diisopropoxyisophthalonitrile (0.75 g) and 3-(4-mercaptophenyl) propanoic acid (0.43 g) instead of 4-(trifluoromethyl) thiophenol as described in Example 142. Yield 0.99 g ¹H NMR (400 MHz, DMSO-d₆) ppm 12.12 (br s, 1H) 7.99 (s, 1H) 7.19-7.27 (m, 2H) 7.10-7.18 (m, 2H) 4.82-4.86 (m, 1H) 4.74-4.83 (m, 1H) 2.79 (t, 2H) 2.51-2.56 (m, 2H) 1.32 (d, 6H) 1.29 (d, 6H)

Methyl 3-(4-(2,6-dicyano-3,4-diisopropoxyphenyl-thio)phenyl)propanoate

To a mixture of 3-(4-(2,6-dicyano-3,4-diisopropoxyphenylthio)phenyl)propanoic acid (1.0 g) in methanol (14 ml) was added thionyl chloride (0.2 ml) over 30 min at 0° C. followed by refluxing for 30 min. The product was extracted to EtOAc and washed with saturated aqueous sodium hydrogen carbonate solution and brine. The organic phase was dried (Na₂SO₄), filtered and evaporated. Yield 0.85 g ¹H NMR (400 MHz, DMSO-d₆) ppm 7.99 (s, 1H) 7.15-7.25 (m, 2H) 7.12-7.18 (m, 2H) 4.82-4.90 (m, 1H) 4.75-4.84 (m, 1H) 3.57 (s, 3H) 2.82 (t, 2H) 2.61 (t, 2H) 1.32 (d, 6H) 1.29 (d, 6H)

Methyl 3-(4-(2,6-dicyano-3,4-dihydroxyphenylthio)phenyl)propanoate

The title compound was prepared from methyl 3-(4-(2,6-dicyano-3,4-diisopropoxyphenylthio)phenyl)propanoate (0.8 g) instead of 4,5-diisopropoxy-2-(4-(trifluoromethyl)phenylthio)isophthalonitrile as described in Example 142. Methyl 3-(4-(2,6-dicyano-3,4-dihydroxyphenylthio)phenyl)propanoate was purified by chromatography. Yield 0.33 g
¹H NMR (400 MHz, DMSO-d₆) ppm 7.36 (s, 1H) 7.21 (m, 2H) 7.12 (m, 2H) 3.57 (s, 3H) 2.81 (t, 2H) 2.61 (t, 2H)

Example 145

4,5-Dihydroxy-2-(p-tolyloxy)isophthalonitrile 4,5-Diisopropoxy-2=(p-tolyloxy)isophthalonitrile 4,5-Diisopropoxy-2-(p-tolyloxy)isophthalonitrile was prepared from 2-bromo-4,5-diisopropoxyisophthalonitrile (0.5 g) and p-cresol (0.18 g) instead of 4-(trifluoromethyl)thiophenol as described in Example 142. After addition of water, 4,5-diisopropoxy-2-(p-tolyloxy)isophthalonitrile was collected by filtration, washed with water, and dried in vacuum. Yield 0.54 g
¹H NMR (400 MHz, DMSO-d₆) ppm 7.97 (s, 1H) 7.13-7.23 (m, 2H) 6.81-6.91 (m, 2H) 4.88 (m, 1H) 4.79 (m, 1H) 2.28 (s, 3H) 1.32 (d, 6H) 1.30 (d, 6H)

4,5-Dihydroxy-2-(p-tolyloxy)isophthalonitrile

The title compound was prepared from 4,5-diisopropoxy-2-(p-tolyloxy)isophthalonitrile (0.3 g) instead of 4,5-diisopropoxy-2-(4-(trifluoromethyl)phenylthio)isophthalonitrile as described in Example 142. The product was further purified by extraction with EtOAc and water. Yield 0.16 g
¹H NMR (400 MHz, DMSO-d₆) ppm 10.5-11.5 (br s, 2H) 7.29 (s, 1H) 7.15 (d, 2H) 6.82 (d, 2H) 2.27 (s, 3H)

Example 146

(E)-2-(2,4-Difluorostyryl)-4,5-dihydroxyisophthalonitrile

The title compound was prepared from 4-bromo-3,5-dicyano-1,2-phenylene diacetate (200 mg) by the procedure analogous to Example 74 using as a reactant trans-2-(2,4-difluorophenyl)vinylboronic acid pinacol ester (231 mg) instead of 3,6-dihydro-2H-pyran-4-boronic acid pinacol ester. Reaction conditions: 30 min at 130° C. Yield 52 mg
¹H NMR (400 MHz, DMSO-d₆) ppm 7.81-7.90 (m, 1H) 7.27-7.46 (m, 4H) 7.20 (t, J=8.03 Hz, 1H)

Example 147

(E)-4,5-Dihydroxy-2-(3-(trifluoromethyl)styryl)isophthalonitrile

The title compound was prepared from 4-bromo-3,5-dicyano-1,2-phenylene diacetate (200 mg) by the procedure analogous to Example 74 using as reactant trans-2-(3-trifluoromethylphenyl)vinylboronic acid pinacol ester (240 mg) instead of 3,6-dihydro-2H-pyran-4-boronic acid pinacol ester. Reaction conditions: 30 min at 130° C. Yield 46 mg
¹H NMR (400 MHz, DMSO-d₆) ppm 7.93-8.01 (m, 2H) 7.65-7.77 (m, 2H) 7.42 (s, 2H) 7.37 (s, 1H)

Example 148

(E)-4,5-Dihydroxy-2-(4-methylpent-1-enyl)isophthalonitrile

The title compound was prepared from 4-bromo-3,5-dicyano-1,2-phenylene diacetate (300 mg) and trans-4-methyl-1-pentenylboronic acid (154 mg) instead of 3,4,5-trifluorophenylboronic acid as described in Example 7. Reaction conditions: 10 min at 140° C. Yield 40 mg
¹H NMR (400 MHz, DMSO-d₆) ppm 11.19 (br s, 2H) 7.25 (s, 1H) 6.44-6.49 (m, 2H) 2.14-2.19 (m, 2H) 1.75 (dt, J=13.30, 6.65 Hz, 1H) 0.95 (d, J=6.78 Hz, 6H)

Example 149

(E)-2-(3,5-Difluorostyryl)-4,5-dihydroxyisophthalonitrile

The title compound was prepared from 4-bromo-3,5-dicyano-1,2-phenylene diacetate (200 mg) by the procedure analogous to Example 74 using as a reactant trans-2-(3,5-difluorophenyl)vinylboronic acid pinacol ester (214 mg) instead of 3,6-dihydro-2H-pyran-4-boronic acid pinacol ester. Reaction conditions: 30 min at 130° C. Yield 91 mg
¹H NMR (400 MHz, DMSO-d₆) ppm 7.62 (s, 1H) 7.17-7.32 (m, 4H) 6.51 (m, 1H)

Example 150

2-(4-(2,6-Dicyano-3,4-dihydroxybenzyl)phenyl)acetic acid

Using the procedure analogous to Example 54, 2-(4-(2,6-dicyano-3-hydroxy-4-methoxybenzyl)phenyl)acetic acid (700 mg), prepared from 2-bromo-4-hydroxy-5-methoxy-isophthalonitrile and 2-(4-((4,4,5,5-tetramethyl-1,3,2-dioxaborolan-2-yl)methyl)phenyl)acetic acid, was demethylated to give the title compound. Yield 490 mg
¹H NMR (400 MHz, DMSO-d₆) ppm 7.28 (s, 1H) 7.19 (d, J=8.03 Hz, 2H) 7.10 (d, J=8.03 Hz, 2H) 4.11 (s, 2H) 3.51 (s, 2H)

Example 151

2-(4-Chlorobenzyl)-4,5-dihydroxyisophthalonitrile

Using the procedure analogous to Example 54, 2-(4-chlorobenzyl)-4-hydroxy-5-methoxyisophthalonitrile (580 mg), prepared from 2-bromo-4-hydroxy-5-methoxy-isophthalonitrile and 2-(4-chlorobenzyl)-4,4,5,5-tetramethyl-1,3,2-dioxaborolane, was demethylated to give the title compound. Yield 280 mg
¹H NMR (400 MHz, DMSO-d₆) ppm 7.36-7.43 (m, 2H) 7.29 (s, 1H) 7.18 (d, J=8.53 Hz, 2H) 4.15 (s, 2H)

Example 152

3,4-Dihydroxy-4'-methylbiphenyl-2,6-dicarbonitrile

The title compound was prepared from 4-bromo-3,5-dicyano-1,2-phenylene diacetate (1.63 g) and 4,4,5,5-tetramethyl-2-p-tolyl-1,3,2-dioxaborolane (1.10 g) instead of 3,4,5-trifluorophenylboronic acid as described in Example 7. Reaction conditions: 120 min at 130° C. Yield 0.21 g $^1$H NMR (400 MHz, DMSO-d$_6$) ppm 7.13-7.32 (m, 4H) 6.64 (s, 1H) 2.36 (s, 3H)

Example 153

3-(4-(2,6-Dicyano-3,4-dihydroxybenzyl)phenyl) propanoic acid

Using the procedure analogous to Example 54, 3-(4-(2, 6-dicyano-3-hydroxy-4-methoxybenzyl)phenyl)propanoic acid (100 mg), prepared from 3-(4-((4,4,5,5-tetramethyl-1, 3,2-dioxaborolan-2-yl)methyl)phenyl)propanoic acid and 2-bromo-4-hydroxy-5-methoxyisophthalonitrile, was demethylated to give the title compound. Yield 12 mg $^1$H NMR (400 MHz, methanol-d$_4$) ppm 7.10-7.24 (m, 5H) 4.20 (s, 2H) 2.82-2.94 (m, 2H) 2.51-2.65 (m, 2H)

Example 154

4,5-Dihydroxy-2-(4-(trifluoromethyl)benzyl) isophthalonitrile

Using the procedure analogous to Example 54, 4-hydroxy-5-methoxy-2-(4-(trifluoromethyl)benzyl)isophthalonitrile (200 mg), prepared from 2-bromo-4-hydroxy-5-methoxyisophthalonitrile and 4,4,5,5-tetramethyl-2-(4-(trifluoromethyl)benzyl)-1,3,2-dioxaborolane, was demethylated to give the title compound. Yield 96 mg $^1$H NMR (400 MHz, methanol-d$_4$) ppm 7.59 (d, J=8.07 Hz, 2H) 7.45 (d, J=8.07 Hz, 2H) 6.96 (br s, 1H) 4.24 (s, 2H)

Example 155

(E)-4,5-Dihydroxy-2-(4-(trifluoromethyl)styryl) isophthalonitrile

Using the procedure described in Example 37, (E)-4-hydroxy-5-methoxy-2-(4-(trifluoromethyl)styryl)isophthalonitrile (43 mg), prepared from 2-bromo-4-hydroxy-5-methoxyisophthalonitrile and trans-2-(4-(trifluoromethyl) phenyl)vinylboronic acid, was demethylated to give the title compound. Yield 10 mg $^1$H NMR (400 MHz, DMSO-d$_6$) ppm 7.50 (d, J=1.00 Hz, 1H) 7.29-7.35 (m, 2H) 7.25 (d, J=1.00 Hz, 2H) 7.18 (d, J=1.00 Hz, 2H)

Example 156

4,5-Dihydroxy-2-(p-tolylsulfinyl)isophthalonitrile

The preparation of 4,5-dihydroxy-2-(p-tolylthio) isophthalonitrile is described in Example 53. To a mixture of 4,5-dihydroxy-2-(p-tolylthio)isophthalonitrile (0.15 g) in DCM was added mCPBA (0.08 g) at 0° C. After 2 h, the solvent was evaporated. Chromatographic purification gave the title compound. Yield 0.1 g $^1$H NMR (400 MHz, DMSO-d$_6$) ppm 7.52 (m, 2H) 7.37 (m, 2H) 6.78 (s, 1H) 2.35 (s, 3H)

Example 157

4-(2,6-Dicyano-3,4-dihydroxyphenylthio)benzoic acid 4-(2,6-Dicyano-3-hydroxy-4-methoxyphenylthio) benzoic acid To a mixture of 3-bromo-2,4-dicyano-6-methoxyphenyl acetate (1.0 g), zinc (1.2 equiv.) and p-mercaptobenzoic acid (0.62 g) in DMF (20 ml) was added Pd(dppf)Cl$_2$ complex with CH$_2$Cl$_2$ (1:1) (0.9 equiv.). The stirred reaction was microwave-irradiated at 160° C. for 30 min after which water was added and solvents were evaporated. 5M NaOH solution was added to the residue and the mixture was stirred for 30 min, extracted with EtOAc, filtered over pall filter, cooled and acidified with HCl to give solid which was filtered and washed with water and diethyl ether. Yield 818 mg $^1$H NMR (400 MHz, DMSO-d$_6$) ppm 7.85 (m, 2H) 7.13 (m, 2H) 6.92 (s, 1H) 3.71 (s, 3H)

4-(2,6-Dicyano-3,4-dihydroxyphenylthio)benzoic acid

To a mixture of 4-(2,6-dicyano-3-hydroxy-4-methoxyphenylthio)benzoic acid (0.7 g) in DCM under nitrogen atmosphere was added 1 M boron tribromide solution in DCM (3-5 equiv.) at 0° C. The reaction mixture was left to warm slowly to room temperature with stirring for 2 h. The reaction mixture was poured into methanol. After evaporation of the solvent, 5 M NaOH solution was added and the mixture was stirred for 30 min, washed with EtOAc, cooled and acidified with HCl to give solid product which was filtered, washed with water and dried in vacuum. 4-(2,6-Dicyano-3,4-dihydroxyphenylthio)benzoic acid was purified by chromatography. Yield 0.2 g $^1$H NMR (400 MHz, DMSO-d$_6$) ppm 7.87 (m, 2H) 7.42 (s, 1H) 7.19 (m, 2H)

Example 158

2-(4-Ethylphenylthio)-4,5-dihydroxyisophthalonitrile 2-(4-Ethylphenylthio)-4-hydroxy-5-methoxyisophthalonitrile 2-(4-Ethylphenylthio)-4-hydroxy-5-methoxyisophthalonitrile was prepared from 3-bromo-2,4-dicyano-6-methoxyphenyl acetate (1.0 g) and 4-ethylthiophenol (0.5 ml) instead of p-mercaptobenzoic acid as described in Example 157. Yield 1.01 g $^1$H NMR (400 MHz, DMSO-d$_6$) ppm 7.26-6.90 (m, 5H) 3.71 (s, 3H) 2.56 (q, 2H) 1.15 (t, 3H)

2-(4-Ethylphenylthio)-4,5-dihydroxyisophthalonitrile

The title compound was prepared from 2-(4-ethylphenylthio)-4-hydroxy-5-methoxyisophthalonitrile (0.7 g) instead of 4-(2,6-dicyano-3-hydroxy-4-methoxyphenylthio)benzoic acid as described in Example 157. Yield 0.213 g $^1$H NMR (400 MHz, DMSO-d$_6$) ppm 7.35 (s, 1H) 7.20 (m, 2H) 7.14 (m, 2H) 2.57 (q, 2H) 1.15 (t, 3H)

Example 159

2-(4-Chlorophenylthio)-4,5-dihydroxyisophthalonitrile 2-(4-Chlorophenylthio)-4-hydroxy-5-methoxyisophthalonitrile 2-(4-Chlorophenylthio)-4-hydroxy-5-methoxyisophthalonitrile was prepared from 3-bromo-2,4-dicyano-6-methoxyphenyl acetate (1.0 g) and bis(p-chlorophenyl)-disulfide (0.58 g) instead of p-mercaptobenzoic acid as described in Example 157. Yield 0.99 g $^1$H NMR (400 MHz, DMSO-$d_6$) ppm 7.41 (m, 2H) 7.23 (s, 1H) 7.15 (m, 2H) 3.68 (s, 3H)

2-(4-Chlorophenylthio)-4,5-dihydroxyisophthalonitrile

The title compound was prepared from 2-(4-chlorophenylthio)-4-hydroxy-5-methoxyisophthalonitrile (0.7 g) instead of 4-(2,6-dicyano-3-hydroxy-4-methoxyphenylthio)benzoic acid as described in Example 157. Yield 0.494 g $^1$H NMR (400 MHz, DMSO-$d_6$) ppm 7.34 (m, 2H) 7.02 (m, 2H) 6.40 (s, 1H)

Example 160

4,5-Dihydroxy-2-(o-tolylthio)isophthalonitrile

The title compound was prepared from 3-bromo-2,4-dicyano-6-methoxyphenyl acetate (1.0 g) and 2-methylthiophenol (0.42 g) instead of p-mercaptobenzoic acid as described in Example 157 followed by demethylation as described in Example 157. 4,5-Dihydroxy-2-(o-tolylthio)isophthalonitrile was purified by chromatography. Yield 0.31 g $^1$H NMR (400 MHz, DMSO-$d_6$) ppm 7.39 (s, 1H) 7.27 (m, 1H) 7.14 (m, 2H) 6.72 (m, 1H) 2.39 (s, 3H)

Example 161

Methyl 4-(2,6-dicyano-3,4-dihydroxyphenylthio)benzoate

The preparation of 4-(2,6-dicyano-3,4-dihydroxyphenylthio)benzoic acid is described in Example 157. To 4-(2,6-dicyano-3,4-dihydroxyphenylthio)benzoic acid (1.0 g) in methanol (16 ml) was added thionyl chloride (0.28 ml) over 30 min at 0° C. followed by refluxing for 30 min. The product was extracted into EtOAc and washed with brine and water. The organic phase was dried ($Na_2SO_4$), filtered and evaporated. Yield 0.73 g $^1$H NMR (400 MHz, DMSO-$d_6$) ppm 7.88 (m, 2H) 7.41 (s, 1H) 7.21 (m, 2H) 3.83 (s, 3H)

Example 162

2-(2-Chlorophenylthio)-4,5-dihydroxyisophthalonitrile

To a mixture of 2-bromo-4,5-dihydroxyisophthalonitrile (0.4 g), zinc (1.2 equiv.) and 2-chlorothiophenol (0.19 ml) in DMF (20 ml) was added Pd(dppf)Cl$_2$ complex with CH$_2$Cl$_2$ (1:1) (0.9 equiv.). The stirred reaction was microwave-irradiated at 160° C. for 30 min after which solvent was evaporated. Water was added and solid was filtered and dissolved in 5 M NaOH solution. Insoluble material was filtered and the filtrate was acidified with 37% HCl to give solid product which was filtered, washed with water and dried in vacuum. 2-(2-chlorophenylthio)-4,5-dihydroxyisophthalonitrile was purified by chromatography. Yield 0.22 g $^1$H NMR (400 MHz, DMSO-$d_6$) ppm 7.74 (m, 1H) 7.41 (s, 1H) 7.26 (m, 2H) 6.70 (m, 1H)

Example 163

Methyl 2-(2,6-dicyano-3,4-dihydroxyphenylthio)benzoate

The title compound was prepared from 2-bromo-4,5-dihydroxyisophthalonitrile (0.9 g) and methyl thiosalicylate (0.63 g) instead of 2-chlorothiophenol as described in Example 162. Methyl 2-(2,6-dicyano-3,4-dihydroxyphenylthio)benzoate was purified by chromatography. Yield 0.43 g $^1$H NMR (400 MHz, DMSO-d) ppm 7.96-8.07 (m, 1H) 7.45-7.51 (m, 1H) 7.43 (s, 1H) 7.28-7.37 (m, 1H) 6.57-6.68 (m, 1H) 3.92 (s, 3H)

Example 164

2-(4-(2,6-Dicyano-3,4-dihydroxyphenylthio)phenyl)acetic acid

The title compound was prepared from 2-bromo-4,5-dihydroxyisophthalonitrile (0.9 g) and 4-mercaptophenylacetic acid (0.63 g) instead of 2-chlorothiophenol as described in Example 162. 2-(4-(2,6-Dicyano-3,4-dihydroxyphenylthio)phenyl)acetic acid was purified by chromatography. Yield 0.36 g $^1$H NMR (400 MHz, DMSO-$d_6$) ppm 7.37 (s, 1H) 7.24 (m, 2H) 7.14 (m, 2H) 3.55 (s, 2H)

Example 165

2-(2,6-Dicyano-3,4-dihydroxyphenylthio)benzoic acid

The preparation of methyl 2-(2,6-dicyano-3,4-dihydroxyphenylthio)benzoate is described in Example 163. A mixture of methyl 2-(2,6-dicyano-3,4-dihydroxyphenylthio)benzoate (0.3 g) and 2.5 M NaOH was stirred for 30 min after which solid material was filtered. The filtrate was collected and made acidic with 37% HCl to give solid product which was filtered, washed with water and dried in vacuum. Yield 0.103 g $^1$H NMR (400 MHz, DMSO-$d_6$) ppm 8.00 (m, 1H) 7.45 (s, 1H) 7.38-7.48 (m, 1H) 7.28 (m, 1H) 6.57 (d, 1H)

Example 166

3-(4-(2,6-Dicyano-3,4-dihydroxyphenylthio)phenyl)propanoic acid

The title compound was prepared from 2-bromo-4,5-dihydroxyisophthalonitrile (0.6 g) and 3-(4-mercaptophenyl)propanoic acid (0.46 g) instead of 2-chlorothiophenol as described in Example 162. 3-(4-(2,6-Dicyano-3,4-dihydroxyphenylthio)phenyl)propanoic acid was purified by chromatography. Yield 0.12 g $^1$H NMR (400 MHz, DMSO-$d_6$) ppm 7.36 (s, 1H) 7.22 (m, 2H) 7.13 (m, 2H) 2.78 (t, 2H) 2.45-2.55 (m, 2H)

Example 167

4,5-Dihydroxy-2-(4-methoxyphenylthio)isophthalonitrile

The title compound was prepared from 2-bromo-4,5-dihydroxyisophthalonitrile (0.9 g) and 4-methoxybenzenethiol (0.53 g) instead of 2-chlorothiophenol as described in Example 162. 4,5-Dihydroxy-2-(4-methoxyphenylthio)isophthalonitrile was purified by chromatography. Yield 0.42 g
$^1$H NMR (400 MHz, DMSO-$d_6$) ppm 7.32 (s, 1H) 7.30 (m, 2H) 6.94 (m, 2H) 3.74 (s, 3H)

Example 168

Methyl 2-(4-(2,6-dicyano-3,4-dihydroxybenzyl)phenyl)acetate

The preparation of 2-(4-(2,6-dicyano-3,4-dihydroxybenzyl)phenyl)acetic acid is described in Example 150. 2-(4-(2,6-Dicyano-3,4-dihydroxybenzyl)phenyl)acetic acid (100 mg) was esterified using thionyl chloride and methanol to give the title compound. Yield 38 mg
$^1$H NMR (400 MHz, methanol-$d_4$) ppm 7.18-7.25 (m, 5H) 4.23 (s, 2H) 3.68 (s, 2H) 3.63 (s, 3H)

Example 169

4,5-Dihydroxy-2-(3-methoxyphenylthio)isophthalonitrile

The title compound was prepared from 2-bromo-4,5-dihydroxyisophthalonitrile (1.0 g) and 3-methoxybenzenethiol (0.64 g) instead of 2-chlorothiophenol as described in Example 162. 4,5-Dihydroxy-2-(3-methoxyphenylthio)isophthalonitrile was purified by chromatography. Yield 0.34 g
$^1$H NMR (400 MHz, DMSO-$d_6$) ppm 7.38 (s, 1H) 7.27 (m, 1H) 6.84 (m, 1H) 6.74 (m, 1H) 6.67 (m, 1H) 3.73 (s, 3H)

Example 170

Methyl 4-(2,6-dicyano-3,4-dihydroxyphenoxy)benzoate

Methyl 4-(2,6-dicyano-3,4-diisopropoxyphenoxy)benzoate

Methyl 4-(2,6-dicyano-3,4-diisopropoxyphenoxy)benzoate was prepared from 2-bromo-4,5-diisopropoxyisophthalonitrile (0.1 g) and methyl 4-hydroxybenzoate (0.047 g) instead of 4-(trifluoromethyl)thiophenol as described in Example 142, except that the reaction mixture was stirred at 80° C. instead of room temperature. After addition of water, methyl 4-(2,6-dicyano-3,4-diisopropoxyphenoxy)benzoate was collected by filtration, washed with water, and dried in vacuum. Yield 0.1 g
$^1$H NMR (400 MHz, DMSO-$d_6$) ppm 8.03 (s, 1H) 7.99 (m, 2H) 7.16 (m, 2H) 4.86-4.97 (m, 1H) 4.76-4.87 (m, 1H) 3.85 (s, 3H) 1.34 (d, 6H) 1.32 (d, 6H)

Methyl 4-(2,6-dicyano-3,4-dihydroxyphenoxy)benzoate

The title compound was prepared from methyl 4-(2,6-dicyano-3,4 diisopropoxyphenoxy)benzoate (0.1 g) instead of 4,5-diisopropoxy-2-(4-(trifluoromethyl)phenylthio)isophthalonitrile as described in Example 142. Yield 0.024 g
$^1$H NMR (400 MHz, DMSO-$d_6$) ppm 7.98 (m, 2H) 7.31 (s, 1H) 7.09 (m, 2H) 3.84 (s, 3H)

Example 171

4,5-Dihydroxy-2-(pyridin-4-ylthio)isophthalonitrile 4,5-Diisopropoxy-2-(pyridin-4-ylthio)isophthalonitrile 4,5-Diisopropoxy-2-(pyridin-4-ylthio)isophthalonitrile was prepared from 2-bromo-4,5-diisopropoxyisophthalonitrile (0.25 g) and 4-mercaptopyridine (0.095 g) instead of 4-(trifluoromethyl)thiophenol as described in Example 142. After addition of water, 4,5-diisopropoxy-2-(pyridin-4-ylthio)isophthalonitrile was collected by filtration, washed with water, and dried in vacuum. Yield 0.22 g
$^1$H NMR (400 MHz, DMSO-$d_6$) ppm 8.43 (m, 2H) 8.12 (s, 1H) 7.09 (m, 2H) 4.85-4.95 (m, 1H) 4.79-4.86 (m, 1H) 1.35 (d, 6H) 1.30 (d, 6H)

4,5-Dihydroxy-2-(pyridin-4-ylthio)isophthalonitrile

The title compound was prepared from 4,5-diisopropoxy-2-(pyridin-4-ylthio)isophthalonitrile (0.21 g) instead of 4,5-diisopropoxy-2-(4-(trifluoromethyl)phenylthio)isophthalonitrile as described in Example 142. Yield 0.06 g
$^1$H NMR (400 MHz, DMSO-$d_6$) ppm 8.56 (m, 2H) 7.55 (s, 1H) 7.44 (m, 2H)

Example 172

3-(2,6-Dicyano-3,4-dihydroxyphenylthio)benzoic acid

The title compound was prepared from 2-bromo-4,5-dihydroxyisophthalonitrile (0.75 g) and m-mercaptobenzoic acid (0.48 g) instead of 2-chlorothiophenol as described in Example 162. 3-(2,6-Dicyano-3,4-dihydroxyphenylthio)benzoic acid was purified by chromatography. Yield 0.28 g
$^1$H NMR (400 MHz, DMSO-$d_6$) ppm 7.81 (m, 1H) 7.67 (m, 1H) 7.36-7.54 (m, 3H)

Example 173

2-(4-Cyanophenylthio)-4,5-dihydroxyisophthalonitrile

The title compound was prepared from 2-bromo-4,5-dihydroxyisophthalonitrile (1.0 g) and 4-mercaptobenzonitrile (0.62 g) instead of 2-chlorothiophenol as described in Example 162. 2-(4-Cyanophenylthio)-4,5-dihydroxyisophthalonitrile was purified by chromatography. Yield 0.03 g
$^1$H NMR (400 MHz, methanol-$d_4$) ppm 7.61-7.69 (m, 2H) 7.34 (s, 1H) 7.23-7.29 (m, 2H)

Example 174

4,5-Dihydroxy-2-(naphthalen-2-ylthio)isophthalonitrile

The title compound was prepared from 2-bromo-4,5-dihydroxyisophthalonitrile (0.8 g) and 2-naphthalenethiol (0.59 g) instead of 2-chlorothiophenol as described in Example 162. 4,5-Dihydroxy-2-(naphthalen-2-ylthio) isophthalonitrile was purified by chromatography. Yield 0.04 g $^1$H NMR (400 MHz, methanol-d$_4$) ppm 7.71-7.86 (m, 5H) 7.42-7.52 (m, 2H) 7.31 (m, 1H)

Example 175

2-(4-(2,6-Dicyano-3,4-dihydroxybenzyl)phenyl)-N,N-diethylacetamide

The preparation of 2-(4-(2,6-dicyano-3,4-dihydroxybenzyl)phenyl)acetic acid is described in Example 150. The title compound was prepared from 2-(4-(2,6-dicyano-3,4-dihydroxybenzyl)phenyl)acetic acid (120 mg) and diethylamine in the presence of thionyl chloride. Yield 36 mg $^1$H NMR (400 MHz, methanol-d$_4$) ppm 7.12-7.29 (m, 5H) 4.21 (s, 2H) 3.70 (s, 2H) 3.37 (qd, J=7.12, 2.66 Hz, 4H) 1.09 (dt, J=11.43, 7.12 Hz, 6H)

Example 176

2-(4-Ethylphenoxy)-4,5-dihydroxyisophthalonitrile 2-(4-Ethylphenoxy)-4,5-diisopropoxyisophthalonitrile 2-(4-Ethylphenoxy)-4,5-diisopropoxyisophthalonitrile was prepared from 2-bromo-4,5-diisopropoxyisophthalonitrile (0.25 g) and 4-ethylphenol (0.095 g) instead of 4-(trifluoromethyl)thiophenol as described in Example 142. After addition of water, 2-(4-ethylphenoxy)-4,5-diisopropoxyisophthalonitrile was collected by filtration, washed with water, and dried in vacuum. Yield 0.27 g $^1$H NMR (400 MHz, DMSO-d$_6$) ppm 7.97 (s, 1H) 7.21 (m, 2H) 6.89 (m, 2H) 4.80-5.00 (m, 1H) 4.60-4.78 (m, 1H) 2.59 (q, 2H) 1.33 (d, 6H) 1.31 (d, 6H) 1.17 (t, 3H)

2-(4-Ethylphenoxy)-4,5-dihydroxyisophthalonitrile

The title compound was prepared from 2-(4-ethylphenoxy)-4,5-diisopropoxyisophthalonitrile (0.29 g) instead of 4,5-diisopropoxy-2-(4-(trifluoromethyl)phenylthio)isophthalonitrile as described in Example 142. Yield 0.18 g $^1$H NMR (400 MHz, DMSO-d$_6$) ppm 7.31 (s, 1H) 7.19 (m, 2H) 6.85 (m, 2H) 2.58 (q, 2H) 1.17 (t, 3H)

Example 177

2-(4-Acetylphenoxy)-4,5-dihydroxyisophthalonitrile

The title compound was prepared from 2-bromo-4,5-diisopropoxyisophthalonitrile (250 mg) and 4'-hydroxyacetophenone (116 mg) instead of 4-(trifluoromethyl)thiophenol as described in Example 142 followed by demethylation as described in Example 142. Reaction conditions for the reaction of 2-bromo-4,5-diisopropoxyisophthalonitrile with 4'-hydroxyacetophenone: 1 d at room temperature and 1 d at 50° C. 2-(4-Acetylphenoxy)-4,5-dihydroxyisophthalonitrile was purified by preparative reversed phase HPLC. Yield 23 mg $^1$H NMR (400 MHz, methanol-d$_4$) ppm 8.03-8.09 (m, 2H) 7.26 (s, 1H) 7.00-7.06 (m, 2H) 2.59 (s, 3H)

Example 178

4,5-Dihydroxy-2-(1-oxo-2,3-dihydro-1H-inden-5-yloxy)isophthalonitrile

The title compound was prepared from 2-bromo-4,5-diisopropoxyisophthalonitrile (250 mg) and 5-hydroxy-1-indanone (155 mg) instead of 4-(trifluoromethyl)thiophenol as described in Example 142 followed by demethylation as described in Example 142. Reaction conditions for the reaction of 2-bromo-4,5-diisopropoxyisophthalonitrile with 5-hydroxy-1-indanone: 1 d at room temperature and 3 d at 50° C. 4,5-Dihydroxy-2-(1-oxo-2,3-dihydro-1H-inden-5-yloxy)isophthalonitrile was purified by preparative reversed phase HPLC. Yield 19 mg $^1$H NMR (400 MHz, methanol-d$_4$) ppm 7.71-7.78 (m, 1H) 7.26 (s, 1H) 7.00-7.07 (m, 2H) 3.08-3.19 (m, 2H) 2.67-2.82 (m, 2H)

Example 179

2-(2',6'-Dicyano-3',4'-dihydroxybiphenyl-4-yl)acetic acid

The title compound was prepared from 4-bromo-3,5-dicyano-1,2-phenylene diacetate (1.63 g) and ethyl 2-(4-(4,4,5,5-tetramethyl-1,3,2-dioxaborolan-2-yl)phenyl)acetate (2.19 g) instead of 3,4,5-trifluorophenylboronic acid as described in Example 7. Reaction conditions: 120 min at 130° C. Yield 1.12 g $^1$H NMR (400 MHz, DMSO-d$_6$) ppm 7.26-7.49 (m, 5H) 3.68 (s, 2H)

Example 180

2-(2,4-Dimethylphenoxy)-4,5-dihydroxyisophthalonitrile 2-(2,4-Dimethylphenoxy)-4,5-diisopropoxyisophthalonitrile 2-(2,4-Dimethylphenoxy)-4,5-diisopropoxyisophthalonitrile was prepared from 2-bromo-4,5-diisopropoxyisophthalonitrile (0.50 g) and 2,4-dimethylphenol (0.19 ml) instead of 4-(trifluoromethyl)thiophenol as described in Example 142, except that the reaction mixture was heated at 60° C. for additional 2 h. After evaporation of solvents and addition of 2 M NaOH solution, 2-(2,4-dimethylphenoxy)-4,5-diisopropoxyisophthalonitrile was collected by filtration, washed with water, and dried in vacuum. Yield 0.52 g $^1$H NMR (400 MHz, DMSO-d$_6$) ppm 7.95 (s, 1H) 7.12 (m, 1H) 6.94 (m, 1H) 6.49 (m, 1H) 4.85-4.93 (m, 1H) 4.75-4.82 (m, 1H) 2.50 (s, 3H) 2.25 (s, 3H) 1.32 (d, 6H) 1.31 (d, 6H)

2-(2,4-Dimethylphenoxy)-4,5-dihydroxyisophthalonitrile

The title compound was prepared from 2-(2,4-dimethylphenoxy)-4,5-diisopropoxyisophthalonitrile (0.52 g) instead of 4,5-diisopropoxy-2-(4-(trifluoromethyl)phenylthio)isophthalonitrile as described in Example 142. Yield 0.35 g ¹H NMR (400 MHz, DMSO-d₆) ppm 7.30 (s, 1H) 7.10 (m, 1H) 6.92 (m, 1H) 6.42 (m, 1H) 2.30 (s, 3H) 2.24 (s, 3H)

Example 181

2-(4-Chlorophenoxy)-4,5-dihydroxyisophthalonitrile 2-(4-Chlorophenoxy)-4,5-diisopropoxyisophthalonitrile 2-(4-Chlorophenoxy)-4,5-diisopropoxyisophthalonitrile was prepared from 2-bromo-4,5-diisopropoxyisophthalonitrile (0.50 g) and 4-chlorophenol (0.20 g) instead of 4-(trifluoromethyl)thiophenol as described in Example 142, except that the reaction mixture was heated at 60° C. for additional 2 h. After addition of water, 2-(4-chlorophenoxy)-4,5-diisopropoxyisophthalonitrile (0.54 g) was collected by filtration, washed with water, and dried in vacuum. Yield 0.54 g ¹H NMR (400 MHz, DMSO-d₆) ppm 8.00 (s, 1H) 7.41-7.48 (m, 2H) 7.04-7.10 (m, 2H) 4.85-4.93 (m, 1H) 4.76-4.84 (m, 1H) 1.33 (d, 6H) 1.31 (d, 6H)

2-(4-Chlorophenoxy)-4,5-dihydroxyisophthalonitrile

The title compound was prepared from 2-(4-chlorophenoxy)-4,5-diisopropoxyisophthalonitrile (0.25 g) instead of 4,5-diisopropoxy-2-(4-(trifluoromethyl)phenylthio) isophthalonitrile as described in Example 142. Yield 0.070 g ¹H NMR (400 MHz, DMSO-d₆) ppm 7.40-7.45 (m, 2H) 7.30 (s, 1H) 6.98-7.04 (m, 2H)

Example 182

4,5-Dihydroxy-2-(4-(trifluoromethyl)phenoxy) isophthalonitrile

The title compound was prepared from 2-bromo-4,5-diisopropoxyisophthalonitrile (500 mg) and p-hydroxybenzotrifluoride (276 mg) instead of 4-(trifluoromethyl)thiophenol as described in Example 142 followed by demethylation as described in Example 142. Reaction conditions for the reaction of 2-bromo-4,5-diisopropoxyisophthalonitrile with p-hydroxybenzotrifluoride 4 d at room temperature and 5 h at 50° C. 4,5-Dihydroxy-2-(4-(trifluoromethyl)phenoxy) isophthalonitrile was purified by reversed phase column chromatography. Yield 196 mg ¹H NMR (400 MHz, DMSO-d₆) ppm 11.04 (br s, 2H) 7.71-7.80 (m, 2H) 7.33 (s, 1H) 7.14-7.22 (m, 2H)

Example 183

4,5-Dihydroxy-2-(1H-inden-3-yl)isophthalonitrile

The title compound was prepared from 4-bromo-3,5-dicyano-1,2-phenylene diacetate (350 mg) and 3H-indene-1-boronic acid (220 mg) instead of 3,4,5-trifluorophenylboronic acid as described in Example 7. 4,5-Dihydroxy-2-(H-inden-3-yl)isophthalonitrile was purified by reversed phase column chromatography. Yield 21 mg ¹H NMR (400 MHz, methanol-d₄) ppm 7.54-7.58 (m, 1H) 7.30 (s, 1H) 7.23-7.29 (m, 2H) 7.06-7.10 (m, 1H) 6.75 (t, 1H) 3.64 (d, 2H)

Example 184

4,5-Dihydroxy-2-(morpholinomethyl)isophthalonitrile 2-(Bromomethyl)-4-hydroxy-5-methoxyisophthalonitrile 4-Hydroxy-5-methoxy-2-methylisophthalonitrile (1.32 g), NBS (2.48 g), and AIBN (164 mg) in DCM (50 ml) were refluxed for 6 h 30 min. The reaction was allowed to cool overnight to room temperature. The mixture was cooled in an ice bath and insoluble material was filtered off. The filtrate was evaporated to dryness. EtOAc (10 ml) and heptane (10 ml) were added to the residue and the mixture was heated to reflux. Insoluble oil was removed from the hot solvent. The mixture was allowed to cool to room temperature and the precipitate was filtered off. The filtrate was evaporated to dryness. The crude product was chromatographed over silica gel (EtOAc/heptane/AcOH). The compound was used without further purification. Yield 646 mg ¹H NMR (400 MHz, DMSO-d₆) ppm 11.05 (br s, 1H) 7.74 (s, 1H) 4.73 (s, 2H) 3.94 (s, 3H)

4-Hydroxy-5-methoxy-2-(morpholinomethyl) isophthalonitrile

Sodium hydride (60% in oil, 116 mg), morpholine (0.25 ml), DMF (1 ml) were cooled in an ice bath. 2-(Bromomethyl)-4-hydroxy-5-methoxyisophthalonitrile (365 mg) was added dropwise in DMF (9 ml). The mixture was stirred for 15 min in an ice bath and 2 h 30 min at room temperature. The reaction was quenched with few drops of water. The mixture was evaporated to dryness. EtOAc (25 ml) was added and insoluble material was filtered off.

The filtrate was evaporated to dryness and the resulting residue was chromatographed over silica gel (EtOAc/heptane/AcOH). Yield 148 mg ¹H NMR (400 MHz, DMSO-d₆) ppm 11.79 (br s, 1H) 7.62 (s, 1H) 3.90 (s, 3H) 3.61 (s, 2H) 3.51-3.56 (m, 4H) 2.40-2.46 (m, 4H)

4,5-Dihydroxy-2-(morpholinomethyl)isophthalonitrile

4-Hydroxy-5-methoxy-2-(morpholinomethyl)isophthalonitrile (140 mg) and acetonitrile (5 ml) were mixed. Boron tribromide (2.05 ml, 1 M in DCM) in DCM (15 ml) was added dropwise to the mixture at room temperature. The reaction was stirred for 2 h, and then quenched with water (0.22 ml). The mixture was stirred in an ice bath. The precipitate was filtered and washed with small amount of DCM. Ethanol (4 ml) was added to the solid and the mixture was heated to reflux. Insoluble material was filtered off from the hot solution. The amount of solvent was reduced to about 1.5 ml and the mixture was heated to reflux followed by cooling to room temperature. Ethanol was slowly evaporated by stream of air until precipitate formed. The mixture was stirred in an ice bath, filtered and washed with few drops of ethanol. Yield 45 mg ¹H NMR (400 MHz, DMSO-d₆) ppm 9.98 (br s, 2H) 7.07 (s, 1H) 4.43 (s, 2H) 3.69-3.98 (m, 4H) 3.39 (br s, 4H)

Example 185

2-((Diethylamino)methyl)-4,5-dihydroxyisophthalonitrile hydrochloride

2-((Diethylamino)methyl)-4-hydroxy-5-methoxyisophthalonitrile hydrochloride

4-Hydroxy-5-methoxy-2-methylisophthalonitrile (188 mg), NBS (354 mg), and AIBN (41 mg) in EtOAc (10 ml) were refluxed for 2 h. The reaction was cooled in an ice bath and diethylamine (0.52 ml) in methanol (10 ml) was added. The mixture was stirred overnight at room temperature and evaporated to dryness. The residue was mixed with toluene and evaporated to dryness. The resulting material was dissolved in EtOAc and cooled in an ice bath. HCl in EtOAc was added dropwise. The precipitate was filtered and washed with cold EtOAc. The crude product was recrystallized from EtOAc/ethanol. Yield 180 mg $^1$H NMR (400 MHz, DMSO-$d_6$) ppm 8.69 (br s, 1H) 7.81 (s, 1H) 4.39 (s, 2H) 3.96 (s, 3H) 3.21 (q, 4H) 1.33 (t, 6H)

2-((Diethylamino)methyl)-4,5-dihydroxyisophthalonitrile hydrochloride 2-((Diethylamino)methyl)-4-hydroxy-5-methoxyisophthalonitrile hydrochloride (170 mg) and acetonitrile (20 ml) were cooled to −20° C. Boron tribromide (1.7 ml, 1 M in DCM) was added dropwise to the mixture. The reaction was allowed to warm overnight to room temperature and then cooled in an ice bath. Methanol was added (10 ml) followed by heating to reflux for 1 h. The mixture was evaporated to dryness. 1 M HCl in diethyl ether was added dropwise. The precipitate was filtered. The solid was triturated with EtOAc/ethanol, toluene/EtOAc/AcOH and EtOAc. The crude product was chromatographed over silica gel (DCM/methanol). The product was dissolved in EtOAc and cooled in an ice bath. 1 M HCl in EtOAc was added dropwise. The precipitate was filtered and washed with cold EtOAc. Yield 20 mg $^1$H NMR (400 MHz, DMSO-$d_6$) ppm 8.37 (br s, 3H) 7.41 (s, 1H) 4.36 (br s, 2H) 3.20 (br s, 4H) 1.31 (t, 6H)

Example 186

4,5-Dihydroxy-2-(((2-hydroxyethyl)amino)methyl)isophthalonitrile hydrochloride (1:1)

4-Hydroxy-2-(((2-hydroxyethyl)amino)methyl)-5-methoxyisophthalonitrile

4-Hydroxy-5-methoxy-2-methylisophthalonitrile (188 mg), NBS (356 mg), and AIBN (41 mg) in EtOAc (10 ml) were refluxed for 2 h. The reaction was cooled in an ice bath. Ethanolamine (0.18 ml) was dissolved in methanol (10 ml) and added to the mixture. The reaction mixture was stirred for 2 h at room temperature and evaporated to dryness. The residue was triturated with EtOAc and methanol. Yield 47 mg $^1$H NMR (400 MHz, DMSO-$d_6$) ppm 8.68 (br s, 1H) 7.14 (s, 1H) 5.04 (br s, 1H) 4.63 (s, 2H) 3.63 (s, 3H) 3.57-3.65 (m, 4H)

4,5-Dihydroxy-2-(((2-hydroxyethyl)amino)methyl)isophthalonitrile hydrochloride (1:1)

4-Hydroxy-2-(((2-hydroxyethyl)amino)methyl)-5-methoxyisophthalonitrile (47 mg), aluminum chloride (76 mg) and sodium iodide (57 mg) in acetonitrile were refluxed for 2 h. The reaction was cooled and quenched with 2 N HCl (1 ml). The organic phase was separated and the aqueous phase was washed with acetonitrile. The combined organic phases were evaporated to dryness. The residue was treated with methanol, and then the solvent was decanted. The solution was treated with 1 M HCl in EtOAc in an ice bath. The product was filtered. Yield 18 mg $^1$H NMR (400 MHz, DMSO-$d_6$) ppm 11.21 (br s, 1H) 9.94 (br s, 1H) 9.29 (br s, 1H) 7.86 (br s, 1H) 4.95 (br s, 2H) 3.82 (br s, 2H) 3.72 (br s, 2H)

Example 187

4,5-Dihydroxy-2-(3-hydroxypropyl)isophthalonitrile

4-Hydroxy-2-(3-hydroxypropyl)-5-methoxyisophthalaldehyde 5-(3-Hydroxypropyl)-2-methoxyphenol (4.51 g) and hexamethylenetetramine (7.29 g) in AcOH (50 ml) were refluxed for 8 h. Concentrated HCl (9.1 ml) was added and the mixture was refluxed for 2 h. Brine (50 ml) was added and the mixture was extracted thrice with DCM (75 ml). The combined organic phases were dried (Na$_2$SO$_4$) and evaporated to dryness. The residue was filtered through silica gel cake using toluene/EtOAc/AcOH (8:1:1) solvent mixture. The mixture was evaporated to dryness. The compound was used without further purification. Yield 8.86 g

4-Hydroxy-2-(3-hydroxypropyl)-5-methoxyisophthalonitrile

4-Hydroxy-2-(3-hydroxypropyl)-5-methoxyisophthalaldehyde (8.86 g), hydroxylamine hydrochloride (7.75 g) and anhydrous sodium acetate (12.20 g) in formic acid (50 ml) were refluxed for 5 h. The reaction mixture was evaporated to dryness. Acetone (100 ml) was added to the residue and insoluble material was filtered off. The filtrate was evaporated to dryness. THF (100 ml), acetic anhydride (18.99 g) and triethylamine (51.9 ml) was added. The reaction was stirred at room temperature until reaction stopped (TLC). The mixture was evaporated to dryness. The remainder was cooled in an ice bath. Water (100 ml) was added to the residue and pH was adjusted to about 1 with concentrated HCl. The aqueous phase was extracted thrice with EtOAc (100 ml) and the combined organic phases were washed with brine (25 ml). The organic phase was extracted twice with 2 N NaOH (75 ml). The combined aqueous phases were cooled in an ice bath and pH was adjusted to about 1 with concentrated HCl. The precipitate was filtered and washed with cold water. Yield 870 mg $^1$H NMR (400 MHz, DMSO-$d_6$) ppm 11.78 (br s, 1H) 7.62 (s, 1H) 3.89 (s, 3H) 3.46 (t, 2H) 2.81-2.87 (m, 2H) 1.68-1.77 (m, 2H)

4,5-Dihydroxy-2-(3-hydroxypropyl)isophthalonitrile

To a mixture of 4-hydroxy-2-(3-hydroxypropyl)-5-methoxyisophthalonitrile (570 mg), DCM (50 ml) under nitrogen atmosphere was added 1 M boron tribromide solution in DCM (8.1 ml) at room temperature. The reaction mixture was refluxed for 10 h. 5% sodium sulfite was added to the reaction mixture until no color change was seen. The precipitate was filtered off and washed with water. The solid was dissolved in 1 M sodium hydrogen carbonate and washed with EtOAc. The aqueous phase was cooled in an ice bath and 6 N HCl was added. The product was filtered and washed with water. Yield 300 mg $^1$H NMR (400 MHz, DMSO-d$_6$) ppm 11.06 (br s, 2H) 7.22 (s, 1H) 4.57 (br s, 1H) 3.45 (t, J=6.32 Hz, 2H) 2.71-2.94 (m, 2H) 1.55-1.80 (m, 2H)

Example 188

2-Amino-4,5-dihydroxyisophthalonitrile 3-(Benzylamino)-2,4-dicyano-6-methoxyphenyl tert-butyl carbonate Sodium hydride (2.48 g) and benzylamine (11.29 ml) in toluene (50 ml) were heated at 70° C. for 15 min under nitrogen atmosphere. The mixture was cooled in an ice bath and Pd$_2$(dba)$_3$ (0.14 g), rac-2,2'-bis(diphenylphosphino)-1, 1'-binaphthalene (0.23 g) and 3-bromo-2,4-dicyano-6-methoxyphenyl tert-butyl carbonate (3.65 g) were added. The mixture was heated at 85° C. for 3 h and then cooled in an ice bath. 4 N HCl was added to the mixture and the mixture was extracted thrice with EtOAc. The combined organic phases were washed thrice with brine, dried (Na$_2$SO$_4$), filtered and evaporated to dryness. The residue was triturated with hot 75% ethanol and cooled in an ice bath. The product was filtered off and washed with 50% ethanol. Yield 2.96 g $^1$H NMR (400 MHz, DMSO-d$_6$) ppm 7.47 (s, 1H) 7.25-7.35 (m, 4H) 7.17-7.25 (m, 1H) 6.56 (t, J=6.90 Hz, 1H) 4.74 (d, J=7.03 Hz, 2H) 3.70 (s, 3H) 1.32 (s, 9H)

2-(Benzylamino)-4-hydroxy-5-methoxyisophthalonitrile 3-(Benzylamino)-2,4-dicyano-6-methoxyphenyl tert-butyl carbonate and DCM (40 ml) were stirred at room temperature. Phosphoric acid (2.1 g, 85%, aq.) was added and the reaction mixture stirred at 40° C. until the reaction was completed. The mixture was cooled in an ice bath. The solvent was decanted and the residue was washed with cold DCM. The remainder was triturated with 10% ethanol and cooled in an ice bath. The solids were filtered off and washed with ice cold water. Yield 1.03 g $^1$H NMR (400 MHz, DMSO-d$_6$) ppm 11.54 (br s, 1H) 7.27-7.36 (m, 5H) 7.19-7.26 (m, 1H) 6.48 (t, J=6.90 Hz, 1H) 4.74 (d, J=6.78 Hz, 2H) 3.68-3.80 (m, 3H)

2-Amino-4,5-dihydroxyisophthalonitrile 2-(Benzylamino)-4-hydroxy-5-methoxyisophthalonitrile (520 mg) was slowly added to a solution of aluminum chloride (993 mg) and sodium iodide (1116 mg) in acetonitrile (15 ml) at 0° C. The reaction mixture was stirred at room temperature for 2 h. The mixture was evaporated to dryness. 1 N HCl (21 ml) was added followed by addition of 1 M sodium sulfite until no color change was seen. The organic phase was separated. The aqueous phase was extracted thrice with EtOAc. The organic phases were combined, washed with brine, dried (Na$_2$SO$_4$), filtered and evaporated to dryness. Heptane (9 ml) and EtOAc (1 ml) was added and heated to reflux. The crude product was filtered from the hot solution and chromatographed over silica gel. Yield 160 mg $^1$H NMR (400 MHz, DMSO-d$_6$) ppm 10.98 (br s, 1H) 9.7 (br s, 1H) 6.97 (s, 1H) 5.85 (s, 2H)

Example 189

4,5-Dihydroxy-2-(pyrrolidin-1-yl)isophthalonitrile tert-Butyl 2,4-dicyano-6-methoxy-3-(pyrrolidin-1-yl)phenyl carbonate Using the procedure analogous to Example 188, 3-bromo-2,4-dicyano-6-methoxyphenyl tert-butyl carbonate (1.06 g) was converted to tert-butyl 2,4-dicyano-6-methoxy-3-(pyrrolidin-1-yl)phenyl carbonate. The crude product was triturated with hot ethanol. Yield 1.03 g $^1$H NMR (400 MHz, DMSO-d$_6$) ppm 7.53 (s, 1H) 3.77 (s, 3H) 3.68-3.73 (m, 4H) 1.88-1.96 (m, 4H) 1.40 (s, 9H)

4-Hydroxy-5-methoxy-2-(pyrrolidin-1-yl)isophthalonitrile

Using the procedure analogous to Example 188, tert-butyl 2,4-dicyano-6-methoxy-3-(pyrrolidin-1-yl)phenyl carbonate (530 mg) was converted to 4-hydroxy-5-methoxy-2-(pyrrolidin-1-yl)isophthalonitrile. Yield 260 mg $^1$H NMR (400 MHz, DMSO-d$_6$) ppm 11.48 (br s, 1H) 7.34 (s, 1H) 3.80 (s, 3H) 3.70 (t, J=6.40 Hz, 4H) 1.88-1.93 (m, 4H)

4,5-Dihydroxy-2-(pyrrolidin-1-yl)isophthalonitrile

Using the procedure analogous to Example 188, 4-hydroxy-5-methoxy-2-(pyrrolidin-1-yl)isophthalonitrile was converted to 4,5-dihydroxy-2-(pyrrolidin-1-yl)isophthalonitrile. The crude product was dissolved in 8 N NaOH and washed twice with EtOAc. The aqueous phase was cooled in an ice bath and concentrated HCl was added. The precipitate was filtered and washed with water. Yield 32 mg $^1$H NMR (400 MHz, DMSO-d$_6$) ppm 10.61 (br s, 2H) 7.02 (s, 1H) 3.64 (t, J=6.30 Hz, 4H) 1.90 (m, 4H)

Example 190

2-(2,6-Dimethylmorpholino)-4,5-dihydroxyisophthalonitrile tert-Butyl 2,4-dicyano-3-(2,6-dimethylmorpholino)-6-methoxyphenyl carbonate Using the procedure analogous to Example 188, 3-bromo-2,4-dicyano-6-methoxyphenyl tert-butyl carbonate (706 mg) was converted to tert-butyl 2,4-dicyano-3-(2,6-dimethylmorpholino)-6-methoxyphenyl carbonate. Yield 159 mg $^1$H NMR (400 MHz, DMSO-d$_6$) ppm 7.69 (s, 1H) 3.82 (s, 3H) 3.67-3.77 (m, 2H) 3.26 (d, J=11.29 Hz, 2H) 2.94 (dd, J=11.80, 10.04 Hz, 2H) 1.40 (s, 9H) 1.11 (d, J=6.27 Hz, 6H)

2-(2,6-Dimethylmorpholino)-4-hydroxy-5-methoxyisophthalonitrile

Using the procedure analogous to Example 188, tert-butyl 2,4-dicyano-3-(2,6-dimethylmorpholino)-6-methoxyphenyl carbonate (159 mg) was converted to 2-(2,6-dimethylmorpholino)-4-hydroxy-5-methoxyisophthalonitrile. To isolate the crude product from the reaction mixture, brine was added. The mixture was extracted thrice with EtOAc. The combined organic phases were dried (Na$_2$SO$_4$), filtered end evaporated to dryness. Yield 139 mg ¹H NMR (400 MHz, DMSO-d₆) ppm 11.74 (br s, 1H) 7.50 (s, 1H) 3.85 (s, 3H) 3.66-3.75 (m, 2H) 3.23 (d, J=11.54 Hz, 2H) 2.88-2.96 (m, 2H) 1.10 (d, J=6.27 Hz, 6H)

2-(2,6-Dimethylmorpholino)-4,5-dihydroxyisophthalonitrile

Using the procedure analogous to Example 188, 2-(2,6-dimethylmorpholino)-4-hydroxy-5-methoxyisophthalonitrile (139 mg) was converted to 2-(2,6-dimethylmorpholino)-4,5-dihydroxyisophthalonitrile. The crude product was triturated with hot toluene. Yield 5.7 mg ¹H NMR (400 MHz, DMSO-d₆) ppm 11.41 (br s, 1H) 10.63 (br s, 1H) 7.14 (s, 1H) 3.53-3.80 (m, 2H) 3.16 (d, J=11.29 Hz, 2H) 2.89 (d, J=11.05 Hz, 2H) 1.09 (d, J=6.27 Hz, 6H)

Example 191

4,5-Dihydroxy-2-morpholinoisophthalonitrile tert-Butyl 2,4-dicyano-6-methoxy-3-morpholinophenyl carbonate Using the procedure analogous to Example 188, 3-bromo-2,4-dicyano-6-methoxyphenyl tert-butyl carbonate (706 mg) was converted to tert-butyl 2,4-dicyano-6-methoxy-3-morpholinophenyl carbonate. The crude product was crystallized from ethanol. Yield 312 mg ¹H NMR (400 MHz, DMSO-d₆) ppm 7.70 (s, 1H) 3.83 (s, 3H) 3.69-3.77 (m, 4H) 3.28-3.34 (m, 4H) 1.40 (s, 9H)

4-Hydroxy-5-methoxy-2-morpholinoisophthalonitrile

Using the procedure analogous to Example 188, tert-butyl 2,4-dicyano-6-methoxy-3-morpholinophenyl carbonate (312 mg) was converted to 4-hydroxy-5-methoxy-2-morpholinoisophthalonitrile. The crude product was triturated with diethyl ether. Yield 109 mg ¹H NMR (400 MHz, DMSO-d₆) ppm 11.76 (br s, 1H) 7.49 (s, 1H) 3.85 (s, 3H) 3.71 (t, J=4.02 Hz, 4H) 3.28 (t, J=4.52 Hz, 4H)

4,5-Dihydroxy-2-morpholinoisophthalonitrile

Using the procedure analogous to Example 188, 4-hydroxy-5-methoxy-2-morpholinoisophthalonitrile (109 mg) was converted to 4,5-dihydroxy-2-morpholinoisophthalonitrile. The crude product was dissolved in 4 N NaOH (5 ml) and washed twice with EtOAc (5 ml). The aqueous phase was cooled in an ice bath and pH was adjusted to <3 with concentrated HCl. The precipitate was filtered and washed thrice with cold water. Yield 26 mg ¹H NMR (400 MHz, DMSO-d₆) ppm 10.91 (br s, 2H) 7.12 (s, 1H) 3.56-3.83 (m, 4H) 3.21-3.26 (m, 4H)

Example 192

4,5-Dihydroxy-2-(isopropylamino)isophthalonitrile tert-Butyl 2,4-dicyano-3-(isopropylamino)-6-methoxyphenyl carbonate Using the procedure analogous to Example 188, 3-bromo-2,4-dicyano-6-methoxyphenyl tert-butyl carbonate (1.41 g) was converted to tert-butyl 2,4-dicyano-3-(isopropylamino)-6-methoxyphenyl carbonate. The crude product was chromatographed over silica gel using heptane/EtOAc solvent mixture. Yield 541 mg ¹H NMR (400 MHz, DMSO-d₆) ppm 7.58 (s, 1H) 5.07 (d, J=9.29 Hz, 1H) 3.98-4.15 (m, 1H) 3.76 (s, 3H) 1.40 (s, 9H) 1.21 (d, J=6.27 Hz, 6H)

4-Hydroxy-2-(isopropylamino)-5-methoxyisophthalonitrile

Using the procedure analogous to Example 188, tert-butyl 2,4-dicyano-3-(isopropylamino)-6-methoxyphenyl carbonate (535 mg) was converted to 4-hydroxy-2-(isopropylamino)-5-methoxyisophthalonitrile. Yield 265 mg ¹H NMR (400 MHz, DMSO-d₆) ppm 11.57 (br s, 1H) 7.39 (s, 1H) 4.94 (d, J=9.29 Hz, 1H) 4.09 (m, 1H) 3.79 (s, 3H) 1.20 (d, J=6.27 Hz, 6H).

4,5-Dihydroxy-2-(isopropylamino)isophthalonitrile

Using the procedure analogous to Example 188, 4-hydroxy-2-(isopropylamino)-5-methoxyisophthalonitrile (250 mg) was converted to 4,5-dihydroxy-2-(isopropylamino)isophthalonitrile. The crude product was chromatographed over silica gel using heptane/EtOAc solvent mixture containing 0.05% TFA. Yield 175 mg ¹H NMR (400 MHz, DMSO-d₆) ppm 11.29 (br s, 1H) 9.98 (br s, 1H) 7.04 (s, 1H) 4.71 (d, J=9.03 Hz, 1H) 3.94-4.06 (m, 1H) 1.18 (d, J=6.27 Hz, 6H)

Example 193

4,5-Dihydroxy-2-(3-methoxypropylamino)isophthalonitrile tert-Butyl 2,4-dicyano-6-methoxy-3-(3-methoxypropylamino)phenyl carbonate Using the procedure analogous to Example 188, 3-bromo-2,4-dicyano-6-methoxyphenyl tert-butyl carbonate (706 mg) was converted to tert-butyl 2,4-dicyano-6-methoxy-3-(3-methoxypropylamino)phenyl carbonate. The product was chromatographed over silica gel using toluene/EtOAc solvent mixture. Yield 355 mg ¹H NMR (400 MHz, DMSO-d₆) ppm 7.52 (s, 1H) 5.98 (t, J=5.90 Hz, 1H) 3.74 (s, 3H) 3.58 (q, J=6.53 Hz, 2H) 3.42 (t, J=5.90 Hz, 2H) 3.23 (s, 3H) 1.82 (quin, J=6.34 Hz, 2H) 1.40 (s, 9H)

4-Hydroxy-5-methoxy-2-(3-methoxypropylamino)isophthalonitrile

Using the procedure analogous to Example 188, tert-butyl 2,4-dicyano-6-methoxy-3-(3-methoxypropylamino)phenyl carbonate (320 mg) was converted to 4-hydroxy-5-methoxy-2-(3-methoxypropylamino)isophthalonitrile. Yield 188 mg ¹H NMR (400 MHz, DMSO-d₆) ppm 11.51 (br s, 1H) 7.34 (s, 1H) 5.89 (t, J=5.90 Hz, 1H) 3.76 (s, 3H) 3.57 (q, J=6.53 Hz, 2H) 3.42 (t, J=6.02 Hz, 2H) 3.23 (s, 3H) 1.81 (m, 2H)

4,5-Dihydroxy-2-(3-methoxypropylamino)isophthalonitrile

Using the procedure analogous to Example 188, 4-hydroxy-5-methoxy-2-(3-methoxypropylamino)isophthalonitrile (188 mg) was converted to 4,5-dihydroxy-2-(3-methoxypropylamino)isophthalonitrile. The product was triturated with toluene/EtOAc (1:1) mixture. Yield 57 mg $^1$H NMR (400 MHz, DMSO-$d_6$) ppm 11.20 (br s, 1H) 9.82 (br s, 1H) 6.99 (s, 1H) 5.68 (br s, 1H) 3.53 (q, J=6.02 Hz, 2H) 3.41 (t, J=5.90 Hz, 2H) 3.23 (s, 3H) 1.69-1.85 (m, 2H)

Example 194

2,4,5-Trihydroxyisophthalonitrile 2,4-Dihydroxy-5-methoxyisophthalaldehyde

4-Methoxybenzene-1,3-diol (2.00 g) was dissolved in TFA (50 ml).

Hexamethylenetetramine (8.00 g) was added and the reaction mixture was heated under reflux for 6 h. TFA was evaporated and 4 M HCl (60 ml) was added. The mixture was refluxed for 3 h and then stirred overnight at room temperature. The solid product was filtered, washed with 4 M HCl solution and dried. Yield 0.64 g $^1$H NMR (400 MHz, DMSO-$d_6$) ppm 11.98 (br s, 1H) 10.30 (s, 1H) 10.10 (s, 1H) 7.50 (s, 1H) 3.84 (s, 3H)

(1E,1'E)-2,6-Dihydroxy-3-((E)-(hydroxyimino)methyl)-5-methoxybenzaldehyde oxime 2,4-Dihydroxy-5-methoxyisophthalaldehyde (0.60 g) was dissolved in THF (25 ml). Hydroxylamine hydrochloride (0.85 g) and pyridine (1.48 ml) were added. The solution was stirred at room temperature for 3½ h. THF was evaporated and ice was added. The solid was filtered, washed with ice cold water and dried. Yield 0.41 g $^1$H NMR (400 MHz, DMSO-$d_6$) ppm 11.68 (s, 1H) 11.11 (s, 1H) 10.58 (s, 1H) 10.43 (s, 1H) 8.49 (s, 1H) 8.26 (s, 1H) 7.14 (s, 1H) 3.74 (s, 3H)

2,4-Dihydroxy-5-methoxyisophthalonitrile (1E,1'E)-2,6-Dihydroxy-3-((E)-(hydroxyimino)methyl)-5-methoxybenzaldehyde oxime (0.41 g) was dissolved in acetic anhydride (20 ml). The mixture was refluxed for 4 h after which it was allowed to cool to room temperature. Toluene and water were added and solvents were evaporated. After stirring with ice, the solid was filtered, washed with water and dried. The solid was dissolved in methanol (10 ml). Sodium methylate (1.68 ml, 21% solution in methanol) was added at 0° C. The solution was stirred at 0° C. for 30 min. Methanol was evaporated. Ice was added and pH was adjusted to 2 with concentrated HCl. The mixture was extracted with EtOAc, washed with water and brine. The organic phase was dried (Na$_2$SO$_4$), filtered and evaporated. Yield 0.32 g $^1$H NMR (400 MHz, DMSO-$d_6$) ppm 11.69 (br s, 1H) 11.52 (br s, 1H) 7.45 (s, 1H) 3.81 (s, 3H)

2,4,5-Trihydroxyisophthalonitrile

Sieve dry acetonitrile (20 ml) was cooled in an ice bath. Aluminum chloride (210 mg) was added slowly to the solvent so that temperature was kept below 30° C. The mixture was stirred at room temperature for 10 min. Sodium iodide (158 mg) was added and the solution was stirred for 15 min. 2,4-Dihydroxy-5-methoxyisophthalonitrile (100 mg) was added and the reaction mixture was heated at 50° C. for 45 min after which it was allowed to cool to room temperature. 2 M HCl (10 ml) and sodium sulfate (50 mg) were successively added to the reaction mixture. The mixture was extracted with EtOAc. The organic phase was washed twice with 2 M HCl, twice with water and once with brine. The organic phase was dried (Na$_2$SO$_4$), filtered and evaporated to dryness. The residue was triturated with DCM. The solid was filtered and washed with DCM. Yield 49 mg $^1$H NMR (400 MHz, DMSO-$d_6$) ppm 11.22 (br s, 2H) 10.15 (br s, 1H) 7.08 (s, 1H)

Example 195

2-Ethyl-4,5-dihydroxyisophthalonitrile

The preparation of 4,5-dihydroxy-2-vinylisophthalonitrile is described in Example 89. 4,5-Dihydroxy-2-vinylisophthalonitrile (70 mg) was dissolved in methanol (8 ml). H-Cube system was charged with Pd/C 10% catridge. The solution was filtered and pumped twice through H-Cube system with a flow rate of 1 ml/min. The collected solution was evaporated. Yield 30 mg $^1$H NMR (400 MHz, DMSO-$d_6$) ppm 11.09 (br s, 2H) 7.23 (s, 1H) 2.78 (q, 2H) 1.19 (t, 3H)

Example 196

3,4-Dihydroxy-4'-methoxybiphenyl-2,6-dicarbonitrile

To a mixture of 2-bromo-4,5-dihydroxyisophthalonitrile (200 mg) and 4-methoxyphenylboronic acid (127 mg) in ethanol (1 ml) and water (1 ml) was added palladium(II) acetate (7.5 mg) and DBU (120 mg). The stirred reaction was microwave-irradiated for 10 min at 150° C. The hot reaction mixture was filtered. After cooling, the filtrate was acidified with 1 M HCl (1 ml). Recrystallization was carried out with ethanol (1 ml). The solid was filtrated and washed with water-ethanol 2:1. Yield 72 mg $^1$H NMR (400 MHz, DMSO-$d_6$) ppm 11.23 (br s, 2H) 7.37-7.45 (m, 2H) 7.33 (s, 1H) 7.02-7.12 (m, 2H) 3.83 (s, 3H)

Example 197

3,4-Dihydroxy-3'-(morpholine-4-carbonyl)biphenyl-2,6-dicarbonitrile

2',6'-Dicyano-3'-hydroxy-4'-methoxybiphenyl-3-carboxylic acid

To a mixture of 2-bromo-4-hydroxy-5-methoxyisophthalonitrile (500 mg) and 3-carboxyphenylboronic acid (426 mg) in ethanol (3 ml) and acetonitrile (6 ml) was added bis(triphenylphosphine)palladium(II) chloride (76 mg) and 2 M sodium carbonate (3 ml). The reaction mixture was microwave-irradiated for 10 min at 150° C. 1 M NaOH (30 ml) was added and the mixture was stirred for 2 h. Ethanol and acetonitrile were evaporated. The water phase was washed thrice with toluene and then made acidic by addition of 4 M HCl under cooling. The product was filtered, washed with water and dried. Yield 570 mg $^1$H NMR (400 MHz, DMSO-$d_6$) ppm 8.08 (d, 1H) 8.01 (s, 1H) 7.72-7.78 (m, 2H) 7.64-7.72 (m, 1H) 3.95 (s, 3H)

3-Hydroxy-4-methoxy-3'-(morpholine-4-carbonyl)biphenyl-2,6-dicarbonitrile

2',6'-Dicyano-3'-hydroxy-4'-methoxybiphenyl-3-carboxylic acid (200 mg), morpholine (0.12 ml), 1-(3-dimethylaminopropyl)-3-ethylcarbodiimide hydrochloride (130 mg), DIPEA (0.30 ml) and 1-hydroxybenzotriazole hydrate (104 mg) were dissolved in DMF (5 ml) and the reaction was stirred overnight at room temperature. The reaction mixture was poured into ice (50 g) and 1 M HCl (5 ml) was added. The solid was filtered and washed with water. The crude mixture was purified by flash column chromatography (DCM/methanol). Yield 70 mg $^1$H NMR (400 MHz, DMSO-$d_6$) ppm 7.49-7.66 (m, 5H) 3.91 (s, 3H) 3.50-3.77 (m, 8H)

3,4-Dihydroxy-3'-(morpholine-4-carbonyl)biphenyl-2,6-dicarbonitrile

To a dry mixture of 3-hydroxy-4-methoxy-3'-(morpholine-4-carbonyl)biphenyl-2,6-dicarbonitrile (70 mg) in DCM (5 ml) under nitrogen atmosphere was added 1 M boron tribromide solution in DCM (0.96 ml) at −10° C. The reaction mixture was warmed slowly to room temperature with stirring for 3 h. The reaction mixture was poured into methanol (1 ml)/ice mixture. The solid was filtrated and washed with water. Yield 30 mg $^1$H NMR (400 MHz, DMSO-$d_6$) ppm 11.26 (br s, 2H) 7.44-7.70 (m, 4H) 7.37 (s, 1H) 3.45-3.75 (m, 8H)

Example 198

N-Butyl-2',6'-dicyano-3',4'-dihydroxybiphenyl-4-carboxamide

2',6'-Dicyano-3'-hydroxy-4'-methoxybiphenyl-4-carboxylic acid

To a mixture of 2-bromo-4-hydroxy-5-methoxyisophthalonitrile (500 mg) and 4-carboxyphenylboronic acid (329 mg) in ethanol (3 ml) and acetonitrile (6 ml) was added bis(triphenylphosphine)palladium(II) chloride (76 mg) and 2 M sodium carbonate (3 ml). The reaction mixture was microwave-irradiated for 10 min at 150° C. 1 M NaOH (30 ml) was added and the mixture was stirred for 2 h. Ethanol and acetonitrile were evaporated. The water phase was washed thrice with toluene and then made acidic by addition of 4 M HCl under cooling. The product was filtered, washed with water and dried. Yield 560 mg $^1$H NMR (400 MHz, DMSO-$d_6$) ppm 13.09 (br s, 1H) 7.93-8.06 (m, 2H) 7.41-7.54 (m, 2H) 6.80 (s, 1H) 3.69 (s, 3H)

N-Butyl-2',6'-dicyano-3'-hydroxy-4'-methoxybiphenyl-4-carboxamide

2',6'-Dicyano-3'-hydroxy-4'-methoxybiphenyl-4-carboxylic acid (200 mg), butylamine (0.13 ml), 1-(3-dimethylaminopropyl)-3-ethylcarbodiimide hydrochloride (130 mg), DIPEA (0.30 ml) and 1-hydroxybenzotriazole hydrate (104 mg) were dissolved in DMF (5 ml) and the reaction was stirred for 72 h at room temperature. 1 M NaOH was added (20 ml). The reaction mixture was washed thrice with toluene and then made acidic by addition of 4 M HCl. EtOAc was added and the organic phase was washed with 1 M HCl, 1 M sodium hydrogen carbonate, water and brine. The washed organic phase was dried (Na$_2$SO$_4$), filtered and evaporated to dryness. Yield 100 mg $^1$H NMR (400 MHz, DMSO-$d_6$) ppm 8.58 (m, 1H) 7.88-8.03 (m, 2H) 7.75 (s, 1H) 7.51-7.65 (m, 2H) 3.96 (s, 3H) 3.25-3.28 (m, 2H) 1.47-1.59 (m, 2H) 1.35 (m, 2H) 0.91 (t, 3H)

N-Butyl-2',6'-dicyano-3',4'-dihydroxybiphenyl-4-carboxamide

To a dry mixture of N-butyl-2',6'-dicyano-3'-hydroxy-4'-methoxybiphenyl-4-carboxamide (90 mg) in DCM (5 ml) under nitrogen atmosphere was added 1 M boron tribromide solution in DCM (1.23 ml) at −10° C. The reaction mixture was warmed slowly to room temperature with stirring for 3 h. The reaction mixture was poured into methanol (1 ml)/ice mixture. The solid was filtrated and washed with water. Yield 58 mg $^1$H NMR (400 MHz, DMSO-$d_6$) ppm 11.29 (br s, 2H) 8.47-8.71 (m, 1H) 7.85-8.08 (m, 2H) 7.49-7.70 (m, 2H) 7.37 (s, 1H) 3.26-3.32 (m, 2H) 1.46-1.64 (m, 2H) 1.27-1.44 (m, 2H) 0.92 (t, 3H)

Example 199

2-(3,3-Dimethylbutyl)-4,5-dihydroxyisophthalonitrile

The preparation of (E)-2-(3,3-dimethylbut-1-enyl)-4,5-dihydroxyisophthalonitrile is described in Example 28. (E)-2-(3,3-Dimethylbut-1-enyl)-4,5-dihydroxyisophthalonitrile (150 mg) was dissolved in methanol (12 ml). H-Cube system was charged with Pd/C 10% catridge. The solution was filtered and pumped through H-Cube system with a flow rate of 1 ml/min. The collected solution was evaporated. Recrystallization was carried out from ethanol-water solution. Yield 30 mg $^1$H NMR (400 MHz, DMSO-$d_6$) ppm 7.17 (s, 1H) 2.73 (dt, 2H) 1.38 (dt, 2H) 0.96 (s, 9H)

Example 200

4,5-Dihydroxy-2-(piperidin-1-yl)isophthalonitrile tert-Butyl 2,4-dicyano-6-methoxy-3-(piperidin-1-yl)phenyl carbonate Using the procedure analogous to Example 188, 3-bromo-2,4-dicyano-6-methoxyphenyl tert-butyl carbonate (353 mg) was converted to tert-butyl 2,4-dicyano-6-methoxy-3-(piperidin-1-yl)phenyl carbonate. The crude product was triturated with hot 90% ethanol. Yield 145 mg $^1$H NMR (400 MHz, DMSO-$d_6$-chloroform-d) ppm 7.43 (s, 1H) 3.83 (s, 3H) 3.23-3.42 (m, 4H) 1.70-1.80 (m, 4H) 1.60-1.70 (m, 2H) 1.43 (s, 9H)

4-Hydroxy-5-methoxy-2-(piperidin-1-yl)isophthalonitrile

Using the procedure analogous to Example 188, tert-butyl 2,4-dicyano-6-methoxy-3-(piperidin-1-yl)phenyl carbonate (140 mg) was converted to 4-hydroxy-5-methoxy-2-(piperidin-1-yl)isophthalonitrile. To isolate the crude product from the reaction mixture, water was added. The mixture was extracted thrice with EtOAc. The organic phase was dried (Na$_2$SO$_4$), filtered end evaporated to dryness. Yield 54 mg $^1$H NMR (400 MHz, DMSO-$d_6$) ppm 11.62 (s, 1H) 7.44 (s, 1H) 3.83 (s, 3H) 3.20-3.26 (m, 4H) 1.60-1.68 (m, 4H) 1.52-1.59 (m, 2H)

4,5-Dihydroxy-2-(piperidin-1-yl)isophthalonitrile

Using the procedure analogous to Example 188, 4-hydroxy-5-methoxy-2-(piperidin-1-yl)isophthalonitrile was converted to 4,5-dihydroxy-2-(piperidin-1-yl)isophthalonitrile. The crude product was dissolved in 2 M NaOH and washed with EtOAc. Concentrated HCl was added and the aqueous phase evaporated to dryness. The residue was triturated with toluene/EtOAc/AcOH (8/3/3) and CDCl$_3$. Yield 10 mg $^1$H NMR (400 MHz, methanol-d$_4$) ppm 7.05 (s, 1H) 3.25-3.30 (m, 4H) 1.70-1.80 (m, 4H) 1.60-1.65 (m, 2H)

Example 201

2-(Hexylamino)-4,5-dihydroxyisophthalonitrile tert-Butyl 2,4-dicyano-3-(hexylamino)-6-methoxyphenyl carbonate Using the procedure analogous to Example 188, 3-bromo-2,4-dicyano-6-methoxyphenyl tert-butyl carbonate (706 mg) was converted to tert-butyl 2,4-dicyano-3-(hexylamino)-6-methoxyphenyl carbonate. The crude product was triturated with hot 90% ethanol. Yield 324 mg $^1$H NMR (400 MHz, DMSO-d$_6$) ppm 7.51 (s, 1H) 5.92 (t, J=6.27 Hz, 1H) 3.74 (s, 3H) 3.49 (q, J=6.78 Hz, 2H) 1.50-1.60 (m, 2H) 1.39 (s, 9H) 1.19-1.35 (m, 6H) 0.85 (t, J=6.78 Hz, 3H)

2-(Hexylamino)-4-hydroxy-5-methoxyisophthalonitrile

Using the procedure analogous to Example 188, tert-butyl 2,4-dicyano-3-(hexylamino)-6-methoxyphenyl carbonate (320 mg) was converted to 2-(hexylamino)-4-hydroxy-5-methoxyisophthalonitrile. Yield 251 mg $^1$H NMR (400 MHz, DMSO-d$_6$) ppm 11.49 (br s, 1H) 7.33 (s, 1H) 5.81 (t, J=5.90 Hz, 1H) 3.77 (s, 3H) 3.48 (q, J=6.69 Hz, 2H) 1.49-1.59 (m, 2H) 1.26 (br s, 6H) 0.85 (t, J=6.53 Hz, 3H)

2-(Hexylamino)-4,5-dihydroxyisophthalonitrile

Using the procedure analogous to Example 188, 2-(hexylamino)-4-hydroxy-5-methoxyisophthalonitrile (251 mg) was converted to 2-(hexylamino)-4,5-dihydroxyisophthalonitrile. The crude product was triturated with heptane/EtOAc (5/2) solvent mixture. Yield 36 mg $^1$H NMR (400 MHz, DMSO-d$_6$) ppm 11.24 (br s, 1H) 9.81 (br s, 1H) 6.97 (s, 1H) 5.61 (t, J=6.32 Hz, 1H) 3.39-3.48 (m, 2H) 1.42-1.59 (m, 2H) 1.20-1.40 (m, 6H) 0.78-0.90 (m, 3H)

Example 202

2-(Cyclohexylamino)-4,5-dihydroxyisophthalonitrile tert-Butyl 2,4-dicyano-3-(cyclohexylamino)-6-methoxyphenyl carbonate Using the procedure analogous to Example 188, 3-bromo-2,4-dicyano-6-methoxyphenyl tert-butyl carbonate (706 mg) was converted to tert-butyl 2,4-dicyano-3-(cyclohexylamino)-6-methoxyphenyl carbonate. The crude product was chromatographed over silica gel (toluene). Yield 257 mg $^1$H NMR (400 MHz, DMSO-d$_6$) ppm 7.56 (s, 1H) 5.12 (d, J=9.29 Hz, 1H) 3.75 (s, 3H) 3.65-3.74 (m, 1H) 1.91 (d, J=10.54 Hz, 2H) 1.66-1.74 (m, 2H) 1.56 (d, J=12.30 Hz, 1H) 1.39 (s, 9H) 1.13-1.37 (m, 5H)

2-(Cyclohexylamino)-4-hydroxy-5-methoxyisophthalonitrile

Using the procedure analogous to Example 188, tert-butyl 2,4-dicyano-3-(cyclohexylamino)-6-methoxyphenyl carbonate (257 mg) was converted to 2-(cyclohexylamino)-4-hydroxy-5-methoxyisophthalonitrile. To isolate the crude product from the reaction mixture, the mixture was evaporated to dryness. Water was added. The mixture was extracted thrice with EtOAc. The organic phases were dried (Na$_2$SO$_4$), filtered end evaporated to dryness. The crude product was chromatographed over silica gel (toluene/EtOAc). Yield 94 mg $^1$H NMR (400 MHz, DMSO-d$_6$) ppm 11.58 (br s, 1H) 7.37 (s, 1H) 4.99 (d, J=8.78 Hz, 1H) 3.78 (s, 3H) 3.66-3.75 (m, 1H) 1.86-1.96 (m, 2H) 1.65-1.74 (m, 2H) 1.56 (d, J=10.29 Hz, 1H) 1.11-1.41 (m, 5H)

2-(Cyclohexylamino)-4,5-dihydroxyisophthalonitrile

Using the procedure analogous to Example 188, 2-(cyclohexylamino)-4-hydroxy-5-methoxyisophthalonitrile (85 mg) was converted to 2-(cyclohexylamino)-4,5-dihydroxyisophthalonitrile. The crude product was triturated with heptane/EtOAc (3/1) solvent mixture Yield 19 mg $^1$H NMR (400 MHz, DMSO-d$_6$) ppm 11.27 (br s, 1H) 9.95 (br s, 1H) 7.03 (s, 1H) 4.78 (d, J=9.03 Hz, 1H) 3.65 (br s, 1H) 1.90 (m, 2H) 1.65-1.73 (m, 2H) 1.56 (d, J=11.80 Hz, 1H) 1.19-1.35 (m, 5H)

Example 203

4,5-Dihydroxy-2-(2-methoxyethylamino)isophthalonitrile tert-Butyl 2,4-dicyano-6-methoxy-3-(2-methoxyethylamino)phenyl carbonate Using the procedure analogous to Example 188, 3-bromo-2,4-dicyano-6-methoxyphenyl tert-butyl carbonate (706 mg) was converted to tert-butyl 2,4-dicyano-6-methoxy-3-(2-methoxyethylamino)phenyl carbonate. The crude product was dissolved in toluene/EtOAc (9/1) solvent mixture. Insoluble material was filtered off. The mixture was evaporated to dryness. Yield 410 mg $^1$H NMR (400 MHz, DMSO-d$_6$) ppm 7.54 (s, 1H) 5.62 (t, J=6.27 Hz, 1H) 3.75 (s, 3H) 3.65 (q, J=5.60 Hz, 2H) 3.51 (t, J=5.63 Hz, 2H) 3.25 (s, 3H) 1.39 (s, 9H)

4-Hydroxy-5-methoxy-2-(2-methoxyethylamino)isophthalonitrile

Using the procedure analogous to Example 188, tert-butyl 2,4-dicyano-6-methoxy-3-(2-methoxyethylamino)phenyl carbonate (400 mg) was converted to 4-hydroxy-5-methoxy-2-(2-methoxyethylamino)isophthalonitrile. The crude product was triturated with heptane. Yield 45 mg $^1$H NMR (400 MHz, DMSO-d$_6$) ppm 11.61 (br s, 1H) 7.36 (s, 1H) 5.56 (t, J=6.06 Hz, 1H) 3.78 (s, 3H) 3.65 (q, J=6.06 Hz, 2H) 3.50 (t, J=5.48 Hz, 2H) 3.26 (s, 3H)

4,5-Dihydroxy-2-(2-methoxyethylamino)isophthalonitrile

Using the procedure analogous to Example 188, 4-hydroxy-5-methoxy-2-(2-methoxyethylamino)isophthalonitrile (40 mg) was converted to 4,5-dihydroxy-2-(2-methoxyethylamino)isophthalonitrile. The crude product was triturated with toluene/EtOAc (4/1) solvent mixture. Yield 18 mg $^1$H NMR (400 MHz, methanol-d$_4$) ppm 6.99 (s, 1H) 3.71 (t, J=1.00 Hz, 2H) 3.59 (t, J=1.00 Hz, 2H) 3.39 (s, 3H)

Example 204

2-(4-Benzylpiperidin-1-yl)-4,5-dihydroxyisophthalonitrile 3-(4-Benzylpiperidin-1-yl)-2,4-dicyano-6-methoxyphenyl tert-butyl carbonate Using the procedure analogous to Example 188, 3-bromo-2,4-dicyano-6-methoxyphenyl tert-butyl carbonate (706 mg) was converted to 3-(4-benzylpiperidin-1-yl)-2,4-dicyano-6-methoxyphenyl tert-butyl carbonate. The crude product was chromatographed over silica gel using toluene/EtOAc solvent mixture. Yield 562 mg $^1$H NMR (400 MHz, DMSO-d$_6$) ppm 7.64 (s, 1H) 7.11-7.34 (m, 5H) 3.80 (s, 3H) 3.39 (m, 2H) 3.16 (t, J=11.12 Hz, 2H) 2.57 (d, J=7.07 Hz, 2H) 1.59-1.77 (m, 3H) 1.29-1.46 (m, 2H) 1.38 (s, 9H)

2-(4-Benzylpiperidin-1-yl)-4-hydroxy-5-methoxyisophthalonitrile

Using the procedure analogous to Example 188, 3-(4-benzylpiperidin-1-yl)-2,4-dicyano-6-methoxyphenyl tert-butyl carbonate (550 mg) was converted to 2-(4-benzylpiperidin-1-yl)-4-hydroxy-5-methoxyisophthalonitrile. To isolate the crude product from the reaction mixture, the mixture was evaporated to dryness. The remainder was cooled in an ice bath and water was added. The product was filtered and washed with ice cold water. Yield 267 mg $^1$H NMR (400 MHz, DMSO-d$_6$) ppm 11.64 (br s, 1H) 7.44 (s, 1H) 7.26-7.32 (m, 2H) 7.18-7.23 (m, 3H) 3.83 (s, 3H) 3.33-3.39 (m, 2H) 3.09-3.19 (m, 2H) 2.57 (d, J=6.78 Hz, 2H) 1.66 (m, 3H) 1.34 (m, 2H)

2-(4-Benzylpiperidin-1-yl)-4,5-dihydroxyisophthalonitrile

Using the procedure analogous to Example 188, 2-(4-benzylpiperidin-1-yl)-4-hydroxy-5-methoxyisophthalonitrile (269 mg) was converted to 2-(4-benzylpiperidin-1-yl)-4,5-dihydroxyisophthalonitrile. The crude product was crystallized from heptane/EtOAc (10/1). Yield 80 mg $^1$H NMR (400 MHz, DMSO-d$_6$) ppm 11.31 (br s, 1H) 10.60 (br s, 1H) 7.25-7.33 (m, 2H) 7.16-7.25 (m, 3H) 7.08 (s, 1H) 3.30 (d, J=1.00 Hz, 2H) 3.12 (t, J=1.00 Hz, 2H) 2.56 (d, J=6.57 Hz, 2H) 1.64 (d, J=10.11 Hz, 3H) 1.26-1.39 (m, 2H)

Example 205

4,5-Dihydroxy-2-(pentan-3-ylamino)isophthalonitrile tert-Butyl 2,4-dicyano-6-methoxy-3-(pentan-3-ylamino)phenyl carbonate Using the procedure analogous to Example 188, 3-bromo-2,4-dicyano-6-methoxyphenyl tert-butyl carbonate (706 mg) was converted to tert-butyl 2,4-dicyano-6-methoxy-3-(pentan-3-ylamino)phenyl carbonate. The crude product was chromatographed over silica gel using heptane/EtOAc solvent mixture. Yield 709 mg $^1$H NMR (400 MHz, DMSO-d$_6$) ppm 7.57 (s, 1H) 5.06 (d, J=9.60 Hz, 1H) 3.77-3.84 (m, 1H) 3.75 (s, 3H) 1.51-1.64 (m, 4H) 1.39 (s, 9H) 0.89 (t, J=7.58 Hz, 6H)

4-Hydroxy-5-methoxy-2-(pentan-3-ylamino)isophthalonitrile

Using the procedure analogous to Example 188, tert-butyl 2,4-dicyano-6-methoxy-3-(pentan-3-ylamino)phenyl carbonate (780 mg) was converted to 4-hydroxy-5-methoxy-2-(pentan-3-ylamino)isophthalonitrile. To isolate the product, the mixture was evaporated to dryness. The remainder was cooled in an ice bath and water was added. The product was filtered and washed with ice cold water Yield 551 mg $^1$H NMR (400 MHz, DMSO-d$_6$) ppm 11.61 (br s, 1H) 7.37 (s, 1H) 4.93 (d, J=9.60 Hz, 1H) 3.81-3.87 (m, 1H) 3.79 (s, 3H) 1.50-1.63 (m, 4H) 0.85-0.92 (m, 6H)

4,5-Dihydroxy-2-(pentan-3-ylamino)isophthalonitrile

Using the procedure analogous to Example 188, 4-hydroxy-5-methoxy-2-(pentan-3-ylamino)isophthalonitrile (540 mg) was converted to 4,5-dihydroxy-2-(pentan-3-ylamino)isophthalonitrile. The crude product was crystallized from heptane/EtOAc (7/3) and chromatographed over silica gel using heptane/EtOAc solvent mixture. Yield 64 mg $^1$H NMR (400 MHz, DMSO-d$_6$) ppm 11.29 (br s, 1H) 10.28 (br s, 1H) 7.02 (s, 1H) 4.73 (d, J=10.04 Hz, 1H) 3.75 (dt, J=10.16, 5.96 Hz, 1H) 1.46-1.59 (m, 4H) 0.88 (t, J=7.40 Hz, 6H)

Example 206

(E)-2-(4-Ethylbenzylideneamino)-4,5-dihydroxyisophthalonitrile

The preparation of 2-amino-4,5-dihydroxyisophthalonitrile is described in Example 188. 2-Amino-4,5-dihydroxyisophthalonitrile (100 mg), 4-ethylbenzaldehyde (306 mg) and ethanol (4 ml) were microwave-irradiated for 15 min at 125° C. The mixture was evaporated to dryness and the residue was triturated with heptane. The product was filtered and washed with heptane. Yield 14 mg $^1$H NMR (400 MHz, chloroform-d) ppm 8.52 (s, 1H) 7.88 (d, J=7.78 Hz, 2H) 7.33 (d, J=8.03 Hz, 2H) 7.19 (s, 1H) 2.73 (q, J=7.61 Hz, 2H) 1.27 (t, J=7.53 Hz, 3H)

Example 207

(E)-4,5-Dihydroxy-2-(4-methoxybenzylideneamino)isophthalonitrile

The preparation of 2-amino-4,5-dihydroxyisophthalonitrile is described in Example 188. 2-Amino-4,5-dihydroxyisophthalonitrile (100 mg), 4-methoxybenzaldehyde (306 mg) and ethanol (4 ml) were microwave-irradiated for 30 min at 130° C. The mixture was evaporated to dryness and the remainder was washed with heptane. The product was crystallized from heptane/EtOAc (3/1). Yield 46 mg $^1$H NMR (400 MHz, DMSO-d$_6$) ppm 10.94 (br s, 2H) 8.58 (s, 1H) 7.92 (d, J=8.78 Hz, 2H) 7.24 (s, 1H) 7.13 (d, J=8.53 Hz, 2H) 3.84 (s, 3H)

Example 208

(E)-2-(4-Fluorobenzylideneamino)-4,5-dihydroxyisophthalonitrile

The preparation of 2-amino-4,5-dihydroxyisophthalonitrile is described in Example 188. 2-Amino-4,5-dihydroxyisophthalonitrile (100 mg), 4-fluorobenzaldehyde (283 mg) and ethanol (4 ml) were microwave-irradiated for 30 min at 130° C. The mixture was evaporated to dryness and the remainder was triturated with heptane/EtOAc (3/1). The product was crystallized from heptane/EtOAc (3/1). Yield 56 mg $^1$H NMR (400 MHz, DMSO-$d_6$) ppm 11.03 (br s, 2H) 8.71 (s, 1H) 8.05 (dd, J=8.66, 5.65 Hz, 2H) 7.48 (t, J=9.03 Hz, 2H) 7.28 (s, 1H)

Example 209

4,5-Dihydroxy-2-tosylisophthalonitrile 4,5-Diisopropoxy-2-(p-tolylthio)isophthalonitrile 4,5-Diisopropoxy-2-(p-tolylthio)isophthalonitrile was prepared from 2-bromo-4,5-diisopropoxyisophthalonitrile (0.25 g) and 4-methylbenzenethiol (0.11 g) instead of 4-(trifluoromethyl)thiophenol as described in Example 142, except that the reaction mixture was heated at 60° C. for additional 2 h. After addition of water, 4,5-diisopropoxy-2-(p-tolylthio)isophthalonitrile was collected by filtration, washed with water, and dried in vacuum. Yield 0.28 g $^1$H NMR (400 MHz, DMSO-$d_6$) ppm 7.99 (s, 1H) 7.08-7.24 (m, 4H) 4.82-4.93 (m, 1H) 4.72-4.85 (m, 1H) 2.27 (s, 3H) 1.33 (d, 6H) 1.29 (d, 6H)

4,5-Diisopropoxy-2-tosylisophthalonitrile

To a mixture of 4,5-diisopropoxy-2-(p-tolylthio)isophthalonitrile (0.27 g) in DCM (4 ml) was added mCPBA (0.66 g) at room temperature. After 8 h, the solvent was evaporated. 1 M NaOH solution was added and solid material was collected, washed with 1 M NaOH, and dried in vacuum. Yield 0.29 g $^1$H NMR (400 MHz, DMSO-$d_6$) ppm 7.99 (s, 1H) 7.45 (m, 2H) 7.06 (m, 2H) 4.85-4.93 (m, 1H) 4.77-4.86 (m, 1H) 2.47-2.53 (s, 3H, overlap with the signal of the solvent) 1.33 (d, 6H) 1.29 (d, 6H) MS-ES m/z 399 (M+1)

4,5-Dihydroxy-2-tosylisophthalonitrile

The title compound was prepared from 4,5-diisopropoxy-2-tosylisophthalonitrile (0.29 g) instead of 4,5-diisopropoxy-2-(4-(trifluoromethyl)phenylthio)isophthalonitrile as described in Example 142. Yield 0.08 g $^1$H NMR (400 MHz, DMSO-$d_6$) ppm 7.90 (m, 2H) 7.53 (m, 2H) 7.33 (s, 1H) 2.41 (s 3H)

Example 210

4-(2,6-Dicyano-3,4-dihydroxyphenoxy)benzoic acid 4-(2,6-Dicyano-3,4-diisopropoxyphenoxy)benzoic acid 4-(2,6-Dicyano-3,4-diisopropoxyphenoxy)benzoic acid was prepared from 2-bromo-4,5-diisopropoxyisophthalonitrile (0.25 g) and 4-hydroxybenzoic acid (0.11 g) instead of 4-(trifluoromethyl)thiophenol as described in Example 142, except that 3 equivalents of cesium carbonate was used and the reaction mixture was heated at 80° C. for 35 h. After addition of water and 37% HCl until pH was acidic, 4-(2,6-dicyano-3,4-diisopropoxyphenoxy)benzoic acid was collected by filtration, washed with water, and dried in vacuum. Yield 0.24 g $^1$H NMR (400 MHz, DMSO-$d_6$) ppm 12.5-13.3 (br s, 1H) 8.03 (s, 1H) 7.93-8.02 (m, 2H) 7.07-7.16 (m, 2H) 4.86-4.94 (m, 1H) 4.77-4.85 (m, 1H) 1.34 (d, 6H) 1.31 (d, 6H)

4-(2,6-Dicyano-3,4-dihydroxyphenoxy)benzoic acid

The title compound was prepared from 4-(2,6-dicyano-3,4-diisopropoxyphenoxy)benzoic acid (0.24 g) instead of 4,5-diisopropoxy-2-(4-(trifluoromethyl)phenylthio)isophthalonitrile as described in Example 142. 4-(2,6-Dicyano-3,4-dihydroxyphenoxy)benzoic acid was purified by chromatography. Yield 0.050 g $^1$H NMR (400 MHz, CD$_3$OD) ppm 8.04-8.10 (m, 2H) 7.26 (s, 1H) 6.98-7.04 (m, 2H)

Example 211

2-(Benzo[d]thiazol-2-ylthio)-4,5-dihydroxyisophthalonitrile 2-(Benzo[d]thiazol-2-ylthio)-4,5-diisopropoxyisophthalonitrile 2-(Benzo[d]thiazol-2-ylthio)-4,5-diisopropoxyisophthalonitrile was prepared from 2-bromo-4,5-diisopropoxyisophthalonitrile (0.25 g) and 2-mercaptobenzothiazole (0.13 g) instead of 4-(trifluoromethyl)thiophenol as described in Example 142, except that the reaction mixture was heated at 80° C. for 33 h. After addition of water and 37% HCl until pH was acidic, 2-(benzo[d]thiazol-2-ylthio)-4,5-diisopropoxyisophthalonitrile was collected by filtration, washed with water, and dried in vacuum. Yield 0.27 g $^1$H NMR (400 MHz, DMSO-$d_6$) ppm 8.19 (s, 1H) 7.96-8.08 (m, 1H) 7.82-7.91 (m, 1H) 7.50 (m, 1) 7.41 (m, 1H) 4.92-5.01 (m, 1H) 4.83-4.89 (m, 1H) 1.35 (d, 6H) 1.33 (d, 6H)

2-(Benzo[d]thiazol-2-ylthio)-4,5-dihydroxyisophthalonitrile

The title compound was prepared from 2-(benzo[d]thiazol-2-ylthio)-4,5-diisopropoxyisophthalonitrile (0.26 g) instead of 4,5-diisopropoxy-2-(4-(trifluoromethyl)phenylthio)isophthalonitrile as described in Example 142. 2-(Benzo[d]thiazol-2-ylthio)-4,5-dihydroxyisophthalonitrile was purified by chromatography. Yield 0.035 g $^1$H NMR (400 MHz, CD$_3$OD) ppm 7.85 (m, 2H) 7.49 (m, 1H) 7.42 (s, 1H) 7.39 (m, 1H)

Example 212

2-(4-Fluorophenylthio)-4,5-dihydroxyisophthalonitrile 2-(4-Fluorophenylthio)-4,5-diisopropoxyisophthalonitrile 2-(4-Fluorophenylthio)-4,5-diisopropoxyisophthalonitrile was prepared from 2-bromo-4,5-diisopropoxyisophthalonitrile (0.30 g) and 4-fluorobenzenethiol (0.10 ml) instead of 4-(trifluoromethyl)thiophenol as described in Example 142. After addition of water, 2-(4-fluorophenylthio)-4,5-diisopropoxyisophthalonitrile was collected by filtration, washed with water, and dried in vacuum. Yield 0.33 g $^1$H NMR (400 MHz, DMSO-$d_6$) ppm 8.00 (s, 1H) 7.29-7.39 (m, 2H) 7.16-7.29 (m, 2H) 4.84-4.89 (m, 1H) 4.71-4.84 (m, 1H) 1.32 (d, 6H) 1.29 (d, 6H)

2-(4-Fluorophenylthio)-4,5-dihydroxyisophthalonitrile

The title compound was prepared from 2-(4-fluorophenylthio)-4,5-diisopropoxyisophthalonitrile (0.33 g) instead of 4,5-diisopropoxy-2-(4-(trifluoromethyl)phenylthio)isophthalonitrile as described in Example 142. 2-(4-Fluorophenylthio)-4,5-dihydroxyisophthalonitrile was purified by chromatography. Yield 0.11 g $^1$H NMR (400 MHz, DMSO-$d_6$) ppm 11.0-12.2 (br s 2H) 7.35 (s, 1H) 7.26-7.32 (m, 2H) 7.18-7.25 (m, 2H)

Example 213

2-(Biphenyl-4-ylmethyl)-4,5-dihydroxyisophthalonitrile 2-(Biphenyl-4-ylmethyl)-4,4,5,5-tetramethyl-1,3,2-dioxaborolane (655 mg), Pd(dppf)Cl$_2$ complex with CH$_2$Cl$_2$ (1:1) (0.09 equiv.) and sodium hydrogen carbonate (4 equiv.) were successively added to a mixture of 2-bromo-4,5-diisopropoxyisophthalonitrile (650 mg) in acetonitrile, ethanol and water. The reaction mixture was microwave-irradiated for 3-4 h at 130° C. After cooling, EtOAc was added and the mixture was filtered through celite. The organic phase was washed with 1 M NaOH solution, water and brine, dried (Na$_2$SO$_4$), filtered and evaporated to dryness. The residue was purified by reversed phase column chromatography to yield 2-(biphenyl-4-ylmethyl)-4,5-diisopropoxyisophthalonitrile. To a mixture of 2-(biphenyl-4-ylmethyl)-4,5-diisopropoxyisophthalonitrile in DCM under nitrogen atmosphere was added 1 M boron tribromide solution in DCM (2.5 equiv.) at 0° C. The reaction mixture was stirred at 0° C. for 1-2 h and poured into methanol. After evaporation of the solvent, 4 M HCl solution was added and the mixture was stirred for 30 min at 0° C. to give solid product which was filtered, washed with water and dried in vacuum. Yield 217 mg $^1$H NMR (400 MHz, DMSO-$d_6$) ppm 11.51 (br s, 1H) 11.02 (br s, 1H) 7.59-7.66 (m, 4H) 7.42-7.48 (m, 2H) 7.32-7.38 (m, 1H) 7.31 (s, 1H) 7.24-7.29 (m, 2H) 4.20 (s, 2H)

Example 214

2-(4-Chloro-2-methylbenzyl)-4,5-dihydroxyisophthalonitrile

The title compound was prepared from 2-bromo-4,5-diisopropoxyisophthalonitrile (650 mg) and 2-(4-chloro-2-methylbenzyl)-4,4,5,5-tetramethyl-1,3,2-dioxaborolane (1072 mg) instead of 2-(biphenyl-4-ylmethyl)-4,4,5,5-tetramethyl-1,3,2-dioxaborolane as described in Example 213. Yield 187 mg $^1$H NMR (400 MHz, DMSO-$d_6$) ppm 11.16 (br s, 2H) 7.32 (s, 2H) 7.13 (dd, 1H) 6.50 (d, 1H) 4.07 (s, 2H) 2.38 (s, 3H)

Example 215

2-(2-Ethylbenzyl)-4,5-dihydroxyisophthalonitrile

The title compound was prepared from 2-bromo-4,5-diisopropoxyisophthalonitrile (750 mg) and 2-(2-ethylbenzyl)-4,4,5,5-tetramethyl-1,3,2-dioxaborolane (1028 mg) instead of 2-(biphenyl-4-ylmethyl)-4,4,5,5-tetramethyl-1,3,2-dioxaborolane as described in Example 213. Yield 111 mg $^1$H NMR (400 MHz, DMSO-$d_6$) ppm 11.26 (br s, 2H) 7.32 (s, 1H) 7.23 (dd, 1H) 7.17 (td, 1H) 7.06 (td, 1H) 6.43 (dd, 1H) 4.16 (s, 2H) 2.75 (q, 2H) 1.22 (t, 3H)

Example 216

2-(2,3-Dihydro-1H-inden-5-yloxy)-4,5-dihydroxyisophthalonitrile

The title compound was prepared from 2-bromo-4,5-diisopropoxyisophthalonitrile (400 mg) and 5-indanol (183 mg) instead of 4-(trifluoromethyl)thiophenol as described in Example 142 followed by demethylation as described in Example 142. Reaction conditions for the reaction of 2-bromo-4,5-diisopropoxyisophthalonitrile with 5-indanol: 3 d at room temperature. 2-(2,3-Dihydro-1H-inden-5-yloxy)-4,5-dihydroxyisophthalonitrile was purified by reversed phase column chromatography. Yield 150 mg $^1$H NMR (400 MHz, DMSO-$d_6$) ppm 10.97 (br s, 2H) 7.27 (s, 1H) 7.17 (d, 1H) 6.77 (d, 1H) 6.67 (dd, 1H) 2.82 (q, 4H) 1.97-2.07 (m, 2H)

Example 217

Enantiomer A and enantiomer B of 4,5-dihydroxy-2-(p-tolylsulfinyl)isophthalonitrile The preparation of 4,5-dihydroxy-2-(p-tolylsulfinyl)isophthalonitrile is described in Example 156. Sulphoxide enantiomers of 4,5-dihydroxy-2-(p-tolylsulfinyl)isophthalonitrile were separated using preparative chiralpak IC column with isocratic elution 25% ethanol (0.2% TFA) in n-hexane (0.1% TFA) with a flow rate of 20 ml/min. Retention time of enantiomer A: 9.99 min. Retention time of enantiomer B: 21.03 min.

Example 218

2-((Cyclohexylmethyl)amino)-4,5-dihydroxyisophthalonitrile tert-Butyl 2,4-dicyano-3-((cyclohexylmethyl)amino)-6-methoxyphenyl carbonate Using the procedure analogous to Example 188, 3-bromo-2,4-dicyano-6-methoxyphenyl tert-butyl carbonate (706 mg) was converted to tert-butyl 2,4-dicyano-3-((cyclohexylmethyl)amino)-6-methoxyphenyl carbonate. The product was triturated with hot 90% ethanol. Yield 355 mg $^1$H NMR (400 MHz, DMSO-$d_6$) ppm 7.51 (s, 1H) 5.94 (t, J=6.27 Hz, 1H) 3.74 (s, 3H) 3.35 (t, J=6.65 Hz, 2H) 1.64-1.77 (m, 4H) 1.51-1.64 (m, 2H) 1.39 (s, 9H) 1.12-1.21 (m, 3H) 0.86-0.97 (m, 2H)

2-((Cyclohexylmethyl)amino)-4-hydroxy-5-methoxyisophthalonitrile

Using the procedure analogous to Example 188, tert-butyl 2,4-dicyano-3-((cyclohexylmethyl)amino)-6-methoxyphenyl carbonate (355 mg) was converted to 2-((cyclohexylmethyl)amino)-4-hydroxy-5-methoxyisophthalonitrile. Yield 156 mg $^1$H NMR (400 MHz, DMSO-$d_6$) ppm 11.50 (br s, 1H) 7.32 (s, 1H) 5.84 (t, J=6.02 Hz, 1H) 3.77 (s, 3H) 3.36 (t, J=6.53 Hz, 2H) 1.70 (t, J=12.92 Hz, 4H) 1.51-1.64 (m, 2H) 1.09-1.25 (m, 3H) 0.82-0.97 (m, 2H)

2-((Cyclohexylmethyl)amino)-4,5-dihydroxy-isophthalonitrile

Using the procedure analogous to Example 188, 2-((cyclohexylmethyl)amino)-4-hydroxy-5-methoxyisophthalonitrile (156 mg) was converted to 2-((cyclohexylmethyl)amino)-4,5-dihydroxyisophthalonitrile. The crude product was triturated with toluene/EtOAc (3:2). Yield 65 mg $^1$H NMR (400 MHz, DMSO-$d_6$) ppm 11.19 (br s, 1H) 9.81 (br s, 1H) 6.98 (s, 1H) 5.60 (t, J=6.06 Hz, 1H) 3.25-3.35 (2H, overlap with the signal of the solvent) 1.70 (t, J=13.39 Hz, 4H) 1.46-1.64 (m, 2H) 1.05-1.25 (m, 3H) 0.82-0.98 (m, 2H) MS-ES m/z 272 (M+1)

Example 219

4,5-Dihydroxy-2-(4-phenoxyphenylthio)isophthalonitrile 2-(4-Hydroxyphenylthio)-4,5-diisopropoxyisophthalonitrile 2-(4-Hydroxyphenylthio)-4,5-diisopropoxyisophthalonitrile was prepared from 2-bromo-4,5-diisopropoxyisophthalonitrile (0.25 g) and 4-hydroxythiophenol (0.10 g) instead of 4-(trifluoromethyl)thiophenol as described in Example 142. After addition of water, 2-(4-hydroxyphenylthio)-4,5-diisopropoxyisophthalonitrile was collected by filtration, washed with water, and dried in vacuum. Yield 0.27 g $^1$H NMR (400 MHz, DMSO-$d_6$) ppm 9.81 (br s, 1H) 7.93 (s, 1H) 7.25 (m, 2H) 6.76 (m, 2H) 4.80-4.87 (m, 1H) 4.73-4.81 (m, 1H) 1.30 (d, 6H) 1.28 (d, 6H)

4,5-Dihydroxy-2-(4-phenoxyphenylthio)isophthalonitrile

To a mixture of 2-(4-hydroxyphenylthio)-4,5-diisopropoxyisophthalonitrile (0.1 g), copper(II) acetate (0.05 g), triethylamine (0.19 ml) in DCM (2.5 ml) containing 4 Å molecular sievers (0.1 g) was added phenylboronic acid (0.21 g) in portions. After stirring for 14 d at room temperature, the product was extracted to EtOAc and washed with 1 M HCl, 1 M NaOH, brine, and water. The organic phase was collected, dried (Na$_2$SO$_4$), and filtrated. The solvent was evaporated to yield 4,5-diisopropoxy-2-(4-phenoxyphenylthio)isophthalonitrile (0.090 g). The title compound was prepared from 4,5-diisopropoxy-2-(4-phenoxyphenylthio)isophthalonitrile instead of 4,5-diisopropoxy-2-(4-(trifluoromethyl)phenylthio)isophthalonitrile as described in Example 142. 4,5-Dihydroxy-2-(4-phenoxyphenylthio)isophthalonitrile was purified by chromatography. Yield 0.11 g $^1$H NMR (400 MHz, DMSO-$d_6$) ppm 7.36-7.43 (m, 2H) 7.32 (s, 1H) 7.25-7.31 (m, 2H) 7.12-7.20 (m, 1H) 6.95-7.05 (m, 4H)

Example 220

4,5-Dihydroxy-2-(pyridin-3-yl)isophthalonitrile 4,5-Diisopropoxyisophthalonitrile A flask was charged with 4,5-dihydroxyisophthalonitrile (1.29 g), potassium carbonate (3.34 g), 2-iodopropane (2.41 ml) and DMF (20 ml). The mixture was stirred at 85° C. for 6.5 h. The mixture was stirred overnight at room temperature. Another portion of 2-iodopropane (0.80 ml) was added and the mixture was stirred at 85° C. for 6 h. The mixture was allowed to cool to room temperature. Water and EtOAc were added. The aqueous phase was extracted with EtOAc. The combined organic phases were washed with 1 M NaOH, dried (Na$_2$SO$_4$) and solvents were evaporated. The crude product was recrystallized from absolute ethanol. Yield 1.03 g $^1$H NMR (400 MHz, DMSO-$d_6$) ppm 7.91-7.93 (m, 1H) 7.87-7.91 (m, 1H) 4.72-4.86 (m, 2H) 1.26-1.33 (m, 12H)

4,5-Diisopropoxy-2-(pyridin-3-yl)isophthalonitrile

A pressure tube was charged with 4,5-diisopropoxyisophthalonitrile (0.244 g), potassium carbonate (0.207 g), triphenylphosphine (0.052 g), palladium(II) acetate (0.011 g), 2-ethylhexanoic acid (0.016 ml), xylenes (3 ml) and 3-bromopyridine (0.12 ml). Air atmosphere was removed and the sealed reaction vessel was heated to 130° C. and stirred for 22 h. The reaction mixture was allowed to cool to room temperature and then diluted with EtOAc. The mixture was filtered through a pad of celite and solvents were removed in reduced pressure. The crude product was purified with column chromatography (SiO$_2$, 20-50% EtOAc/heptane). Yield 0.14 g $^1$H NMR (400 MHZ, chloroform-d) ppm 8.70-8.80 (m, 2H) 7.83 (m, 1H) 7.47 (m, 1H) 7.37 (d, 1H) 4.95 (m, 1H) 4.65 (m, 1H) 1.45 (d, 6H) 1.42 (d, 6H)

4,5-Dihydroxy-2-(pyridin-3-yl)isophthalonitrile

The title compound was prepared from 4,5-diisopropoxy-2-(pyridin-3-yl)isophthalonitrile (0.14 g) instead of 4,5-diisopropoxy-2-(4-(trifluoromethyl)phenylthio)isophthalonitrile as described in Example 142. 4,5-Dihydroxy-2-(pyridin-3-yl)isophthalonitrile was purified by chromatography. Yield 0.039 g $^1$H NMR (400 MHz, DMSO-$d_6$) ppm 11.0-12.0 (br s, 2H) 8.70 (m, 2H) 7.97 (m, 1H) 7.58 (m, 1H) 7.39 (s, 1H)

Example 221

4,5-Dihydroxy-2-(4-(2,2,2-trifluoroethyl)benzyl)isophthalonitrile

Methyl 4-(2,2,2-trifluoroethyl)benzoate 1,1,1-Trifluoro-2-iodoethane (5.5 ml), xantphos (1.6 g), Pd$_2$(dba)$_3$ (1.3 g) and cesium carbonate (36.2 g) were added to a solution of 4-(methoxycarbonyl)phenylboronic acid (5 g) in 1,4-dioxane (75 ml) and water (9 ml) under argon atmosphere. The reaction mixture was heated at 80° C. for 24 h. The reaction was quenched with water and the mixture extracted with EtOAc. The organic layer was washed with brine, dried (Na$_2$SO$_4$) and concentrated under reduced pressure. The crude product was purified by flash chromatography. Yield 4.56 g $^1$H NMR (400 MHz, chloroform-d) ppm 8.03 (d, J=8.4 Hz, 2H) 7.38 (d, J=8.4 Hz, 2H) 3.92 (s, 3H) 3.42 (q, J=10.8 Hz, 2H)

(4-(2,2,2-Trifluoroethyl)phenyl)methanol

Methyl 4-(2,2,2-trifluoroethyl)benzoate (11.0 g) dissolved in THF (40 ml) was added to a suspension of lithium aluminum hydride (2.3 g) in THF (100 ml) at 0° C. The reaction mixture was stirred for 1 h at room temperature and then the reaction was quenched with saturated aqueous sodium sulfate solution. The reaction mass was filtered through celite. The filtrate was evaporated to remove THF, extracted with EtOAc and washed with water. The organic layer was dried (Na$_2$SO$_4$) and concentrated under vacuum. Yield 9.6 g $^1$H NMR (400 MHz, chloroform-d) ppm 7.37 (d, J=8.0 Hz, 2H) 7.30 (d, J=8.0 Hz, 2H) 4.71 (d, J=5.6 Hz, 2H) 3.37 (q, J=10.8 Hz, 2H) 1.67 (t, J=5.6 Hz, 1H)

1-(Chloromethyl)-4-(2,2,2-trifluoroethyl)benzene

Phosphorus pentachloride (8.2 g) was added in portions to a solution of (4-(2,2,2-trifluoroethyl)phenyl)methanol (5 g) in chloroform (100 ml) at 0° C. After stirring for 1 h at 0° C., the reaction mixture was poured into cold water and extracted with DCM. The organic layer was dried (Na$_2$SO$_4$) and concentrated under vacuum. Yield 5.2 g $^1$H NMR (400 MHz, chloroform-d) ppm 7.39 (d, J=8.0 Hz, 2H) 7.30 (d, J=8.0 Hz, 2H) 4.59 (s, 2H) 3.37 (q, J=10.4 Hz, 2H)

4,4,5,5-Tetramethyl-2-(4-(2,2,2-trifluoroethyl)benzyl)-1,3,2-dioxaborolane

A flask containing magnesium (9.0 g) was heated at 250° C. for 30 min under vacuum. After cooling to room temperature, THF (300 ml) was added and heated at 60° C. for 30 min. The flask was again cooled to room temperature and 4,4,5,5-tetramethyl-1,3,2-dioxaborolane (16.3 ml) was added slowly. A solution of 1-(chloromethyl)-4-(2,2,2-trifluoroethyl)benzene (15.6 g) in THF (60 ml) was added slowly under nitrogen atmosphere. The reaction mixture was stirred at room temperature for 8 h. The reaction mass was poured into ice water and filtered through celite. The filtrate was extracted with EtOAc and washed with brine. The organic layer was dried (Na$_2$SO$_4$) and concentrated under vacuum. The crude product was purified by column chromatography. Yield 9.5 g $^1$H NMR (400 MHz, chloroform-d) ppm 7.17 (br s, 4H) 3.31 (q, J=10.8 Hz, 2H) 2.29 (s, 2H) 1.24 (s, 12H)

4-Hydroxy-5-methoxy-2-(4-(2,2,2-trifluoroethyl)benzyl)isophthalonitrile 4,4,5,5-Tetramethyl-2-(4-(2,2,2-trifluoroethyl)benzyl)-1,3,2-dioxaborolane (498 mg), Pd(dppf)Cl$_2$ complex with CH$_2$Cl$_2$ (1:1) (75 mg) and sodium hydrogen carbonate (350 mg) were added to a solution of 2-bromo-4-hydroxy-5-methoxyisophthalonitrile (210 mg) in ethanol (1 ml) and water (10 ml) under nitrogen atmosphere and refluxed for 4 h. The reaction mixture was filtered through celite. The filtrate was evaporated to dryness. The crude reaction mass was acidified with 1 N HCl and extracted with DCM. The organic layer was dried (Na$_2$SO$_4$) and concentrated under reduced pressure. The product was purified by flash chromatography. Yield 88 mg $^1$H NMR (400 MHz, chloroform-d) ppm 7.35 (d, J=8.0 Hz, 2H) 7.23 (d, J=8.0 Hz, 2H) 7.21 (s, 1H) 6.70 (br s, 1H) 4.31 (s, 2H) 3.97 (s, 3H) 3.33 (q, J=10.8 Hz, 2H)

4,5-Dihydroxy-2-(4-(2,2,2-trifluoroethyl)benzyl)isophthalonitrile

A solution of boron tribromide in DCM (3 M, 2.5 ml) was added to a solution of 4-hydroxy-5-methoxy-2-(4-(2,2,2-trifluoroethyl)benzyl)isophthalonitrile (88 mg) in DCM (10 ml) at 0° C. The reaction mixture was stirred at room temperature for 3 h. The reaction was quenched with methanol and the mixture evaporated to dryness. The crude product was treated with water and extracted with EtOAc. The organic layer was dried (Na$_2$SO$_4$) and concentrated under reduced pressure. Yield 60 mg $^1$H NMR (400 MHz, DMSO-d$_6$) ppm 7.28-7.33 (m, 3H) 7.17 (d, J=8.0 Hz, 2H) 4.14 (s, 2H) 3.59 (q, J=10.8 Hz, 2H)

Example 222

4,5-Dihydroxy-2-(4-methyl-2-(trifluoromethyl)benzyl)isophthalonitrile

Methyl 4-bromo-2-(trifluoromethyl)benzoate

4-Bromo-2-trifluoromethyl benzoic acid (25 g) was dissolved in methanol (300 ml) and cooled to 0° C. Thionyl chloride (88.8 g) was added and the mixture was refluxed for 18 h.

The reaction mixture was concentrated under vacuum. Yield 25.8 g $^1$H NMR (400 MHz, chloroform-d) ppm 7.89 (d, J=1.6 Hz, 1H) 7.75 (dd, J=8.0, 1.6 Hz, 1H) 7.68 (d, J=8.0 Hz, 1H) 3.93 (s, 3H)

Methyl 4-methyl-2-(trifluoromethyl)benzoate

Trimethylboroxine (16.2 g), tetrakis(triphenylphosphine) palladium(0) (8.2 g) and cesium carbonate (69.0 g) were added to a solution of methyl 4-bromo-2-(trifluoromethyl) benzoate (20.0 g) in 1,4-dioxane (500 ml) under argon atmosphere. The reaction mixture was heated at 120° C. for 18 h. The mixture was diluted with water and extracted with EtOAc. The organic layer was washed with water, dried (Na$_2$SO$_4$) and concentrated at 40° C. under vacuum. The crude product was purified by column chromatography. Yield 12.4 g $^1$H NMR (400 MHz, chloroform-d) ppm 7.71 (d, J=8.0 Hz, 1H) 7.55 (s, 1H) 7.40 (d, J=8.0 Hz, 1H) 3.92 (s, 3H) 2.45 (s, 3H)

(4-Methyl-2-(trifluoromethyl)phenyl)methanol (4-Methyl-2-(trifluoromethyl)phenyl)methanol was prepared using the procedure described in Example 221 starting from methyl 4-methyl-2-(trifluoromethyl)benzoate (24.0 g). Yield 17.9 g $^1$H NMR (400 MHz, chloroform-d) ppm 7.56 (d, J=8.0 Hz, 1H) 7.45 (s, 1H) 7.35 (d, J=8.0 Hz, 1H) 4.81 (s, 2H) 2.40 (s, 3H) 1.82 (br s, 1H)

1-(Chloromethyl)-4-methyl-2-(trifluoromethyl)benzene 1-(Chloromethyl)-4-methyl-2-(trifluoromethyl)benzene was prepared using the procedure described in Example 221 starting from (4-methyl-2-(trifluoromethyl)phenyl)methanol (28.9 g) and phosphorus pentachloride (79.0 g). Yield 24.1 g $^1$H NMR (400 MHz, chloroform-d) ppm 7.50 (d, J=8.0 Hz, 1H) 7.47 (s, 1H) 7.37 (d, J=8.0 Hz, 1H) 4.72 (s, 2H) 2.72 (s, 3H)

4,4,5,5-Tetramethyl-2-(4-methyl-2-(trifluoromethyl) benzyl)-1,3,2-dioxaborolane 4,4,5,5-Tetramethyl-2-(4-methyl-2-(trifluoromethyl)benzyl)-1,3,2-dioxaborolane was prepared using the procedure described in Example 221 starting from 1-(chloromethyl)-4-methyl-2-(trifluoromethyl)benzene (12 g) and 4,4,5,5-tetramethyl-1,3,2-dioxaborolane (10 g). The crude product was purified by flash chromatography. Yield 7.2 g $^1$H NMR (400 MHz, chloroform-d) ppm 7.38 (s, 1H) 7.21 (d, J=8.4 Hz, 1H) 7.15 (d, J=8.4 Hz, 1H) 2.41 (s, 2H) 2.33 (s, 3H) 1.17 (s, 12H)

4-Hydroxy-5-methoxy-2-(4-methyl-2-(trifluoromethyl)benzyl)isophthalonitrile

4-Hydroxy-5-methoxy-2-(4-methyl-2-(trifluoromethyl) benzyl)isophthalonitrile was prepared using the procedure described in Example 221 starting from 2-bromo-4-hydroxy-5-methoxyisophthalonitrile (0.40 g) and 4,4,5,5-tetramethyl-2-(4-methyl-2-(trifluoromethyl) benzyl)-1,3,2-dioxaborolane (0.71 g). The crude product was purified by flash chromatography. Yield 33 mg $^1$H NMR (400 MHz, DMSO-d$_6$) ppm 7.54 (s, 1H) 7.33 (d, J=8.4 Hz, 1H) 6.68 (s, 1H) 6.66 (d, J=8.4 Hz, 1H) 4.07 (s, 2H) 3.63 (s, 3H) 2.34 (s, 3H)

4,5-Dihydroxy-2-(4-methyl-2-(trifluoromethyl)benzyl)isophthalonitrile

The title compound was prepared using the procedure described in Example 221 starting from 4-hydroxy-5-methoxy-2-(4-methyl-2-(trifluoromethyl)benzyl)isophthalonitriie (33 mg). Yield 22 mg $^1$H NMR (400 MHz, DMSO-d$_6$) ppm 7.60 (s, 1H) 7.34 (d, J=8.0 Hz, 1H) 7.28 (s, 1H) 6.56 (d, J=8.0 Hz, 1H) 4.27 (s, 2H) 2.35 (s, 3H)

Example 223

4,5-Dihydroxy-2-((4-(morpholine-4-carbonyl)phenyl)thio)isophthalonitrile (Disulfanediylbis(4,1-phenylene))bis(morpholinoethanone)

Oxalyl chloride (0.7 ml) and catalytic DMF were added to a solution of 4,4'-disulfanediyldibenzoic acid (0.5 g) in THF (10 ml) at 0° C. The reaction mixture was stirred at room temperature for 1 h under nitrogen atmosphere. The solvent was evaporated under reduced pressure. The crude product was dissolved in DCM (10 ml) and cooled to 0° C. Triethylamine (2.26 ml) and morpholine (0.7 ml) were added and the mixture was stirred at room temperature for 2 h. The reaction was quenched with water and the mixture extracted with DCM. The organic layer was washed with water, dried (Na$_2$SO$_4$) and concentrated under vacuum. Yield 650 mg $^1$H NMR (400 MHz, DMSO-d$_6$) ppm 7.60 (d, J=8.4 Hz, 4H) 7.44 (d, J=8.4 Hz, 4H) 3.57 (br s, 16H)

(4-Mercaptophenyl)(morpholino)methanone

Sodium borohydride (139 mg) was added to a solution of (disulfanediylbis(4,1-phenylene))bis(morpholinoethanone) (0.65 g) in ethanol (10 ml) under nitrogen atmosphere and stirred at room temperature for 6 h. The reaction was quenched with saturated aqueous ammonium chloride solution. Ethanol was removed by distillation and the aqueous solution was extracted with EtOAc. The organic layer was washed with brine, dried (Na$_2$SO$_4$) and concentrated under vacuum. Yield 300 mg (crude)

$^1$H NMR (400 MHz, chloroform-d) ppm 7.30 (br s, 5H) 3.68 (br s, 8H)

4,5-Diisopropoxy-2-((4-(morpholine-4-carbonyl) phenyl)thio)isophthalonitrile

2-Bromo-4,5-diisopropoxyisophthalonitrile (270 mg) and (4-mercaptophenyl)(morpholino)methanone (187 mg) were dissolved in dry toluene (10 ml) under nitrogen atmosphere. Diisopropylamine (0.23 ml), DPEPhos (34 mg) and Pd$_2$(dba)$_3$ (38 mg) were added. The reaction mixture was heated at 110° C. for 12 h. Water was added to quench the reaction and the mixture was extracted with EtOAc. The organic layer was washed with brine, dried (Na$_2$SO$_4$) and concentrated under vacuum. The crude product was purified by flash chromatography. Yield 200 mg $^1$H NMR (400 MHz, DMSO-d$_6$) ppm 8.06 (s, 1H) 7.39 (d, J=8.4 Hz, 2H) 7.22 (d, J=8.4 Hz, 2H) 4.79-4.92 (m, 2H) 3.57 (br s, 8H) 1.34 (d, J=6.4 Hz, 6H) 1.30 (d, J=6.0 Hz, 6H)

4,5-Dihydroxy-2-((4-(morpholine-4-carbonyl)phenyl)thio)isophthalonitrile

The title compound was prepared from 4,5-diisopropoxy-2-((4-(morpholine-4-carbonyl)phenyl)thio)isophthalonitrile (160 mg) instead of 4-hydroxy-5-methoxy-2-(4-(2,2,2-trifluoroethyl)benzyl)isophthalonitrile as described in Example 221. Yield 60 mg $^1$H NMR (400 MHz, DMSO-d$_6$) ppm 7.36-7.40 (m, 3H) 7.18 (d, J=8.4 Hz, 2H) 3.56 (br s, 8H)

Example 224

4,5-Dihydroxy-2-(methyl(p-tolyl)amino)isophthalonitrile 4,5-Diisopropoxy-2-(methyl(p-tolyl)amino)isophthalonitrile N,4-dimethylaniline (124 mg), palladium(II) acetate (21 mg), rac-2,2'-bis(diphenylphosphino)-1,1'-binaphthalene (87 mg) and cesium carbonate (911 mg) were added to a solution of 2-bromo-4,5-diisopropoxyisophthalonitrile (300 mg) in THF (15 ml) under argon atmosphere and heated at 75° C. for 16 h. The reaction was quenched with water and the mixture extracted with EtOAc. The organic layer was washed with water, dried (Na$_2$SO$_4$) and concentrated under reduced pressure. The crude product was purified by column chromatography. Yield 130 mg $^1$H NMR (400 MHz, chloroform-d) ppm 7.24 (s, 1H) 7.04 (d, J=8.4 Hz, 2H) 6.56 (d, J=8.4 Hz, 2H) 4.86-4.92 (m, 1H) 4.53-4.58 (m, 1H) 3.39 (s, 3H) 2.26 (s, 3H) 1.34-1.41 (m, 12H)

4,5-Dihydroxy-2-(methyl(p-tolyl)amino)isophthalonitrile

The title compound was prepared from 4,5-diisopropoxy-2-(methyl(p-tolyl)amino)isophthalonitrile (120 mg) instead of 4-hydroxy-5-methoxy-2-(4-(2,2,2-trifluoroethyl)benzyl) isophthalonitrile as described in Example 221. 4,5-Dihydroxy-2-(methyl(p-tolyl)amino)isophthalonitrile was purified by flash chromatography. Yield 35 mg $^1$H NMR (400 MHz, DMSO-$d_6$) ppm 7.29 (s, 1H) 7.00 (d, J=8.4 Hz, 2H) 6.46 (d, J=8.4 Hz, 2H) 3.23 (s, 3H) 2.20 (s, 3H)

Example 225

4,5-Dihydroxy-2-((6-methoxynaphthalen-2-yl)methyl)isophthalonitrile

6-Methoxy-2-naphthaldehyde n-Butyllithium (18.5 ml) was added slowly to a solution of 2-bromo-6-methoxynaphthalene (10.0 g) in diethyl ether (200 ml) at −78° C. The reaction mixture was stirred at −78° C. for 1 h. DMF (3.25 ml) was added dropwise and the mixture was stirred again for 30 min. The reaction mixture was allowed to warm to 0° C. The reaction was quenched with saturated aqueous ammonium chloride solution and the mixture extracted with EtOAc. The organic layer was washed with water, dried ($Na_2SO_4$) and concentrated at 40° C. under vacuum. The crude product was purified by column chromatography. Yield 7.4 g $^1$H NMR (400 MHz, chloroform-d) ppm 10.10 (s, 1H) 8.26 (s, 1H) 7.88-7.94 (m, 2H) 7.81 (d, J=8.4 Hz, 1H) 7.15-7.24 (m, 2H) 3.91 (s, 3H)

(6-Methoxynaphthalen-2-yl)methanol

Sodium borohydride (1.8 g) was added in portions to a solution of 6-methoxy-2-naphthaldehyde (7.4 g) in methanol (80 ml) at 0° C. The reaction mixture was stirred at room temperature for 1.5 h and the reaction was quenched with saturated aqueous ammonium chloride solution. Methanol was removed under vacuum and the aqueous solution was extracted with EtOAc. The organic layer was washed with water, dried ($Na_2SO_4$) and concentrated at 40° C. under vacuum. The crude product was purified by flash chromatography. Yield 7.1 g $^1$H NMR (400 MHz, chloroform-d) ppm 7.72-7.77 (m, 3H) 7.45 (d, J=8.8 Hz, 1H) 7.09-7.19 (m, 2H) 4.82 (d, J=6.0 Hz, 2H) 3.93 (s, 3H) 1.70 (t, J=6.0 Hz, 1H)

2-(Chloromethyl)-6-methoxynaphthalene 2-(Chloromethyl)-6-methoxynaphthalene was prepared using the procedure described in Example 221 starting from (6-methoxynaphthalen-2-yl)methanol (6.0 g) and phosphorus pentachloride (9.95 g). Yield 5.0 g $^1$H NMR (400 MHz, chloroform-d) ppm 7.71-7.79 (m, 3H) 7.47 (d, J=8.8 Hz, 1H) 7.12-7.18 (m, 2H) 4.74 (s, 2H) 3.93 (s, 3H)

2-((6-Methoxynaphthalen-2-yl)methyl)-4,4,5,5-tetramethyl-1,3,2-dioxaborolane 2-((6-Methoxynaphthalen-2-yl)methyl)-4,4,5,5-tetramethyl-1,3,2-dioxaborolane was prepared using the procedure described in Example 221 starting from 2-(chloromethyl)-6-methoxynaphthalene (15.2 g) and 4,4,5,5-tetramethyl-1,3,2-dioxaborolane (16.0 ml). Yield 18.9 g $^1$H NMR (400 MHz, chloroform-d) ppm 7.60-7.68 (m, 2H) 7.55 (s, 1H) 7.30 (d, J=8.0 Hz, 1H) 7.07-7.10 (m, 2H) 3.90 (s, 3H) 2.42 (s, 2H) 1.23 (s, 12H)

5-(Benzyloxy)-4-hydroxy-2-((6-methoxynaphthalen-2-yl)methyl)isophthalonitrile 2-((6-Methoxynaphthalen-2-yl)methyl)-4,4,5,5-tetramethyl-1,3,2-dioxaborolane (700 mg), Pd(dppf)$Cl_2$ complex with $CH_2Cl_2$ (1:1) (83 mg) and sodium carbonate (493 mg) were added to a solution of 5-(benzyloxy)-2-bromo-4-hydroxyisophthalonitrile (300 mg) in isopropanol (2.5 ml) and water (10 ml) under nitrogen atmosphere and refluxed for 1.5 h. The reaction mixture was filtered through celite. The filtrate was evaporated to dryness. The crude reaction mass was acidified with 1 N HCl and extracted with DCM. The organic layer was dried ($Na_2SO_4$) and concentrated under reduced pressure. The product was purified by flash chromatography. Yield 450 mg (crude)

$^1$H NMR (400 MHz, chloroform-d) ppm 7.63-7.73 (m, 3H) 7.37-7.48 (m, 6H) 7.27 (s, 1H) 7.08-7.14 (m, 2H) 6.86 (br s, 1H) 5.15 (s, 2H) 4.43 (s, 2H) 3.90 (s, 3H)

4,5-Dihydroxy-2-((6-methoxynaphthalen-2-yl)methyl)isophthalonitrile

Palladium on carbon (10%, 300 mg) was added to a solution of 5-(benzyloxy)-4-hydroxy-2-((6-methoxynaphthalen-2-yl)methyl)isophthalonitrile (450 mg) in ethanol (20 ml) and stirred under hydrogen atmosphere (1 atm) for 30 min. The reaction mixture was filtered through celite. The filtrate was concentrated under reduced pressure. The crude product was purified by reverse phase HPLC. Yield 75 mg $^1$H NMR (400 MHz, DMSO-$d_6$) ppm 7.72-7.79 (m, 2H) 7.50 (s, 1H) 7.26-7.33 (m, 3H) 7.13 (dd, J=8.4, 1.6 Hz, 1H) 4.28 (s, 2H) 3.85 (s, 3H)

As already mentioned hereinbefore, the compounds of formula I show interesting pharmacological properties, namely they exhibit COMT inhibiting activity and provide in levodopa therapy an improved levodopa concentration in plasma. Said properties are demonstrated with the pharmacological tests presented below.

Experiment 1

Determination of COMT Inhibiting Activity In Vitro

The inhibitory potency was determined by measuring recombinant human soluble COMT (S-COMT) activity at various compound concentrations. COMT activity measurements were performed according to the method published in Kurkela, M. et al. *Analytical Biochemistry*, 331 (2004) 198 with slight modifications according to Assay 1 or Assay 2 described below.

Assay 1

Recombinant human S-COMT (12 nM) was preincubated with the COMT inhibitor and 400 μM S-adenosyl-L-methionine in 100 mM $Na_2HPO_4$ buffer, pH 7.4, containing 5 mM $MgCl_2$ for 60 min at 37° C. The reaction was started with the addition of the substrate esculetin for a final concentration of 2 M and the production of O-methylated esculetin was followed with the FlexStation fluorescence plate reader (Molecular Probes, USA) using excitation at 355 nm and emission at 460 nm. The inhibitor dissociation constant, $K_i$, of the studied compounds was calculated using the Morrison equation, which takes the tight binding inhibition into account (Copeland, R. A. *Evaluation of Enzyme Inhibitors in Drug Discovery. A Guide for Medicinal Chemists and Pharmacologists*, John Wiley & Sons, Inc., Hoboken, N.J., 2005, pp. 185-187):

$$\frac{v_i}{v_0} = 1 - \frac{(E+I+K_i) - \sqrt{(E+I+K_i)^2 - 4E \cdot I}}{2E}$$

wherein $v_0$ and $v_i$ are the reaction velocities in the absence and presence, respectively, of the inhibitor, E is the active enzyme concentration, and I is the inhibitor concentration. The data were analyzed with GraphPad Prism version 4.00 software (GraphPad Software, San Diego, Calif., USA).

Assay 2

Recombinant human S-COMT (0.8 nM) was incubated with the COMT inhibitor and 200 µM S-adenosyl-L-methionine in 100 mM $Na_2HPO_4$ buffer, pH 7.4, containing 5 mM $MgCl_2$ for 30 min at 37° C. The reaction was started with the addition of esculetin for a final concentration of 0.5 µM and the reaction mixture with total volume of 200 µl was incubated for 30 min at 37° C. The reaction was stopped with 20 µl of 4 M $HClO_4$ and the precipitated protein was removed by Sirocco protein precipitation plate (centrifuged at 4° C. for 10 min at 3000 g). O-Methylated esculetin was detected by Waters HT Alliance HPLC setup with Waters 474 fluorescence detector (Ex 460 nm, Em 460 nm, Gain 100). The analytes were separated isocratically using 0.1 M $Na_2HPO_4$, 20 mM citric acid, 0.15 mM EDTA, pH 3.2, in 40% methanol as mobile phase and Waters Spherisorb ODS2 (3 µm, 4.6 mm×100 mm) column. O-Methylated esculetin concentrations were calculated based on the standard curve and the $K_i$ values were calculated using the Morrison equation as in Assay 1.

The results of the determination of COMT inhibiting activity in vitro are shown in Table 1. The results show that the compounds of formula I are capable of inhibiting COMT activity in vitro.

TABLE 1

COMT inhibiting activity in vitro.

| Compound | $K_i$/nM | Method |
|---|---|---|
| Compound of Example 5 | 0.84 | Assay 1 |
| Compound of Example 23 | 0.19 | Assay 1 |
| Compound of Example 26 | 0.12 | Assay 1 |
| Compound of Example 32 | 2.0 | Assay 1 |
| Compound of Example 38 | 9.5 | Assay 1 |
| Compound of Example 45 | 8.2 | Assay 1 |
| Compound of Example 74 | 2.0 | Assay 1 |
| Compound of Example 76 | 3.3 | Assay 1 |
| Compound of Example 89 | 2.0 | Assay 1 |
| Compound of Example 100 | 6.5 | Assay 1 |
| Compound of Example 118 | 0.33 | Assay 2 |
| Compound of Example 121 | 18 | Assay 1 |
| Compound of Example 122 | 1.5 | Assay 1 |
| Compound of Example 144 | 0.7 | Assay 2 |
| Compound of Example 152 | 1.6 | Assay 2 |
| Compound of Example 153 | 0.4 | Assay 2 |
| Compound of Example 154 | 1.3 | Assay 2 |
| Compound of Example 156 | 0.26 | Assay 2 |
| Compound of Example 158 | 0.53 | Assay 2 |
| Compound of Example 159 | 0.94 | Assay 2 |
| Compound of Example 160 | 0.7 | Assay 2 |
| Compound of Example 161 | 0.3 | Assay 2 |
| Compound of Example 164 | 0.2 | Assay 2 |
| Compound of Example 167 | 0.3 | Assay 2 |
| Compound of Example 171 | 0.9 | Assay 2 |
| Compound of Example 172 | 0.2 | Assay 2 |
| Compound of Example 174 | 0.5 | Assay 2 |
| Compound of Example 177 | 0.8 | Assay 2 |
| Compound of Example 180 | 0.5 | Assay 2 |
| Compound of Example 187 | 3.2 | Assay 1 |
| Compound of Example 191 | 2.9 | Assay 1 |
| Compound of Example 209 | 0.1 | Assay 2 |

Experiment 2

Determination of Levodopa Concentration in Rat Plasma

Levodopa concentration in rat plasma was determined substantially as described in e.g. Kim, T. K. et al. *European Journal of Pharmaceutical Sciences*, 38 (2009) 525. The studies were performed in adult male Wistar rats. The COMT inhibitor was dosed orally over a range of doses and several sampling time points were chosen between 0 min and 300 min after drug administration (levodopa+carbidopa and COMT inhibitor). Blood samples were collected by cardiac puncture under $CO_2$ anaesthesia into pre-cooled $K_2$EDTA tubes and kept on ice until the separation of plasma by centrifugation. For levodopa analysis, 75 µl of separated plasma was pipetted without delay into pre-cooled polypropylene tubes containing a conserving agent. All the samples were stored at −80° C. nominal until analyzed. Plasma levels of levodopa were determined by LC-MS/MS (or HPLC). Standard pharmacokinetic methods were used to evaluate the concentration—time data by non-compartmental analysis modeling. The analyses were performed using WinNonlin® Professional v. 5.0.1.

The results of the determination of levodopa concentration in rat plasma are shown in Table 2. The results show that the compounds of formula I provide an improved levodopa concentration in plasma.

TABLE 2

Relative levodopa concentration in rat plasma (entacapone = 1.00).

| Compound | Relative levodopa concentration |
|---|---|
| Compound of Example 1 | 1.65 |
| Compound of Example 6 | 1.64 |
| Compound of Example 23 | 1.34 |
| Compound of Example 28 | 2.69 |
| Compound of Example 55 | 1.31 |
| Compound of Example 60 | 1.13 |
| Compound of Example 87 | 1.51 |
| Compound of Example 92 | 1.42 |
| Entacapone | 1.00 |

The compounds of formula I exhibit COMT inhibiting activity. The present invention thus provides compounds for use as a medicament. Compounds for use in the treatment of a disease or condition where a COMT inhibiting agent is indicated to be useful are also provided. Furthermore, a method for the treatment of a disease or condition where a COMT inhibiting agent is indicated to be useful is provided. In said method a therapeutically effective amount of at least one compound of formula I is administered to a mammal, e.g. human, in need of such treatment. Use of the compounds of formula I for the manufacture of a medicament for the treatment of a disease or condition where a COMT inhibiting agent is indicated to be useful is also provided.

In one embodiment of the invention the disease where a COMT inhibiting agent is indicated to be useful is Parkinson's disease.

In one embodiment of the invention potentiation of therapy with a dopamine precursor, e.g. levodopa, is provided.

The compounds of formula I can be administered, for example, enterally, topically or parenterally by means of any pharmaceutical formulation useful for said administration and comprising as active ingredient at least one compound of formula I in pharmaceutically acceptable and effective amounts together with pharmaceutically acceptable diluents, carriers and/or excipients known in the art.

The therapeutic dose to be given to a patient in need of the treatment will vary depending on the compound being administered, the age and the sex of the subject being treated, the particular condition being treated, as well as the route and method of administration, and is easily determined by a person skilled in the art. Accordingly, the typical dosage for oral administration is from 5 μg/kg to 100 mg/kg per day and for parenteral administration from 0.5 g/kg to 10 mg/kg for an adult mammal.

The compounds according to this invention are given to a patient as such or in combination with one or more other active ingredients and/or suitable pharmaceutical excipients. The latter group comprises conventionally used excipients and formulation aids, such as fillers, binders, disintegrating agents, lubricants, solvents, gel forming agents, emulsifiers, stabilizers, colorants and/or preservatives.

The compounds of formula I are formulated into dosage forms using commonly known pharmaceutical manufacturing methods. The dosage forms can be e.g. tablets, capsules, granules, suppositories, emulsions, suspensions or solutions. Depending on the route of administration and the galenic form, the amount of the active ingredient in a formulation can typically vary between 0.01% and 100% (w/w).

For the treatment of Parkinson's disease the compounds of formula I can be administered together with levodopa or another dopamine precursor, each in its own composition or combined in a single composition. Also a dopa decarboxylase (DDC) inhibitor, such as benserazide or carbidopa, and/or a monoamine oxidase type B (MAO-B) inhibitor, such as lazabemide, rasagiline, safinamide or selegiline, can be present. The amount of levodopa can be from 50 mg to 400 mg, e.g. from 50 mg to 300 mg, such as from 50 mg to 200 mg. The amount of carbidopa can be from 5 mg to 200 mg, e.g. from 10 mg to 150 mg, such as from 20 mg to 110 mg.

If all active ingredients are not combined in a single composition, the amount of daily administrations of the active ingredients can vary. For instance, the composition comprising a compound of formula I can be administered once a day and the composition comprising a dopamine precursor and a DDC inhibitor can be administered three times a day.

The DDC inhibitor and the dopamine precursor, such as levodopa, are typically administered in a ratio of from 1:1 to 1:40, e.g. from 1:4 to 1:10.

The daily dose of lazabemide is typically from 100 mg to 800 mg, e.g. from 100 mg to 200 mg, divided into 1 to 10 individual doses, e.g. 1 to 2 individual doses. The daily dose of rasagiline is typically from 0.1 mg to 5 mg, e.g. from 0.5 mg to 2 mg, divided into 1 to 10 individual doses, e.g. 1 to 2 individual doses. The daily dose of safinamide is typically from 10 mg to 600 mg, e.g. from 50 mg to 150 mg, divided into 1 to 10 individual doses, e.g. 1 to 2 individual doses. The daily dose of selegiline is typically from 1 mg to 20 mg, e.g. from 2 ing to 10 mg, divided into 1 to 10 individual doses, e.g. 1 to 2 individual doses.

A person skilled in the art will appreciate that the embodiments described in this application can be modified without departing from the inventive concept. A person skilled in the art also understands that the invention is not limited to the particular embodiments disclosed but is intended to also cover modifications of the embodiments that are within the spirit and scope of the invention.

The invention claimed is:
1. A compound of formula I,

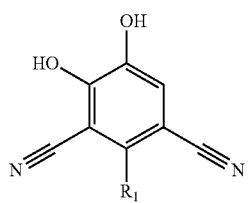

wherein
$R_1$ is $(C_1$-$C_6)$alkyl, $(C_2$-$C_6)$alkenyl, $(C_2$-$C_6)$alkynyl, $(C_3$-$C_7)$cycloalkyl, $(C_4$-$C_{10})$cycloalkenyl, aryl, $(R_2)_2C\!=\!C\!-\!$, halogen, hydroxy, $(C_1$-$C_6)$alkoxy, $(C_1$-$C_6)$alkyl-S—, $(C_4$-$C_{10})$cycloalkenyloxy, $(C_4$-$C_{10})$cycloalkenyl-S—, aryloxy, aryl-S—, heteroaryloxy, heteroaryl-S—, $(R_3)_2N$—, $(R_4)_2C\!=\!N$—, heterocyclyl, heteroaryl, aryl$(C_1$-$C_6)$alkyl, (1-amino-1-carboxymethyl)-$(C_1$-$C_6)$alkyl, halo$(C_1$-$C_6)$alkyl, hydroxy$(C_1$-$C_6)$alkyl, $(C_1$-$C_6)$alkoxy$(C_1$-$C_6)$alkyl, $(C_1$-$C_6)$alkyl-S—$(C_1$-$C_6)$alkyl, $(R_3)_2N$—$(C_1$-$C_6)$alkyl, carboxy$(C_2$-$C_6)$alkenyl, $(C_3$-$C_7)$cycloalkyl$(C_2$-$C_6)$alkenyl, aryl$(C_2$-$C_6)$alkenyl, $(C_1$-$C_6)$alkoxy$(C_2$-$C_6)$alkenyl, heterocyclyl$(C_2$-$C_6)$alkenyl, heteroaryl$(C_2$-$C_6)$alkenyl, carboxy$(C_2$-$C_6)$alkynyl, $(C_3$-$C_7)$cycloalkyl$(C_2$-$C_6)$alkynyl, aryl$(C_2$-$C_6)$alkynyl, $(C_1$-$C_6)$alkoxy$(C_2$-$C_6)$alkynyl, heterocyclyl$(C_2$-$C_6)$alkynyl, heteroaryl$(C_2$-$C_6)$alkynyl, halo$(C_1$-$C_6)$alkoxy, hydroxy$(C_1$-$C_6)$alkoxy, $(C_1$-$C_6)$alkoxy$(C_1$-$C_6)$alkoxy, $(C_1$-$C_6)$alkyl-$(C\!=\!O)$—O—, $R_5$—$(S\!=\!O)$—, $R_5$—$(O\!=\!S\!=\!O)$—, hydroxy$(C_1$-$C_6)$alkoxy$(C_1$-$C_6)$alkyl, $(C_1$-$C_6)$alkoxy-$(C\!=\!O)$—$(C_2$-$C_6)$alkenyl or $(C_1$-$C_6)$alkyl-$(C\!=\!O)$—O—$(C_1$-$C_6)$alkyl, wherein said $(C_4$-$C_{10})$cycloalkenyl, aryl, heterocyclyl, heteroaryl or $(C_3$-$C_7)$cycloalkyl as such or as part of another group is unsubstituted or substituted with 1, 2 or 3 substituent(s) $R_6$;

$R_2$ is, independently at each occurrence, carboxy or aryl, wherein said aryl is, independently at each occurrence, unsubstituted or substituted with 1, 2 or 3 substituent(s) $R_6$;

$R_3$ is, independently at each occurrence, H, $(C_1$-$C_6)$alkyl, $(C_3$-$C_7)$cycloalkyl, aryl, $(C_3$-$C_7)$cycloalkyl$(C_1$-$C_6)$alkyl, hydroxy$(C_1$-$C_6)$alkyl or $(C_1$-$C_6)$alkoxy$(C_1$-$C_6)$alkyl, wherein said $(C_3$-$C_7)$cycloalkyl or aryl as such or as part of another group is, independently at each occurrence, unsubstituted or substituted with 1 substituent being $(C_1$-$C_6)$alkyl, halogen, hydroxy, $(C_1$-$C_6)$alkoxy or hydroxy$(C_1$-$C_6)$alkyl;

$R_4$ is, independently at each occurrence, H or aryl, wherein said aryl is, independently at each occurrence, unsubstituted or substituted with 1 substituent being $(C_1$-$C_6)$alkyl, halogen or $(C_1$-$C_6)$alkoxy;

$R_5$ is $(C_1$-$C_6)$alkyl, aryl, hydroxy or $(C_1$-$C_6)$alkoxy, wherein said aryl is unsubstituted or substituted with 1, 2 or 3 substituent(s) $R_6$;

$R_6$ is, independently at each occurrence, $(C_1$-$C_6)$alkyl, $(C_2$-$C_6)$alkenyl, cyano, aryl, halogen, hydroxy, $(C_1$-$C_6)$alkoxy, $(C_1$-$C_6)$alkyl-S—, $(C_4$-$C_{10})$cycloalkenyloxy, $(C_4$-$C_{10})$cycloalkenyl-S—, aryloxy, aryl-S—, heteroaryloxy, heteroaryl-S—, $(R_7)_2N$—, carboxy$(C_1$-$C_6)$alkyl, aryl$(C_1$-$C_6)$alkyl, halo$(C_1$-$C_6)$alkyl, hydroxy$(C_1$-$C_6)$alkyl, $(C_1$-$C_6)$alkoxy$(C_1$-$C_6)$alkyl, heterocyclyl$(C_1$-$C_6)$alkyl, $(C_1$-$C_6)$alkyl-$(C\!=\!O)$—, $(C_1$-$C_6)$alkoxy- (C=O)—, heterocyclyl-(C=O)—, $(R_7)_2$N—(C=O)—, halo($C_1$-$C_6$)alkoxy, $R_8$—(S=O)—, $R_8$—(O=S=O)—, ($C_1$-$C_6$)alkoxy-(C=O)—($C_1$-$C_6$)alkyl, $(R_7)_2$N—(C=O)—($C_1$-$C_6$)alkyl or ($C_1$-$C_6$)alkoxy($C_1$-$C_6$)alkoxy-(C=O)—, wherein said aryl, heteroaryl or heterocyclyl as such or as part of another group is, independently at each occurrence, unsubstituted or substituted with 1 substituent being ($C_1$-$C_6$)alkyl;

or $R_6$ and $R_6$ both attached to the same carbon ring atom form, together with the carbon ring atom to which they are attached, a —(C=O)— group;

$R_7$ is, independently at each occurrence, H, ($C_1$-$C_6$)alkyl, ($C_3$-$C_7$)cycloalkyl or carboxy($C_1$-$C_6$)alkyl, wherein said ($C_3$-$C_7$)cycloalkyl is, independently at each occurrence, unsubstituted or substituted with 1 substituent being ($C_1$-$C_6$)alkyl;

$R_8$ is, independently at each occurrence, ($C_1$-$C_6$)alkyl, hydroxy, ($C_1$-$C_6$)alkoxy or $(R_9)_2$N—;

$R_9$ is, independently at each occurrence, ($C_1$-$C_6$)alkyl;

or a pharmaceutically acceptable salt or ester thereof.

2. The compound according to claim 1, wherein $R_1$ is ($C_1$-$C_6$)alkyl, ($C_2$-$C_6$)alkenyl, ($C_2$-$C_6$)alkynyl, ($C_4$-$C_{10}$)cycloalkenyl, aryl, halogen, hydroxy, ($C_4$-$C_{10}$)cycloalkenyloxy, aryloxy, aryl-S—, heteroaryl-S—, $(R_3)_2$N—, $(R_4)_2$C=N—, heterocyclyl, heteroaryl, aryl($C_1$-$C_6$)alkyl, hydroxy($C_1$-$C_6$)alkyl, $(R_3)_2$N—($C_1$-$C_6$)alkyl, carboxy($C_2$-$C_6$)alkenyl, ($C_3$-$C_7$)cycloalkyl($C_2$-$C_6$)alkenyl, aryl($C_2$-$C_6$)alkenyl, ($C_1$-$C_6$)alkoxy($C_2$-$C_6$)alkenyl, heteroaryl($C_2$-$C_6$)alkenyl, aryl($C_2$-$C_6$)alkynyl, ($C_1$-$C_6$)alkoxy($C_2$-$C_6$)alkynyl, $R_5$—(S=O)—, $R_5$—(O=S=O)— or ($C_1$-$C_6$)alkoxy-(C=O)—($C_2$-$C_6$)alkenyl, wherein said ($C_4$-$C_{10}$)cycloalkenyl, aryl, heterocyclyl, heteroaryl or ($C_3$-$C_7$)cycloalkyl as such or as part of another group is unsubstituted or substituted with 1, 2 or 3 substituent(s) $R_6$;

$R_3$ is, independently at each occurrence, H, ($C_1$-$C_6$)alkyl, ($C_3$-$C_7$)cycloalkyl, aryl, ($C_3$-$C_7$)cycloalkyl($C_1$-$C_6$)alkyl, hydroxy($C_1$-$C_6$)alkyl or ($C_1$-$C_6$)alkoxy($C_1$-$C_6$)alkyl, wherein said ($C_3$-$C_7$)cycloalkyl or aryl as such or as part of another group is unsubstituted or substituted with 1 substituent being ($C_1$-$C_6$)alkyl;

$R_4$ is, independently at each occurrence, H or aryl, wherein said aryl is, independently at each occurrence, substituted with 1 substituent being ($C_1$-$C_6$)alkyl, halogen or ($C_1$-$C_6$)alkoxy;

$R_5$ is aryl, wherein said aryl is substituted with 1 substituent $R_6$;

$R_6$ is, independently at each occurrence, ($C_1$-$C_6$)alkyl, ($C_2$-$C_6$)alkenyl, carboxy, cyano, aryl, halogen, hydroxy, ($C_1$-$C_6$)alkoxy, ($C_1$-$C_6$)alkyl-S—, aryloxy, heteroaryl, carboxy($C_1$-$C_6$)alkyl, aryl($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, heterocyclyl($C_1$-$C_6$)alkyl, ($C_1$-$C_6$)alkyl-(C=O)—, ($C_1$-$C_6$)alkoxy-(C=O)—, heterocyclyl-(C=O)—, $(R_7)_2$N—(C=O)—, halo($C_1$-$C_6$)alkoxy, $R_8$—(O=S=O)—, ($C_1$-$C_6$)alkoxy-(C=O)—($C_1$-$C_6$)alkyl, $(R_7)_2$N—(C=O)—($C_1$-$C_6$)alkyl or ($C_1$-$C_6$)alkoxy($C_1$-$C_6$)alkoxy-(C=O)—, wherein said aryl, heteroaryl or heterocyclyl as such or as part of another group is, independently at each occurrence, unsubstituted or substituted with 1 substituent being ($C_1$-$C_6$)alkyl;

or $R_6$ and $R_6$ both attached to the same carbon ring atom form, together with the carbon ring atom to which they are attached, a —(C=O)— group;

$R_7$ is, independently at each occurrence, H, ($C_1$-$C_6$)alkyl, ($C_3$-$C_7$)cycloalkyl or carboxy($C_1$-$C_6$)alkyl, wherein said ($C_3$-$C_7$)cycloalkyl is unsubstituted;

$R_8$ is, independently at each occurrence, ($C_1$-$C_6$)alkyl or $(R_9)_2$N—;

$R_9$ is, independently at each occurrence, ($C_1$-$C_6$)alkyl.

3. The compound according to claim 2, wherein $R_1$ is ($C_1$-$C_6$)alkyl, ($C_2$-$C_6$)alkenyl, ($C_2$-$C_6$)alkynyl, ($C_4$-$C_{10}$)cycloalkenyl, aryl, halogen, ($C_4$-$C_{10}$)cycloalkenyloxy, aryloxy, aryl-S—, heteroaryl-S—, $(R_3)_2$N—, $(R_4)_2$C=N—, heterocyclyl, heteroaryl, aryl($C_1$-$C_6$)alkyl, $(R_3)_2$N—($C_1$-$C_6$)alkyl, carboxy($C_2$-$C_6$)alkenyl, ($C_3$-$C_7$)cycloalkyl($C_2$-$C_6$)alkenyl or aryl($C_2$-$C_6$)alkenyl, wherein said ($C_4$-$C_{10}$)cycloalkenyl, aryl, heterocyclyl, heteroaryl or ($C_3$-$C_7$)cycloalkyl as such or as part of another group is unsubstituted or substituted with 1, 2 or 3 substituent(s) $R_6$;

$R_3$ is, independently at each occurrence, H, ($C_1$-$C_6$)alkyl or ($C_1$-$C_6$)alkoxy($C_1$-$C_6$)alkyl;

$R_4$ is, independently at each occurrence, H or aryl, wherein said aryl is, independently at each occurrence, substituted with 1 substituent being ($C_1$-$C_6$)alkyl, halogen or ($C_1$-$C_6$)alkoxy;

$R_6$ is, independently at each occurrence, ($C_1$-$C_6$)alkyl, cyano, aryl, halogen, hydroxy, ($C_1$-$C_6$)alkoxy, ($C_1$-$C_6$)alkyl-S—, carboxy($C_1$-$C_6$)alkyl, aryl($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, heterocyclyl-(C=O)—, $(R_7)_2$N—(C=O)—$R_8$—(O=S=O)— or ($C_1$-$C_6$)alkoxy-(C=O)—($C_1$-$C_6$)alkyl, wherein said aryl or heterocyclyl as such or as part of another group is unsubstituted;

$R_7$ is, independently at each occurrence, H, ($C_1$-$C_6$)alkyl or ($C_3$-$C_7$)cycloalkyl, wherein said ($C_3$-$C_7$)cycloalkyl is unsubstituted;

$R_8$ is, independently at each occurrence, ($C_1$-$C_6$)alkyl or $(R_9)_2$N—;

$R_9$ is, independently at each occurrence, ($C_1$-$C_6$)alkyl.

4. The compound according to claim 3, wherein $R_1$ is ($C_1$-$C_6$)alkyl, ($C_2$-$C_6$)alkenyl, aryl, halogen, aryloxy, aryl-S—, $(R_3)_2$N—, $(R_4)_2$C=N—, heterocyclyl, heteroaryl, aryl($C_1$-$C_6$)alkyl, ($C_3$-$C_7$)cycloalkyl($C_2$-$C_6$)alkenyl or aryl($C_2$-$C_6$)alkenyl, wherein said aryl, heterocyclyl, heteroaryl or ($C_3$-$C_7$)cycloalkyl as such or as part of another group is unsubstituted or substituted with 1, 2 or 3 substituent(s) $R_6$;

$R_3$ is, independently at each occurrence, H or ($C_1$-$C_6$)alkyl;

$R_4$ is, independently at each occurrence, H or aryl, wherein said aryl is, independently at each occurrence, substituted with 1 substituent being ($C_1$-$C_6$)alkyl, halogen or ($C_1$-$C_6$)alkoxy;

$R_6$ is, independently at each occurrence, ($C_1$-$C_6$)alkyl, cyano, aryl, halogen, hydroxy, ($C_1$-$C_6$)alkoxy, ($C_1$-$C_6$)alkyl-S—, carboxy($C_1$-$C_6$)alkyl, halo($C_1$-$C_6$)alkyl, hydroxy($C_1$-$C_6$)alkyl, ($C_1$-$C_6$)alkoxy($C_1$-$C_6$)alkyl, heterocyclyl-(C=O)—, $(R_7)_2$N—(C=O)— or $R_8$—(O=S=O)—, wherein said aryl or heterocyclyl as such or as part of another group is unsubstituted;

$R_7$ is, independently at each occurrence, H or ($C_1$-$C_6$)alkyl;

$R_8$ is, independently at each occurrence, ($C_1$-$C_6$)alkyl.

5. The compound according to claim 4, wherein $R_1$ is ($C_1$-$C_6$)alkyl, ($C_2$-$C_6$)alkenyl, aryl, halogen, aryloxy, aryl-S—, $(R_3)_2$N—, heterocyclyl, heteroaryl, aryl($C_1$-$C_6$)alkyl or aryl($C_2$-$C_6$)alkenyl, wherein said aryl, heterocyclyl or heteroaryl as such or as part of another group is unsubstituted or substituted with 1, 2 or 3 substituent(s) R$_6$;

R$_3$ is, independently at each occurrence, H or (C$_1$-C$_6$) alkyl;

R$_6$ is, independently at each occurrence, (C$_1$-C$_6$)alkyl, halogen, hydroxy, (C$_1$-C$_6$)alkoxy, carboxy(C$_1$-C$_6$) alkyl, halo(C$_1$-C$_6$)alkyl or (R$_7$)$_2$N—(C=O)—;

R$_7$ is, independently at each occurrence, H or (C$_1$-C$_6$) alkyl.

6. The compound according to claim 5, wherein

R$_1$ is (C$_2$-C$_6$)alkenyl, aryl, halogen, aryloxy, aryl-S—, (R$_3$)$_2$N—, heteroaryl, aryl(C$_1$-C$_6$)alkyl or aryl(C$_2$-C$_6$) alkenyl, wherein said aryl or heteroaryl as such or as part of another group is unsubstituted or substituted with 1 or 2 substituent(s) R$_6$;

R$_3$ is, independently at each occurrence, H or (C$_1$-C$_6$) alkyl;

R$_6$ is, independently at each occurrence, (C$_1$-C$_6$)alkyl, halogen, (C$_1$-C$_6$)alkoxy, carboxy(C$_1$-C$_6$)alkyl or halo (C$_1$-C$_6$)alkyl.

7. The compound according to claim 6, wherein

R$_1$ is (C$_2$-C$_6$)alkenyl, aryl, halogen, aryl-S—, heteroaryl or aryl(C$_1$-C$_6$)alkyl, wherein said aryl or heteroaryl as such or as part of another group is unsubstituted or substituted with 1 or 2 substituent(s) R$_6$;

R$_6$ is, independently at each occurrence, (C$_1$-C$_6$)alkyl, halogen or (C$_1$-C$_6$)alkoxy.

8. The compound according to claim 7, wherein

R$_1$ is (C$_2$-C$_6$)alkenyl, halogen, aryl-S— or aryl(C$_1$-C$_6$) alkyl, wherein said aryl as part of another group is unsubstituted or substituted with 1 or 2 substituent(s) R$_6$;

R$_6$ is, independently at each occurrence, (C$_1$-C$_6$)alkyl, halogen or (C$_1$-C$_6$)alkoxy.

9. The compound according to claim 7, wherein

R$_1$ is (C$_2$-C$_6$)alkenyl, aryl, aryl-S—, heteroaryl or aryl (C$_1$-C$_6$)alkyl, wherein said aryl or heteroaryl as such or as part of another group is substituted with 1 or 2 substituent(s) R$_6$;

R$_6$ is, independently at each occurrence, (C$_1$-C$_6$)alkyl or (C$_1$-C$_6$)alkoxy.

10. The compound according to claim 9, wherein

R$_1$ is (C$_2$-C$_6$)alkenyl, aryl-S— or aryl(C$_1$-C$_6$)alkyl, wherein said aryl as part of another group is substituted with 1 or 2 substituent(s) R$_6$;

R$_6$ is, independently at each occurrence, (C$_1$-C$_6$)alkyl or (C$_1$-C$_6$)alkoxy.

11. The compound according to claim 7, wherein R$_1$ is (C$_2$-C$_6$)alkenyl.

12. The compound according to claim 7, wherein

R$_1$ is aryl, wherein said aryl is unsubstituted or substituted with 1 or 2 substituent(s) R$_6$;

R$_6$ is, independently at each occurrence, (C$_1$-C$_6$)alkyl, halogen or (C$_1$-C$_6$)alkoxy.

13. The compound according to claim 7, wherein

R$_1$ is aryl-S—, wherein said aryl is unsubstituted or substituted with 1 or 2 substituent(s) R$_6$;

R$_6$ is, independently at each occurrence, (C$_1$-C$_6$)alkyl, halogen or (C$_1$-C$_6$)alkoxy.

14. The compound according to claim 7, wherein

R$_1$ is heteroaryl, wherein said heteroaryl is unsubstituted or substituted with 1 or 2 substituent(s) R$_6$;

R$_6$ is, independently at each occurrence, (C$_1$-C$_6$)alkyl, halogen or (C$_1$-C$_6$)alkoxy.

15. The compound according to claim 7, wherein

R$_1$ is aryl(C$_1$-C$_6$)alkyl, wherein said aryl is substituted with 1 or 2 substituent(s) R$_6$;

R$_6$ is, independently at each occurrence, (C$_1$-C$_6$)alkyl or (C$_1$-C$_6$)alkoxy.

16. The compound according to claim 1, wherein the compound is 2-bromo-4,5-dihydroxyisophthalonitrile, 4,5-dihydroxy-2-(phenylethynyl)isophthalonitrile, 4,5-dihydroxy-2-(prop-1-ynyl)isophthalonitrile, 4,5-dihydroxy-2-(1-methyl-1H-pyrrol-2-yl)isophthalonitrile, 4,5-dihydroxy-2-(thiophen-2-yl)isophthalonitrile, 2-(furan-2-yl)-4,5-dihydroxyisophthalonitrile, 3',4',5'-trifluoro-3,4-dihydroxybiphenyl-2,6-dicarbonitrile, 4,5-dihydroxy-2-(naphthalen-1-yl)isophthalonitrile, 4'-tert-butyl-3,4-dihydroxybiphenyl-2,6-dicarbonitrile, 3,4-dihydroxy-4'-(hydroxymethyl)biphenyl-2,6-dicarbonitrile, 4,5-dihydroxy-2-(naphthalen-2-yl)isophthalonitrile, 3,4-dihydroxy-4'-(isopropylthio)biphenyl-2,6-dicarbonitrile, 3,4-dihydroxy-4'-(methylthio)biphenyl-2,6-dicarbonitrile, 3,4-dihydroxy-4'-isopropoxybiphenyl-2,6-dicarbonitrile, 4'-(ethylthio)-3,4-dihydroxybiphenyl-2,6-dicarbonitrile, 3,4-dihydroxy-4'-isopropoxy-3',5'-dimethylbiphenyl-2,6-dicarbonitrile, 4'-butyl-3,4-dihydroxybiphenyl-2,6-dicarbonitrile, 3,4-dihydroxy-2',4',5'-trimethylbiphenyl-2,6-dicarbonitrile, 3,4-dihydroxy-2',5'-dimethylbiphenyl-2,6-dicarbonitrile, 2-cyclohexenyl-4,5-dihydroxyisophthalonitrile, 3'-ethyl-3,4-dihydroxybiphenyl-2,6-dicarbonitrile, 3,4-dihydroxybiphenyl-2,4',6-tricarbonitrile, 3,4-dihydroxy-4'-(isopropylsulfonyl)biphenyl-2,6-dicarbonitrile, 2',6'-dicyano-3',4'-dihydroxy-N,N-dimethylbiphenyl-4-sulfonamide, (E)-4,5-dihydroxy-2-(pent-1-enyl)isophthalonitrile, 3,4-dihydroxy-4'-(1-methoxyethyl)biphenyl-2,6-dicarbonitrile, (E)-2-(3,3-dimethylbut-1-enyl)-4,5-dihydroxyisophthalonitrile, 3,4-dihydroxy-2'-methylbiphenyl-2,6-dicarbonitrile, (E)-2-(2-cyclohexylvinyl)-4,5-dihydroxyisophthalonitrile, (Z)-4,5-dihydroxy-2-(prop-1-enyl)isophthalonitrile, 3-(2',6'-dicyano-3',4'-dihydroxybiphenyl-4-yl)propanoic acid, 3,4-dihydroxy-3'-(hydroxymethyl)biphenyl-2,6-dicarbonitrile, 3,4-dihydroxy-3'-(methoxymethyl)biphenyl-2,6-dicarbonitrile, 2',6'-dicyano-3',4'-dihydroxy-N,N-dipropylbiphenyl-4-carboxamide, (E)-4,5-dihydroxy-2-(prop-1-enyl)isophthalonitrile, 3,4-dihydroxybiphenyl-2,6-dicarbonitrile, 3',4'-dichloro-3,4-dihydroxybiphenyl-2,6-dicarbonitrile, 3,4-dihydroxy-3'-(trifluoromethyl)biphenyl-2,6-dicarbonitrile, 2-(furan-3-yl)-4,5-dihydroxyisophthalonitrile, 3,4-dihydroxy-4'-(trifluoromethyl)biphenyl-2,6-dicarbonitrile, 4,5-dihydroxy-2-(thiophen-3-yl)isophthalonitrile, 4,5-dihydroxy-2-(5-methylfuran-2-yl)isophthalonitrile, 4,5-dihydroxy-2-(5-methylthiophen-2-yl)isophthalonitrile, 2-benzyl-4,5-dihydroxyisophthalonitrile, 2-(benzofuran-2-yl)-4,5-dihydroxyisophthalonitrile, 2-(5-chlorothiophen-2-yl)-4,5-dihydroxyisophthalonitrile, 2-(benzo[b]thiophen-2-yl)-4,5-dihydroxyisophthalonitrile, (E)-4,5-dihydroxy-2-styrylisophthalonitrile, 4'-ethyl-3,4-dihydroxybiphenyl-2,6-dicarbonitrile, 3,4-dihydroxy-3',5'-dimethylbiphenyl-2,6-dicarbonitrile, 4,5-dihydroxy-2-(phenylthio) isophthalonitrile, 4,5-dihydroxy-2-(p-tolylthio) isophthalonitrile, 4,5-dihydroxy-2-(4-methylbenzyl) isophthalonitrile, 2-(4-fluorobenzyl)-4,5-dihydroxyisophthalonitrile, 4,5-dihydroxy-2-(4-hydroxybenzyl)isophthalonitrile, 4,5-dihydroxy-2-(2-methoxybenzyl)isophthalonitrile, 4,5-dihydroxy-2-(4-(trifluoromethoxy)benzyl)isophthalonitrile, 2-(3-fluoro-4-methoxybenzyl)-4,5-dihydroxyisophthalonitrile, 2-(2-fluorobenzyl)-4,5-dihydroxyisophthalonitrile, 4,5-dihydroxy-2-(2-methylbenzyl)isophthalonitrile, 2-(2,5-dimethylbenzyl)-4,5-dihydroxyisophthalonitrile, 2-(3- fluoro-5-methylbenzyl)-4,5-dihydroxyisophthalonitrile, 2-(4 fluoro-3-methylbenzyl)-4,5-dihydroxyisophthalonitrile, 4,5-dihydroxy-2-(3-methylbenzyl)isophthalonitrile, 2-(5-fluoro-2-methoxybenzyl)-4,5-dihydroxyisophthalonitrile, 2-(3,5-dimethylbenzyl)-4,5-dihydroxyisophthalonitrile, 4,5-dihydroxy-2-(4-isopropylbenzyl)isophthalonitrile, 2-(4-ethylbenzyl)-4,5-dihydroxyisophthalonitrile, 4,5-dihydroxy-2-(naphthalen-1-ylmethyl)isophthalonitrile, 2-(2,4-dimethylbenzyl)-4,5-dihydroxyisophthalonitrile, 2-(3,6-dihydro-2H-pyran-4-yl)-4,5-dihydroxyisophthalonitrile, 2-cyclopentenyl-4,5-dihydroxyisophthalonitrile, (E)-3-(2,6-dicyano-3,4-dihydroxyphenyl)acrylic acid, (E)-4,5-dihydroxy-2-(3-methoxyprop-1-enyl)isophthalonitrile, 4,5-dihydroxy-2-(5-(morpholinomethyl)thiophen-2-yl) isophthalonitrile, 3,4-dihydroxy-4'-(morpholine-4-carbonyl) biphenyl-2,6-dicarbonitrile, 2-(1-benzyl-1H-pyrazol-4-yl)-4,5-dihydroxyisophthalonitrile, 2-(5-hexylthiophen-2-yl)-4,5-dihydroxyisophthalonitrile, (Z)-2-(but-2-enyl)-4,5-dihydroxyisophthalonitrile, 4,5-dihydroxy-2-(3-methylbut-2-enyl)isophthalonitrile, (E)-2-(but-2-enyl)-4,5-dihydroxyisophthalonitrile, 4,5-dihydroxy-2-methylisophthalonitrile, 4,5-dihydroxy-2-(2-methylprop-1-enyl)isophthalonitrile, 3,4-dihydroxy-3'-methylbiphenyl-2,6-dicarbonitrile, 4,5-dihydroxy-2-vinylisophthalonitrile, 4,5-dihydroxy-2-(prop-1-en-2-yl)isophthalonitrile, 2-(2-ethoxythiazol-5-yl)-4, 5-dihydroxyisophthalonitrile, 2-allyl-4,5-dihydroxyisophthalonitrile, 3'-(tert-butoxymethyl)-3,4-dihydroxybiphenyl-2,6-dicarbonitrile, tert-butyl 2',6'-dicyano-3',4'-dihydroxybiphenyl-3-carboxylate, 3,4-dihydroxybiphenyl-2,3',6-tricarbonitrile, 2',6'-dicyano-3',4'-dihydroxy-N,N-dipropylbiphenyl-3-carboxamide, 2',6'-dicyano-N-cyclohexyl-3',4'-dihydroxybiphenyl-4-carboxamide, 2',6'-dicyano-N-cyclohexyl-3',4'-dihydroxybiphenyl-3-carboxamide, 2',6'-dicyano-N,N-diethyl-3',4'-dihydroxybiphenyl-4-carboxamide, 2',6'-dicyano-N,N-diethyl-3',4'-dihydroxybiphenyl-3-carboxamide, 2',6'-dicyano-N-ethyl-3',4'-dihydroxybiphenyl-3-carboxamide, 2',6'-dicyano-3',4'-dihydroxy-N,N-dimethylbiphenyl-3-carboxamide, 4'-fluoro-3,4-dihydroxybiphenyl-2,6-dicarbonitrile, 3',4'-difluoro-3,4-dihydroxybiphenyl-2,6-dicarbonitrile, 4'-fluoro-3,3',4-trihydroxybiphenyl-2,6-dicarbonitrile, (E)-4,5-dihydroxy-2-(3-phenylprop-1-enyl)isophthalonitrile, 4'-fluoro-3,4-dihydroxy-3'-methoxybiphenyl-2,6-dicarbonitrile, 3,4-dihydroxy-4'-(methylsulfonyl)biphenyl-2,6-dicarbonitrile, 3,4-dihydroxy-4'-propoxybiphenyl-2,6-dicarbonitrile, 4'-chloro-3,4-dihydroxy-3'-methylbiphenyl-2,6-dicarbonitrile, 4,5-dihydroxy-2-(5-phenylthiophen-2-yl)isophthalonitrile, 3,4-dihydroxy-4'-isopropylbiphenyl-2,6-dicarbonitrile, 3,4-dihydroxy-4'-propylbiphenyl-2,6-dicarbonitrile, 4,5-dihydroxy-2-(1-phenylvinyl)isophthalonitrile, (E)-4,5-dihydroxy-2-(4-methoxystyryl)isophthalonitrile, 3,4-dihydroxy-3',4'-dimethylbiphenyl-2,6-dicarbonitrile, (E)-4,5-dihydroxy-2-(4-methylstyryl)isophthalonitrile, 4,5-dihydroxy-2-(6-hydroxynaphthalen-2-yl)isophthalonitrile, 4'-fluoro-3,4-dihydroxy-3'-methylbiphenyl-2,6-dicarbonitrile, 4,5-dihydroxy-2-(3-methylbut-2-en-2-yl)isophthalonitrile, dimethylthiophen-3-yl)-4,5-dihydroxyisophthalonitrile, 2-(2,3-difluoro-4-methylbenzyl)-4,5-dihydroxyisophthalonitrile, 2-(4-(2,6-dicyano-3,4-dihydroxybenzyl)phenyl)propanoic acid, (E)-2-(3-cyclopentylprop-1-enyl)-4,5-dihydroxyisophthalonitrile, 4,5-dihydroxy-2-(1-isobutyl-1H-pyrazol-4-yl)isophthalonitrile, 2-(4-(2,6-dicyano-3,4-dihydroxyphenyl)-1H-pyrazol-1-yl) acetic acid, 4,5-dihydroxy-2-(1-methyl-1H-pyrazol-4-yl)isophthalonitrile, 4,5-dihydroxy-2-(3-methoxyprop-1-ynyl)isophthalonitrile, (E)-4,5-dihydroxy-2-(2-(thiophen-3-yl)vinyl)isophthalonitrile, (E)-2-(2-cyclopropylvinyl)-4,5-dihydroxyisophthalonitrile, 2',6'-dicyano-3',4'-dihydroxybiphenyl-4-carboxamide, 3,4-dihydroxy-3',4'-dimethoxybiphenyl-2,6-dicarbonitrile, 3,4-dihydroxy-3'-isopropylbiphenyl-2,6-dicarbonitrile, 2-(2,3-dihydrobenzofuran-5-yl)-4,5-dihydroxyisophthalonitrile, 4,5-dihydroxy-2-(6-methoxynaphthalen-2-yl)isophthalonitrile, 4,5-dihydroxy-2-(4-(hydroxymethyl)benzyl)isophthalonitrile, 2-(2,6-difluoro-3-methylbenzyl)-4,5-dihydroxyisophthalonitrile, 4,5-dihydroxy-2-(4-(trifluoromethyl) phenylthio)isophthalonitrile, 2-(2,4-dimethylphenylthio)-4,5-dihydroxyisophthalonitrile, methyl 3-(4-(2,6-dicyano-3,4-dihydroxyphenylthio)phenyl)propanoate, 4,5-dihydroxy-2-(p-tolyloxy)isophthalonitrile, (E)-2-(2,4-difluorostyryl)-4,5-dihydroxyisophthalonitrile, (E)-4,5-dihydroxy-2-(3-(trifluoromethyl)styryl)isophthalonitrile, (E)-4,5-dihydroxy-2-(4-methylpent-1-enyl)isophthalonitrile, (E)-2-(3,5-difluorostyryl)-4,5-dihydroxyisophthalonitrile, 2-(4-(2,6-dicyano-3,4-dihydroxybenzyl)phenyl)acetic acid, 2-(4-chlorobenzyl)-4,5-dihydroxyisophthalonitrile, 3,4-dihydroxy-4'-methylbiphenyl-2,6-dicarbonitrile, 3-(4-(2,6-dicyano-3,4-dihydroxybenzyl)phenyl)propanoic acid, 4,5-dihydroxy-2-(4-(trifluoromethyl)benzyl)isophthalonitrile, (E)-4,5-dihydroxy-2-(4-(trifluoromethyl)styryl)isophthalonitrile, 4,5-dihydroxy-2-(p-tolylsulfinyl)isophthalonitrile, 2-(4-ethylphenylthio)-4,5-dihydroxyisophthalonitrile, 2-(4-chlorophenylthio)-4,5-dihydroxyisophthalonitrile, 4,5-dihydroxy-2-(o-tolylthio)isophthalonitrile, methyl 4-(2,6-dicyano-3,4-dihydroxyphenylthio)benzoate, 2-(2-chlorophenylthio)-4,5-dihydroxyisophthalonitrile, methyl 2-(2,6-dicyano-3,4-dihydroxyphenylthio)benzoate, 2-(4-(2,6-dicyano-3,4-dihydroxyphenylthio)phenyl)acetic acid, 3-(4 (2,6-dicyano-3,4-dihydroxyphenylthio)phenyl)propanoic acid, 4,5-dihydroxy-2-(4-methoxyphenylthio)isophthalonitrile, methyl 2-(4-(2,6-dicyano-3,4-dihydroxybenzyl)phenyl)acetate, 4,5-dihydroxy-2-(3-methoxyphenylthio) isophthalonitrile, methyl 4-(2,6-dicyano-3,4-dihydroxyphenoxy)benzoate, 4,5-dihydroxy-2-(pyridin-4-ylthio)isophthalonitrile, 2-(4-cyanophenylthio)-4,5-dihydroxyisophthalonitrile, 4,5-dihydroxy-2-(naphthalen-2-ylthio)isophthalonitrile, 2-(4-(2,6-dicyano-3,4-dihydroxybenzyl)phenyl)-N,N-diethylacetamide, 2-(4-ethylphenoxy)-4,5-dihydroxyisophthalonitrile, 2-(4-acetylphenoxy)-4,5-dihydroxyisophthalonitrile, 4,5-dihydroxy-2-(1-oxo-2,3-dihydro-1H-inden-5-yloxy) isophthalonitrile, 2-(2',6'-dicyano-3',4'-dihydroxybiphenyl-4-yl)acetic acid, 2-(2,4-dimethylphenoxy)-4,5-dihydroxyisophthalonitrile, 2-(4-chlorophenoxy)-4,5-dihydroxyisophthalonitrile, 4,5-dihydroxy-2-(4-(trifluoromethyl)phenoxy)isophthalonitrile, 4,5-dihydroxy-2-(1H-inden-3-yl)isophthalonitrile, 2-((diethylamino)methyl)-4,5-dihydroxyisophthalonitrile hydrochloride, 4,5-dihydroxy-2-(((2-hydroxyethyl)amino)methyl) isophthalonitrile hydrochloride (1:1), 4,5-dihydroxy-2-(3-hydroxypropyl)isophthalonitrile, 2-amino-4,5-dihydroxyisophthalonitrile, 4,5-dihydroxy-2-(pyrrolidin-1-yl)isophthalonitrile, 2-(2,6-dimethylmorpholino)-4,5-dihydroxyisophthalonitrile, 4,5-dihydroxy-2-morpholinoisophthalonitrile, 4,5-dihydroxy-2-(isopropylamino)isophthalonitrile, 4,5-dihydroxy-2-(3-methoxypropylamino)isophthalonitrile, 2,4,5-trihydroxyisophthalonitrile, 2-ethyl-4,5-dihydroxyisophthalonitrile, 3,4-dihydroxy-4'-methoxybiphenyl-2,6-dicarbonitrile, 3,4-dihydroxy-3'-(morpholine-4-carbonyl)biphenyl-2,6-dicarbonitrile, N-butyl-2',6'-dicyano-3',4'-dihydroxybiphenyl-4-carboxamide, 2-(3,3-dimethylbutyl)-4,5-dihydroxyisophthalonitrile, 4,5-dihydroxy-2-(piperidin-1-yl)isophthalonitrile, 2-(hexylamino)-4,5-dihydroxyisophthalonitrile, 2-(cyclohexylamino)-4,5-dihydroxyisophthalonitrile, 4,5-dihydroxy-2-(2-methoxyethylamino)isophthalonitrile, 2-(4-benzylpiperidin-1-yl)-4,5-dihydroxyisophthalonitrile, 4,5-dihydroxy-2-(pentan-3-ylamino)isophthalonitrile, (E)-2-(4-ethylbenzylideneamino)-4,5-dihydroxyisophthalonitrile, (E)-4,5-dihydroxy-2-(4-methoxybenzylideneamino) isophthalonitrile, (E)-2-(4-fluorobenzylideneamino)-4,5-dihydroxyisophthalonitrile, 4,5-dihydroxy-2-tosylisophthalonitrile, 2-(benzo[d]thiazol-2-ylthio)-4,5-dihydroxyisophthalonitrile, 2-(4-fluorophenylthio)-4,5-dihydroxyisophthalonitrile, 2-(biphenyl-4-ylmethyl)-4,5-dihydroxyisophthaldnitrile, 2-(4-chloro-2-methylbenzyl)-4,5-dihydroxyisophthalonitrile, 2-(2-ethylbenzyl)-4,5-dihydroxyisophthalonitrile, 2-(2,3-dihydro-1H-inden-5-yloxy)-4,5-dihydroxyisophthalonitrile, enantiomer A of 4,5-dihydroxy-2-(p-tolylsulfinyl)isophthalonitrile, enantiomer B of 4,5-dihydroxy-2-(p-tolylsulfinyl)isophthalonitrile, 2-((cyclohexylmethyl)amino)-4,5-dihydroxyisophthalonitrile, 4,5-dihydroxy-2-(4-phenoxyphenylthio)isophthalonitrile, 4,5-dihydroxy-2-(pyridin-3-yl)isophthalonitrile, 4,5-dihydroxy-2-(4-(2,2,2-trifluoroethyl)benzyl)isophthalonitrile, 4,5-dihydroxy-2-(4-methyl-2-(trifluoromethyl)benzyl)isophthalonitrile, 4,5-dihydroxy-2-((4-(morpholine-4-carbonyl)phenyl)thio)isopththalonitrile, 4,5-dihydroxy-2-(methyl(p-tolyl)amino)isophthalonitrile or 4,5-dihydroxy-2-((6-methoxynaphthalen-2-yl)methyl) isophthalonitrile.

17. A method for the treatment of Parkinson's disease, comprising administering to a mammal in need of such treatment an effective amount of at least one compound according to claim 1.

18. The method according to claim 17, wherein levodopa therapy is potentiated.

19. A pharmaceutical composition, comprising as active ingredient at least one compound according to claim 1 and a pharmaceutically acceptable carrier, diluent, excipient or a mixture thereof.

20. The pharmaceutical composition according to claim 19, wherein the composition further comprises at least one other active ingredient.

21. The pharmaceutical composition according to claim 20, wherein the composition comprises levodopa and carbidopa.

22. The compound according to claim 11, wherein the compound is (E)-4,5-dihydroxy-2-(pent-1-enyl)isophthalonitrile, (E)-2-(3,3-dimethylbut-1-enyl)-4,5-dihydroxyisophthalonitrile, (Z)-4,5-dihydroxy-2-(prop-1-enyl)isophthalonitrile, (E)-4,5-dihydroxy-2-(prop-1-enyl)isophthalonitrile, (Z)-2-(but-2-enyl)-4,5-dihydroxyisophthalonitrile, 4,5-dihydroxy-2-(3-methylbut-2-enyl)isophthalonitrile, (E)-2-(but-2-enyl)-4,5-dihydroxyisophthalonitrile, 4,5-dihydroxy-2-(2-methylprop-1-enyl)isophthalonitrile, 4,5-dihydroxy-2-vinylisophthalonitrile, 4,5-dihydroxy-2-(prop-1-en-2-yl)isophthalonitrile, 2-allyl-4,5-dihydroxyisophthalonitrile, 4,5-dihydroxy-2-(3-methylbut-2-en-2-yl)isophthalonitrile, or (E)-4,5-dihydroxy-2-(4-methylpent-1-enyl)isophthalonitrile.

23. The compound according to claim 12, wherein the compound is 4,5-dihydroxy-2-(naphthalen-1-yl)isophthalonitrile, 4'-tert-butyl-3,4-dihydroxybiphenyl-2,6-dicarbonitrile, 4,5-dihydroxy-2-(naphthalen-2-yl)isophthalonitrile, 3,4-dihydroxy-4'-isopropoxybiphenyl-2,6-dicarbonitrile, 4'-butyl-3,4-dihydroxybiphenyl-2,6-dicarbonitrile, 3,4-dihydroxy-2',5'-dimethylbiphenyl-2,6-dicarbonitrile, 3'-ethyl-3,4-dihydroxybiphenyl-2,6-dicarbonitrile, 3,4-dihydroxy-2'-methylbiphenyl-2,6-dicarbonitrile, 3,4-dihydroxybiphenyl-2,6-dicarbonitrile, 3',4'-dichloro-3,4-dihydroxybiphenyl-2,6-dicarbonitrile, 4'-ethyl-3,4-dihydroxybiphenyl-2,6-dicarbonitrile, 3,4-dihydroxy-3',5'-dimethylbiphenyl-2,6-dicarbonitrile, 3,4-dihydroxy-3'-methylbiphenyl-2,6-dicarbonitrile, 4'-fluoro-3,4-dihydroxybiphenyl-2,6-dicarbonitrile, 3',4'-difluoro-3,4-dihydroxybiphenyl-2,6-dicarbonitrile, 4'-fluoro-3,4-dihydroxy-3'-methoxybiphenyl-2,6-dicarbonitrile, 3,4-dihydroxy-4'-propoxybiphenyl-2,6-dicarbonitrile, 4'-chloro-3,4-dihydroxy-3'-methylbiphenyl-2,6-dicarbonitrile, 3,4-dihydroxy-4'-isopropylbiphenyl-2,6-dicarbonitrile, 3,4-dihydroxy-4'-propylbiphenyl-2,6-dicarbonitrile, 3,4-dihydroxy-3',4'-dimethylbiphenyl-2,6-dicarbonitrile, 4'-fluoro-3,4-dihydroxy-3'-methylbiphenyl-2,6-dicarbonitrile, 3,4-dihydroxy-3',4'-dimethoxybiphenyl-2,6-dicarbonitrile, 3,4-dihydroxy-3'-isopropylbiphenyl-2,6-dicarbonitrile, 4,5-dihydroxy-2-(6-methoxynaphthalen-2-yl)isophthalonitrile, 3,4-dihydroxy-4'-methylbiphenyl-2,6-dicarbonitrile, or 3,4-dihydroxy-4'-methoxybiphenyl-2,6-dicarbonitrile.

24. The compound according to claim 13, wherein the compound is 4,5-dihydroxy-2-(phenylthio)isophthalonitrile, 4,5-dihydroxy-2-(p-tolylthio)isophthalonitrile, 2-(2,4-dimethylphenylthio)-4,5-dihydroxyisophthalonitrile, 2-(4-ethylphenylthio)-4,5-dihydroxyisophthalonitrile, 2-(4-chlorophenylthio)-4,5-dihydroxyisophthalonitrile, 4,5-dihydroxy-2-(o-tolylthio)isophthalonitrile, 2-(2-chlorophenylthio)-4,5-dihydroxyisophthalonitrile, 4,5-dihydroxy-2-(4-methoxyphenylthio)isophthalonitrile, 4,5-dihydroxy-2-(3-methoxyphenylthio)isophthalonitrile, or 2-(4-fluorophenylthio)-4,5-dihydroxyisophthalonitrile.

25. The compound according to claim 14, wherein the compound is 4,5-dihydroxy-2-(1-methyl-1H-pyrrol-2-yl)isophthalonitrile, 4,5-dihydroxy-2-(thiophen-2-yl)isophthalonitrile, 2-(furan-2-yl)-4,5-dihydroxyisophthalonitrile, 2-(furan-3-yl)-4,5-dihydroxyisophthalonitrile, 4,5-dihydroxy-2-(thiophen-3-yl)isophthalonitrile, 4,5-dihydroxy-2-(5-methylfuran-2-yl)isophthalonitrile, 4,5-dihydroxy-2-(5-methylthiophen-2-yl)isophthalonitrile, 2-(benzofuran-2-yl)-4,5-dihydroxyisophthalonitrile, 2-(5-chlorothiophen-2-yl)-4,5-dihydroxyisophthalonitrile, 2-(benzo[b]thiophen-2-yl)-4,5-dihydroxyisophthalonitrile, 2-(5-hexylthiophen-2-yl)-4,5-dihydroxyisophthalonitrile, 2-(2-ethoxythiazol-5-yl)-4,5-dihydroxyisophthalonitrile, 2-(2,5-dimethylthiophen-3-yl)-4,5-dihydroxyisophthalonitrile, 4,5-dihydroxy-2-(1-isobutyl-1H-pyrazol-4-yl)isophthalonitrile, 4,5-dihydroxy-2-(1-methyl-1H-pyrazol-4-yl)isophthalonitrile, or 4,5-dihydroxy-2-(pyridin-3-yl)isophthalonitrile.

26. The compound according to claim 15, wherein the compound is 4,5-dihydroxy-2-(4-methylbenzyl)isophthalonitrile, 4,5-dihydroxy-2-(2-methoxybenzyl)isophthalonitrile, 4,5-dihydroxy-2-(2-methylbenzyl)isophthalonitrile, 2-(2,5-dimethylbenzyl)-4,5-dihydroxyisophthalonitrile, 4,5-dihydroxy-2-(3-methylbenzyl)isophthalonitrile, 2-(3,5-dimethylbenzyl)-4,5-dihydroxyisophthalonitrile, 4,5-dihydroxy-2-(4-isopropylbenzyl)isophthalonitrile, 2-(4-ethylbenzyl)-4,5-dihydroxyisophthalonitrile, 2-(2,4-dimethylbenzyl)-4,5-dihydroxyisophthalonitrile, 2-(2-ethylbenzyl)-4,5-dihydroxyisophthalonitrile, or 4,5-dihydroxy-2-((6-methoxynaphthalen-2-yl)methyl) isophthalonitrile.

27. The compound according to claim 11, wherein the compound is (E)-2-(3,3-dimethylbut-1-enyl) -4,5-dihydroxyisophthalonitrile.

28. The compound according to claim 11, wherein the compound is (E)-4,5- dihydroxy-2-(prop-1-enyl)isophthalonitrile.

29. The compound according to claim 11, wherein the compound is 4,5- dihydroxy-2-(2-methylprop-1-enyl)isophthalonitrile.

30. The compound according to claim 11, wherein the compound is 4,5- dihydroxy-2-vinylisophthalonitrile.

31. The compound according to claim 11, wherein the compound is 4,5- dihydroxy-2-(prop-1-en-2-yl)isophthalonitrile.

32. The compound according to claim 11, wherein the compound is 2-allyl- 4,5-dihydroxyisophthalonitrile.

33. The compound according to claim 12, wherein the compound is 4'-tert- butyl-3,4-dihydroxybiphenyl-2,6-dicarbonitrile.

34. The compound according to claim 12, wherein the compound is 3,4- dihydroxy-2',5'-dimethylbiphenyl-2,6-dicarbonitrile.

35. The compound according to claim 12, wherein the compound is 4'-ethyl- 3,4-dihydroxybiphenyl-2,6-dicarbonitrile.

36. The compound according to claim 12, wherein the compound is 3,4- dihydroxy-4'-isopropylbiphenyl-2,6-dicarbonitrile.

37. The compound according to claim 12, wherein the compound is 3,4- dihydroxy-4'-propylbiphenyl-2,6-dicarbonitrile.

38. The compound according to claim 12, wherein the compound is 3,4- dihydroxy-3',4'-dimethylbiphenyl-2,6-dicarbonitrile.

39. The compound according to claim 12, wherein the compound is 3,4- dihydroxy-4'-methylbiphenyl-2,6-dicarbonitrile.

40. The compound according to claim 12, wherein the compound is 3,4- dihydroxy-4'-methoxybiphenyl-2,6-dicarbonitrile.

41. The compound according to claim 13, wherein the compound is 2-(4- ethylphenylthio)-4,5-dihydroxyisophthalonitrile.

42. The compound according to claim 13, wherein the compound is 4,5- dihydroxy-2-(o-tolylthio)isophthalonitrile.

43. The compound according to claim 13, wherein the compound is 4,5- dihydroxy-2-(4-methoxyphenylthio)isophthalonitrile.

44. The compound according to claim 14, wherein the compound is 4,5- dihydroxy-2-(1-methyl-1H-pyrrol-2-yl)isophthalonitrile.

45. The compound according to claim 14, wherein the compound is 2-(2- ethoxythiazol-5-yl)-4,5-dihydroxyisophthalonitrile.

46. The compound according to claim 14, wherein the compound is 2-(2,5- dimethylthiophen-3-yl)-4,5-dihydroxyisophthalonitrile.

47. The compound according to claim 14, wherein the compound is 4,5- dihydroxy-2-(1-isobutyl-1H-pyrazol-4-yl)isophthalonitrile.

48. The compound according to claim 15, wherein the compound is 4,5- dihydroxy-2-(4-methylbenzyl)isophthalonitrile.

49. The compound according to claim 15, wherein the compound is 4,5- dihydroxy-2-(2-methoxybenzyl)isophthalonitrile.

50. The compound according to claim 15, wherein the compound is 2-(3,5- dimethylbenzyl)-4,5-dihydroxyisophthalonitrile.

51. The compound according to claim 15, wherein the compound is 2-(4- ethylbenzyl)-4,5-dihydroxyisophthalonitrile.

52. The compound according to claim 15, wherein the compound is 2-(2- ethylbenzyl)-4,5-dihydroxyIsophthalonitrile.

\* \* \* \* \*

UNITED STATES PATENT AND TRADEMARK OFFICE
CERTIFICATE OF CORRECTION

PATENT NO. : 9,458,128 B2
APPLICATION NO. : 14/403023
DATED : October 4, 2016
INVENTOR(S) : Marko Ahlmark et al.

It is certified that error appears in the above-identified patent and that said Letters Patent is hereby corrected as shown below:

In the Claims

Claim 16, Column 105, Lines 58-59, "dimethylthiophen-3-yl)4,5-dihydroxyisophthalonitrile," should read -- 2-(2,5-dimethylthiophen-3-yl)-4,5-dihydroxyisophthalonitrile, --.

Claim 16, Column 106, Line 32, "3-(4" should read -- 3-(4- --.

Claim 16, Column 107, Line 14, "dihydroxyisophthaldnitrile" should read -- dihydroxyisophthalonitrile --.

Claim 52, Column 110, Lines 35-36, "dihydroxylsophthalonitrile" should read -- dihydroxyisophthalonitrile --.

Signed and Sealed this
Tenth Day of January, 2017

Michelle K. Lee
*Director of the United States Patent and Trademark Office*